US006358885B1

(12) United States Patent
Selby et al.

(10) Patent No.: US 6,358,885 B1
(45) Date of Patent: Mar. 19, 2002

(54) SUBSTITUTED PHENYLHETEROCYCLIC HERBICIDES

(75) Inventors: Thomas P. Selby, Wilmington; Thomas M. Stevenson, Newark, both of DE (US)

(73) Assignees: Mississippi State University; Research Technology Corporation Mississippi State, both of MS (US)

( * ) Notice: Subject to any disclaimer, the term of this patent is extended or adjusted under 35 U.S.C. 154(b) by 0 days.

(21) Appl. No.: 09/292,417

(22) Filed: Apr. 15, 1999

Related U.S. Application Data

(60) Division of application No. 08/852,719, filed on May 7, 1997, now Pat. No. 5,977,028, which is a division of application No. 08/256,622, filed as application No. PCT/US92/11300 on Dec. 30, 1992, now Pat. No. 5,670,455, which is a continuation-in-part of application No. 07/827,788, filed on Jan. 29, 1992, now abandoned.

(51) Int. Cl.[7] .................. A01N 43/84; A01N 43/72; A01N 43/40; A01N 43/78; A01N 43/56
(52) U.S. Cl. .................. 504/225; 504/221; 504/255; 504/267; 504/275; 504/281; 504/270; 544/58.2; 544/139; 544/145; 544/148; 544/176; 544/105; 548/152; 548/159; 548/178; 548/221; 548/302.7; 548/303.7; 548/304.4; 548/311.1; 548/311.4; 548/311.7; 548/360.1; 548/360.5
(58) Field of Search ................. 504/225, 281, 504/270, 267, 221, 275, 277; 544/139, 145, 148, 176, 58.2, 105; 548/360.1, 360.5, 221, 159, 178, 152, 311.1, 303.7, 304.4, 302.7, 311.4, 311.7

(56) References Cited

U.S. PATENT DOCUMENTS

| 4,578,387 A | 3/1986 | Spitzer ................ 514/249 |
| 4,670,445 A | 6/1987 | Spitzer ................ 514/300 |
| 4,925,849 A | 5/1990 | Shiokawa et al. ........ 546/121 |
| 5,032,165 A | 7/1991 | Miura et al. ............. 71/92 |
| 5,281,571 A | 1/1994 | Woodward et al. ........ 504/225 |

FOREIGN PATENT DOCUMENTS

| EP | 0 231 622 | 8/1987 | ......... C07D/513/04 |
| EP | 0 299 209 | 1/1989 | ......... C07D/471/04 |
| FR | 2 593 817 | 1/1986 | ......... C07D/471/04 |

OTHER PUBLICATIONS

Chemical Abstracts, 117, p. 702, Abstract No. 26424a (1992).
Alcaide, B. et al, *J. Org. Chem.*, 54, 5763–5768 (1989).
Lantos, I. et al, *J. Org. Chem.*, 4223–4227 (1988).
Lantos, I. et al, *Heterocycles*, 24(4), 991–996 (1986).
Lantos, I. et al, *J. Med. Chem.*, 27, 72–75 (1984).
Ranganathan, D. et al, *Tetrahedron Letters*, 24(10), 1067–1070 (1983).
Larsen, S. et al, *Tetrahedron Letters*, 30(35), 4625–4628 (1989).
Ranganathan, D. et al, *Synthetic Communication*, 15(3), 259–265 (1985).
Padwa, A. et al, *J. Org. Chem.*, 43(9), 1664–1671 (1978).
Suzue, S. et al, *Chem. Pharm. Bull.*, 21(10), 2146–2160 (1973).
Chemical Abstracts, 115(5), Abstract No. 115:49686k, (1991).
Chemical Abstracts, 115(9), Abstract No. 115:92260d (1991).
Chemical Abstracts, 115(7), Abstract No. 115:182, 910v (1991).
Chemical Abstracts, 114(17) Abstract No. 114:164, 226b (1991).

*Primary Examiner*—Amelia Owens
(74) *Attorney, Agent, or Firm*—Steven B. Kelber; Piper Marbury Rudnick and Wolfe LLP

(57) ABSTRACT

This invention relates to certain phenylheterocyclic compounds, herbicidal compositions thereof and a method for their use as general and selective preemergent or postemergent herbicides or plant growth regulants.

8 Claims, No Drawings

SUBSTITUTED PHENYLHETEROCYCLIC HERBICIDES

CROSS REFERENCE TO RELATED APPLICATIONS

This application is a divisional of Ser. No. 08/852,719, filed May 7, 1997 now U.S. Pat. No. 5,977,028, which is a divisional of Ser. No. 08/256,622, filed Jul. 27, 1994, now U.S. Pat. No. 5,670,455, which was filed under 371 from PCT/US92/11300, filed Dec. 30, 1992, which is a continuation in part of Ser. No. 07/827,788 filed Jan. 29, 1992, now abandoned.

BACKGROUND OF THE INVENTION

This invention relates to certain substituted fused heterocyclic compounds which are useful as herbicides and their agriculturally suitable compositions as well as methods for their use as general or selective preemergent or postemergent herbicides or as plant growth regulants.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked weed growth in such crops can cause significant losses, reducing profit to the farmer and increasing costs to the consumer. In other situations, herbicides are desired which will control all plant growth. Examples of areas in which complete control of all vegetation is desired are areas around railroad tracks, storage tanks and industrial storage areas. There are many products commercially available for these purposes, but the search continues for products which are more effective, less costly and environmentally safe.

U.S. Pat. No. 5,032,165 discloses herbicidal compounds of the formula

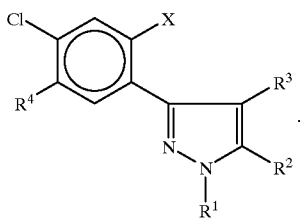

SUMMARY OF THE INVENTION

The invention comprises novel compounds of Formula I, agriculturally suitable compositions containing them, and their method-of-use as preemergent and/or postemergent herbicides and/or plant growth regulants

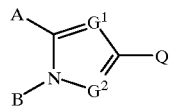

I wherein
Q is

Q-1

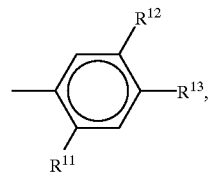

Q-2

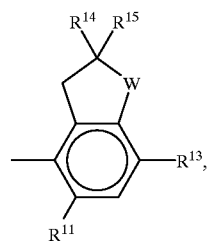

Q-3

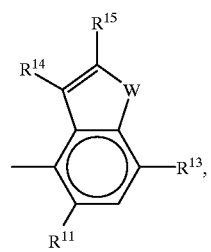

Q-4

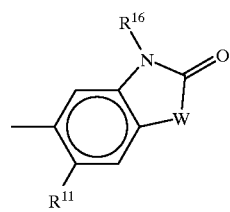

Q-5

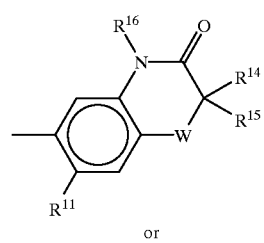

or

Q-6

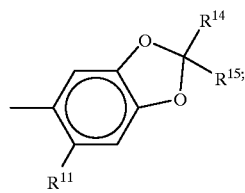

$G^1$ is $CR^1$ or N;
$G^2$ is $CR^4$ or N;
A is $C_1$–$C_4$ alkyl, $C_1$–$C_4$ haloalkyl, $C_2$–$C_4$ alkenyl, $C_2$–$C_4$ alkynyl, $OR^{10}$, $SR^{10}$ or halogen;
B is $C_1$–$C_4$ alkyl, $C_1$–$C_4$ haloalkyl, $C_3$–$C_4$ alkenyl or $C_3$–$C_4$ alkynyl;

A and B can be taken together as X—Y—Z to form a fused ring such that X is connected to nitrogen and Z is connected to carbon;

X is $CHR^2$, $CH_2CH_2$ or $CR^2=CR^3$;

Y is $CHR^5$, $CR^5=CR^6$, $CHR^5CHR^6$, $NR^7$, O or $S(O)_n$;

Z is $CHR^8$, $CH_2CH_2$, $CR^8=CR^9$, $NR^7$, O or $S(O)_n$;

n is 0, 1 or 2;

$R^1$ and $R^4$ are independently halogen or CN;

$R^2$, $R^3$, $R^5$, $R^6$, $R^8$ and $R^9$ are independently H, halogen, $C_1$–$C_4$ alkyl or $C_1$–$C_4$ haloalkyl;

$R^7$ is H, $C_1$–$C_4$ alkyl or $C_1$–$C_4$ haloalkyl;

W is O or S;

$R^{10}$ is $C_1$–$C_4$ alkyl or $C_1$–$C_4$ haloalkyl;

$R^{11}$ is halogen;

$R^{12}$ is H, $C_1$–$C_8$ alkyl, $C_1$–$C_8$ haloalkyl, halogen, OH, $OR^{17}$, SH, $S(O)_nR^{17}$, $COR^{17}$, $CO_2R^{17}$, $C(O)SR^{17}$, $C(O)NR^{19}R^{20}$, CHO, $CR^{19}=NOR^{26}$, $CH=CR^{27}CO_2R^{17}$, $CH_2CHR^{27}CO_2R^{17}$, $CO_2N=CR^{21}R^{22}$, $NO_2$, CN, $NHSO_2R^{23}$, $NHSO_2NHR^{23}$, $NR^{17}R^{28}$, $NH_2$ or phenyl optionally substituted with $R^{29}$;

$R^{13}$ is $C_1$–$C_2$ alkyl, $C_1$–$C_2$ haloalkyl, $OCH_3$, $SCH_3$, $OCHF_2$, halogen, CN or $NO_2$;

$R^{14}$ is H, $C_1$–$C_3$ alkyl or halogen;

$R^{15}$ is H, $C_1$–$C_3$ alkyl, halogen, $C_1$–$C_3$ haloalkyl, cyclopropyl, vinyl, $C_2$ alkynyl, CN, $C(O)R^{28}$, $CO_2R^{28}$, $C(O)NR^{28}R^{30}$, $CR^{24}R^{25}CN$, $CR^{24}R^{25}C(O)R^{28}$, $CR^{24}R^{25}CO_2R^{28}$, $CR^{24}R^{25}C(O)NR^{28}R^{30}$, $CHR^{24}OH$, $CHR^{24}OC(O)R^{28}$ or $OCHR^{24}OC(O)NR^{28}R^{30}$;

when Q is Q-2 or Q-6, $R^{14}$ and $R^{15}$ together with the carbon to which they are attached can be C=O;

$R^{16}$ is H, $C_1$–$C_6$ alkyl, $C_1$–$C_6$ haloalkyl, $C_2$–$C_6$ alkoxyalkyl, $C_3$–$C_6$ alkenyl, $C_3$–$C_6$ alkynyl or

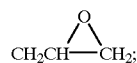

$R^{17}$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl, $C_4$–$C_8$ alkoxyalkoxyalkyl; $C_4$–$C_8$ cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with halogen, $C_1$–$C_3$ alkyl or $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkyl carbonyl; benzyl optionally substituted with halogen, $C_1$–$C_3$ alkyl or $C_1$–$C_3$ haloalkyl; $CHR^{24}COR^{18}$; $CHR^{24}P(O)$ $(OR^{18})_2$; $CHR^{24}P(S)$ $(OR^{18})_2$; $CHR^{24}C(O)NR^{19}R^{20}$; $CHR^{24}C(O)NH_2$; $CHR^{24}CO_2R^{18}$;

$CO_2R^{18}$; $SO_2R^{18}$; phenyl optionally substituted with $R^{29}$;

$R^{18}$ is $C_1$–$C_6$ alkyl, $C_1$–$C_6$ haloalkyl, $C_3$–$C_6$ alkenyl or $C_3$–$C_6$ alkynyl;

$R^{19}$ and $R^{21}$ are independently H or $C_1$–$C_4$ alkyl;

$R^{20}$ and $R^{22}$ are independently $C_1$–$C_4$ alkyl or phenyl optionally substituted with halogen, $C_1$–$C_3$ alkyl or $C_1$–$C_3$ haloalkyl;

$R^{19}$ and $R^{20}$ may be taken together as —$(CH_2)_5$—, —$(CH_2)_4$— or —$CH_2CH_2OCH_2CH_2$—, each ring optionally substituted with $C_1$–$C_3$ alkyl, phenyl or benzyl;

$R^{21}$ and $R^{22}$ may be taken together with the carbon to which they are attached to form $C_3$–$C_8$ cycloalkyl;

$R^{23}$ is $C_1$–$C_4$ alkyl or $C_1$–$C_4$ haloalkyl;

$R^{24}$ and $R^{25}$ are independently H or $C_1$–$C_4$ alkyl;

$R^{26}$ is H, $C_1$–$C_6$ alkyl, $C_3$–$C_6$ alkenyl or $C_3$–$C_6$ alkynyl;

$R^{27}$ is H, $C_1$–$C_4$ alkyl or halogen;

$R^{28}$ and $R^{30}$ are independently H or $C_1$–$C_4$ alkyl; and $R^{29}$ is $C_1$–$C_2$ alkyl, $C_1$–$C_2$ haloalkyl, $OCH_3$, $SCH_3$, $OCHF_2$, halogen, CN or $NO_2$;

and their corresponding N-oxides and agriculturally suitable salts provided that 1) the sum of X, Y, and Z is no greater than 5 atoms in length and only one of Y and Z can be other than a carbon containing link;
2) when A and B are other than taken together as X—Y—Z then $G^1$ is N and $G^2$ is $CR^4$;
3) when $R^{12}$ is $CO_2R^{17}$, $C(O)SR^{17}$, $CH=CR^{27}CO_2R^{17}$ or $CH_2CHR^{27}CO_2R^{17}$ then $R^{17}$ is other than $C_1$ haloalkyl and when $R^{17}$ is $CHR^{24}CO_2R^{18}$ or $CO_2R^{18}$ then $R^{18}$ is other than $C_1$ haloalkyl; and
4) when $G^1$ is N then $G^2$ is $CR^4$, and when $G^2$ is N then $G^1$ is $CR^1$.

In the above definitions, the term "alkyl", used either alone or in compound words such as "alkylthio" or "haloalkyl", includes straight chain or branched alkyl, e.g., methyl, ethyl, n-propyl, isopropyl or the different butyl isomers. Alkoxy includes methoxy, ethoxy, n-propyloxy, isopropyloxy, the different butoxy isomers, etc. Alkenyl and alkynyl include straight chain or branched alkenes and alkynes, e.g., 1-propenyl, 2-propenyl, 3-propenyl and the different butenyl isomers. Cycloalkyl includes cyclopropyl, cyclobutyl, cyclopentyl, cyclohexyl, etc. The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

The compounds of the invention preferred for reasons including ease of synthesis and/or greater herbicidal efficacy are:

1) Compounds of Formula I wherein $R^2$, $R^3$, $R^5$, $R^6$, $R^8$ and $R^9$ are independently H, F, $CH_3$ or $CF_3$.
2) Compounds of Preferred 1 wherein
   $R^{12}$ is H, $OR^{17}$, $SR^{17}$ or $CO_2R^{17}$;
   $R^{13}$ is halogen or CN.
3) Compounds of Preferred 2 wherein Q is Q-1, Q-2, Q-4 or Q-5;
A and B are taken together as X—Y—Z;
X is $CHR^2$;
Y is $CHR^5$ or $CHR^5CHR^6$;
Z is $CHR^8$;
$R^2$, $R^3$, $R^5$, $R^6$, $R^8$ and $R^9$ are independently H or F;
$R^{17}$ is $C_1$–$C_4$ alkyl, $C_3$–$C_4$ alkenyl, $C_3$–$C_4$ alkynyl, $C_2$–$C_4$ alkoxyalkyl, $C_1$–$C_4$ haloalkyl, $C_3$–$C_4$ haloalkenyl or $C_3$–$C_4$ haloalkynyl.

4) Compounds of Formula I wherein $G^1$ is N.

5) Compounds of Formula I wherein $G^2$ is N.

The compounds of the invention specifically preferred for reasons of greatest ease of synthesis and/or greatest herbicidal efficacy are the compounds of Preferred 3 which are:
3-bromo-2-[4-chloro-2-fluoro-5-(2-propynyloxy)-phenyl]-4,5,6,7-tetrahydropyrazolo[1,5-a]pyridine;
3-chloro-2-[4-chloro-2-fluoro-5-(2-propynyloxy)-5,6,7,8-tetrahydoimidazo[1,2-a]pyridine; and
6-(3-chloro-4,5,6,7-tetrahydropyrazolo[1,5-a]pyridin-2-yl)-7-fluoro-4-(1-methyl-2-propynyl)-2H-1,4-benzoxazin-3(4H)-one.

Another embodiment of the invention is an agriculturally suitable composition for controlling the growth of undesired vegetation comprising an effective amount of a compound of Formula I with the substituents as defined above.

A further embodiment of the invention is a method for controlling the growth of undesired vegetation which comprises applying to the locus to be protected an effective amount of a compound of Formula I with the substituents as defined above.

Compounds of Formula I may exist as one or more stereoisomers. The various stereoisomers include enantiomers, diastereomers and geometric isomers. One skilled in the art will appreciate that one stereoisomer may be the more active. One skilled in the art knows how to separate said enantiomers, diasteriomers and geometric isomers. Accordingly, the present invention comprises racemic mixtures, individual stereoisomers, and optically active mixtures.

DETAILED DESCRIPTION OF THE INVENTION

Synthesis

By using one or more of the reactions and techniques described in Schemes 1–18 of this section as well as by following the specific procedures given in Examples 1–20, compounds of General Formula I can be prepared.

Compounds of Formula Ia, where Q, X, Y, and Z are defined as above, can be prepared by the method in Scheme 1. Reaction of an aminoheterocycle of Formula II with an alpha-bromo or chloroketone of Formula III in a solvent such as acetonitrile or methanol at room temperature or by heating followed by neutralization with a base such as saturated aqueous sodium bicarbonate affords compounds of Formula Ia. Aminoheterocycles of Formula II are known and can be commercially purchased in some cases.

Halogenation of compounds of Formula Ia with halogenating agents such as N-halosuccinimides or bromine affords compounds of Formula Ib (where $R^1$ is halogen). Treatment of compounds of Formula Ia with Vilsmeier Reagent (phosphorous oxychloride, N,N-dimethylformamide) gives aldehyde adducts (of Formula Ib where $R^1$ is a formyl group) which can be condensed with hydroxylamine hydrochloride to give oxime intermediates (Ib where $R^1$ is C=NOH) which in turn can be heated in phosphorous oxychloride to yield cyano substituted analogs of Formula Ic.

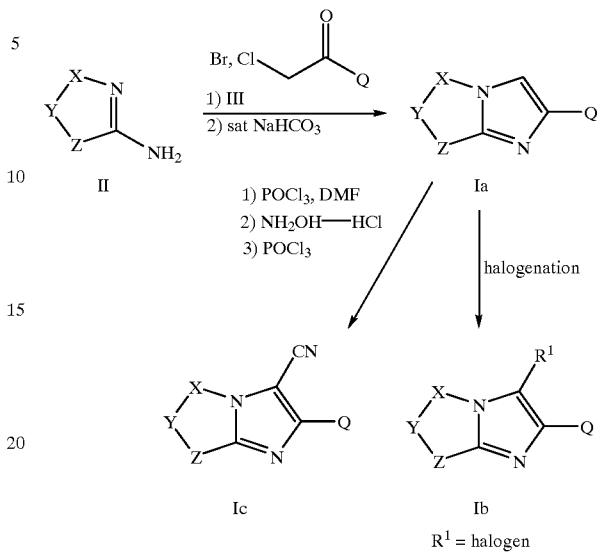

SCHEME 1

The alpha-bromo and chloroketone of Formula III can be made by the methods summarized in Scheme 2. Carboxylic acids of Formula IV can be treated with thionyl chloride to give an acid chloride which in turn is allowed to react with Grignard reagent of Formula MeMgBr or MeMgCl or with methyl lithium to furnish ketone intermediates of Formula V. Lithiation of arylhalides of Formula VI followed by treatment with reagents of formula MeCOL (where L represents a leaving group such as halogen, dialkylamine, or alkoxide) gives ketones V as well. By the method of Beech [J. Chem. Soc. 1297 (1954)], ketones of Formula V can also be prepared from arylamines of Formula VII by diazotization followed by reaction of the generated diazonium salt with acetaldehyde oxime (MeCH=NOH) and hydrolysis. The starting materials IV, VI, and VII are known and can be commercially obtained in some cases.

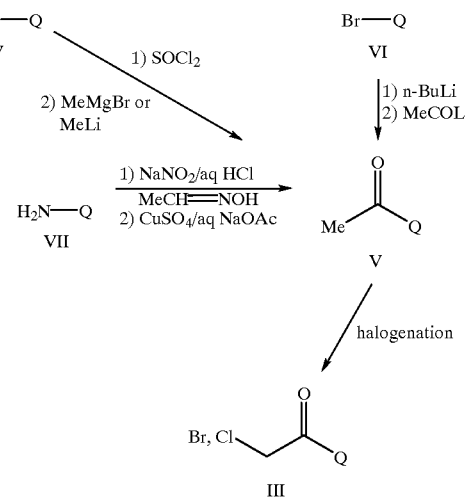

SCHEME 2

An alternative and more specific method for preparing tetrahydroimidazo[1,2-a]pyridine intermediates of Formula Id where $R^2$, $R^5$, $R^6$, $R^8$, and Q are defined as above (except when $R^{16}$ or $R^{17}$ on Q is an unsaturated group) is shown in Scheme 3. Heating 2-aminopyridines of Formula VIII with an alpha-bromo or chloroketone of Formula III followed by neutralization with saturated aqueous sodium bicarbonate gives imidazo[1,2-a]pyridines of Formula IX. Catalytic hydrogenation of imidazopyridines IX with a transition metal catalyst such as platinum oxide affords the tetrahydro analogs Id. Use of 2-aminothiazoles, 2-aminoxazoles, 2-aminopyrimidines, 2-aminopyridazines, and 2-aminopyrazines in place of the 2-aminopyridine starting materials in Scheme 3 and following this same method of synthesis also gives compounds of Formula Ia where X, Y, and Z are heteroatoms.

SCHEME 3

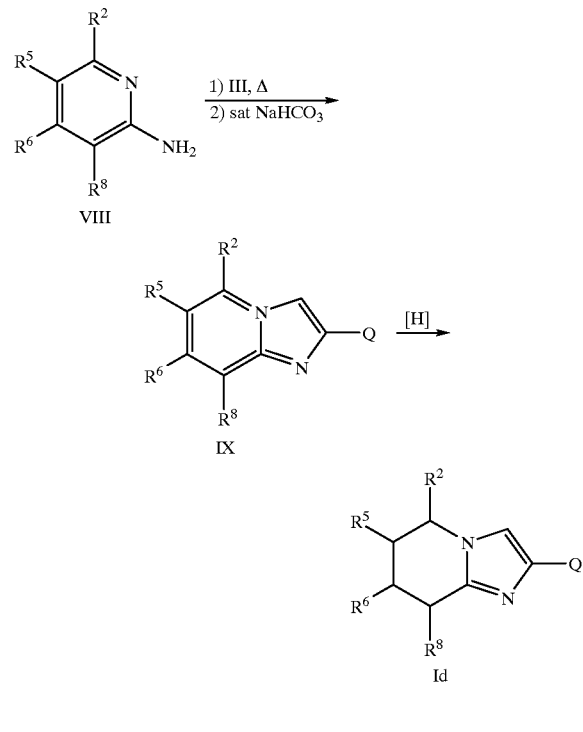

Tetrahydroimidazo[1,2-a]pyridines of Formula Ib or Id where $R^{16}$ or $R^{17}$ on Q is methyl or benzyl can be deprotected with borontribromide to give dealkylated intermediates (where $R^{16}$ and $R^{17}$ are hydrogen) which on realkylation with alkenyl or alkynyl halides give compounds of Formula Ib or Id where $R^{16}$ or $R^{17}$ represents an alkenyl or alkynyl moiety.

Intermediate imidazo[1,2-a]pyridines of Formula IX can also be made by the route shown in Scheme 4. Condensing aminopyridines of Formula X with bromoacetic acid followed by heating the obtained condensation adducts with phosphorous oxybromide gives 2-bromoimidazo[1,2-a] pyridines of Formula XI. Palladium-catalyzed cross-couplings [using bis(triphenylphosphine)palladium(II) chloride or tetrakis(triphenylphosphine)palladium(0)] of these bromoimidazopyridines with boronic acids of formula QB(OH)$_2$ in a solvent such as glyme in the presence of base such as aqueous sodium bicarbonate yields imidazo[1,2-a] pyridines of Formula IX.

SCHEME 4

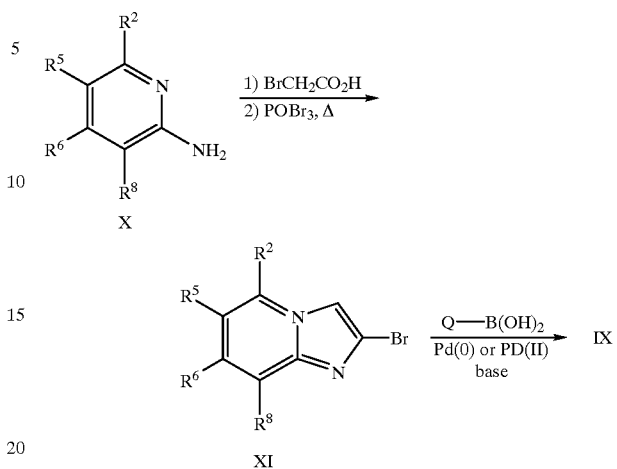

Dihydroimidazo[1,2-a]pyridines of Formula Ie and If can be synthesized by the chemistry shown in Scheme 5. Warming tetrahydroimidazopyridines of Formula Id with an excess of N-halosuccinimides (2.0–2.5 equivalents) in dimethylformamide at 60–100° C. produces Ie and If.

SCHEME 5

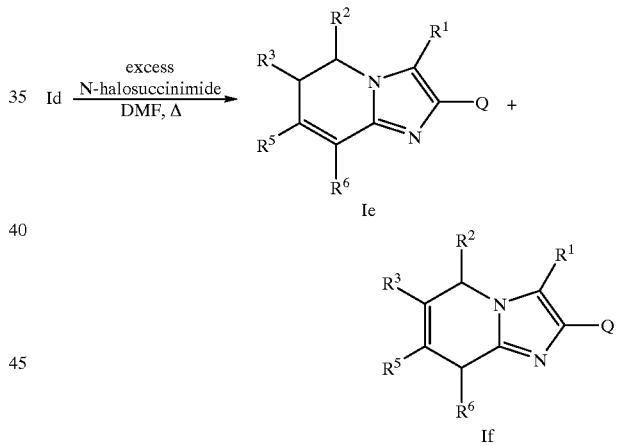

Scheme 6 illustrates the preparation of imidazoles of Formula Ig where $R^1$ is halogen, and Q, A, and B are as previously defined. Amidines, isoureas, and isothioureas of Formula XII can be heated with alpha-bromo and chloroketones of Formula III, or with a corresponding alpha-hydroxyketone, in a solvent such as ethanol or dimethylformamide to give, after neutralization with a base such as aqueous saturated sodium bicarbonate, intermediates of Formula XIII. Alkylation of intermediates of Formula XIII with alkylating agents of Formula BL$^1$ (where L$^1$ is a leaving group) affords imidazoles of Formula XIV which on halogenation gives 5-haloimidazoles of Formula Ig where $R^1$ is halogen. Halogenation of compounds of Formula XIV where A is hydrogen with an excess of the halogenating reagent produces imidazoles of Formula Ig where both A and $R^1$ is halogen.

SCHEME 6

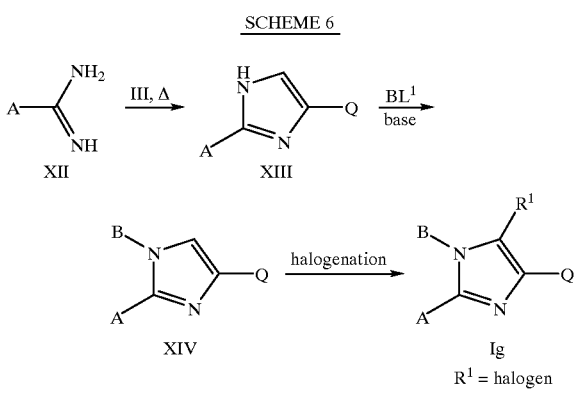

An alternative method of preparing compounds of Formula XIV is shown in Scheme 7. Palladium-catalyzed cross-couplings [using for example bis(triphenylphosphine)palladium(II) chloride or tetrakis(triphenylphosphine)palladium(0)] of 4-bromoimidazoles of Formula XV with boronic acids of Formula $QB(OH)_2$ in a solvent such as glyme in the presence of base such as aqueous sodium bicarbonate yields compounds of Formula XIV. Bromoimidazoles of Formula XV can be prepared by established methods.

SCHEME 7

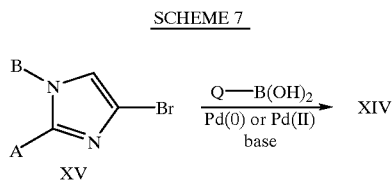

Salts (e.g., hydrochlorides and N-oxides) of I and II can be made by reaction of the free bases with an appropriate acid or oxidizing agent such as meta-chlorperoxybenzoic acid.

Scheme 8 describes how compounds of Formula I (where $G^2=N$, $G^1=CR^1$ and A and B are X—Y—Z) can be made by the reaction of sydnones of Formula XVI with appropriately substituted alkynes XVII. The reaction takes place at elevated temperatures generally between 80° C. and 200° C. The reaction may be performed in a variety of solvents with aromatic hydrocarbons such as xylenes being preferred.

SCHEME 8

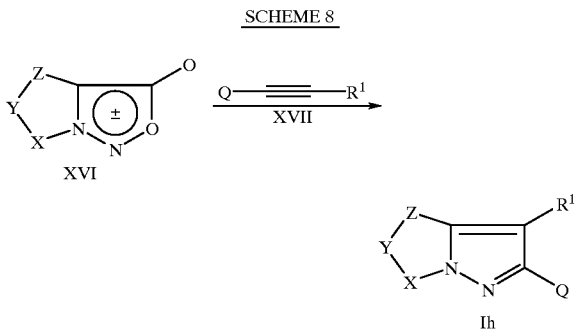

Scheme 9 describes how compounds of Formula I can be made by the reaction of sydnones with appropriately substituted alkenes XVIII. The initial product of the reaction is a dihydro aromatic compound. Often this is converted directly to the desired structure (Ih) in situ. It is also possible to include an oxidant such as chloranil or other mild oxidizing agent in the reaction mixture so as to make the aromatization process more facile (this has been shown with simpler sydnones: Huisgen et al.; Chem. Ber. 1968, 101, 829). The conditions for the reaction are as described above. The sydnones used in the above-mentioned processes can be made using procedures known in the art. (see S. D. Larsen and E. Martinborough, Tet. Lett. 1989, 4625) The chemistry of bicyclic sydnones has been reviewed (see Kevin Potts in "1,3-Dipolar Cycloaddition Chemistry", Volume II, pages 50–57; A. Padwa editor, Wiley Interscience, New York, 1984).

SCHEME 9

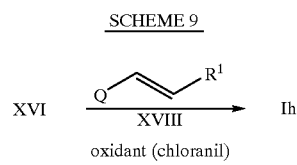

Scheme 10 describes an alternative synthesis of compounds of the invention by the photochemical cycloaddition of alkynyl substituted tetrazoles (XIX). The reaction can be performed in a variety of solvents, but is preferably carried out in inert solvents such as benzene or toluene. The reaction must be carried out in a vessel that allows the passage of light at wavelengths between 250 and 300 nm such as those made from quartz or vycor. The photolysis is preferably performed with a high pressure mercury arc lamp or other lamp which produces light above 250 nm. The reaction is carried out at room temperature or above.

SCHEME 10

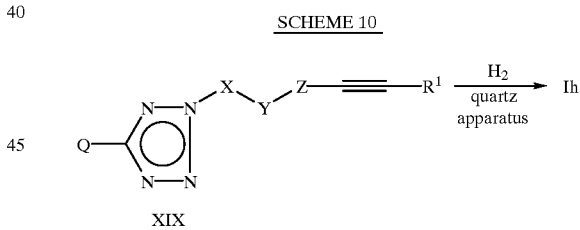

Scheme 11 describes how the tetrazoles XIX are made by alkylation of the free tetrazole XX with a halide or sulfonate in the presence of an acid acceptor or base. Many different bases such as alkali carbonates, hydroxides or hydrides are suitable. A variety of solvents can be used, but solvents of high polarity such as dimethylformamide or dimethyl acetamide are preferred. Tetrazoles XX can also be alkylated with alcohols XXI using the Mitsonobu reaction with a phosphine and a diazodicarboxylate. There are many different solvents and conditions that can be used. (See O. Mitsonobu, Synthesis, 1981, 1) Especially useful conditions for the instant invention include carrying out the reaction in tetrahydrofuran with diethyl azodicarboxylate and triphenylphosphine. Under these conditions the desired 3-alkynyl tetrazole (V) is produced predominantly.

SCHEME 11

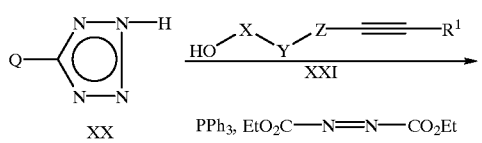

Scheme 12 describes how compounds of the instant invention (Ih or Ij, $R^1$=H) can be converted to other compounds of the present invention (Ih or Ij, $R^1$=Cl or Br) by reaction with halogenating agents. The reaction may be carried out with elemental halogens and also with N-halosuccinimides. The reaction with N-halosuccinimides gives particularly good results when conducted in dipolar aprotic solvents such as dimethylformamide.

SCHEME 12

Ih or Ij ($R^1$=H) →[NCS(NBS) or $Br_2$($Cl_2$)]→ Ih or Ij ($R^1$=Br, Cl)

Scheme 13 shows how compounds of Formula Ih can also be prepared by coupling compounds of Formula Ih, Q=$SnR^3$, with aryl halides or sulfonates (XXVII) in the presence of palladium catalysts such as those described in Scheme 7. For an example of this type of coupling with monocyclic pyrazoles, see Yamanaka et al., *Heterocycles*, 33, 813–818 (1992). Compounds of Formula Ih, Q=$SnR^3$, can be made by sydnone cycloaddition as described in Scheme 8 using stannylated acetylenes.

SCHEME 13

Ih (Q=SnBu₃) + XXVII (X=Br, I, OSO₂CF₃) →[Pd° catalyst]→ Ih

As shown in Scheme 14 some compounds of formula Ii where $G^2$=N can be prepared by catalytic hydrogenation of compounds of Formula XXIII. The conditions are those disclosed in Scheme 3. Compounds of Formula XXIII can be prepared by cyclization of N-aminopicoline salts (XXI) with acid chlorides (XXII). The reaction is best performed in the presence of a base, preferably an amine base. Specifically preferred conditions are to run the reaction at elevated temperature (50–80° C.) in the amine base, such as pyridine, as solvent (see Potts et al., *J. Org. Chem.*, 33, 3767–3770 (1969).

SCHEME 14

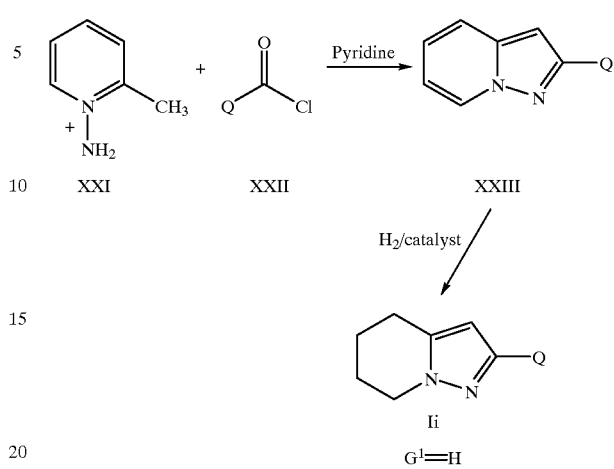

Scheme 15 describes how other compounds of the invention (Ij) can be obtained by the reaction of Munchnones (reactive mesoionic intermediates) with acetylenes (III). The Munchnones are prepared in the presence of the dipolarphile by dehydrating N-acyl-aminoacids (XXIV). The cycloaddition reaction occurs at elevated temperatures, generally between 50° C. and 160° C. Dehydrating agents such as acetic anhydride are very useful in this process. Other reagents and conditions for generating Munchnones have been described by Huisgen et al., *Chem. Ber.*, 1970, 103, 2315.

SCHEME 15

XXIV + XVII →[Dehydration Agent]→ [Munchnone] → Ij

Scheme 16 describes how munchnones can also be made by the reaction of imides of structure (XXV) and a dehydrating agent in the presence of the alkene or alkyne. Many dehydrating reagents can be used. If the reagent used is acetic anhydride, it is convenient to use it as the solvent of the reaction. If a reagent such as a dicyclohexylcarbodiimide (DCC) is used, aromatic hydrocarbons such as benzene, toluene, or xylenes are preferred as solvents. The reaction is generally carried out at elevated temperature from 50° C. to 180° C. The chemistry of the bicyclic munchnones has been reviewed by Kevin Potts in "1,3-Dipolar Cycloaddition Chemistry", Volume II, pages 41–49 (A. Padwa editor, Wiley Interscience, New York, 1984).

SCHEME 16

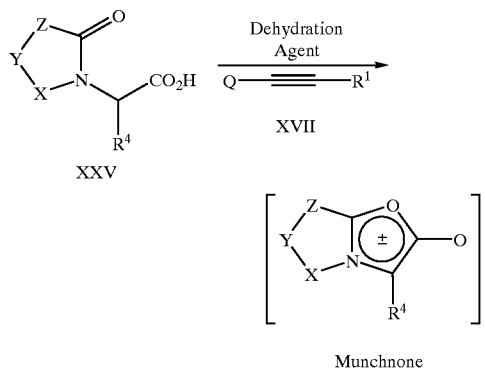

Munchnone

The alkenes and alkynes (XVII and XVIII) are often commercially available. Scheme 7 describes how a generally useful method of synthesis is to couple aryl bromides and iodides (XXVII) with alkenes and alkynes in the presence of palladium catalysts. Appropriate catalysts and conditions are described in detail by Heck in "Palladium Reagents in Organic Syntheses", Academic Press, New York, 1985. The aryl halides (XXVII) used for the instant invention are either commercially available or synthesized via diazotization of known arylamines (XXVI). Suitable conditions for diazotization of arylamines (XXVI) and their conversion to aryl halides (XXVII) can be found in Furniss et al, "Vogel's Textbook of Practical Organic Chemistry, Fifth Edition", Longman Scientific and Technical, Essex, England, pages 922–946. There are many other known methods to incorporate iodine into aromatic molecules (see, Merkushev, *Synthesis*, 9213–937 (1988).

SCHEME 17

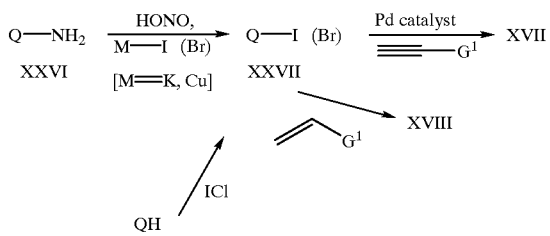

Compounds of Formula Ik where $R^{12}$=OH can serve as intermediates for the synthesis of compounds of Formula I containing many different $R^{12}$ substituents. Scheme 18 shows some, but not all of the more useful transformations. In addition to well known alkylation and acylation chemistry, through the intermediacy of the triflate Il($R^{12}$=OSO$_2$CF$_3$) a wide variety of $R^{12}$ substituents can be introduced. To form esters (Im) ($R^{12}$=CO$_2$R$^{17}$)Il may be reacted with carbon monoxide and an alcohol in the presence of a suitable palladium catalyst (see *Chem. Comm.* 1987, 904–905). To form alkenes (In) the triflates (Il) may be reacted with an alkene in the presence of a palladium catalyst (see *Heterocycles*, 26, 355–358 (1987)). Ketones (Ip) may be formed by reaction of enol ethers under similar conditions (see *J. Org. Chem.*, 57, 1481–1486 (1992)). Aryl groups (Iq) can be introduced by reaction of aryl boronic acids ArB(OH)2 with palladium catalysts (see *Tetrahedron Lett.*, 32, 2273–2276 (1991) and references cited therein)). Alkyl groups (Ir) may be introduced by nickel or palladium catalyzed reaction with grignard reagents (see, *J. Org. Chem.*, 57, 4066–4068 (1992) and references cited therein).

SCHEME 18

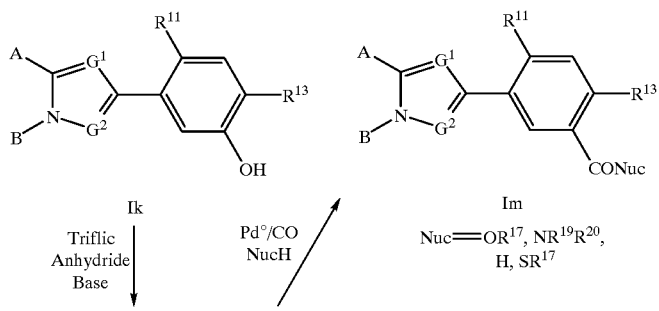

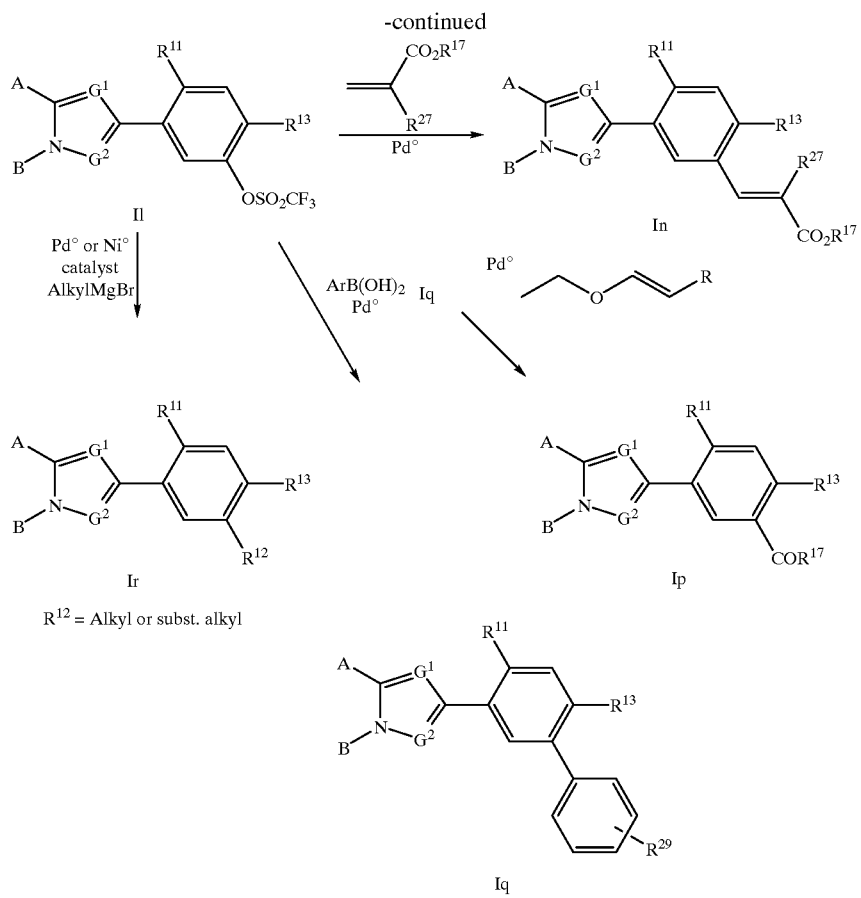

The preparation of the compounds of this invention is further illustrated by the following specific examples.

EXAMPLE 1

Preparation of 2-(2,4-dichlorophenyl)-imidazo[1,2-a]pyridine

A mixture of 8.4 g (89.2 mmol) 2-aminopyridine and 20.1 g (89.9 mmol) of 2,2',4'-trichloroacetophenone in 300 ml of ethanol was heated at reflux with stirring for 14 h. At this point, another 5.0 g (22.4 mmol) of 2,2', 4'-trichloroacetophenone was added and the reaction mixture heated an additional 6 h. Ethyl acetate (400 ml) and excess saturated aqueous sodium bicarbonate were slowly added. After thorough mixing, the ethyl acetate layer was separated and washed with two fold excess water, saturated brine, and dried over magnesium sulfate. Evaporating the solvent in vacuo to almost dryness gave a wet solid residue to which n-butyl chloride was added. This solid was filtered and washed thoroughly with n-butyl chloride before drying. A yield of 9.0 g of the title compound was obtained (m.p. 173–175° C.) as a technical material which was not purified further but used directly in the next step.

EXAMPLE 2

Preparation of 2-(2,4-dichlorophenyl)-5,6,7,8-tetrahydro-imidazo[1,2-a]pyridine

To 4.5 g (17.1 mmol) of the above 2-(2,4-dichlorophenyl)-imidazo[1,2-a]pyridine in a Paar bottle, 100 ml of ethanol, 1.5 ml of concentrated hydrochloric acid, and 0.4 g of platinum oxide were added. This mixture was placed on a Paar hydrogenator at 45 psi of hydrogen at room temperature for 15 minutes. Thin layer chromatography revealed that the reaction was complete. The mixture was filtered through celite and washed with 300 ml of ethyl acetate. To the filtrate, excess saturated aqueous sodium bicarbonate was slowly added. The ethyl acetate layer was separated, washed with saturated brine, and dried over magnesium sulfate. Evaporating the solvent in vacuo gave a solid residue to which n-butyl chloride was added. The solid was filtered, washed with n-butyl chloride, and dried to give 1.2 g of the title compound (m.p. 134–136° C.). The filtrate was also concentrated in vacuo to give a sludge which on silica gel chromatography (5:1 followed by 3:1 followed in turn by 1:1 hexane/ethyl acetate) afforded another 2.1 g of the title compound.

EXAMPLE 3

Preparation of 3-bromo-2-(2,4-dichlorophenyl)-5,6,7,8-tetrahydroimidazo[1,2-a]pyridine To 0.8 g (3.0 mmol) of the above 2-(2,4-dichlorophenyl)-5,6,7,8-tetrahydroimidazo[1,2-a]pyridine stirring in 50 ml of methylene chloride at room temperature, 0.5 g (3.1 mmol) of bromine in 5 ml of methylene chloride was added dropwise. The solution was stirred for 2 h. Another 20 ml of methylene chloride and excess saturated aqueous sodium bicarbonate were added. After sufficient mixing, the methylene chloride layer was separated, washed with water and brine, and dried over magnesium sulfate. Evaporating the solvent in vacuo gave a yellow solid residue which was purified by silica gel column chromatography (5:1 followed by 3:1 followed in turn by 1:1 hexane/ethyl acetate) to yield a 0.55 g sample of the title compound (m.p. 112–113° C.).

EXAMPLE 4

Preparation of 3-chloro-2-(2,4-dichlorophenyl)-5,6,7,8-tetrahydroimidazo[1,2-a]pyridine A mixture of 1.0 g (3.7 mmol) of 2-(2,4-dichlorophenyl)-5,6,7,8-tetrahydroimidazo[1,2-a]pyridine and 0.6 g (4.5 mmol) of N-chlorosuccinimide was stirred in 15 ml of dimethylformamide at room temperature overnight followed by heating at 70° C. for 20 minutes. An excess of water was added and the aqueous mixture extracted with 200 ml of ethyl acetate. The separated organic layer layer was washed with water, saturated aqueous sodium bicarbonate, and brine. After drying over magnesium sulfate, the solvent was removed in vacuo to give a oily residue. Silica gel column chromatography (3:1 followed by 1:1 hexane/ethyl acetate followed in turn by 2:1 ethyl acetate/hexane) afforded the title compound as the main component (0.65 g, m.p. 99–101° C.).

EXAMPLE 5

Preparation of 3-chloro-2-(2,4-dichlorophenyl)-5,8-dihydroimidazopyridine and 3-chloro-2-(2,4-diphenylphenyl)-5,6-dihydroimidazo[1,2-a]pyridine A mixture of 1.1 g (4.1 mmol) of 2-(2,4-difluorophenyl)-5,6,7,8-tetrahydroimidazo[1,2-a]pyridine and 1.0 g (7.5 mmol) of N-chlorosuccinimide was stirred in 15 ml of dimethylformamide at room temperature overnight followed by heating at 60° C. for 45 minutes. At this point, another 0.5 g (3.7 mmol) of N-chlorosuccinimide was added and the reaction mixture heated at 60° C. for an additional 30 minutes. A mixture of components were observed by thin layer chromatography. The two main components were isolated by silica gel column chromato-graphy (5:1 followed by 3:1 followed in turn by 1:1 hexane/ethyl acetate). The first to elute was isolated as an oil (0.7 g) and identified as 3-chloro-2-(2,4-dichlorophenyl)-5,8-dihydroimidazo[1,2-a]pyridine. NMR (CDCl$_3$, 200 MHz), δ: 2.30–2.47 (m, 1H), 2.85–3.10 (m, 1H), 4.00–4.47 (m, 2H), 4.73 (broad s, 1H), 5.38 (broad s, 1H), 7.28–7.57 (m, 3H).

The second main component to elute was isolated as a solid (150 mg) and identified as 3-chloro-2-(2,4-dichlorophenyl)-5,6-dihydroimidazo[1,2-a]pyridine (m.p. 104–105° C.).

EXAMPLE 6

Preparation of 5-bromo-6-(2,4-dichlorophenyl)-2,3-dihydroimidazo[2,1-b]thiazole

Step A

2-Aminothiazoline (4.7 g) and 2,2',4'-trichloro-acetophenone (6.0 g) were dissolved in ethanol (50 ml) and treated with sodium acetate (5.0 g). The mixture was stirred at room temperature for 1 h and then heated to reflux for 3.5 h. The cooled reaction mixture was evaporated to dryness and partitioned between water and methylene chloride. The organic layer was dried and evaporated. The residue was chromatographed on silica gel with hexanes/ethyl acetate (5:1–3:1) as eluent. The product was isolated as a yellow solid (m.p. 110–112° C.); NMR (CDCl$_3$, 200 MHz) δ: 8.0 (1H), 7.7 (1H), 7.3 (m, 2H), 4.1 (m, 2H), 3.8 (m, 2H).

Step B

The 6-(2,4-dichlorophenyl)-2,3-dihydroimidazo[2,1-b]thiazole (0.6 g) prepared above and N-bromosuccinimide (0.45 g) were dissolved in dimethylformamide (5 ml). The mixture was heated to reflux and stirred for 18 h at room temperature. The mixture was diluted with water (60 ml) and allowed to crystallize. The liquid was decanted and the residue was dissolved in methylene chloride and dried with magnesium sulfate. The organic residue was chromatographed on silica gel with hexanes/ethyl acetate (3:1) as eluent to give the desired product as a solid (m.p. 200–202° C.); NMR (CDCl$_3$, 200 MHz) δ: 7.4–7.2 (3H), 4.2 (m, 2H), 3.9 (m, 2H).

EXAMPLE 7

Preparation of 2-(4-chloro-2-fluoro-5-methoxyphenyl)-imidazo[1,2-a]pyridine

Step A

By a known method [*Chem. Ber.* 57, 1381 (1924)], solid potassium carbonate (24 g, 174 mmol) was added portion-wise to a solution of 30 g (319 mmol) of chloroacetic acid stirring in 150 ml of water until efferescence ceased. A 30 g (102 mmol) sample of 2-aminopyridine was added and the reaction mixture heated at reflux for 8 h. After standing overnight, the solid that precipitated was filtered, washed with a minimal amount of water, and oven dried (yield: 14.0 g, m.p. 247–254° C. dec.).

To 7.0 g of the above dried solid stirring as a suspension in xylene, 50 g of phosphorous oxybromide was added and the stirred mixture heated at reflux for 1.5 h. On heating, a thick grey precipitate gradually resulted and stirring became difficult. The reaction mixture was quenched with ice/water followed by neutralization with aqueous sodium hydroxide. The dark aqueous mixture was extracted with 300 ml of ethyl acetate which was separated and washed with water, brine, and dried over magnesium sulfate. Evaporating in vacuo gave a dark oily residue which was flash chromatographed on silice gel (1:1 hexane/ethyl acetate) to give 3.9 g of 2-bromoimidazo[1,2-a]pyridine (m.p. 83–85° C.)

Step B

To 2.0 g (7.0 mmol) of 2-chloro-4-fluoro-5-iodo-anisole (made from the compound of Example 11, Step A by methylation) stirring in 30 ml of diethyl ether at –78° C., 4.8 ml (7.7 mmol) of 1.6M n-butyl lithium was added dropwise (keeping the temperature below –69° C.). After stirring 0.5 h, 0.91 ml (8.0 mmol) of trimethyl borate in 15 ml of diethyl ether was added dropwise and the reaction mixture stirred 3 h before allowing to warm to room temperature. Slowly, 1N aqueous hydrogen chloride was added and the resulting biphase system stirred 1 h. The separated aqueous phase was separated and washed with an additional 30 ml of diethyl ether. Combined organic layers were washed with brine and dried over magnesium sulfate. Evaporating in vacuo gave a white solid which was suspended in hexane, filtered, and dried to afford 0.86 g of a technical sample of 4-chloro-2-fluoro-5-methoxyphenylboronic acid (m.p. 280–296° C.).

Step C

A mixture of 0.8 g (4.1 mmol) of 2-bromoimidazo[1,2-a]pyridine, 0.8 g (4.2 mmol) of 4-chloro-2-fluoro-5-methoxyphenylboronic acid, and 0.2 g (0.28 mmol) of bis(triphenylphosphine)palladium(II) chloride were heated in 30 ml of glyme at reflux for 2 h. The reaction mixture was partitioned between 250 ml of ethyl acetate and 100 ml of water and the separated organic layer washed with brine and dried over magnesium sulfate. On evaporating in vacuo, the remaining residue was flash chromatographed on silice gel (1:1 hexane/ethyl acetate) to afford 0.7 g of the title compound (m.p. 139–141° C.). NMR (CDCl$_3$, 400 MHz); δ4.03 (s, 3H), 6.81 (t, 1H), 7.21 (m, 2H), 8.63 (d, 1H), 7.92 (d, 1H), 8.04 (s, 1H), 8.14 (d, 1H).

EXAMPLE 8

Preparation of 3-chloro-2-(4-chloro-2-fluoro-5-methoxyphenyl)-5,6,7,8-tetrahydroimidazo[1,2-a]pyridine Step A A mixture of 1.05 g (3.8 mmol) of 2-(4-chloro-2-fluoro-5-methoxy)imidazo[1,2-a]pyridine, 3 ml of conc. hydrochloric acid, and a catalytic amount of platinum oxide in 85 ml of ethanol was shaken on a paar hydrogenator at 45 psi at room temperature for 45 minutes. The reaction mixture was filtered through celite and the filtrate concentrated in vacuo. An excess of saturated sodium bicarbonate and 250 ml of ethyl acetate were added. The separated organic extract was washed with water, brine, and dried over magnesium sulfate. Evaporating in vacuo gave 1.2 g of solid which was taken directly to the next step.

Step B

To 1.2 g of the above solid prepared in Step A stirring in 40 ml of N,N-dimethylformamide, 0.48 g (3.6 mmol) of N-chlorosuccinimide was added and the mixture heated at 63° C. for 6 h. The reaction mixture was partitioned between excess water and 125 ml of ethyl acetate. The organic layer was separated and washed with water (3×), brine, and dried over magnesium sulfate. Evaporating in vacuo gave a dark brown oil which was flash chromatographed on silica gel (10:1–1:1–1:3 hexane/ethyl acetate) to afford the main component as an oil. The title compound crystallized as a white solid on addition of hexane (yield: 0.7 g, m.p. 132–134° C.). NMR (CDCl$_3$, 200 MHz): $\delta$2.02 (m, 4H), 2.93 (t, 2H), 3.92 (broad s, 5H), 7.18, 7.22 (dd, 2H).

EXAMPLE 9

Preparation of 3-chloro-2-[4-chloro-2-fluoro-5-(2-propynoxy)phenyl]-5,6,7,8-tetrahydroimidazo[1,2-a]pyridine Step A At 0° C., 5.0 ml of 1.0M boron tribromide in dichloromethane was added dropwise to a solution of 0.7 g (2.2 mmol) of 3-chloro-2-(4-chloro-2-fluoro-5-methoxy)-5,6,7,8-tetrahydroimidazo[1,2-a]pyridine stirring in 25 ml of dichloromethane. After the addition, the reaction mixture was allowed to warm to room temperature and stirred 1.5 h. Water (10 ml) was slowly added and the resulting thick suspension concentrated in vacuo. Diethyl ether (15 ml) was added and the solid filtered and washed with water/diethyl ether followed by drying. This solid was taken directly to the next step.

Step B

To the above solid prepared in Step A and 3.5 g (25.4 mmol) of potassium carbonate stirring in 20 ml of N,N-dimethylformamide, 3.5 ml of propargyl chloride were added and the mixture heated at 60–70° C. for 2 h. The reaction mixture was partitioned between 200 ml of ethyl acetate and 125 ml of water. The organic layer was separated and washed with water (2×), brine, and dried over magnesium sulfate. Evaporating in vacuo gave an oily solid residue which was flash chromatographed on silica gel (1:1 ethyl acetate/hexane) to afford 0.5 g the title compound as a white solid (m.p. 142–145° C.). NMR (CDCl$_3$, 200 MHz): $\delta$1.96 (m, 2H), 2.05 (m, 2H), 2.54 (broad s, 1H), 2.91 (t, 2H), 3.90 (t, 2H), 4.79 (s, 2H), 7.20 (d, 1H), 7.31 (d, 1H).

EXAMPLE 10

Preparation of 3-chloro-2-(2,4-dichloro-5-nitrophenyl)-5,6,7,8-tetrahydroimidazo[1,2-a]pyridine A 1.1 g (3.85 mmol) sample of 3-chloro-2-(2,4-dichlorophenyl)-5,6,7,8-tetrahydroimidazo[1,2-a]pyridine was added to 8.0 ml of a 1:1 mixture of concentrated sulfuric/nitric acid at 0° C. The reaction mixture was stirred at 0° C. for 20 minutes followed by warming to 20° C. After pouring the reaction mixture onto ice/water, the resulting aqueous mixture was extracted with 400 ml of ethyl acetate. The separated organic layer was washed with water, brine, and dried over magnesium sulfate. The yellow oily solid residue obtained after evaporating in vacuo was flash chromatographed on silica gel (1:1 hexane/ethyl acetate) to provide 0.8 g of the title compound as a yellow solid (m.p. 111–112° C.). NMR (CDCl$_3$, 200 MHz): $\delta$1.95 (m, 2H), 2.05 (m, 2H), 2.91 (t, 2H), 3.92 (t, 2H), 7.66 (s, 1H), 8.09 (s, 1H).

EXAMPLE 11

Preparation of 3-chloro-2-(4-chloro-2-fluoro-5-hydroxyphenyl)-4,5,6,7-tetrahydropyrazolo[1,5-a]pyridine Step A: 2-Chloro-4-fluoro-5-iodophenol 5-Amino-2-chloro-4-fluorophenol (35 g, previously crystallized from ethyl acetate) was treated with 165 ml of aqueous HCl (6N) and stirred mechanically in a 2 liter flask. The mixture was cooled to 5° C. and treated dropwise with a solution of sodium nitrite (16.6 g) in 80 ml of water while keeping the temperature below 10° C. The mixture was treated dropwise with aqueous potassium iodide (41 g in 100 ml of water). The addition is accompanied by foaming and control of stirring is maintained by the addition of cold water (200 ml) during the course of the iodide addition. The mixture was allowed to come to room temperature and stirred for 1 h. The dark mixture was extracted with ether and washed with sodium thiosulfate sodium. The ether extract was subjected to silica gel chromatography in hexanes/ethyl acetate (15:1) to give a yellow oil (39.8 g).

Step B: 2-Chloro-4-fluoro-5-ethynylphenol

The product from Step A (39 g) was dissolved in triethylamine (200 ml) and treated with trimethylsilylacetylene (26 ml), dichlorobis(triphenylphosphine)palladium (1.95 g) and copper iodide (0.6 g). The reaction slowly heats up and a precipitate forms. After stirring for 2 h the triethylamine is removed by evaporation at reduced pressure. The residue is partitioned between saturated ammonium chloride and ether. The ether phase was dried over magnesium sulfate and the ether evaporated. The residue was dissolved in methanol (200 ml) and treated with potassium hydroxide (10 g). The black mixture was stirred for 45 minutes and the volatiles were removed by evaporation at reduced pressure. The residue was partitioned between aqueous hydrochloric acid (1N) and ether. The ether layer was dried over magnesium sulfate and subjected to silica gel chromatography with hexanes/ethyl acetate (15:1) to give the desired product (13.4 g). NMR (CDCl$_3$): $\delta$7.1 (2H, ArH), 5.3 (1H, OH), 3.3 (1H, CH).

Step C: 2-(4-Chloro-2-fluoro-5-hydroxyphenyl)-4, 5,6,7-tetrahydropyrazolo 8 1, 5-a]pyridine The product of Step B (13 g) was dissolved in xylenes (250 ml) and treated with 1',2',3',4'-tetrahydropyrido[1',2'-3,4]sydnone (13 g, J. Chem. Soc., 3303 (1961))., The mixture was refluxed for 5.5 h, cooled, and the solvent was removed at reduced pressure. The residue was triturated with butyl chloride and a small amount of ethyl acetate to afford the product as a white solid (8.8 g), m.p.=218–220° C. NMR (DMSO-D$_6$): $\delta$10.3 (1H, OH), 7.8 (1H, ArH), 7.3 (1H, ArH), 4.0 (2H, CH$_2$N), 2.85 (2H, CH$_2$pyrazole), 2.1 (2H, CH$_2$), 1.9 (2H, CH$_2$).

Step D: 3-Chloro-2- (4-chloro-2-fluoro-5-hydroxyphenyl)-4,5,6, 7-tetrahydropyrazolo[1,5-a]pyridine The product from Step C (8.3 g) was dissolved in dimethylformamide (40 ml) and was treated with N-chlorosuccinimide (4.4 g). The mixture was heated and at 65° C. a color change from yellow to red occurred. Heating was discontinued and the reaction was allowed to stir at room temperature overnight. The reaction mixture was diluted with water and ice and the solid was filtered and washed with water. After air drying the solid was taken up in ethyl acetate and dried further with magnesium sulfate. The ethyl acetate was removed by evaporation at reduced pressure to afford the product as a slightly pink solid (9.2 g), m.p.=177–178° C. NMR (DMSO-$D_6$): δ8 10.2 (OH), 7.3 (1H), 6.9 (1H), 3.9 (2H), 2.6 (2H), 1.9 (2H), 1.7 (2H).

EXAMPLE 12

Preparation of 3-chloro-2-(4-chloro-2-fluoro-5-(2-propenyloxy) phenyl)-4,5,6,7-tetrahydropyrazolo[1,5-a]pyridine The compound of Example 1 (0.7 g) was dissolved in dimethylformamide (7 ml) and treated successively with potassium carbonate (1 g) and allyl bromide (0.6 ml). The mixture was stirred for 24 h, diluted with water and filtered. The solid was air dried and then dissolved in dichloromethane and dried further with magnesium sulfate. Evaporation of the solvent afforded the product as a solid (0.7 g), m.p.=91–92° C. NMR (CDCl$_3$): δ7.3–7.1 (2H, ArH), 6.1 (1H, CH=), 5.4 (2H, CH$_2$=), 4.5 (2H, CH$_2$C=), 4.1 (2H, CH$_2$N), 2.8 (2H, CH$_2$pyrazole), 2.1 (2H, CH$_2$), 1.9 (2H, CH$_2$).

EXAMPLE 13

Preparation of 3-chloro-2-(4-chloro-2-fluoro-5-(trifluoromethanesulfonoxyphenyl)-4,5,6,7-tetrahydropyrazolo[1,5-a]pyridine The compound of Example 1 (9.1 g) was dissolved in pyridine (80 ml) and cooled in a water bath. Trifluoromethanesulfonic anhydride (9.9 g) was added dropwise and the reaction was stirred at room temperature overnight. The pyridine was evaporated at reduced pressure and the residue was partitioned between dichloromethane and aqueous HCl (1N). The aqueous phase was reextracted with dichloromethane and the combined organic layers were dried over magnesium sulfate and evaporated. The product was an oil which solidified (10 g), m.p.=64–65° C. NMR (CDCl$_3$): δ7.3 (1H, ArH), 7.2 (1H, ArH), 4.2 (2H, CH$_2$N), 2.8 (2H, CH$_2$), 2.1 (2H, CH$_2$), 1.9 (2H, CH$_2$).

EXAMPLE 14

Preparation of ethyl 2-chloro-5-(3-chloro-4,5,6,7-tetrahydropyrazolo[1,5-a]pyridin-2-yl)-4-fluorobenzoate The compound from Example 3 (2.73 g) was dissolved in dimethylsulfoxide (15 ml) and ethanol (4 ml) and treated with triethylamine (1.5 ml). To this solution was added bis(1,3-diphenylphosphinopropane) (0.13 g) and palladium acetate (0.12 g) and then carbon monoxide was bubbled through the solution for 2 minutes at room temperature. The mixture was then heated under a carbon monoxide atmosphere (balloon) at 65–70° C. for 3 h. The mixture was partitioned between dichloromethane and water. The dichloromethane was washed with water and dried over magnesium sulfate. After evaporation of the solvent under reduced pressure the residue was subjected to silica gel chromatography with hexanes/ethyl acetate (10:1). The product (1.6 g) was isolated as a solid, m.p.=72–73° C. NMR (CDCl$_3$): δ8.1 (1H, ArH), 7.3 (1H, ArH), 4.4 (2H, CH$_2$O), 4.2 (2H, CH$_2$N), 2.8 (2H, CH$_2$), 2.1 (2H, CH$_2$), 1.9 (2H, CH$_2$), 1.4 (3H, CH$_3$).

EXAMPLE 15

Preparation of 1-((2-chloro-5-(3-chloro-4,5,6,7-tetrahydropyrazolo[1,5-a]pyridine-2yl)-4-fluorophenyl))-ethanone The compound of Example 3 (1.5 g) was dissolved in dimethylformamide (10 ml) and treated with butylvinylether (2.5 ml), triethylamine (1.5 ml), bis(1,3-diphenylphosphinopropane) (0.1 g) and palladium acetate (0.05 g). The reaction was heated to 80–90° C. for 2.5 h. The reaction was cooled and treated with ether and aqueous HCl (1N). The ether layer was dried, evaporated at reduced pressure, and subjected to silica gel chromatography with hexanes/ethyl acetate (4:1–2:1). The desired product was isolated as an oil which solidified (0.3 g), m.p.=108–109° C. NMR (CDCl$_3$): δ7.9 (1H, ArH), 7.3 (1H, ArH), 4.2 (2H, CH$_2$N), 2.8 (2H, CH$_2$), 2.6 (3H, CH$_3$), 2.1 (2H, CH$_2$), 1.9 (2H, CH$_2$).

EXAMPLE 16

Preparation of 3-chloro-2-(6-chloro-4-fluoro-(1,1-biphenyl))-3-yl)-4,5,6,7-tetrahydropyrazolo[1,5-a]pyridine The compound of Example 3 (1 g) was dissolved in dimethoxyethane (30 ml) and treated with phenylboronic acid (0.5 g), tetrakis(triphenylphosphine) palladium (0.2 g), and sodium carbonate (1 g in 5 ml of water). The mixture was heated at reflux for 4.5 h and then partitioned between water and dichloromethane. The organic layer was washed two times with water and then dried over magnesium sulfate and evaporated under reduced pressure. The residue was purified by silica gel chromatography with butyl chloride/ethyl acetate (15:1). The product (0.53 g) was an oil which eventually solidified. NMR (CDCl$_3$): δ7.6–7.2 (7H, ArH), 4.2 (2H, CH$_2$N), 2.8 (2H, CH$_2$), 2.1 (2H, CH$_2$), 1.9 (2H, CH$_2$).

EXAMPLE 17

Preparation of 3-chloro-2-(4-chloro-2-fluoro-5-(1-methyl-2-propynyloxy)phenyl)-4,5,6,7-tetrahydropyrazolo[1,5-a]pyridine The product of Example 1 (0.75 g) and triphenylphosphine (0.7 g) were dissolved in tetrahydrofuran (15 ml) and treated with 2-butynol (0.3 ml) and diethylazodicarboxylate (1.35 ml of 40% solution in toluene). The mixture was stirred at room temperature and evaporated directly onto silica gel and subjected to chromatography on silica gel in hexanes/ethyl acetate (4:1 to 2:1). The product was isolated as a solid (0.7 g), m.p.=116–120° C. NMR (CDCl$_3$): δ7.4 (1H, ArH), 7.1 (1H, ArH), 4.9 (1H, OCH), 4.2 (2H, CH$_2$), 2.8 (2H, CH$_2$), 2.5 (1H, CH), 2.1 (2H, CH$_2$), 1.9 (2H, CH$_2$) 1.7 (3H, CH$_3$).

EXAMPLE 18

Preparation of 6-(3-chloro-4,5,6,7-tetrahydropyrazolo-[1,5-a]pyridin-2-yl-7-fluoro-2H-1,4-benzoxazin-3(4H)-one Step A: 6-Iodo-7-fluoro-2H-1,4-benzoxazin-3(4H)-one 7-Fluoro-2H-1,4-benzoxazin-3(4H)-one (15.8 g) was mixed with iodine monochloride (15.6 g) in acetic acid (150 ml) and heated to reflux for 36 h. The cooled mixture was treated with saturated aqueous sodium bisulfite until the color was dissipated. The solid was filtered and washed well with water. The solid was air dried and dried further by dissolution in dimethylformamide (100 ml) and evaporated to dryness under reduced pressure to give the desired product (26.3 g) contaminated with some starting material. (The reaction can be taken to completion by addition of more iodine monochloride and refluxing for 24 h longer.) The crude product was used in Step B.

Step B: 6-Ethynyl-7-fluoro-2H-1,4-benzoxazin-3(4H)-one

The product of Step A (26.3 g) was converted to the desired compound (5.7 g) by following the procedures used in Step B of Example 11. Final purification was done by silica gel chromatography in hexanes/ethyl acetate 3:1 to 1:3), m.p.=224–228° C. (decomp). NMR (CDCl$_3$): δ10.8 (1H, NH), 6.9 (2H, ArH), 4.5 (2H, CH$_2$), 3.3 (1H, CH).

Step C: 6-(4,5,6,7-Tetrahydropyrazolo[1,5-a]pyridin-2-yl-7-fluoro-2H-1,4-benzoxazin-3(4H)-one The compound of Step B (5 g) and 1',2',3',4'-tetrahydropyrido[1',2'-3,4]sydnone (5 g), following the procedure of Step C of Example 1 gave the desired product (5 g), m.p.=249–251° C. NMR (CDCl$_3$): δ8.2 (1H, NH), 7.5 (1H, ArH), 6.8 (1H, ArH), 6.4 (1H, ArH), 4.6 (2H, OCH$_2$N), 4.2 (2H, CH$_2$N), 2.9 (2H, CH$_2$), 2.1 (2H, CH$_2$), 1.9 (2H, CH$_2$).

Step D: 6-(3-Chloro-4,5,6,7-tetrahydropyrazolo[1,5-a]pyridine-2-yl-7-fluoro-2H-1,4-benzoxazin-3(4H)-one The compound of Step C (5 g) was converted with N-chlorosuccinimide (2.4 g) to the desired product (5.1 g) by the procedure of Example 11 Step D, m.p.=231–234° C. NMR (CDCl$_3$): δ10.7 (1H, NH), 7.0 (2H, ArH), 4.7 (2H, OCH$_2$N), 4.1 (2H, CH$_2$), 2.7 (2H, CH$_2$), 2.1 (2H, CH$_2$), 1.9 (2H, CH$_2$).

EXAMPLE 19

Preparation of 6-(3-chloro-4,5,6,7-tetrahydropyrazolo-[1,5-a]pyridin-2-yl-7-fluoro-4-2-propynyl)-2H-1,4-benzoxazin-3(4H)-one The compound of Example 18 (1 g) was dissolved in dimethylformamide (10 ml) and treated with sodium hydride (0.27 g, 60% in mineral oil) and then stirred for 30 min at room temperature. A solution of propargyl bromide (0.4 ml of 80% in toluene) was added and stirring was continued for an hour. The reaction was quenched by addition of water and the aqueous phase was extracted with ether and then ethyl acetate. The combined organic layers were washed with water 3 times and then dried with magnesium sulfate. The residue from the organic layer was subjected to silica gel chromatography with hexanes/ethyl acetate (5:1 to 1:1) to give the product as a solid (0.65 g), m.p.=140–141° C. NMR (CDCl$_3$): δ7.4 (1H, ArH), 6.9 (1H, ArH), 4.7 (4H, 2×CH$_2$), 4.2 (2H, CH$_2$), 2.8 (2H, CH$_2$), 2.4 (1H, CH), 2.1 (2H, CH$_2$), 1.9 (2H, CH$_2$).

EXAMPLE 20

Preparation of 5-Bromo-4-(2,4-dichlorophenyl)-1-difluoromethyl-2-methylimidazole Step A A mixture of 8.0 g (32.4 mmol) of 2-acetoxy-2',4'-dichloroacetophenone and 23 ml of formamide was heated neat at reflux for 3.5 h. On cooling, the reaction mixture was partitioned between 300 ml of ethyl acetate and 300 ml of water. The separated organic layer was washed with water (2×) and brine and dried over magnesium sulfate. Evaporating in vacuo gave a dark oily solid residue which was flash chromatographed on silica gel (100:5:2–75:5:2-methylene chloride/methanol/glacial acetic acid followed by 5:1 methylene chloride/methanol) to afford two solids. The first component to elute was 4-(2,4-dichlorophenyl)-1H-imidazole (1.2 g, m.p. 130–136° C.) and the second was a crude sample of 4-(2,4-dichlorophenyl)-2-methyl-1H-imidazole (1.8 g, m.p. 185–190° C.).

Step B

To 1.7 g (7.5 mmol) of 4-(2,4-dichlorophenyl)-2-methyl-1H-imidazole stirring in a mixture of 75 ml of tetrahydrofuran and 8 ml of 50% aqueous sodium hydroxide at room temperature, 8 ml of condensed chlorodifluoromethane was added dropwise from a gas addition funnel. The reaction mixture was stirred at ambient temperature overnight. After partitioning between an excess of ethyl acetate and water, the organic layer was separated, washed with water (3×) and brine, dried over magnesium sulfate, and evaporated in vacuo. The resulting dark red oil was flash chromatographed on silica gel (10:1–5:1–3:1–1:1 hexane/ethyl acetate) to give 940 mg of slightly impure 4-(2,4-dichlorophenyl)-1-difluoromethyl-2-methylimidazole, obtained as an oily solid residue and taken directly to the next step.

Step C

Bromine (0.54 g, 3.1 mmol), in 7 ml of methylene chloride, was added dropwise to a solution of 0.9 g (3.2 mmol) of 4-(2,4-dichlorophenyl)-1-difluoromethyl-2-methylimidazole stirring in 35 ml of methylene chloride. The reaction mixture was stirred at room temperature overnight. Another 0.3 g of bromine, in 5 ml of methylene chloride, were added and the reaction stirred overnight. Methylene chloride (250 ml) and saturated sodium bicarbonate (200 ml) were added and the organic layer separated and washed with saturated sodium bicarbonate and brine followed by drying over magnesium sulfate. Evaporating in vacuo gave a red oil residue. Flash chromatography on silica gel (20:1–10:1–5:1–3:1 hexane/ethyl acetate) afforded 0.7 g of 5-bromo-4-(2,4-dichlorophenyl)-1-difluoromethyl-2-methylimidazole as a white solid (m.p. 81–83° C.). NMR (CDCl$_3$, 200 MHz) δ: 2.65 (s, 3H), 7.20 (t, 1H), 7.27–7.40 (m, 2H), 7.52 (s, 1H).

Using the techniques and procedures outlined in Schemes 1–18 and Examples 1–20, the compounds in the following tables can be prepared.

TABLE 1

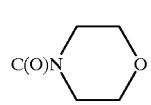

| X | Y | Z | R$^1$ | R$^{11}$ | R$^{12}$ | R$^{13}$ |
|---|---|---|---|---|---|---|
| CH$_2$ | CH$_2$ | CH$_2$CH$_2$ | Cl | Cl | H | Cl |
| CH$_2$ | CH$_2$ | CH$_2$CH$_2$ | Br | Cl | H | Cl |
| CH$_2$ | CH$_2$ | CH$_2$CH$_2$ | Cl | F | H | Cl |
| CH$_2$ | CH$_2$ | CH$_2$CH$_2$ | Br | F | H | Cl |
| CH$_2$ | CH$_2$ | CH$_2$CH$_2$ | F | Cl | H | Cl |
| CH$_2$ | CH$_2$ | CH$_2$CH$_2$ | I | F | H | Cl |
| CH$_2$ | CH$_2$ | CH$_2$CH$_2$ | CN | Cl | H | Cl |
| CH$_2$ | CH$_2$ | CH$_2$CH$_2$ | CN | F | H | Cl |
| CH$_2$ | CH$_2$ | CH$_2$CH$_2$ | Cl | F | H | Br |
| CH$_2$ | CH$_2$ | CH$_2$CH$_2$ | Br | F | H | Br |
| CH$_2$ | CH$_2$ | CH$_2$CH$_2$ | Cl | Cl | OMe | Cl |
| CH$_2$ | CH$_2$ | CH$_2$CH$_2$ | Br | F | OMe | Cl |
| CH$_2$ | CH$_2$ | CH$_2$CH$_2$ | Cl | Cl | OCHMe$_2$ | Cl |
| CH$_2$ | CH$_2$ | CH$_2$CH$_2$ | Cl | F | OCHMe$_2$ | Cl |
| CH$_2$ | CH$_2$ | CH$_2$CH$_2$ | Br | F | OCHMe$_2$ | Cl |
| CH$_2$ | CH$_2$ | CH$_2$CH$_2$ | Cl | Cl | OCH$_2$CH=CH$_2$ | Cl |
| CH$_2$ | CH$_2$ | CH$_2$CH$_2$ | Cl | Cl | OCH$_2$C≡CH | Cl |
| CH$_2$ | CH$_2$ | CH$_2$CH$_2$ | Cl | H | OCH$_2$C≡CH | Cl |
| CH$_2$ | CH$_2$ | CH$_2$CH$_2$ | Br | Cl | OCH$_2$C≡CH | Cl |
| CH$_2$ | CH$_2$ | CH$_2$CH$_2$ | Cl | F | OCH$_2$C≡CH | Cl |
| CH$_2$ | CH$_2$ | CH$_2$CH$_2$ | Br | F | OCH$_2$C≡CH | Cl |
| CH$_2$ | CH$_2$ | CH$_2$CH$_2$ | Cl | Cl | OCH$_2$C≡CH | Br |
| CH$_2$ | CH$_2$ | CH$_2$CH$_2$ | Cl | Cl | OCH$_2$CO$_2$Me | Cl |
| CH$_2$ | CH$_2$ | CH$_2$CH$_2$ | Br | F | OCH(Me)CO$_2$Me | Cl |
| CH$_2$ | CH$_2$ | CH$_2$CH$_2$ | Cl | F | OCH$_2$C(O)NMe$_2$ | Cl |
| CH$_2$ | CH$_2$ | CH$_2$CH$_2$ | Cl | F | OCH$_2$C(O)NHMe | Cl |
| CH$_2$ | CH$_2$ | CH$_2$CH$_2$ | Cl | F | OCH$_2$C(O)NHPh | Cl |
| CH$_2$ | CH$_2$ | CH$_2$CH$_2$ | Cl | Br | OCH$_2$CH=CMe$_2$ | Cl |
| CH$_2$ | CH$_2$ | CH$_2$CH$_2$ | Cl | F | OCH$_2$CH$_2$Me | Cl |
| CH$_2$ | CH$_2$ | CH$_2$CH$_2$ | Cl | Cl | OCH$_2$CHMe$_2$ | Cl |
| CH$_2$ | CH$_2$ | CH$_2$CH$_2$ | Cl | Cl | OCH$_2$CH$_2$OCHF$_2$ | Cl |
| CH$_2$ | CH$_2$ | CH$_2$CH$_2$ | Cl | Cl | SMe | Cl |
| CH$_2$ | CH$_2$ | CH$_2$CH$_2$ | Cl | F | SO$_2$Me | Cl |
| CH$_2$ | CH$_2$ | CH$_2$CH$_2$ | Cl | F | OCH$_2$CH$_2$OMe | Cl |
| CH$_2$ | CH$_2$ | CH$_2$CH$_2$ | Cl | Cl | OCH$_2$CF$_3$ | Cl |
| CH$_2$ | CH$_2$ | CH$_2$CH$_2$ | Cl | Cl | OCHF$_2$ | Cl |
| CH$_2$ | CH$_2$ | CH$_2$CH$_2$ | Br | Cl | OCH$_2$CH$_2$OMe | Cl |
| CH$_2$ | CH$_2$ | CH$_2$CH$_2$ | Cl | Cl | OCH$_2$OCH$_2$C≡CH | Cl |
| CH$_2$ | CH$_2$ | CH$_2$CH$_2$ | Cl | Cl | OCH$_2$Ph | Cl |
| CH$_2$ | CH$_2$ | CH$_2$CH$_2$ | Cl | F | OCH$_2$OEt | Cl |
| CH$_2$ | CH$_2$ | CH$_2$CH$_2$ | Cl | F | SCH$_2$C≡CH | Cl |
| CH$_2$ | CH$_2$ | CH$_2$CH$_2$ | Cl | F | SCH$_2$CF$_3$ | Cl |
| CH$_2$ | CH$_2$ | CH$_2$CH$_2$ | Cl | Cl | OCF$_2$CHF$_2$ | Cl |
| CH$_2$ | CH$_2$ | CH$_2$CH$_2$ | Cl | F | OCH$_2$P(O)(OMe)$_2$ | Cl |
| CH$_2$ | CH$_2$ | CH$_2$CH$_2$ | Cl | F | OCH$_2$C(O)NH$_2$ | Cl |
| CH$_2$ | CH$_2$ | CH$_2$CH$_2$ | Cl | F | OCH$_2$SiMe$_3$ | Cl |
| CH$_2$ | CH$_2$ | CH$_2$CH$_2$ | Cl | Cl | CO$_2$Me | Cl |
| CH$_2$ | CH$_2$ | CH$_2$CH$_2$ | Cl | Cl | C(O)NMe$_2$ | |
| CH$_2$ | CH$_2$ | CH$_2$CH$_2$ | Cl | F | CO$_2$Me | Cl |
| CH$_2$ | CH$_2$ | CH$_2$CH$_2$ | Cl | F | C(O)NH$_2$ | Cl |
| CH$_2$ | CH$_2$ | CH$_2$CH$_2$ | Cl | F | C(O)NHPh | Cl |
| CH$_2$ | CH$_2$ | CH$_2$CH$_2$ | Cl | F | C(O)NHMe | Cl |
| CH$_2$ | CH$_2$ | CH$_2$CH$_2$ | Cl | F | C(O)N-morpholinyl | Cl |
| CH$_2$ | CH$_2$ | CH$_2$CH$_2$ | Cl | F | C(O)NHn-Bu | Br |
| CH$_2$ | CH$_2$ | CH$_2$CH$_2$ | Br | F | C(O)NHn-Pr | Cl |
| CH$_2$ | CH$_2$ | CH$_2$CH$_2$ | Cl | F | CO$_2$CH$_2$C≡CH | Cl |
| CH$_2$ | CH$_2$ | CH$_2$CH$_2$ | Cl | F | CO$_2$n-Pr | Cl |
| CH$_2$ | CH$_2$ | CH$_2$CH$_2$ | Br | F | CO$_2$CH$_2$CH=CH$_2$ | Cl |
| CH$_2$ | CH$_2$ | CH$_2$CH$_2$ | Cl | Cl | CO$_2$N=CMe$_2$ | Cl |
| CH$_2$ | CH$_2$ | CH$_2$CH$_2$ | Cl | F | C(O)Me | Cl |
| CH$_2$ | CH$_2$ | CH$_2$CH$_2$ | Cl | F | CO$_2$n-Pr | Cl |

TABLE 1-continued

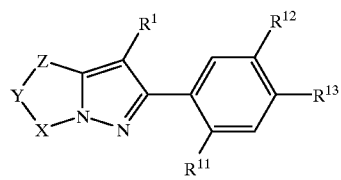

| X | Y | Z | R¹ | R¹¹ | R¹² | R¹³ |
|---|---|---|---|---|---|---|
| CH$_2$ | CH$_2$ | CH$_2$CH$_2$ | Cl | F | CO$_2$Et | Cl |
| CH$_2$ | CH$_2$ | CH$_2$CH$_2$ | Cl | Cl | CO$_2$CH$_2$CF$_3$ | Cl |
| CH$_2$ | CH$_2$ | CH$_2$CH$_2$ | Cl | Cl | NHSO$_2$Me | Cl |
| CH$_2$ | CH$_2$ | CH$_2$CH$_2$ | Cl | F | NHSO$_2$Me | Cl |
| CH$_2$ | CH$_2$ | CH$_2$CH$_2$ | Cl | F | NHSO$_2$NHMe | Cl |
| CH$_2$ | CH$_2$ | CH$_2$CH$_2$ | Cl | F | NHSO$_2$CF$_3$ | Cl |
| CH$_2$ | CH$_2$ | CH$_2$CH$_2$ | Cl | F | CF$_3$ | Cl |
| CH$_2$ | CH$_2$ | CH$_2$CH$_2$ | Cl | F | CH(Me)$_2$ | Cl |
| CH$_2$ | CH$_2$ | CH$_2$CH$_2$ | Cl | F | Me | Cl |
| CH$_2$ | CH$_2$ | CH$_2$CH$_2$ | Cl | F | NO$_2$ | Cl |
| CH$_2$ | CH$_2$ | CH$_2$CH$_2$ | Cl | CN | OCH$_2$C≡CH | Cl |
| CH$_2$ | CH$_2$ | CH$_2$CH$_2$ | Cl | F | CH═CHCO$_2$Me | Cl |
| CH$_2$ | CH$_2$ | CH$_2$CH$_2$ | Br | F | CN | Cl |
| CH$_2$ | CH$_2$ | CH$_2$CH$_2$ | Cl | F | Cl | Cl |
| CH$_2$ | CH$_2$ | CH$_2$CH$_2$ | Cl | Cl | Br | Cl |
| CH$_2$ | CH$_2$ | CH$_2$CH$_2$ | Cl | F | CH$_2$CH═CH$_2$ | Cl |
| CH$_2$ | CH$_2$ | CH$_2$CH$_2$ | Cl | F | OCH$_2$C≡CMe | Br |
| CH$_2$ | CH$_2$ | S | Cl | Cl | H | Cl |
| CH$_2$ | CH$_2$ | S | Cl | Cl | OCH$_2$C≡CH | Cl |
| CH$_2$ | CH$_2$ | S | Cl | F | OCH$_2$C≡CH | Cl |
| CH$_2$ | CH$_2$ | CH$_2$ | Cl | F | OCH$_2$C≡CH | Cl |
| CH$_2$ | CH$_2$ | CH═CH | Cl | F | OCH$_2$C≡CH | Cl |
| CH$_2$ | CH$_2$ | CH═CH | Cl | Cl | H | Cl |
| CH$_2$ | CH$_2$ | CH═CH | Cl | Cl | OCH$_2$C≡CH | Cl |
| CH$_2$ | CH═CH | CH$_2$ | Cl | Cl | OCH$_2$C≡CH | Cl |
| CH$_2$ | CH═CH | CH$_2$ | Cl | F | OCH$_2$C≡CH | Cl |
| CH$_2$ | CH$_2$ | O | Cl | F | OCH$_2$C≡CH | Cl |
| CHMe | CH$_2$ | CH$_2$CH$_2$ | Br | Cl | OCH$_2$C≡CH | Cl |
| CH$_2$ | CHMe | CH$_2$CH$_2$ | Cl | F | OCH$_2$C≡CH | Cl |
| CH$_2$CH$_2$ | CH$_2$ | CHMe | Cl | F | OCH$_2$C≡CH | Cl |
| CH$_2$ | NMe | CH$_2$CH$_2$ | Cl | F | OCH$_2$C≡CH | Cl |
| CHF | CH$_2$ | CH$_2$CH$_2$ | Cl | F | OCH$_2$C≡CH | Cl |
| CHFC$_3$ | CH$_2$ | O | Cl | F | OCH$_2$C≡CH | Cl |
| CH$_2$CH$_2$ | CH$_2$ | O | Cl | F | OCH$_2$C≡CH | Cl |
| CH$_2$ | CH$_2$ | CH$_2$CH$_2$ | CN | F | OCH$_2$C≡CH | Cl |
| CH$_2$ | CH$_2$ | CH$_2$CH$_2$ | Cl | F | CCH$_2$C≡CH | CF$_3$ |
| CH$_2$ | CH$_2$ | CH$_2$CH$_2$ | Cl | F | OCH$_2$C≡CH | OCHF$_2$ |
| CH$_2$ | CH$_2$ | CH$_2$CH$_2$ | Cl | F | OCH$_2$C≡CH | OMe |
| CH$_2$ | O | CH$_2$CH$_2$ | Cl | F | OCH$_2$CH═CH$_2$ | Cl |
| CH$_2$ | O | CH$_2$CH$_2$ | Cl | F | OCH$_2$C≡CH | Cl |
| CH$_2$ | S | CH$_2$CH$_2$ | Cl | F | OCH$_2$C≡CH | Cl |
| CH$_2$ | CH$_2$ | CH$_2$CH$_2$ | Cl | F | OCH(Me)CH═CH$_2$ | Cl |
| CH$_2$ | CH$_2$ | CH$_2$CH$_2$ | Cl | F | OCH(Me)C≡CH | Cl |
| CH$_2$ | CH$_2$ | CH$_2$CH$_2$ | Cl | F | OCH(Me)CO$_2$CH$_2$CH═CH$_2$ | Cl |
| CH$_2$CH$_2$ | CH$_2$ | CH$_2$CH$_2$ | Cl | F | OCH$_2$CH═CH$_2$ | Cl |
| CH$_2$CH$_2$ | CH$_2$ | CH$_2$CH$_2$ | Cl | F | OCH$_2$C≡CH | Cl |
| CH$_2$CH$_2$ | CH$_2$ | CH$_2$CH$_2$ | Cl | F | COOi-Pr | Cl |
| CH$_2$CH$_2$ | CH$_2$ | CH$_2$CH$_2$ | Cl | F | H | Cl |
| CH$_2$CH$_2$ | CH$_2$ | CH$_2$CH$_2$ | Cl | F | OCH$_2$C≡CH | CN |
| CH$_2$CH$_2$ | CH$_2$ | CH$_2$CH$_2$ | Cl | F | OCH$_2$CH═CH$_2$ | CN |
| CH$_2$ | CH$_2$ | CH$_2$CH$_2$ | Cl | F | OCH$_2$C≡CH | Br |
| CH$_2$ | CH$_2$ | CH$_2$CH$_2$ | Cl | F | OCH$_2$CH═CH$_2$ | Br |
| CH$_2$ | CH$_2$ | CH$_2$CH$_2$ | Cl | F | COOn-iPr | Cl |
| CH$_2$ | CH$_2$ | CH$_2$CH$_2$ | Cl | Cl | OCH$_2$CH═CH$_2$ | Cl |
| CH$_2$ | CH$_2$ | CH$_2$ | CN | F | H | Br |
| CH$_2$ | CH$_2$ | CH$_2$ | Cl | F | OCH(Me)CO$_2$Me | Cl |
| CH$_2$ | CH$_2$ | CH$_2$ | Cl | Cl | H | Cl |
| CH$_2$ | CH$_2$ | CH$_2$ | Br | Cl | H | Cl |
| CH$_2$ | CH$_2$ | CH$_2$ | Br | F | H | Cl |
| CH$_2$CH$_2$ | O | CH$_2$ | Cl | F | H | Cl |
| CH$_2$CH$_2$ | O | CH$_2$ | Br | F | H | Cl |
| CH$_2$CH$_2$ | O | CH$_2$ | Cl | Cl | H | Cl |
| CH$_2$CH$_2$ | O | CH$_2$ | Br | Cl | H | Cl |
| CH$_2$CH$_2$ | S | CH$_2$ | Cl | F | H | Cl |
| CH$_2$CH$_2$ | S | CH$_2$ | Br | F | H | Cl |
| CH$_2$CH$_2$ | S | CH$_2$ | Cl | Cl | H | Cl |
| CH$_2$CH$_2$ | S | CH$_2$ | Br | Cl | H | Cl |

TABLE 1-continued

| X | Y | Z | R¹ | R¹¹ | R¹² | R¹³ |
|---|---|---|---|---|---|---|
| $CH_2$ | $CH_2$ | $CH_2CH_2$ | Cl | F | H | CN |
| $CH_2$ | $CH_2$ | $CH_2CH_2$ | Br | F | H | CN |
| $CH_2$ | $CH_2$ | $CH_2CH_2$ | Cl | Cl | H | CN |
| $CH_2$ | $CH_2$ | $CH_2CH_2$ | Br | Cl | H | CN |
| $CH_2$ | $CH_2$ | $CH_2CH_2$ | Cl | F | H | Cl |
| $CH_2$ | $CH_2$ | $CH_2CH_2$ | Cl | F | OEt | Cl |
| $CH_2$ | $CH_2$ | $CH_2CH_2$ | Cl | F | On-Pr | Cl |
| $CH_2$ | $CH_2$ | $CH_2CH_2$ | Cl | F | On-Bu | Cl |
| $CH_2$ | $CH_2$ | $CH_2CH_2$ | Cl | F | On-Hex | Cl |
| $CH_2$ | $CH_2$ | $CH_2CH_2$ | Cl | F | S-Me | Cl |
| $CH_2$ | $CH_2$ | $CH_2CH_2$ | Cl | F | S-Et | Cl |
| $CH_2$ | $CH_2$ | $CH_2CH_2$ | Cl | F | S-i-Pr | Cl |
| $CH_2$ | $CH_2$ | $CH_2CH_2$ | Cl | F | $SCH_2CO_2Me$ | Cl |
| $CH_2$ | $CH_2$ | $CH_2CH_2$ | Cl | F | $SCH_2CH=CH_2$ | Cl |
| $CH_2$ | $CH_2$ | $CH_2CH_2$ | Cl | F | $SCH_2CO_2$-i-Pr | Cl |
| $CH_2$ | $CH_2$ | $CH_2CH_2$ | Cl | F | $NHCH_2\equiv CH$ | Cl |
| $CH_2$ | $CH_2$ | $CH_2CH_2$ | Cl | F | $NHCH_2CH=CH_2$ | Cl |
| $CH_2$ | $CH_2$ | $CH_2CH_2$ | Cl | F | $NMe_2$ | Cl |
| $CH_2$ | $CH_2$ | $CH_2CH_2$ | Cl | F | $NHCH(Me)C\equiv CH$ | Cl |
| $CH_2$ | $CH_2$ | $CH_2CH_2$ | Cl | F | $NHSO_2Et$ | Cl |
| $CH_2$ | $CH_2$ | $CH_2CH_2$ | Cl | F | $NHSO_2$i-Pr | Cl |
| $CH_2$ | $CH_2$ | $CH_2CH_2$ | Cl | F | $OCH_2CO_2Et$ | Cl |
| $CH_2$ | $CH_2$ | $CH_2CH_2$ | Cl | F | $OCH_2CO_2$i-Pr | Cl |
| $CH_2$ | $CH_2$ | $CH_2CH_2$ | Cl | F | $OCH_2CN$ | Cl |
| $CH_2$ | $CH_2$ | $CH_2CH_2$ | Cl | F | $OCH(Me)CO_2Et$ | Cl |
| $CH_2$ | $CH_2$ | $CH_2CH_2$ | Cl | F | $OCH(Me)CO_2$i-Pr | Cl |
| $CH_2$ | $CH_2$ | $CH_2CH_2$ | Cl | F | Et | Cl |
| $CH_2$ | $CH_2$ | $CH_2CH_2$ | Cl | F | n-Pr | Cl |
| $CH_2$ | $CH_2$ | $CH_2CH_2$ | Cl | F | n-Bu | Cl |
| $CH_2$ | $CH_2$ | $CH_2CH_2$ | Cl | F | i-Bu | Cl |
| $CH_2$ | $CH_2$ | $CH_2$ | Cl | F | $CH=C(CH_3)CO_2Me$ | Cl |
| $CH_2$ | $CH_2$ | $CH_2$ | Cl | F | $CH=C(Cl)CO_2Me$ | Cl |
| $CH_2$ | $CH_2$ | $CH_2$ | Cl | F | $CH=C(Br)CO_2Me$ | Cl |
| $CH_2$ | $CH_2$ | $CH_2$ | Cl | F | $CH_2CH(Cl)CO_2Me$ | Cl |
| $CH_2$ | $CH_2$ | $CH_2$ | Cl | F | $CH_2CH(Cl)CO_2Et$ | Cl |
| $CH_2$ | $CH_2$ | $CH_2$ | Cl | r | COSMe | Cl |
| $CH_2$ | $CH_2$ | $CH_2$ | Cl | F | COSEt | Cl |
| $CH_2$ | $CH_2$ | $CH_2$ | Cl | F | CH=NOMe | Cl |
| $CH_2$ | $CH_2$ | $CH_2$ | Cl | F | CH=NOEt | Cl |
| $CH_2$ | $CH_2$ | $CH_2$ | Cl | F | $CH=NOCH_2CH=CH_2$ | Cl |
| $CH_2$ | $CH_2$ | $CH_2$ | Cl | F | CH=NOn-Pr | Cl |
| $CH_2$ | $CH_2$ | $CH_2$ | Cl | F | COi-Pr | Cl |
| $CH_2$ | $CH_2$ | $CH_2$ | Cl | F | COn-Bu | Cl |
| $CH_2$ | $CH_2$ | $CH_2$ | Cl | F | COEt | Cl |
| $CH_2$ | $CH_2$ | $CH_2$ | Cl | F | $OSO_2CF_3$ | Cl |
| $CH_2$ | $CH_2$ | $CH_2$ | Cl | F | OCOEt | Cl |
| $CH_2$ | $CH_2$ | $CH_2$ | Cl | F | $OCOCHMe_2$ | Cl |
| $CH_2$ | $CH_2$ | $CH_2$ | Cl | F | $OCO_2Et$ | Cl |
| $CH_2$ | $CH_2$ | $CH_2$ | Cl | F | OPh | Cl |
| $CH_2$ | $CH_2$ | $CH_2CH_2$ | Cl | Cl | OEt | Cl |
| $CH_2$ | $CH_2$ | $CH_2CH_2$ | Cl | Cl | On-Pr | Cl |
| $CH_2$ | $CH_2$ | $CH_2CH_2$ | Cl | Cl | On-Bu | Cl |
| $CH_2$ | $CH_2$ | $CH_2CH_2$ | Cl | Cl | On-Hex | Cl |
| $CH_2$ | $CH_2$ | $CH_2CH_2$ | Cl | Cl | S-Me | Cl |
| $CH_2$ | $CH_2$ | $CH_2CH_2$ | Cl | Cl | S-Et | Cl |
| $CH_2$ | $CH_2$ | $CH_2CH_2$ | Cl | Cl | S-i-Pr | Cl |
| $CH_2$ | $CH_2$ | $CH_2CH_2$ | Cl | Cl | $SCH_2CO_2Me$ | Cl |
| $CH_2$ | $CH_2$ | $CH_2CH_2$ | Cl | Cl | $SCH_2CH=CH_2$ | Cl |
| $CH_2$ | $CH_2$ | $CH_2CH_2$ | Cl | Cl | $SCH_2CO_2$i-Pr | Cl |
| $CH_2$ | $CH_2$ | $CH_2CH_2$ | Cl | Cl | $NHCH_2C\equiv CH$ | Cl |
| $CH_2$ | $CH_2$ | $CH_2CH_2$ | Cl | Cl | $NHCH_2CH=CH_2$ | Cl |
| $CH_2$ | $CH_2$ | $CH_2CH_2$ | Cl | Cl | $NMe_2$ | Cl |
| $CH_2$ | $CH_2$ | $CH_2CH_2$ | Cl | Cl | $NHCH(Me)C\equiv CH$ | Cl |
| $CH_2$ | $CH_2$ | $CH_2CH_2$ | Cl | Cl | $NHSO_2Et$ | Cl |
| $CH_2$ | $CH_2$ | $CH_2CH_2$ | Cl | Cl | $NHSO_2$i-Pr | Cl |
| $CH_2$ | $CH_2$ | $CH_2CH_2$ | Cl | Cl | $OCH_2CO_2Et$ | Cl |
| $CH_2$ | $CH_2$ | $CH_2CH_2$ | Cl | Cl | $OCH_2CO_2$i-Pr | Cl |

TABLE 1-continued

| X | Y | Z | R¹ | R¹¹ | R¹² | R¹³ |
|---|---|---|----|-----|-----|-----|
| $CH_2$ | $CH_2$ | $CH_2CH_2$ | Cl | Cl | $OCH_2CN$ | Cl |
| $CH_2$ | $CH_2$ | $CH_2CH_2$ | Cl | Cl | $OCH(Me)CO_2Et$ | Cl |
| $CH_2$ | $CH_2$ | $CH_2CH_2$ | Cl | Cl | $OCH(Me)CO_2i$-Pr | Cl |
| $CH_2$ | $CH_2$ | $CH_2CH_2$ | Cl | Cl | Et | Cl |
| $CH_2$ | $CH_2$ | $CH_2CH_2$ | Cl | Cl | n-Pr | Cl |
| $CH_2$ | $CH_2$ | $CH_2CH_2$ | Cl | Cl | n-Bu | Cl |
| $CH_2$ | $CH_2$ | $CH_2CH_2$ | Cl | Cl | i-Bu | Cl |
| $CH_2$ | $CH_2$ | $CH_2$ | Cl | Cl | $CH=C(CH_3)CO_2Me$ | Cl |
| $CH_2$ | $CH_2$ | $CH_2$ | Cl | Cl | $CH=C(Cl)CO_2Me$ | Cl |
| $CH_2$ | $CH_2$ | $CH_2$ | Cl | Cl | $CH=C(Br)CO_2Me$ | Cl |
| $CH_2$ | $CH_2$ | $CH_2$ | Cl | Cl | $CH_2CH(Cl)CO_2Me$ | Cl |
| $CH_2$ | $CH_2$ | $CH_2$ | Cl | Cl | $CH_2CH(Cl)CO_2Et$ | Cl |
| $CH_2$ | $CH_2$ | $CH_2$ | Cl | Cl | COSMe | Cl |
| $CH_2$ | $CH_2$ | $CH_2$ | Cl | Cl | COSEt | Cl |
| $CH_2$ | $CH_2$ | $CH_2$ | Cl | Cl | CH=NOMe | Cl |
| $CH_2$ | $CH_2$ | $CH_2$ | Cl | Cl | CH=NOEt | Cl |
| $CH_2$ | $CH_2$ | $CH_2$ | Cl | Cl | $CH=NOCH_2CH=CH_2$ | Cl |
| $CH_2$ | $CH_2$ | $CH_2$ | Cl | Cl | CH=NOn-Pr | Cl |
| $CH_2$ | $CH_2$ | $CH_2$ | Cl | Cl | COi-Pr | Cl |
| $CH_2$ | $CH_2$ | $CH_2$ | Cl | Cl | COn-Bu | Cl |
| $CH_2$ | $CH_2$ | $CH_2$ | Cl | Cl | COEt | Cl |
| $CH_2$ | $CH_2$ | $CH_2$ | Cl | Cl | $OSO_2CF_3$ | Cl |
| $CH_2$ | $CH_2$ | $CH_2$ | Cl | Cl | OCOEt | Cl |
| $CH_2$ | $CH_2$ | $CH_2$ | Cl | Cl | $OCOCHMe_2$ | Cl |
| $CH_2$ | $CH_2$ | $CH_2$ | Cl | Cl | $OCO_2Et$ | Cl |
| $CH_2$ | $CH_2$ | $CH_2$ | Cl | Cl | OPh | Cl |
| $CH_2$ | $CH_2$ | $CH_2CH_2$ | Br | F | OMe | Cl |
| $CH_2$ | $CH_2$ | $CH_2CH_2$ | Br | F | OEt | Cl |
| $CH_2$ | $CH_2$ | $CH_2CH_2$ | Br | F | On-Pr | Cl |
| $CH_2$ | $CH_2$ | $CH_2CH_2$ | Br | F | $OCH_2CH=CH_2$ | Cl |
| $CH_2$ | $CH_2$ | $CH_2CH_2$ | Br | F | $OCH(Me)C\equiv CH$ | Cl |
| $CH_2$ | $CH_2$ | $CH_2CH_2$ | Br | F | $OCH_2CO_2Me$ | Cl |
| $CH_2$ | $CH_2$ | $CH_2CH_2$ | Br | F | $OCH_2CO_2Et$ | Cl |
| $CH_2$ | $CH_2$ | $CH_2CH_2$ | Br | F | $OCH_2CO_2i$-Pr | Cl |
| $CH_2$ | $CH_2$ | $CH_2CH_2$ | Br | F | S—Me | Cl |
| $CH_2$ | $CH_2$ | $CH_2CH_2$ | Br | F | S—Et | Cl |
| $CH_2$ | $CH_2$ | $CH_2CH_2$ | Br | F | S-i-Pr | Cl |
| $CH_2$ | $CH_2$ | $CH_2CH_2$ | Br | F | $SCH_2CO_2Me$ | Cl |
| $CH_2$ | $CH_2$ | $CH_2CH_2$ | Br | F | $SCH_2C\equiv CH$ | Cl |
| $CH_2$ | $CH_2$ | $CH_2CH_2$ | Br | F | Me | Cl |
| $CH_2$ | $CH_2$ | $CH_2CH_2$ | Br | F | i-Pr | Cl |
| $CH_2$ | $CH_2$ | $CH_2CH_2$ | Br | F | $CO_2Me$ | Cl |
| $CH_2$ | $CH_2$ | $CH_2CH_2$ | Br | F | $CO_2Et$ | Cl |
| $CH_2$ | $CH_2$ | $CH_2CH_2$ | Br | F | $CO_2i$-Pr | Cl |
| $CH_2$ | $CH_2$ | $CH_2CH_2$ | Br | F | $NHSO_2Me$ | Cl |
| $CH_2$ | $CH_2$ | $CH_2CH_2$ | Br | F | $NHSO_2Et$ | Cl |
| $CH_2$ | $CH_2$ | $CH_2CH_2$ | Br | F | $OCH_2OMe$ | Cl |
| $CH_2$ | $CH_2$ | $CH_2CH_2$ | Br | F | $OCH_2OEt$ | Cl |
| $CH_2$ | $CH_2$ | $CH_2CH_2$ | Br | F | $CH=C(Br)CO_2Me$ | Cl |
| $CH_2$ | $CH_2$ | $CH_2CH_2$ | Br | F | $CH=C(Me)CO_2Et$ | Cl |
| $CH_2$ | $CH_2$ | $CH_2CH_2$ | Br | Cl | OMe | Cl |
| $CH_2$ | $CH_2$ | $CH_2CH_2$ | Br | Cl | OEt | Cl |
| $CH_2$ | $CH_2$ | $CH_2CH_2$ | Br | Cl | On-Pr | Cl |
| $CH_2$ | $CH_2$ | $CH_2CH_2$ | Br | Cl | $OCH_2CH=CH_2$ | Cl |
| $CH_2$ | $CH_2$ | $CH_2CH_2$ | Br | Cl | $OCH(Me)C\equiv CH$ | Cl |
| $CH_2$ | $CH_2$ | $CH_2CH_2$ | Br | Cl | $OCH_2CO_2Me$ | Cl |
| $CH_2$ | $CH_2$ | $CH_2CH_2$ | Br | Cl | $OCH_2CO_2Et$ | Cl |
| $CH_2$ | $CH_2$ | $CH_2CH_2$ | Br | Cl | $OCH_2CO_2i$-Pr | Cl |
| $CH_2$ | $CH_2$ | $CH_2CH_2$ | Br | Cl | S—Me | Cl |
| $CH_2$ | $CH_2$ | $CH_2CH_2$ | Br | Cl | S—Et | Cl |
| $CH_2$ | $CH_2$ | $CH_2CH_2$ | Br | Cl | S-i-Pr | Cl |
| $CH_2$ | $CH_2$ | $CH_2CH_2$ | Br | Cl | $SCH_2CO_2Me$ | Cl |
| $CH_2$ | $CH_2$ | $CH_2CH_2$ | Br | Cl | $SCH_2C\equiv CH$ | Cl |
| $CH_2$ | $CH_2$ | $CH_2CH_2$ | Br | Cl | Me | Cl |
| $CH_2$ | $CH_2$ | $CH_2CH_2$ | Br | Cl | i-Pr | Cl |
| $CH_2$ | $CH_2$ | $CH_2CH_2$ | Br | Cl | $CO_2Me$ | Cl |
| $CH_2$ | $CH_2$ | $CH_2CH_2$ | Br | Cl | $CO_2Et$ | Cl |

TABLE 1-continued

| X | Y | Z | $R^1$ | $R^{11}$ | $R^{12}$ | $R^{13}$ |
|---|---|---|---|---|---|---|
| $CH_2$ | $CH_2$ | $CH_2CH_2$ | Br | Cl | $CO_2$i-Pr | Cl |
| $CH_2$ | $CH_2$ | $CH_2CH_2$ | Br | Cl | $NHSO_2Me$ | Cl |
| $CH_2$ | $CH_2$ | $CH_2CH_2$ | Br | Cl | $NHSO_2Et$ | Cl |
| $CH_2$ | $CH_2$ | $CH_2CH_2$ | Br | Cl | $OCH_2OMe$ | Cl |
| $CH_2$ | $CH_2$ | $CH_2CH_2$ | Br | Cl | $OCH_2OEt$ | Cl |
| $CH_2$ | $CH_2$ | $CH_2CH_2$ | Br | Cl | $CH=C(Br)CO_2Me$ | Cl |
| $CH_2$ | $CH_2$ | $CH_2CH_2$ | Br | Cl | $CH=C(Me)CO_2Et$ | Cl |
| $CH_2$ | $CH_2$ | $CH_2CH_2$ | CN | F | $OCH_2CH=CH_2$ | Cl |
| $CH_2$ | $CH_2$ | $CH_2CH_2$ | CN | F | $OCH_2CH_3$ | Cl |
| $CH_2$ | $CH_2$ | $CH_2CH_2$ | CN | F | $OCH_2CO_2Me$ | Cl |
| $CH_2$ | $CH_2$ | $CH_2CH_2$ | CN | F | $OCH_2CO_2$i-Pr | Cl |
| $CH_2$ | $CH_2$ | $CH_2CH_2$ | CN | F | $OCH_2OMe$ | Cl |
| $CH_2$ | $CH_2$ | $CH_2CH_2$ | CN | F | $OCH_2CH_2OMe$ | Cl |
| $CH_2$ | $CH_2$ | $CH_2CH_2$ | CN | F | $OCH(Me)C≡CH$ | Cl |
| $CH_2$ | $CH_2$ | $CH_2CH_2$ | CN | F | $CO_2Et$ | Cl |
| $CH_2$ | $CH_2$ | $CH_2CH_2$ | CN | F | $CO_2$i-Pr | Cl |
| $CH_2$ | $CH_2$ | $CH_2CH_2$ | CN | F | $SCH_2C≡CH$ | Cl |
| $CH_2$ | $CH_2$ | $CH_2CH_2$ | CN | F | $SCH_2CO_2Me$ | Cl |
| $CH_2$ | $CH_2$ | $CH_2CH_2$ | CN | Cl | $OCH_2CH=CH_2$ | Cl |
| $CH_2$ | $CH_2$ | $CH_2CH_2$ | CN | Cl | $OCH_2CH_3$ | Cl |
| $CH_2$ | $CH_2$ | $CH_2CH_2$ | CN | Cl | $OCH_2CO_2Me$ | Cl |
| $CH_2$ | $CH_2$ | $CH_2CH_2$ | CN | Cl | $OCH_2CO_2$i-Pr | Cl |
| $CH_2$ | $CH_2$ | $CH_2CH_2$ | CN | Cl | $OCH_2OMe$ | Cl |
| $CH_2$ | $CH_2$ | $CH_2CH_2$ | CN | Cl | $OCH_2CH_2OMe$ | Cl |
| $CH_2$ | $CH_2$ | $CH_2CH_2$ | CN | Cl | $OCH(Me)C≡CH$ | Cl |
| $CH_2$ | $CH_2$ | $CH_2CH_2$ | CN | Cl | $CO_2Et$ | Cl |
| $CH_2$ | $CH_2$ | $CH_2CH_2$ | CN | Cl | $CO_2$i-Pr | Cl |
| $CH_2$ | $CH_2$ | $CH_2CH_2$ | CN | Cl | $SCH_2C≡CH$ | Cl |
| $CH_2$ | $CH_2$ | $CH_2CH_2$ | CN | Cl | $SCH_2CO_2Me$ | Cl |
| $CH_2$ | $CH_2$ | $CH_2$ | Cl | F | OMe | Cl |
| $CH_2$ | $CH_2$ | $CH_2$ | Cl | F | On-Pr | Cl |
| $CH_2$ | $CH_2$ | $CH_2$ | Cl | F | $OCH(Me)C≡H$ | Cl |
| $CH_2$ | $CH_2$ | $CH_2$ | Cl | F | $OCH_2CO_2Me$ | Cl |
| $CH_2$ | $CH_2$ | $CH_2$ | Cl | F | $OCH_2CO_2$i-Pr | Cl |
| $CH_2$ | $CH_2$ | $CH_2$ | Cl | F | $SCH_2C≡CH$ | Cl |
| $CH_2$ | $CH_2$ | $CH_2$ | Cl | F | $SCH_2CO_2Me$ | Cl |
| $CH_2$ | $CH_2$ | $CH_2$ | Cl | F | $CO_2Et$ | Cl |
| $CH_2$ | $CH_2$ | $CH_2$ | Cl | F | $CO_2$i-Pr | Cl |
| $CH_2$ | $CH_2$ | $CH_2$ | Cl | F | $OCH_2OCH_3$ | Cl |
| $CH_2$ | $CH_2$ | $CH_2$ | Cl | F | $OCH_2CH_2OMe$ | Cl |
| $CH_2$ | $CH_2$ | $CH_2$ | Cl | Cl | OMe | Cl |
| $CH_2$ | $CH_2$ | $CH_2$ | Cl | Cl | On-Pr | Cl |
| $CH_2$ | $CH_2$ | $CH_2$ | Cl | Cl | $OCH(Me)C≡CH$ | Cl |
| $CH_2$ | $CH_2$ | $CH_2$ | Cl | Cl | $OCH_2CO_2Me$ | Cl |
| $CH_2$ | $CH_2$ | $CH_2$ | Cl | Cl | $OCH_2CO_2$i-Pr | Cl |
| $CH_2$ | $CH_2$ | $CH_2$ | Cl | Cl | $SCH_2C≡CH$ | Cl |
| $CH_2$ | $CH_2$ | $CH_2$ | Cl | Cl | $SCH_2CO_2Me$ | Cl |
| $CH_2$ | $CH_2$ | $CH_2$ | Cl | Cl | $CO_2Et$ | Cl |
| $CH_2$ | $CH_2$ | $CH_2$ | Cl | Cl | $CO_2$i-Pr | Cl |
| $CH_2$ | $CH_2$ | $CH_2$ | Cl | Cl | $OCH_2OCH_3$ | Cl |
| $CH_2$ | $CH_2$ | $CH_2$ | Cl | Cl | $OCH_2CH_2OMe$ | Cl |
| $CH_2$ | $CH_2$ | $CH_2$ | Br | F | OMe | Cl |
| $CH_2$ | $CH_2$ | $CH_2$ | Br | F | On-Pr | Cl |

TABLE 1-continued

| X | Y | Z | R$^1$ | R$^{11}$ | R$^{12}$ | R$^{13}$ |
|---|---|---|---|---|---|---|
| CH$_2$ | CH$_2$ | CH$_2$ | Br | F | OCH(Me)C≡CH | Cl |
| CH$_2$ | CH$_2$ | CH$_2$ | Br | F | OCH$_2$CO$_2$Me | Cl |
| CH$_2$ | CH$_2$ | CH$_2$ | Br | F | OCH$_2$CO$_2$i-Pr | Cl |
| CH$_2$ | CH$_2$ | CH$_2$ | Br | F | SCH$_2$C≡CH | Cl |
| CH$_2$ | CH$_2$ | CH$_2$ | Br | F | SCH$_2$CO$_2$Me | Cl |
| CH$_2$ | CH$_2$ | CH$_2$ | Br | F | CO$_2$Et | Cl |
| CH$_2$ | CH$_2$ | CH$_2$ | Br | F | CO$_2$i-Pr | Cl |
| CH$_2$ | CH$_2$ | CH$_2$ | Br | F | OCH$_2$OCH$_3$ | Cl |
| CH$_2$ | CH$_2$ | CH$_2$ | Br | F | OCH$_2$CH$_2$OMe | Cl |
| CH$_2$CH$_2$ | O | CH$_2$ | Cl | F | OMe | Cl |
| CH$_2$CH$_2$ | O | CH$_2$ | Cl | F | On-Pr | Cl |
| CH$_2$CH$_2$ | O | CH$_2$ | Cl | F | OCH(Me)C≡CH | Cl |
| CH$_2$CH$_2$ | O | CH$_2$ | Cl | F | OCH$_2$CO$_2$Me | Cl |
| CH$_2$CH$_2$ | O | CH$_2$ | Cl | F | OCH$_2$CO$_2$i-Pr | Cl |
| CH$_2$CH$_2$ | O | CH$_2$ | Cl | F | SCH$_2$C≡CH | Cl |
| CH$_2$CH$_2$ | O | CH$_2$ | Cl | F | SCH$_2$CO$_2$Me | Cl |
| CH$_2$CH$_2$ | O | CH$_2$ | Cl | F | CO$_2$Et | Cl |
| CH$_2$CH$_2$ | O | CH$_2$ | Cl | F | CO$_2$i-Pr | Cl |
| CH$_2$CH$_2$ | O | CH$_2$ | Cl | F | OCH$_2$OCH$_3$ | Cl |
| CH$_2$CH$_2$ | O | CH$_2$ | Cl | F | OCH$_2$CH$_2$OMe | Cl |
| CH$_2$CH$_2$ | O | CH$_2$ | Cl | Cl | OMe | Cl |
| CH$_2$CH$_2$ | O | CH$_2$ | Cl | Cl | On-Pr | Cl |
| CH$_2$CH$_2$ | O | CH$_2$ | Cl | Cl | OCH(Me)C≡CH | Cl |
| CH$_2$CH$_2$ | O | CH$_2$ | Cl | Cl | OCH$_2$CO$_2$Me | Cl |
| CH$_2$CH$_2$ | O | CH$_2$ | Cl | Cl | OCH$_2$CO$_2$i-Pr | Cl |
| CH$_2$CH$_2$ | O | CH$_2$ | Cl | Cl | SCH$_2$C≡CH | Cl |
| CH$_2$CH$_2$ | O | CH$_2$ | Cl | Cl | SCH$_2$CO$_2$Me | Cl |
| CH$_2$CH$_2$ | O | CH$_2$ | Cl | Cl | CO$_2$Et | Cl |
| CH$_2$CH$_2$ | O | CH$_2$ | Cl | Cl | CO$_2$i-Pr | Cl |
| CH$_2$CH$_2$ | O | CH$_2$ | Cl | Cl | OCH$_2$OCH$_3$ | Cl |
| CH$_2$CH$_2$ | O | CH$_2$ | Cl | Cl | OCH$_2$CH$_2$OMe | Cl |
| CH$_2$CH$_2$ | S | CH$_2$ | Cl | F | OMe | Cl |
| CH$_2$CH$_2$ | S | CH$_2$ | Cl | F | On-Pr | Cl |
| CH$_2$CH$_2$ | S | CH$_2$ | Cl | F | OCH(Me)C≡CH | Cl |
| CH$_2$CH$_2$ | S | CH$_2$ | Cl | F | OCH$_2$CO$_2$Me | Cl |
| CH$_2$CH$_2$ | S | CH$_2$ | Cl | F | OCH$_2$CO$_2$i-Pr | Cl |
| CH$_2$CH$_2$ | S | CH$_2$ | Cl | F | SCH$_2$C≡CH | Cl |
| CH$_2$CH$_2$ | S | CH$_2$ | Cl | F | SCH$_2$CO$_2$Me | Cl |
| CH$_2$CH$_2$ | S | CH$_2$ | Cl | F | CO$_2$Et | Cl |
| CH$_2$CH$_2$ | S | CH$_2$ | Cl | F | CO$_2$i-Pr | Cl |
| CH$_2$CH$_2$ | S | CH$_2$ | Cl | F | OCH$_2$OCH$_3$ | Cl |
| CH$_2$CH$_2$ | S | CH$_2$ | Cl | F | CCH$_2$CH$_2$OMe | Cl |
| CH$_2$CH$_2$ | S | CH$_2$ | Br | F | OMe | Cl |
| CH$_2$CH$_2$ | S | CH$_2$ | Br | F | On-Pr | Cl |
| CH$_2$CH$_2$ | S | CH$_2$ | Br | F | OCH(Me)C≡CH | Cl |
| CH$_2$CH$_2$ | S | CH$_2$ | Br | F | OCH$_2$CO$_2$Me | Cl |
| CH$_2$CH$_2$ | S | CH$_2$ | Br | F | OCH$_2$CO$_2$i-Pr | Cl |
| CH$_2$CH$_2$ | S | CH$_2$ | Br | F | SCH$_2$C≡CH | Cl |
| CH$_2$CH$_2$ | S | CH$_2$ | Br | F | SCH$_2$CO$_2$Me | Cl |
| CH$_2$CH$_2$ | S | CH$_2$ | Br | F | CO$_2$Et | Cl |
| CH$_2$CH$_2$ | S | CH$_2$ | Br | F | CO$_2$i-Pr | Cl |
| CH$_2$CH$_2$ | S | CH$_2$ | Br | F | OCH$_2$OCH$_3$ | Cl |
| CH$_2$CH$_2$ | S | CH$_2$ | Br | F | OCH$_2$CH$_2$OMe | Cl |
| CH$_2$ | CH$_2$ | O | Cl | F | H | Cl |
| CH$_2$ | CH$_2$ | O | Cl | Cl | H | Cl |
| CH$_2$ | CH$_2$ | O | Cl | F | OCH$_2$C≡CH | Cl |
| CH$_2$ | CH$_2$ | O | Br | F | OCH$_2$C≡CH | Cl |
| CH$_2$ | CH$_2$ | S | Cl | F | H | Cl |
| CH$_2$ | CH$_2$ | S | Cl | F | OCH$_2$C≡CH | Cl |
| CH$_2$ | CH$_2$ | S | Br | F | OCH$_2$C≡CH | Cl |

TABLE 2

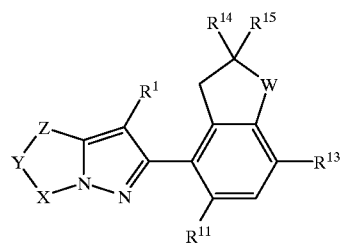

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | Cl | F | Cl | H | H | O |
| CH₂ | CH₂ | CH₂CH₂ | Cl | F | Cl | Me | H | O |
| CH₂ | CH₂ | CH₂CH₂ | Cl | F | Cl | Me | Me | S |
| CH₂ | CH₂ | CH₂CH₂ | Cl | Cl | Cl | Me | H | O |
| CH₂ | CH₂ | CH₂CH₂ | Br | Cl | Cl | Me | H | O |
| CH₂ | CH₂ | CH₂CH₂ | CN | Cl | Cl | Me | H | O |
| CH₂ | CH₂ | CH₂CH₂ | F | F | Cl | Me | H | O |
| CH₂ | CH₂ | CH₂CH₂ | Br | Cl | Cl | Me | Me | O |
| CH₂ | CH₂ | CH₂CH₂ | I | F | Cl | Me | H | O |
| CH₂ | CH₂ | CH₂CH₂ | Br | F | Cl | Me | H | O |
| CH₂ | CHMe | CH₂CH₂ | Cl | F | Cl | Me | H | O |
| CHMe | CH | CH₂CH₂ | Cl | F | Cl | Me | H | O |
| CH₂ | CH₂ | S | Cl | F | Cl | Me | H | O |
| CH₂CH₂ | CH₂ | O | Cl | F | Cl | H | H | O |
| CH₂ | CH₂ | CH₂CH₂ | Cl | F | Br | Me | H | O |
| CH₂ | CH₂ | CH₂CH₂ | Cl | Br | Cl | Me | H | O |
| CH₂ | CHCF₃ | CH₂CH₂ | Cl | F | Cl | Me | H | O |
| CH₂ | CH=CH | CH₂ | Cl | F | Cl | Me | H | O |
| CH₂ | CH₂ | CH₂CH₂ | Cl | F | OMe | H | H | O |
| CH₂ | NHMe | CH₂CH₂ | Cl | F | Cl | H | H | O |
| CH₂ | CH₂ | CH₂CH₂ | Cl | F | Cl | Me | H | S |
| CH₂ | CH₂ | CH₂ | Cl | F | Cl | Me | H | O |
| CH₂ | CH₂ | CH₂ | Cl | F | Cl | Me | H | S |

TABLE 3

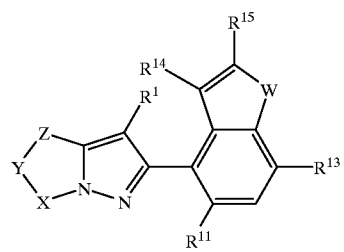

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | Cl | F | Cl | H | Me | O |
| CH₂ | CH₂ | CH₂CH₂ | Cl | F | Cl | H | H | O |
| CH₂ | CH₂ | CH₂CH₂ | Cl | F | Cl | H | H | S |
| CH₂ | CH₂ | CH₂CH₂ | Br | F | Cl | H | H | O |
| CH₂ | CH₂ | CH₂CH₂ | Cl | F | Cl | Me | H | O |
| CH₂ | CH₂ | CH₂CH₂ | F | Cl | Cl | H | H | O |
| CH₂ | CH₂ | CH₂CH₂ | Cl | Cl | Br | H | H | O |
| CH₂ | CH₂ | CH₂CH₂ | Cl | Br | Cl | H | Me | O |

TABLE 3-continued

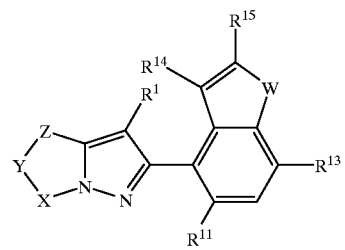

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | CN | F | Cl | H | H | O |
| CH₂ | CH₂ | CH₂CH₂ | Br | F | Cl | H | H | O |
| CH₂ | CH₂ | CH₂CH₂ | Cl | F | CF₃ | H | H | O |
| CH₂ | CH₂ | CH₂CH₂ | Cl | F | OMe | H | H | O |
| CHMe | CH₂ | CH₂CH₂ | Cl | F | Cl | H | H | O |
| CH₂ | CHMe | CH₂CH₂ | Cl | F | Cl | H | Me | O |
| CH₂ | CH₂ | S | Cl | F | Cl | H | Me | O |
| CH₂CH₂ | CH₂ | O | Cl | F | Cl | H | H | O |
| CH₂ | CH₂ | CH₂CH₂ | Cl | Br | Cl | H | Me | S |
| CH₂ | CH=CH | CH₂ | Cl | F | Cl | H | H | O |
| CH₂ | CH₂ | CH₂ | Cl | F | Cl | H | H | O |
| CH₂ | CH₂ | CH₂CH₂ | Cl | H | Cl | H | H | O |

TABLE 4

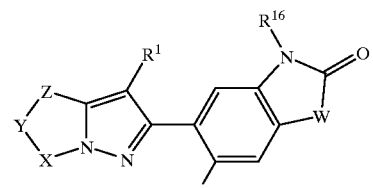

| X | Y | Z | R¹ | R¹¹ | R¹⁶ | W |
|---|---|---|---|---|---|---|
| CH₂ | CH₂ | CH₂CH₂ | Cl | F | Me | O |
| CH₂ | CH₂ | CH₂CH₂ | Cl | Cl | Et | O |
| CH₂ | CH₂ | CH₂CH₂ | Br | F | n-Pr | O |
| CH₂ | CH₂ | CH₂CH₂ | Cl | F | CH₂CH=CH₂ | O |
| CH₂ | CH₂ | CH₂CH₂ | Cl | F | CH₂C≡CH | O |
| CH₂ | CH₂ | CH₂CH₂ | Cl | Br | CH₂C≡CH | O |
| CH₂ | CH₂ | CH₂CH₂ | Cl | H | CH₂C≡CH | O |
| CH₂ | CH₂ | CH₂CH₂ | F | Cl | CH₂C≡CH | O |
| CH₂ | CH₂ | CH₂CH₂ | Br | Cl | CH₂C≡CH | S |
| CH₂ | CH₂ | CH₂CH₂ | Cl | F | CH₂C≡CH | S |
| CH₂ | CH₂ | CH₂CH₂ | Cl | F | CH₂CF₃ | O |
| CH₂ | CH₂ | CH₂CH₂ | Cl | F | CH₂CH=CHCl | O |
| CHMe | CH₂ | CH₂CH₂ | Cl | F | CH₂C≡CH | O |
| CH₂ | NMe | CH₂CH₂ | Cl | F | CH₂C≡CH | O |
| CH₂ | CH₂ | CH₂CH₂ | CN | F | CH₂C≡CH | S |
| CH₂ | CH₂ | CH₂CH₂ | CN | F | CH₂C≡CH | O |
| CH₂ | CH₂ | S | Cl | F | CH₂C≡CH | O |
| CH₂CH₂ | CH₂ | O | Cl | F | CH₂C≡CH | O |
| CH₂ | CH₂ | CH₂CH₂ | Br | F | CH₂C≡CH | O |
| CH₂ | CH₂ | CH₂CH₂ | Cl | H | CH₂C≡CH | O |
| CH₂ | CH₂ | CH₂CH₂ | Cl | F | CH₂OMe | O |
| CH₂ | CH₂ | CH₂ | Br | F | CH₂C≡CH | O |
| CH₂ | CH₂ | CH₂ | Br | F | CH₂C≡CH | S |
| CH₂ | CH₂ | CH₂CH₂ | Br | F | CH₂C≡CH | S |
| CH₂ | CH₂ | CH₂CH₂ | CN | F | CH₂C≡CH | S |
| CH₂CH₂ | O | CH₂ | Cl | F | CH₂C≡CH | O |
| CH₂CH₂ | S | CH₂ | Cl | F | CH₂C≡CH | O |
| CH₂ | CH₂ | CH₂CH₂ | Cl | F | CH(Me)C≡CH | O |
| CH₂ | CH₂ | CH₂CH₂ | Br | F | CH(Me)C≡CH | O |

TABLE 5

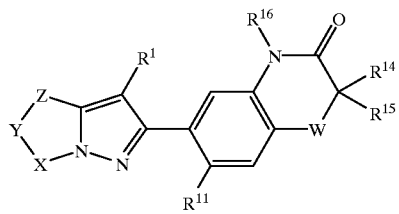

| X | Y | Z | R¹ | R¹¹ | R¹⁶ | R¹⁴ | R¹⁵ | W |
|---|---|---|---|---|---|---|---|---|
| CH₂ | CH₂ | CH₂CH₂ | Cl | F | Me | H | H | O |
| CH₂ | CH₂ | CH₂CH₂ | Cl | Cl | Et | H | H | O |
| CH₂ | CH₂ | CH₂CH₂ | Cl | F | CH₂CH=CH₂ | H | H | O |
| CH₂ | CH₂ | CH₂CH₂ | Cl | F | CH₂C≡CH | H | H | O |
| CH₂ | CH₂ | CH₂CH₂ | Cl | Cl | CH₂C≡CH | H | H | O |
| CH₂ | CH₂ | CH₂CH₂ | Cl | Br | CH₂C≡CH | H | H | O |
| CH₂ | CH₂ | CH₂CH₂ | Br | Cl | CH₂C≡CH | H | H | S |
| CH₂ | CH₂ | CH₂CH₂ | Br | F | CH₂C≡CH | H | H | S |
| CH₂ | CH₂ | CH₂CH₂ | Cl | F | n-Pr | H | H | O |
| CH₂ | CH₂ | CH₂CH₂ | Cl | F | OCH₂CH₂OMe | H | H | O |
| CH₂ | CH₂ | CH₂CH₂ | Cl | F | CH₂OMe | H | H | O |
| CH₂ | CH₂ | CH₂CH₂ | Cl | F | CHMe₂ | H | H | O |
| CH₂ | CH₂ | CH₂ | Cl | F | CH₂C≡CH | H | H | O |
| CH₂ | CH₂ | CH₂ | CN | Cl | CH₂C≡CH | H | H | O |
| CH₂ | CH₂ | CH₂CH₂ | CN | F | CH₂C≡CH | H | H | O |
| CH₂ | CH₂ | CH₂CH₂ | CN | F | CH₂C≡CH | H | H | O |
| CH₂ | CHMe | CH₂CH₂ | Cl | Cl | CH₂C≡CH | H | H | O |
| CH₂CH₂ | S | CH₂ | Cl | F | CH₂C≡CH | H | H | O |
| CH₂CH₂ | O | CH₂ | Cl | F | CH₂C≡CH | H | H | O |
| CH₂ | CH₂ | CH₂CH₂ | Cl | F | CH₂C≡CH | Me | Me | O |
| CH₂ | CH₂ | CH₂CH₂ | Cl | H | CH₂C≡CH | H | H | O |
| CH₂ | CH₂ | CH₂CH₂ | Cl | F | CH(Me)C≡CH | H | H | O |
| CH₂ | CH₂ | CH₂CH₂ | Br | F | CH(Me)C≡CH | H | H | O |
| CH₂ | CH₂ | CH₂CH₂ | Cl | F | CH₂CO₂Me | H | H | O |
| CH₂ | CH₂ | CH₂CH₂ | Cl | F | CH(CH₃)CO₂Me | H | H | O |
| CH₂ | CH₂ | CH₂CH₂ | Cl | F | H | H | H | O |
| CH₂ | CH₂ | CH₂CH₂ | Br | F | H | H | H | O |
| CH₂ | CH₂ | CH₂ | Cl | F | CH₂CH=CH₂ | H | H | O |
| CH₂ | CH₂ | CH₂ | Cl | F | n-Pr | H | H | O |
| CH₂ | CH₂ | CH₂ | Cl | F | CH₂CH₂OMe | H | H | O |

TABLE 6

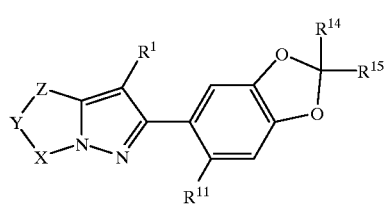

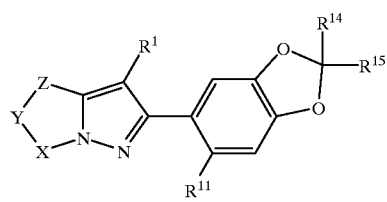

| X | Y | Z | R¹ | R¹¹ | R¹⁴ | R¹⁵ |
|---|---|---|---|---|---|---|
| CH₂ | CH₂ | CH₂CH₂ | Cl | F | H | H |
| CH₂ | CH₂ | CH₂CH₂ | Cl | Cl | H | H |
| CH₂ | CH₂ | CH₂CH₂ | Cl | F | F | F |
| CH₂ | CH₂ | CH₂CH₂ | Cl | Cl | F | F |
| CH₂ | CH₂ | CH₂CH₂ | Cl | F | Me | Me |
| CH₂ | CH₂ | CH₂CH₂ | Cl | F | Me | H |
| CH₂ | CH₂ | CH₂CH₂ | Br | F | F | F |
| CH₂ | CH₂ | CH₂CH₂ | Br | Cl | F | F |
| CH₂ | CH₂ | CH₂CH₂ | Br | F | H | H |
| CH₂ | CH₂ | CH₂CH₂ | Cl | H | F | F |
| CH₂ | CH₂ | CH₂CH₂ | CN | H | F | F |
| CH₂ | CH₂ | CH₂CH₂ | I | H | F | F |
| CH₂CH₂ | S | CH₂ | Cl | F | F | F |
| CH₂ | CH₂ | CH₂ | Cl | F | F | F |
| CH₂ | CH₂ | CH₂CH₂ | Cl | Br | F | F |
| CH₂ | CH₂ | CH₂CH₂ | Br | Cl | H | H |
| CH₂CH₂ | O | CH₂ | Cl | F | F | F |
| CH₂ | CH₂ | CH₂ | Br | F | F | F |

TABLE 7

| X | Y | Z | R$^1$ | R$^4$ | R$^{11}$ | R$^{12}$ | R$^{13}$ |
|---|---|---|---|---|---|---|---|
| CH$_2$ | CH$_2$ | CH$_2$CH$_2$ | Cl | Cl | Cl | H | Cl |
| CH$_2$ | CH$_2$ | CH$_2$CH$_2$ | Br | CN | Cl | H | Cl |
| CH$_2$ | CH$_2$ | CH$_2$CH$_2$ | Cl | Cl | F | H | Cl |
| CH$_2$ | CH$_2$ | CH$_2$CH$_2$ | Br | Br | F | H | Cl |
| CH$_2$ | CH$_2$ | CH$_2$CH$_2$ | F | Br | Cl | H | Cl |
| CH$_2$ | CH$_2$ | CH$_2$CH$_2$ | I | Br | F | H | Cl |
| CH$_2$ | CH$_2$ | CH$_2$CH$_2$ | CN | Br | Cl | H | Cl |
| CH$_2$ | CH$_2$ | CH$_2$CH$_2$ | CN | Br | F | H | Cl |
| CH$_2$ | CH$_2$ | CH$_2$CH$_2$ | Cl | Cl | F | H | Br |
| CH$_2$ | CH$_2$ | CH$_2$CH$_2$ | Br | Br | Cl | H | Br |
| CH$_2$ | CH$_2$ | CH$_2$CH$_2$ | Cl | Cl | Cl | OMe | Cl |
| CH$_2$ | CH$_2$ | CH$_2$CH$_2$ | Br | Br | F | OMe | Cl |
| CH$_2$ | CH$_2$ | CH$_2$CH$_2$ | Cl | Cl | Cl | OCHMe$_2$ | Cl |
| CH$_2$ | CH$_2$ | CH$_2$CH$_2$ | Cl | Cl | F | OCHMe$_2$ | Cl |
| CH$_2$ | CH$_2$ | CH$_2$CH$_2$ | Cl | Cl | Cl | OCH$_2$CH=CH$_2$ | Cl |
| CH$_2$ | CH$_2$ | CH$_2$CH$_2$ | Cl | Cl | Cl | OCH$_2$C≡CH | Cl |
| CH$_2$ | CH$_2$ | CH$_2$CH$_2$ | Cl | Cl | H | OCH$_2$C≡CH | Cl |
| CH$_2$ | CH$_2$ | CH$_2$CH$_2$ | Br | Br | Cl | OCH$_2$C≡CH | Cl |
| CH$_2$ | CH$_2$ | CH$_2$CH$_2$ | Cl | Cl | F | OCH$_2$C≡CH | Cl |
| CH$_2$ | CH$_2$ | CH$_2$CH$_2$ | Br | Br | F | OCH$_2$C≡CH | Cl |
| CH$_2$ | CH$_2$ | CH$_2$CH$_2$ | Cl | Cl | Cl | OCH$_2$C≡CH | Br |
| CH$_2$ | CH$_2$ | CH$_2$CH$_2$ | Cl | Cl | Cl | OCH$_2$CO$_2$Me | Cl |
| CH$_2$ | CH$_2$ | CH$_2$CH$_2$ | Br | Br | F | OCH(Me)CO$_2$Me | Cl |
| CH$_2$ | CH$_2$ | CH$_2$CH$_2$ | Cl | Cl | F | OCH$_2$C(O)NMe$_2$ | Cl |
| CH$_2$ | CH$_2$ | CH$_2$CH$_2$ | Cl | Cl | F | OCH$_2$C(O)NHMe | Cl |
| CH$_2$ | CH$_2$ | CH$_2$CH$_2$ | Cl | Cl | F | COH$_2$C(O)NHPh | Cl |
| CH$_2$ | CH$_2$ | CH$_2$CH$_2$ | Cl | Cl | Br | OCH$_2$CH=CMe$_2$ | Cl |
| CH$_2$ | CH$_2$ | CH$_2$CH$_2$ | Cl | Cl | F | OCH$_2$CH$_2$Me | Cl |
| CH$_2$ | CH$_2$ | CH$_2$CH$_2$ | Cl | Cl | Cl | OCH$_2$CHMe$_2$ | Cl |
| CH$_2$ | CH$_2$ | CH$_2$CH$_2$ | Cl | Cl | Cl | OCH$_2$CH$_2$OCHF$_2$ | Cl |
| CH$_2$ | CH$_2$ | CH$_2$CH$_2$ | Cl | Cl | Cl | SMe | Cl |
| CH$_2$ | CH$_2$ | CH$_2$CH$_2$ | Cl | Cl | F | SO$_2$Me | Cl |
| CH$_2$ | CH$_2$ | CH$_2$CH$_2$ | Cl | Cl | F | OCH$_2$CH$_2$OMe | Cl |
| CH$_2$ | CH$_2$ | CH$_2$CH$_2$ | Cl | Cl | Cl | OCH$_2$CF$_3$ | Cl |
| CH$_2$ | CH$_2$ | CH$_2$CH$_2$ | Cl | Cl | Cl | OCHF$_2$ | Cl |
| CH$_2$ | CH$_2$ | CH$_2$CH$_2$ | Br | Br | Cl | OCH$_2$CH$_2$OMe | Cl |
| CH$_2$ | CH$_2$ | CH$_2$CH$_2$ | Cl | Cl | Cl | OCH$_2$OCH$_2$C≡CH | Cl |
| CH$_2$ | CH$_2$ | CH$_2$CH$_2$ | Cl | Cl | Cl | OCH$_2$Ph | Cl |
| CH$_2$ | CH$_2$ | CH$_2$CH$_2$ | Cl | Cl | F | OCH(CF$_3$)$_2$ | Cl |
| CH$_2$ | CH$_2$ | CH$_2$CH$_2$ | Cl | Cl | F | OCH$_2$OEt | Cl |
| CH$_2$ | CH$_2$ | CH$_2$CH$_2$ | Cl | Cl | F | SCH$_2$C≡CH | Cl |
| CH$_2$ | Cl | CH$_2$CH$_2$ | Cl | Cl | F | SCH$_2$CF$_3$ | Cl |
| CH$_2$ | Cl | CH$_2$CH$_2$ | Cl | Cl | Cl | OCF$_2$CHF$_2$ | Cl |
| CH$_2$ | Cl | CH$_2$CH$_2$ | Cl | Cl | F | OCH$_2$P(O)(OMe)$_2$ | Cl |
| CH$_2$ | CH$_2$ | CH$_2$CH$_2$ | Cl | Cl | F | OCH$_2$C(O)NH$_2$ | Cl |
| CH$_2$ | CH$_2$ | CH$_2$CH$_2$ | Cl | Cl | F | OCH$_2$SiMe$_3$ | Cl |
| CH$_2$ | CH$_2$ | CH$_2$CH$_2$ | Cl | Cl | Cl | CO$_2$Me | Cl |
| CH$_2$ | CH$_2$ | CH$_2$CH$_2$ | Cl | Cl | Cl | C(O)NMe$_2$ | Cl |
| CH$_2$ | CH$_2$ | CH$_2$CH$_2$ | Cl | Cl | F | CO$_2$Me | Cl |
| CH$_2$ | CH$_2$ | CH$_2$CH$_2$ | Cl | Cl | F | C(O)NH$_2$ | Cl |
| CH$_2$ | CH$_2$ | CH$_2$CH$_2$ | Cl | Cl | F | C(O)NHPh | Cl |
| CH$_2$ | CH$_2$ | CH$_2$CH$_2$ | Cl | Cl | F | C(O)NHMe | Cl |
| CH$_2$ | CH$_2$ | CH$_2$CH$_2$ | Cl | Cl | F | C(O)N-morpholine | Cl |
| CH$_2$ | CH$_2$ | CH$_2$CH$_2$ | Cl | Cl | F | C(O)NHn-Bu | Br |
| CH$_2$ | CH$_2$ | CH$_2$CH$_2$ | Br | Cl | F | C(O)NHn-Pr | Cl |
| CH$_2$ | CH$_2$ | CH$_2$CH$_2$ | Cl | Cl | F | CO$_2$CH$_2$C≡CH | Cl |
| CH$_2$ | CH$_2$ | CH$_2$CH$_2$ | Cl | Cl | F | CO$_2$n-Pr | Cl |
| CH$_2$ | CH$_2$ | CH$_2$CH$_2$ | Br | Me | F | CO$_2$CH$_2$CH=CH$_2$ | Cl |
| CH$_2$ | CH$_2$ | CH$_2$CH$_2$ | Cl | Cl | Cl | CO$_2$N=CMe$_2$ | Cl |
| CH$_2$ | CH$_2$ | CH$_2$CH$_2$ | Cl | Cl | F | C(O)Me | Cl |
| CH$_2$ | CH$_2$ | CH$_2$CH$_2$ | Cl | Cl | F | CO$_2$n-Pr | Cl |

TABLE 7-continued

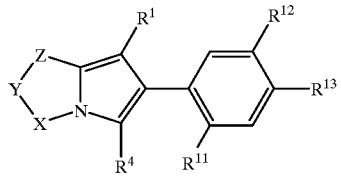

| X | Y | Z | R¹ | R⁴ | R¹¹ | R¹² | R¹³ |
|---|---|---|---|---|---|---|---|
| $CH_2$ | $CH_2$ | $CH_2CH_2$ | Br | Cl | F | $CO_2Et$ | Br |
| $CH_2$ | $CH_2$ | $CH_2CH_2$ | Cl | Cl | Cl | $CO_2CH_2CF_3$ | Cl |
| $CH_2$ | $CH_2$ | $CH_2CH_2$ | Cl | Cl | Cl | $NHSO_2Me$ | Cl |
| $CH_2$ | $CH_2$ | $CH_2CH_2$ | Cl | Cl | F | $NHSO_2Me$ | Cl |
| $CH_2$ | $CH_2$ | $CH_2CH_2$ | Cl | Cl | F | $NHSO_2NHMe$ | Cl |
| $CH_2$ | $CH_2$ | $CH_2CH_2$ | Cl | Cl | F | $NHSO_2CF_3$ | Cl |
| $CH_2$ | $CH_2$ | $CH_2CH_2$ | Cl | Cl | F | $CF_3$ | Cl |
| $CH_2$ | $CH_2$ | $CH_2CH_2$ | Cl | Cl | F | $CH(Me)_2$ | Cl |
| $CH_2$ | $CH_2$ | $CH_2CH_2$ | Cl | Cl | F | Me | Cl |
| $CH_2$ | $CH_2$ | $CH_2CH_2$ | Cl | Cl | F | $NO_2$ | Cl |
| $CH_2$ | $CH_2$ | $CH_2CH_2$ | Cl | Cl | Br | $OCH_2C\equiv CH$ | Cl |
| $CH_2$ | $CH_2$ | $CH_2CH_2$ | Cl | Cl | F | $CH=CHCO_2Me$ | Cl |
| $CH_2$ | $CH_2$ | $CH_2CH_2$ | Br | Cl | F | CN | Cl |
| $CH_2$ | $CH_2$ | $CH_2CH_2$ | Cl | Cl | F | Cl | Cl |
| $CH_2$ | $CH_2$ | $CH_2CH_2$ | Cl | Cl | Cl | Br | Cl |
| $CH_2$ | $CH_2$ | $CH_2CH_2$ | Cl | Cl | F | $CH_2CH=CH_2$ | Cl |
| $CH_2$ | $CH_2$ | $CH_2CH_2$ | Cl | Cl | F | $OCH_2C\equiv CMe$ | Br |
| $CH_2$ | $CH_2$ | S | Cl | Cl | Cl | H | Cl |
| $CH_2$ | $CH_2$ | S | Cl | Cl | Cl | $OCH_2C\equiv CH$ | Cl |
| $CH_2$ | $CH_2$ | S | Cl | Cl | F | $OCH_2C\equiv CH$ | Cl |
| $CH_2$ | $CH_2$ | $CH_2$ | Cl | Cl | F | $OCH_2C\equiv CH$ | Cl |
| $CH_2$ | $CH_2$ | CH=CH | Cl | Cl | F | $OCH_2C\equiv CH$ | Cl |
| $CH_2$ | $CH_2$ | CH=CH | Cl | Cl | Cl | H | Cl |
| $CH_2$ | $CH_2$ | CH=CH | Cl | Cl | Cl | $OCH_2C\equiv CH$ | Cl |
| $CH_2$ | CH=CH | $CH_2$ | Cl | Cl | Cl | $OCH_2C\equiv CH$ | Cl |
| $CH_2$ | CH=CH | $CH_2$ | Cl | Cl | F | $OCH_2C\equiv CH$ | Cl |
| $CH_2$ | $CH_2$ | O | Cl | Cl | F | $OCH_2C\equiv CH$ | Cl |
| CHMe | $CH_2$ | $CH_2CH_2$ | Br | Me | Cl | $OCH_2C\equiv CH$ | Cl |
| $CH_2$ | CHMe | $CH_2CH_2$ | Cl | Cl | F | $OCH_2C\equiv CH$ | Cl |
| $CH_2CH_2$ | $CH_2$ | CHMe | Cl | Cl | F | $OCH_2C\equiv CH$ | Cl |
| $CH_2$ | NMe | $CH_2CH_2$ | Cl | Cl | F | $OCH_2C\equiv CH$ | Cl |
| CHF | $CH_2$ | $CH_2CH_2$ | Cl | Cl | F | $OCH_2C\equiv CH$ | Cl |
| $CHCF_3$ | $CH_2$ | $CH_2CH_2$ | Cl | Cl | F | $OCH_2C\equiv CH$ | Cl |
| $CH_2CH_2$ | $CH_2$ | O | Cl | Cl | F | $OCH_2C\equiv CH$ | Cl |
| $CH_2$ | $CH_2$ | $CH_2CH_2$ | CN | Br | F | $OCH_2C\equiv CH$ | Cl |
| $CH_2$ | $CH_2$ | $CH_2CH_2$ | Cl | Br | F | $OCH_2C\equiv CH$ | $CF_3$ |
| $CH_2$ | $CH_2$ | $CH_2CH_2$ | Cl | Br | F | $OCH_2C\equiv CH$ | $OCHF_2$ |
| $CH_2$ | $CH_2$ | $CH_2CH_2$ | Cl | Br | F | $OCH_2C\equiv CH$ | OMe |

TABLE 8

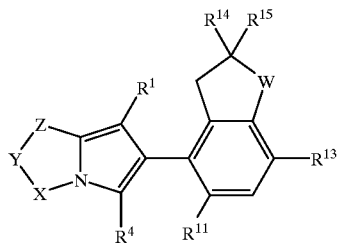

| X | Y | Z | R¹ | R⁴ | R¹¹ | R¹³ | R¹⁴ | R¹⁵ | W |
|---|---|---|---|---|---|---|---|---|---|
| $CH_2$ | $CH_2$ | $CH_2CH_2$ | Cl | Cl | F | Cl | H | H | O |
| $CH_2$ | $CH_2$ | $CH_2CH_2$ | Cl | Cl | F | Cl | Me | H | O |
| $CH_2$ | $CH_2$ | $CH_2CH_2$ | Cl | Cl | F | Cl | Me | Me | S |
| $CH_2$ | $CH_2$ | $CH_2CH_2$ | Cl | Cl | Cl | Cl | Me | H | O |
| $CH_2$ | $CH_2$ | $CH_2CH_2$ | Br | Br | Cl | Cl | Me | H | O |
| $CH_2$ | $CH_2$ | $CH_2CH_2$ | CN | Cl | Cl | Cl | Me | H | O |
| $CH_2$ | $CH_2$ | $CH_2CH_2$ | F | Cl | F | Cl | Me | H | O |
| $CH_2$ | $CH_2$ | $CH_2CH_2$ | I | Cl | F | Cl | Me | H | O |
| $CH_2$ | CHMe | $CH_2CH_2$ | Cl | Cl | F | Cl | Me | H | O |

TABLE 8-continued

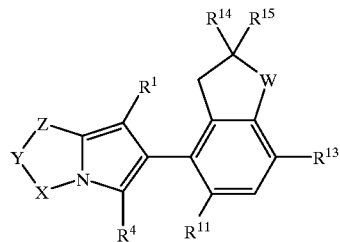

| X | Y | Z | $R^1$ | $R^4$ | $R^{11}$ | $R^{13}$ | $R^{14}$ | $R^{15}$ | W |
|---|---|---|---|---|---|---|---|---|---|
| CHMe | CH | CH$_2$CH$_2$ | Cl | Cl | F | Cl | Me | H | O |
| CH$_2$ | CH$_2$ | S | Cl | Cl | F | Cl | Me | H | O |
| CH$_2$CH$_2$ | CH$_2$ | O | Cl | Cl | F | Cl | H | H | O |
| CH$_2$ | CH$_2$ | CH$_2$CH$_2$ | Cl | Cl | F | Br | Me | H | O |
| CH$_2$ | CH$_2$ | CH$_2$CH$_2$ | Cl | Cl | F | CF$_3$ | Me | H | O |
| CH$_2$ | CH$_2$ | CH$_2$CH$_2$ | Cl | Cl | Br | Cl | Me | H | O |
| CH$_2$ | CHCF$_3$ | CH$_2$CH$_2$ | Cl | Cl | F | Cl | Me | H | O |
| CH$_2$ | CH=CH | CH$_2$ | Cl | Cl | F | Cl | Me | H | O |
| CH$_2$ | CH$_2$ | CH$_2$CH$_2$ | Cl | Cl | F | OMe | H | H | O |
| CH$_2$ | NHMe | CH$_2$CH$_2$ | Cl | Cl | F | Cl | H | H | O |
| CH$_2$ | CH$_2$ | CH$_2$CH$_2$ | Cl | Cl | H | Cl | H | H | O |

TABLE 9

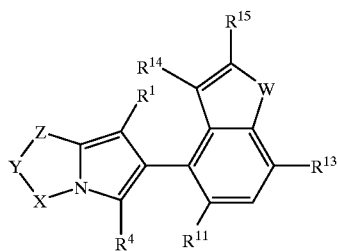

| X | Y | Z | $R^1$ | $R^4$ | $R^{11}$ | $R^{13}$ | $R^{14}$ | $R^{15}$ | W |
|---|---|---|---|---|---|---|---|---|---|
| CH$_2$ | CH$_2$ | CH$_2$CH$_2$ | Cl | Cl | F | Cl | H | Me | O |
| CH$_2$ | CH$_2$ | CH$_2$CH$_2$ | Cl | Cl | F | Cl | H | H | O |
| CH$_2$ | CH$_2$ | CH$_2$CH$_2$ | Cl | Cl | F | Cl | H | H | S |
| CH$_2$ | CH$_2$ | CH$_2$CH$_2$ | Br | Cl | F | Cl | H | H | O |
| CH$_2$ | CH$_2$ | CH$_2$CH$_2$ | Cl | Cl | F | Cl | Me | H | O |
| CH$_2$ | CH$_2$ | CH$_2$CH$_2$ | Br | Br | Cl | Cl | H | H | O |
| CH$_2$ | CH$_2$ | CH$_2$CH$_2$ | Cl | Cl | Cl | Br | H | H | O |
| CH$_2$ | CH$_2$ | CH$_2$CH$_2$ | Cl | Cl | Br | Cl | H | Me | O |
| CH$_2$ | CH$_2$ | CH$_2$CH$_2$ | CN | Cl | F | Cl | H | H | O |
| CH$_2$ | CH$_2$ | CH$_2$CH$_2$ | Cl | Cl | F | CF$_3$ | H | H | O |
| CH$_2$ | CH$_2$ | CH$_2$CH$_2$ | Cl | Cl | F | OMe | H | H | O |
| CHMe | CH$_2$ | CH$_2$CH$_2$ | Cl | Cl | F | Cl | H | H | O |
| CH$_2$ | CHMe | CH$_2$CH$_2$ | Cl | Cl | F | Cl | H | Me | O |
| CH$_2$ | CH$_2$ | S | Cl | Cl | F | Cl | H | Me | O |
| CH$_2$CH$_2$ | CH$_2$ | O | Cl | Cl | F | Cl | H | H | O |
| CH$_2$ | CH$_2$ | CH$_2$CH$_2$ | Cl | Cl | Br | Cl | H | Me | S |
| CH$_2$ | CH=CH | CH$_2$ | Cl | Cl | F | Cl | H | H | O |
| CH$_2$ | CH$_2$ | CH$_2$ | Cl | Cl | F | Cl | H | H | O |
| CH$_2$ | CH$_2$ | CH$_2$CH$_2$ | Cl | Cl | H | Cl | H | H | O |

TABLE 10

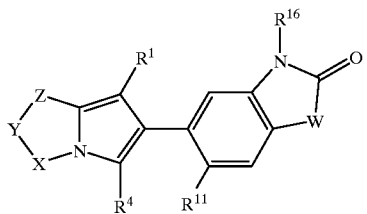

| X | Y | Z | R¹ | R⁴ | R¹¹ | R¹⁶ | W |
|---|---|---|---|---|---|---|---|
| CH₂ | CH₂ | CH₂CH₂ | Cl | Cl | F | Me | O |
| CH₂ | CH₂ | CH₂CH₂ | Cl | Cl | Cl | Et | O |
| CH₂ | CH₂ | CH₂CH₂ | Br | Br | F | n-Pr | O |
| CH₂ | CH₂ | CH₂CH₂ | Cl | Cl | F | CH₂CH=CH₂ | O |
| CH₂ | CH₂ | CH₂CH₂ | Cl | Cl | F | CH₂C≡CH | O |
| CH₂ | CH₂ | CH₂CH₂ | Cl | Cl | Br | CH₂C≡CH | O |
| CH₂ | CH₂ | CH₂CH₂ | Cl | Cl | H | CH₂C≡CH | O |
| CH₂ | CH₂ | CH₂CH₂ | CN | Br | Cl | CH₂C≡CH | O |
| CH₂ | CH₂ | CH₂CH₂ | Br | Cl | Cl | CH₂C≡CH | S |
| CH₂ | CH₂ | CH₂CH₂ | Cl | Cl | F | CH₂C≡CH | S |
| CH₂ | CH₂ | CH₂CH₂ | Cl | Cl | F | CH₂CF₃ | O |
| CH₂ | CH₂ | CH₂CH₂ | Cl | Cl | F | CH₂CH=CHCl | O |
| CHMe | CH₂ | CH₂CH₂ | Cl | Cl | F | CH₂C≡CH | O |
| CH₂ | NMe | CH₂CH₂ | Cl | Cl | F | CH₂C≡CH | O |
| CH₂ | CH₂ | CH₂CH₂ | CN | Me | F | CH₂C≡CH | O |
| CH₂ | CH₂ | S | Cl | Cl | F | CH₂C≡CH | O |
| CH₂CH₂ | CH₂ | O | Cl | Cl | F | CH₂C≡CH | O |
| CH₂ | CH₂ | CH₂ | Br | Br | F | CH₂C≡CH | O |
| CH₂ | CH₂ | CH₂CH₂ | Cl | Cl | H | CH₂C≡CH | O |
| CH₂ | CH 2 | CH₂CH₂ | Cl | Cl | F | CH₂OMe | O |

TABLE 11

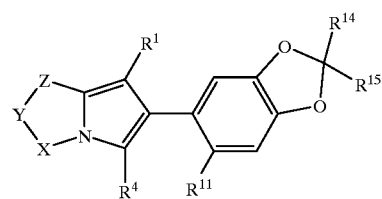

| X | Y | Z | R¹ | R⁴ | R¹¹ | R¹⁶ | R¹⁴ | R¹⁵ | W |
|---|---|---|---|---|---|---|---|---|---|
| CH₂ | CH₂ | CH₂CH₂ | Cl | Cl | F | Me | H | H | O |
| CH₂ | CH₂ | CH₂CH₂ | Cl | Cl | Cl | Et | H | H | O |
| CH₂ | CH₂ | CH₂CH₂ | Cl | Cl | F | CH₂CH=CH₂ | H | H | O |
| CH₂ | CH₂ | CH₂CH₂ | Cl | Cl | F | CH₂C≡CH | H | H | O |
| CH₂ | CH₂ | CH₂CH₂ | Cl | Cl | Cl | CH₂C≡CH | H | H | O |
| CH₂ | CH₂ | CH₂CH₂ | Cl | Cl | Br | CH₂C≡CH | H | H | O |
| CH₂ | CH₂ | CH₂CH₂ | Br | Cl | Cl | CH₂C≡CH | H | H | S |
| CH₂ | CH₂ | CH₂CH₂ | Br | Br | F | CH₂C≡CH | H | H | S |
| CH₂ | CH₂ | CH₂CH₂ | Cl | Cl | F | n-Pr | H | H | O |
| CH₂ | CH₂ | CH₂CH₂ | Cl | Cl | F | CH₂CF₃ | H | H | O |
| CH₂ | CH₂ | CH₂CH₂ | Cl | Cl | F | CH₂OMe | H | H | O |
| CH₂ | CH₂ | CH₂CH₂ | Cl | Cl | F | CHMe₂ | H | H | O |
| CH₂ | CH₂ | CH₂CH₂ | Cl | Cl | Cl | CH₂C≡CH | Me | H | O |
| CH₂ | CH₂ | CH₂CH₂ | | | Cl | CH₂C≡CH | H | H | O |
| CH₂ | CH₂ | CH₂CH₂ | | Cl | Cl | CH₂C≡CH | H | H | O |
| CH₂ | CH₂ | CH₂CH₂ | CN | CN | F | CH₂C≡CH | H | H | O |
| CH₂ | CHMe | CH₂CH₂ | Cl | Cl | Cl | CH₂C≡CH | H | H | O |
| CH₂ | CH₂ | S | Cl | Cl | F | CH₂C≡CH | H | H | O |
| CH₂CH₂ | CH₂ | O | Cl | Cl | F | CH₂C≡CH | W | H | O |
| CH₂ | CH₂ | CH₂CH₂ | Cl | Cl | F | CH₂C≡CH | Me | Me | O |
| CH₂ | CH₂ | CH₂CH₂ | Cl | Cl | H | CH₂C≡CH | H | H | O |

TABLE 12

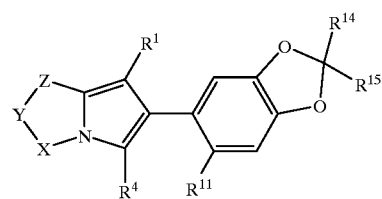

| X | Y | Z | R¹ | R⁴ | R¹¹ | R¹⁴ | R¹⁵ |
|---|---|---|---|---|---|---|---|
| CH₂ | CH₂ | CH₂CH₂ | Cl | Cl | F | H | H |
| CH₂ | CH₂ | CH₂CH₂ | Cl | Cl | Cl | H | H |
| CH₂ | CH₂ | CH₂CH₂ | Cl | Cl | F | F | F |
| CH₂ | CH₂ | CH₂CH₂ | Cl | Cl | Cl | F | F |
| CH₂ | CH₂ | CH₂CH₂ | Cl | Cl | F | Me | Me |
| CH₂ | CH₂ | CH₂CH₂ | Cl | Cl | F | Me | H |
| CH₂ | CH₂ | CH₂CH₂ | Br | Br | F | F | F |
| CH₂ | CH₂ | CH₂CH₂ | Br | Cl | Cl | F | F |
| CH₂ | CH₂ | CH₂CH₂ | Br | I | F | H | H |
| CH₂ | CH₂ | CH₂CH₂ | Cl | Cl | H | F | F |
| CH₂ | CH₂ | CH₂CH₂ | CN | Cl | H | F | F |
| CH₂ | CH₂ | CH₂CH₂ | CN | Br | H | F | F |
| CH₂ | CH₂ | S | Cl | Cl | F | F | F |
| CH₂ | CH₂ | CH₂ | Cl | Cl | F | F | F |
| CH₂ | CH₂ | CH₂CH₂ | Cl | Cl | Br | F | F |
| CH₂ | CH₂ | CH₂CH₂ | Br | Me | Cl | H | H |
| CH₂CH₂ | CH₂ | O | Cl | Cl | F | F | F |

TABLE 13

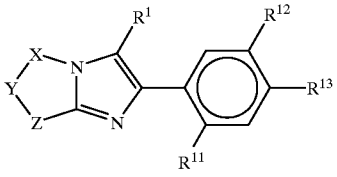

| X | Y | Z | $R^1$ | $R^{11}$ | $R^{12}$ | $R^{13}$ |
|---|---|---|---|---|---|---|
| $CH_2$ | $CH_2$ | $CH_2CH_2$ | Cl | Cl | H | Cl |
| $CH_2$ | $CH_2$ | $CH_2CH_2$ | Br | Cl | H | Cl |
| $CH_2$ | $CH_2$ | $CH_2CH_2$ | Cl | F | H | Cl |
| $CH_2$ | $CH_2$ | $CH_2CH_2$ | Br | F | H | Cl |
| $CH_2$ | $CH_2$ | $CH_2CH_2$ | F | Cl | H | Cl |
| $CH_2$ | $CH_2$ | $CH_2CH_2$ | I | F | H | Cl |
| $CH_2$ | $CH_2$ | $CH_2CH_2$ | CN | Cl | H | Cl |
| $CH_2$ | $CH_2$ | $CH_2CH_2$ | CN | F | H | Cl |
| $CH_2$ | $CH_2$ | $CH_2CH_2$ | Cl | F | H | Br |
| $CH_2$ | $CH_2$ | $CH_2CH_2$ | Br | F | H | Br |
| $CH_2$ | $CH_2$ | $CH_2CH_2$ | Cl | Cl | $SCH_2CO_2Et$ | Cl |
| $CH_2$ | $CH_2$ | $CH_2CH_2$ | Cl | F | $OCH_2OCHF_2$ | Cl |
| $CH_2$ | $CH_2$ | $CH_2CH_2$ | Cl | Cl | $OCH_2OCH_2CH=CH_2$ | Cl |
| $CH_2$ | $CH_2$ | $CH_2CH_2$ | Br | Cl | $OCH_2OMe$ | Cl |
| $CH_2$ | $CH_2$ | $CH_2CH_2$ | Cl | F | $OCH_2CH=CH_2$ | Cl |
| $CH_2$ | $CH_2$ | $CH_2CH_2$ | Cl | Cl | OMe | Cl |
| $CH_2$ | $CH_2$ | $CH_2CH_2$ | Br | F | OMe | Cl |
| $CH_2$ | $CH_2$ | $CH_2CH_2$ | Cl | Cl | $OCHMe_2$ | Cl |
| $CH_2$ | $CH_2$ | $CH_2CH_2$ | Cl | F | $OCHMe_2$ | Cl |
| $CH_2$ | $CH_2$ | $CH_2CH_2$ | Br | F | $OCHMe_2$ | Cl |
| $CH_2$ | $CH_2$ | $CH_2CH_2$ | Cl | Cl | $OCH_2CH=CH_2$ | Cl |
| $CH_2$ | $CH_2$ | $CH_2CH_2$ | Cl | Cl | $OCH_2C\equiv CH$ | Cl |
| $CH_2$ | $CH_2$ | $CH_2CH_2$ | Cl | F | $OCH_2C\equiv CH$ | Cl |
| CHF | $CH_2$ | $CH_2CH_2$ | Cl | F | $OCH_2C\equiv CH$ | Cl |
| $CH_2$ | $CH_2$ | $CH_2CHF$ | Cl | F | $OCH_2C\equiv CH$ | Cl |
| $CH_2$ | CHF | $CH_2CH_2$ | Cl | Cl | $OCH_2C\equiv CH$ | Cl |
| $CH_2$ | $CH_2$ | CHFCHF | Cl | Cl | $OCH_2C\equiv CH$ | Cl |
| $CH_2$ | $CH_2$ | $CH_2CH_2$ | Br | Cl | $OCH_2C\equiv CH$ | Cl |
| $CH_2$ | $CH_2$ | $CH_2CH_2$ | Cl | F | $OCH_2C\equiv CH$ | Cl |
| $CH_2$ | $CH_2$ | $CH_2CH_2$ | Br | F | $OCH_2C\equiv CH$ | Cl |
| $CH_2$ | $CH_2$ | $CH_2CH_2$ | Cl | Cl | $OCH_2C\equiv CH$ | Br |
| $CH_2$ | $CH_2$ | $CH_2CH_2$ | Cl | Cl | $OCH_2CO_2Me$ | Cl |
| $CH_2$ | $CH_2$ | $CH_2CH_2$ | Br | F | $OCH(Me)CO_2Me$ | Cl |
| $CH_2$ | $CH_2$ | $CH_2CH_2$ | Cl | F | $OCH_2C(O)NMe_2$ | Cl |
| $CH_2$ | $CH_2$ | $CH_2CH_2$ | Cl | F | $OCH_2C(O)NHMe$ | Cl |
| $CH_2$ | $CH_2$ | $CH_2CH_2$ | Cl | F | $OCH_2C(O)NHPh$ | Cl |
| $CH_2$ | $CH_2$ | $CH_2CH_2$ | Cl | Br | $OCH_2CH=CMe_2$ | Cl |
| $CH_2$ | $CH_2$ | $CH_2CH_2$ | Cl | F | $OCH_2CH_2Me$ | Cl |
| $CH_2$ | $CH_2$ | $CH_2CH_2$ | Cl | Cl | $OCH_2CHMe_2$ | Cl |
| $CH_2$ | $CH_2$ | $CH_2CH_2$ | Cl | Cl | $OCH_2CH_2OCHF_2$ | Cl |
| $CH_2$ | $CH_2$ | $CH_2CH_2$ | Cl | Cl | SMe | Cl |
| $CH_2$ | $CH_2$ | $CH_2CH_2$ | Cl | F | $SO_2Me$ | Cl |
| $CH_2$ | $CH_2$ | $CH_2CH_2$ | Cl | F | $OCH_2CH_2OMe$ | Cl |
| $CH_2$ | $CH_2$ | $CH_2CH_2$ | Cl | Cl | $OCH_2CF_3$ | Cl |
| $CH_2$ | $CH_2$ | $CH_2CH_2$ | Cl | Cl | $OCHF_2$ | Cl |
| $CH_2$ | $CH_2$ | $CH_2CH_2$ | Br | Cl | $OCH_2CH_2OMe$ | Cl |
| $CH_2$ | $CH_2$ | $CH_2CH_2$ | Cl | Cl | $OCH_2OCH_2C\equiv CH$ | Cl |
| $CH_2$ | $CH_2$ | $CH_2CH_2$ | Cl | Cl | $OCH_2Ph$ | Cl |

TABLE 13-continued

| X | Y | Z | $R^1$ | $R^{11}$ | $R^{12}$ | $R^{13}$ |
|---|---|---|---|---|---|---|
| $CH_2$ | $CH_2$ | $CH_2CH_2$ | Cl | F | $OCH(CF_3)_2$ | Cl |
| $CH_2$ | $CH_2$ | $CH_2CH_2$ | Cl | F | $OCH_2OEt$ | Cl |
| $CH_2$ | $CH_2$ | $CH_2CH_2$ | Cl | F | $SCH_2C{\equiv}CH$ | Cl |
| $CH_2$ | Cl | $CH_2CH_2$ | Cl | F | $SCH_2CF_3$ | Cl |
| $CH_2$ | Cl | $CH_2CH_2$ | Cl | Cl | $OCF_2CHF_2$ | Cl |
| $CH_2$ | Cl | $CH_2CH_2$ | Cl | F | $OCH_2P(O)(OMe)_2$ | Cl |
| $CH_2$ | $CH_2$ | $CH_2CH_2$ | Cl | F | $OCH_2C(O)NH_2$ | Cl |
| $CH_2$ | $CH_2$ | $CH_2CH_2$ | Cl | F | $OCH_2TMS$ | Cl |
| $CH_2$ | $CH_2$ | $CH_2CH_2$ | Cl | Cl | $CO_2Me$ | Cl |
| $CH_2$ | $CH_2$ | $CH_2CH_2$ | Cl | Cl | $C(O)NMe_2$ | Br |
| $CH_2$ | $CH_2$ | $CH_2CH_2$ | Cl | F | $CO_2Me$ | Cl |
| $CH_2$ | $CH_2$ | $CH_2CH_2$ | Cl | F | $C(O)NH_2$ | Cl |
| $CH_2$ | $CH_2$ | $CH_2CH_2$ | Cl | F | $C(O)NHPh$ | Cl |
| $CH_2$ | $CH_2$ | $CH_2CH_2$ | Cl | F | $C(O)NHMe$ | Cl |
| $CH_2$ | $CH_2$ | $CH_2CH_2$ | Cl | F | C(O)N-morpholinyl | Cl |
| $CH_2$ | $CH_2$ | $CH_2CH_2$ | Cl | F | $C(O)NHn$-Bu | Br |
| $CH_2$ | $CH_2$ | $CH_2CH_2$ | Br | F | $C(O)NHn$-Pr | Cl |
| $CH_2$ | $CH_2$ | $CH_2CH_2$ | Cl | F | $CO_2CH_2C{\equiv}CH$ | Cl |
| $CH_2$ | $CH_2$ | $CH_2CH_2$ | Cl | F | $CO_2n$-Pr | Cl |
| $CH_2$ | $CH_2$ | $CH_2CH_2$ | Br | F | $CO_2CH_2CH{=}CH_2$ | Cl |
| $CH_2$ | $CH_2$ | $CH_2CH_2$ | Cl | Cl | $CO_2N{-}CMe_2$ | Cl |
| $CH_2$ | $CH_2$ | $CH_2CH_2$ | Cl | F | $C(O)Me$ | Cl |
| $CH_2$ | $CH_2$ | $CH_2CH_2$ | Cl | F | $CO_2n$-Pr | Cl |
| $CH_2$ | $CH_2$ | $CH_2CH_2$ | Br | F | $CO_2Et$ | Br |
| $CH_2$ | $CH_2$ | $CH_2CH_2$ | Cl | Cl | $CO_2CH_2CF_3$ | Cl |
| $CH_2$ | $CH_2$ | $CH_2CH_2$ | Cl | Cl | $NHSO_2Me$ | Cl |
| $CH_2$ | $CH_2$ | $CH_2CH_2$ | Cl | F | $NHSO_2Me$ | Cl |
| $CH_2$ | $CH_2$ | $CH_2CH_2$ | Cl | F | $NHSO_2NHMe$ | Cl |
| $CH_2$ | $CH_2$ | $CH_2CH_2$ | Cl | F | $NHSO_2CF_3$ | Cl |
| $CH_2$ | $CH_2$ | $CH_2CH_2$ | Cl | F | $CF_3$ | Cl |
| $CH_2$ | $CH_2$ | $CH_2CH_2$ | Cl | F | $CH(Me)_2$ | Cl |
| $CH_2$ | $CH_2$ | $CH_2CH_2$ | Cl | F | Me | Cl |
| $CH_2$ | $CH_2$ | $CH_2CH_2$ | Cl | F | $NO_2$ | Cl |
| $CH_2$ | $CH_2$ | $CH_2CH_2$ | Cl | Br | $OCH_2C{\equiv}CH$ | Cl |
| $CH_2$ | $CH_2$ | $CH_2CH_2$ | Cl | F | $CH{=}CHCO_2Me$ | Cl |
| $CH_2$ | $CH_2$ | $CH_2CH_2$ | Br | F | CN | Cl |
| $CH_2$ | $CH_2$ | $CH_2CH_2$ | Cl | F | Cl | Cl |
| $CH_2$ | $CH_2$ | $CH_2CH_2$ | Cl | Cl | Br | Cl |
| $CH_2$ | $CH_2$ | $CH_2CH_2$ | Cl | F | $CH_2CH{=}CH_2$ | Cl |
| $CH_2$ | $CH_2$ | $CH_2CH_2$ | Cl | F | $OCH_2C{\equiv}CMe$ | Br |
| $CH_2$ | $CH_2$ | S | Cl | Cl | H | Cl |
| $CH_2$ | $CH_2$ | S | Cl | Cl | $OCH_2C{\equiv}CH$ | Cl |
| $CH_2$ | $CH_2$ | S | Cl | F | $OCH_2C{\equiv}CH$ | Cl |
| $CH_2$ | $CH_2$ | $CH_2$ | Cl | F | $OCH_2C{\equiv}CH$ | Cl |
| $CH_2$ | $CH_2$ | $CH{=}CH$ | Cl | F | $OCH_2C{\equiv}CH$ | Cl |
| $CH_2$ | $CH_2$ | $CH{=}CH$ | Cl | Cl | H | Cl |
| $CH_2$ | $CH_2$ | $CH{=}CH$ | Cl | Cl | $OCH_2C{\equiv}CH$ | Cl |
| $CH_2$ | $CH{=}CH$ | $CH_2$ | Cl | Cl | $OCH_2C{\equiv}CH$ | Cl |
| $CH_2$ | $CH{=}CH$ | $CH_2$ | Cl | F | $OCH_2C{\equiv}CH$ | Cl |
| $CH_2$ | $CH_2$ | O | Cl | F | $OCH_2C{\equiv}CH$ | Cl |
| CHMe | $CH_2$ | $CH_2CH_2$ | Br | Cl | $OCH_2C{\equiv}CH$ | Cl |
| $CH_2$ | CHMe | $CH_2CH_2$ | Cl | F | $OCH_2C{\equiv}CH$ | Cl |
| $CH_2CH_2$ | $CH_2$ | CHMe | Cl | F | $OCH_2C{\equiv}CH$ | Cl |
| NMe | $CH_2$ | $CH_2CH_2$ | Cl | F | $OCH_2C{\equiv}CH$ | Cl |
| $CH_2$ | NMe | $CH_2CH_2$ | Cl | F | $OCH_2C{\equiv}CH$ | Cl |
| CHF | $CH_2$ | $CH_2CH_2$ | Cl | F | $OCH_2C{\equiv}CH$ | Cl |
| $CHCF_3$ | $CH_2$ | $CH_2CH_2$ | Cl | F | $OCH_2C{\equiv}CH$ | Cl |
| $CH_2CH_2$ | $CH_2$ | O | Cl | F | $OCH_2C{\equiv}CH$ | Cl |
| $CH_2$ | $CH_2$ | $CH_2CH_2$ | CN | F | $OCH_2C{\equiv}CH$ | Cl |
| $CH_2$ | $CH_2$ | $CH_2CH_2$ | Cl | F | $OCH_2C{\equiv}CH$ | $CF_3$ |
| $CH_2$ | $CH_2$ | $CH_2CH_2$ | Cl | F | $OCH_2C{\equiv}CH$ | $OCHF_2$ |
| $CH_2$ | $CH_2$ | $CH_2CH_2$ | Cl | F | $OCH_2C{\equiv}CH$ | OMe |

TABLE 14

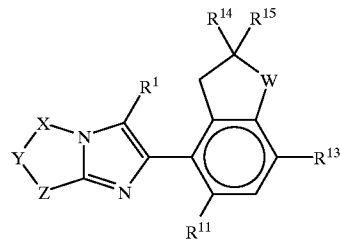

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | Cl | F | Cl | H | H | O |
| CH₂ | CH₂ | CH₂CH₂ | Cl | F | Cl | Me | H | O |
| CH₂ | CH₂ | CH₂CH₂ | Cl | F | Cl | Me | Me | S |
| CH₂ | CH₂ | CH₂CH₂ | Cl | Cl | Cl | Me | H | O |
| CH₂ | CH₂ | CH₂CH₂ | Br | Cl | Cl | Me | H | O |
| CH₂ | CH₂ | CH₂CH₂ | CN | Cl | Cl | Me | H | O |
| CH₂ | CH₂ | CH₂CH₂ | F | F | Cl | Me | H | O |
| CH₂ | CH₂ | CH₂CH₂ | Br | Cl | Cl | Me | Me | O |
| CH₂ | CH₂ | CH₂CH₂ | I | F | Cl | Me | H | O |
| CH₂ | CH₂ | CH₂CH₂ | Br | F | Cl | Me | H | O |
| CH₂ | CHMe | CH₂CH₂ | Cl | F | Cl | Me | H | O |
| CHMe | CH | CH₂CH₂ | Cl | F | Cl | Me | H | O |
| CH₂ | CH₂ | S | Cl | F | Cl | Me | H | O |
| CH₂CH₂ | CH₂ | O | Cl | F | Cl | H | H | O |
| CH₂ | CH₂ | CH₂CH₂ | Cl | F | Br | Me | H | O |
| CH₂ | CH₂ | CH₂CH₂ | Cl | F | CF₃ | Me | H | O |
| CH₂ | CH₂ | CH₂CH₂ | Cl | Br | Cl | Me | H | O |
| CH₂ | CHCF₃ | CH₂CH₂ | Cl | F | Cl | Me | H | O |
| CH₂ | CH=CH | CH₂CH₂ | Cl | F | Cl | Me | H | O |
| CH₂ | CH₂ | CH₂CH₂ | Cl | F | OMe | H | H | O |
| CH₂ | NHMe | CH₂CH₂ | Cl | F | Cl | H | H | O |
| CH₂ | CH₂ | CH₂CH₂ | Cl | F | Cl | Me | H | S |

TABLE 15

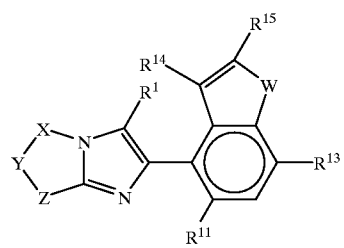

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | Cl | F | Cl | H | Me | O |
| CH₂ | CH₂ | CH₂CH₂ | Cl | F | Cl | H | H | O |
| CH₂ | CH₂ | CH₂CH₂ | Cl | F | Cl | H | H | O |
| CH₂ | CH₂ | CH₂CH₂ | Br | F | Cl | H | H | O |
| CH₂ | CH₂ | CH₂CH₂ | Cl | F | Cl | Me | H | O |
| CH₂ | CH₂ | CH₂CH₂ | F | Cl | Cl | H | H | O |
| CH₂ | CH₂ | CH₂CH₂ | Cl | Cl | Br | H | H | O |
| CH₂ | CH₂ | CH₂CH₂ | Cl | Br | Cl | H | Me | O |
| CH₂ | CH₂ | CH₂CH₂ | CN | F | Cl | H | H | O |
| CH₂ | CH₂ | CH₂CH₂ | Br | F | Cl | H | Me | O |
| CH₂ | CH₂ | CH₂CH₂ | Cl | F | CF₃ | H | H | O |
| CH₂ | CH₂ | CH₂CH₂ | Cl | F | OMe | H | H | O |
| CHMe | CH₂ | CH₂CH₂ | Cl | F | Cl | H | H | O |
| CH₂ | CHMe | CH₂CH₂ | Cl | F | Cl | H | Me | O |
| CH₂ | CH₂ | S | Cl | F | Cl | H | Me | O |
| CH₂CH₂ | CH₂ | O | Cl | F | Cl | H | H | O |
| NMe | CH₂ | CH₂CH₂ | Cl | F | Cl | H | H | O |
| CH₂ | CH₂ | CH₂CH₂ | Cl | Br | Cl | H | Me | S |
| CH₂ | CH=CH | CH₂ | Cl | F | Cl | H | H | O |
| CH₂ | CH₂ | CH₂ | Cl | F | Cl | H | H | O |

TABLE 15-continued

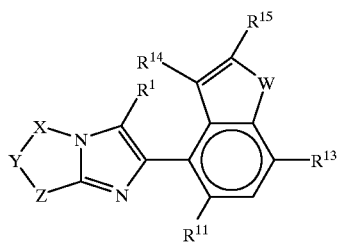

| X | Y | Z | R¹ | R¹¹ | R¹³ | R¹⁴ | R¹⁵ | W |
|---|---|---|---|---|---|---|---|---|
| CH₂ | CH₂ | CH₂CH₂ | Cl | H | Cl | H | H | O |
| CH₂ | CH₂ | CH₂CH₂ | Cl | Cl | Cl | H | H | O |
| CH₂ | CH₂ | CH₂CH₂ | Cl | Cl | Cl | H | Me | O |
| CH₂ | CH₂ | CH₂CH₂ | Br | Cl | Cl | H | Me | O |

TABLE 16

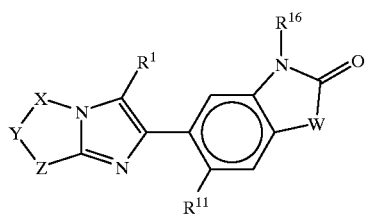

| X | Y | Z | R¹ | R¹¹ | R¹⁶ | W |
|---|---|---|---|---|---|---|
| CH₂ | CH₂ | CH₂CH₂ | Cl | F | Me | O |
| CH₂ | CH₂ | CH₂CH₂ | Cl | Cl | Et | O |
| CH₂ | CH₂ | CH₂CH₂ | Br | F | n-Pr | O |
| CH₂ | CH₂ | CH₂CH₂ | Cl | F | CH₂CH=CH₂ | O |
| CH₂ | CH₂ | CH₂CH₂ | Cl | F | CH₂C≡CH | O |
| CH₂ | CH₂ | CH₂CH₂ | Cl | Br | CH₂C≡CH | O |
| CH₂ | CH₂ | CH₂CH₂ | Cl | H | CH₂C≡CH | O |
| CH₂ | CH₂ | CH₂CH₂ | F | Cl | CH₂C≡CH | O |
| CH₂ | CH₂ | CH₂CH₂ | Br | Cl | CH₂C≡CH | S |
| CH₂ | CH₂ | CH₂CH₂ | Cl | F | CH₂C≡CH | S |
| CH₂ | CH₂ | CH₂CH₂ | Cl | F | CH₂CF₃ | O |
| CH₂ | CH₂ | CH₂CH₂ | Cl | F | CH₂CH=CHCl | O |
| CHMe | CH₂ | CH₂CH₂ | Cl | F | CH₂C≡CH | O |
| CH₂ | NMe | CH₂CH₂ | Cl | F | CH₂C≡CH | O |
| CH₂ | CH₂ | CH₂CH₂ | Br | F | CH₂C≡CH | O |
| CH₂ | CH₂ | CH₂CH₂ | CN | F | CH₂C≡CH | O |
| CH₂ | CH₂ | S | Cl | F | CH₂C≡CH | O |
| OH₂CH₂ | CH₂ | O | Cl | F | CH₂C≡CH | O |
| CH₂ | CH₂ | CH₂CH₂ | Br | F | CH₂C≡CH | O |
| CH₂ | CH₂ | CH₂CH₂ | Cl | H | CH₂C≡CH | O |
| CH₂ | CH₂ | CH₂CH₂ | Cl | F | CH₂OMe | O |
| CH₂ | CH₂ | CH₂CH₂ | Cl | Cl | CH₂C≡H | O |
| CH₂ | CH₂ | CH₂CH₂ | Br | Cl | CH₂C≡CH | O |

TABLE 17

| X | Y | Z | R¹ | R¹¹ | R¹⁶ | R¹⁴ | R¹⁵ | W |
|---|---|---|---|---|---|---|---|---|
| CH₂ | CH₂ | CH₂CH₂ | Cl | F | Me | H | H | O |
| CH₂ | CH₂ | CH₂CH₂ | Cl | Cl | Et | H | H | O |
| CH₂ | CH₂ | CH₂CH₂ | Cl | F | CH₂CH=CH₂ | H | H | O |
| CH₂ | CH₂ | CH₂CH₂ | Cl | F | CH₂C≡CH | H | H | O |
| CH₂ | CH₂ | CH₂CH₂ | Cl | Cl | CH₂C≡CH | H | H | O |
| CH₂ | CH₂ | CH₂CH₂ | Cl | Cl | CH₂C≡CH | H | H | O |
| CH₂ | CH₂ | CH₂CH₂ | Br | Cl | CH₂C≡CH | H | H | S |
| CH₂ | CH₂ | CH₂CH₂ | Br | F | CH₂C≡CH | H | H | S |
| CH₂ | CH₂ | CH₂CH₂ | Cl | F | n-Pr | H | H | O |
| CH | CH₂ | CH₂CH₂ | Cl | F | CH₂CF₃ | H | H | O |
| CH₂ | CH₂ | CH₂CH₂ | Cl | F | CH₂OMe | H | H | O |
| CH₂ | CH₂ | CH₂CH₂ | Cl | F | CHMe₂ | H | H | O |
| CH₂ | CH₂ | CH₂CH₂ | Cl | Cl | CH₂C≡CH | Me | H | O |
| CH₂ | CH₂ | CH₂CH₂ | Cl | Cl | CHF₂ | H | H | O |
| CH₂ | CH₂ | CH₂CH₂ | Cl | Cl | Me | H | H | O |
| CH₂ | CH₂ | CH₂CH₂ | CN | F | CH₂C≡CH | H | H | O |
| CH₂ | CHMe | CH₂CH₂ | Cl | Cl | CH₂C≡CH | H | H | O |
| CH₂ | CH₂ | O | Cl | F | CH₂C≡CH | H | H | O |
| CH₂CH₂ | CH₂ | O | Cl | F | CH₂C≡CH | H | H | O |
| NMe | CH₂ | CH₂CH₂ | Cl | F | CH₂C≡CH | H | H | O |
| CH₂ | CH₂ | CH₂CH₂ | Cl | F | CH₂C≡CH | Me | Me | O |
| CH₂ | CH₂ | CH₂CH₂ | Cl | H | CH₂C≡CH | H | H | O |
| CH₂ | CH₂ | CH₂CH₂ | Br | C | CH₂C≡CH | H | H | O |
| CH₂ | CH₂ | CH₂CH₂ | Br | F | CH₂C≡CH | H | H | O |

TABLE 18

| X | Y | Z | R¹ | R¹¹ | R¹⁴ | R¹⁵ |
|---|---|---|---|---|---|---|
| CH₂ | CH₂ | CH₂CH₂ | Cl | F | H | H |
| CH₂ | CH₂ | CH₂CH₂ | Cl | Cl | H | H |
| CH₂ | CH₂ | CH₂CH₂ | Cl | F | F | F |
| CH₂ | CH₂ | CH₂CH₂ | Cl | Cl | F | F |
| CH₂ | CH₂ | CH₂CH₂ | Cl | F | Me | Me |
| CH₂ | CH₂ | CH₂CH₂ | Cl | F | Me | H |
| CH₂ | CH₂ | CH₂CH₂ | Br | F | F | F |
| CH₂ | CH₂ | CH₂CH₂ | Br | Cl | F | F |
| CH₂ | CH₂ | CH₂CH₂ | Br | F | H | H |
| CH₂ | CH₂ | CH₂CH₂ | Cl | H | F | F |
| CH₂ | CH₂ | CH₂CH₂ | CN | H | F | F |
| CH₂ | CH₂ | CH₂CH₂ | Cl | Cl | Et | Et |
| CH₂ | CH₂ | S | Cl | F | F | F |
| NMe | CH₂ | CH₂CH₂ | Cl | F | F | F |
| CH₂ | CH₂ | CH₂ | Cl | F | F | F |
| CH₂ | CH₂ | CH₂CH₂ | Cl | Br | F | F |
| CH₂ | CH₂ | CH₂CH₂ | Br | Cl | H | H |
| CH₂CH₂ | CH₂ | O | Cl | F | F | F |
| CH₂ | CH₂ | CH₂CH₂ | Cl | Br | F | F |

TABLE 19

| A | B | $R^1$ | $R^{11}$ | $R^{12}$ | $R^{13}$ |
|---|---|---|---|---|---|
| Me | $CHF_2$ | Cl | F | H | Cl |
| Me | $CHF_2$ | Cl | Cl | H | Cl |
| Me | $CHF_2$ | Cl | Br | H | Cl |
| Me | $CHF_2$ | Br | Cl | H | Cl |
| Me | $CHF_2$ | Br | F | H | Cl |
| Me | $CHF_2$ | Cl | F | H | Br |
| Me | $CHF_2$ | CN | Cl | H | Cl |
| Me | $CHF_2$ | Cl | F | $OCHMe_2$ | Br |
| Me | $CHF_2$ | Br | Cl | $OCH_2CH=CH_2$ | Cl |
| Me | $CHF_2$ | Cl | Cl | $OCHF_2$ | Cl |
| Me | $CHF_2$ | Br | F | Cl | Cl |
| Me | $CHF_2$ | Br | Cl | $OCH_2CO_2Me$ | Cl |
| Me | $CHF_2$ | F | Cl | H | Cl |
| Et | $CHF_2$ | Cl | F | H | Cl |
| n-Pr | $CHF_2$ | Cl | Cl | H | Cl |
| iso-Pr | $CHF_2$ | Cl | F | H | Cl |
| Me | $CHF_2$ | Cl | F | H | $CF_3$ |
| Me | $CHF_2$ | Cl | F | H | $OCHF_2$ |
| Me | $CHF_2$ | Cl | F | H | OMe |
| Me | $CHF_2$ | Cl | F | H | SMe |
| CH=CHMe | $CHF_2$ | Cl | Cl | H | Cl |
| Me | $CHF_2$ | Cl | F | Cl | Cl |
| Me | $CHF_2$ | Cl | F | CN | Cl |
| Me | $CHF_2$ | Cl | F | $NO_2$ | Cl |
| Me | $CHF_2$ | Cl | F | Me | Cl |
| Me | $CHF_2$ | Cl | F | $CF_3$ | Cl |
| Me | $CHF_2$ | Cl | F | OMe | Cl |
| Me | $CHF_2$ | Cl | F | $OCH_2C\equiv CH$ | Cl |
| Me | $CHF_2$ | Br | F | $OCH_2C\equiv CH$ | Cl |
| Me | $CHF_2$ | Cl | Cl | $CCH_2C\equiv CH$ | Cl |
| Me | $CHF_2$ | Cl | F | $OCH_2C\equiv CH$ | Br |
| Me | $CHF_2$ | Cl | H | $OCH_2C\equiv CH$ | Cl |
| Me | $CHF_2$ | Cl | Cl | OEt | Cl |
| Me | $CHF_2$ | Cl | F | $OCHMe_2$ | Cl |
| Me | $CHF_2$ | Cl | Cl | $OCH_2CH_2Me$ | Cl |
| Me | $CHF_2$ | Br | F | $OCH_2CH=CH_2$ | Cl |
| Me | $CHF_2$ | Cl | Cl | $OCH_2CH=CH_2$ | Br |
| Me | $CHF_2$ | Cl | F | $OCH_2CO_2Me$ | Cl |
| Me | $CHF_2$ | Cl | Cl | $OCH_2C(O)NMe_2$ | Cl |
| Me | $CHF_2$ | Cl | F | $OCH_2C(O)NH_2$ | Cl |
| Me | $CHF_2$ | Cl | F | $OCH_2C(O)NHPh$ | Cl |
| Me | $CHF_2$ | Cl | Cl | $OCH(Me)CO_2Et$ | Cl |
| Me | $CHF_2$ | Cl | F | $OCH_2CH=CMe_2$ | Cl |
| Me | $CHF_2$ | Cl | F | $OCH_2OMe$ | Cl |
| Me | $CHF_2$ | Cl | F | $OCH_2OEt$ | Cl |
| Me | $CHF_2$ | Cl | Cl | $OCH_2CH_2OMe$ | Cl |
| Me | $CHF_2$ | Cl | F | SMe | Cl |
| Me | $CHF_2$ | Cl | F | $SO_2Me$ | Cl |
| Me | $CHF_2$ | Cl | F | $OCH_2CF_3$ | Cl |
| Me | $CHF_2$ | Cl | F | $SCH_2CF_3$ | Cl |
| Me | $CHF_2$ | Cl | F | $OCH_2CHF_2$ | Br |
| Me | $CHF_2$ | Cl | Cl | $OCF_2CHF_2$ | Cl |
| Me | $CHF_2$ | Cl | Cl | $SCH_2C\equiv CH$ | Cl |
| Me | $CHF_2$ | Cl | F | $OCH_2P(O)(OMe)_2$ | Cl |
| Me | $CHF_2$ | Cl | Cl | $OCH_2P(S)(OMe)_2$ | Cl |
| Me | $CHF_2$ | Cl | F | $OCH_2CH_2OCHF_2$ | Cl |
| Me | $CHF_2$ | Cl | F | $OCH_2OCH_2C\equiv CH$ | Cl |
| Me | $CHF_2$ | Cl | F | $OCH_2OCH_2CH=CH_2$ | Cl |
| Me | $CHF_2$ | Cl | F | $OCHF_2$ | Cl |
| Me | $CHF_2$ | Cl | Cl | $CO_2Me$ | Cl |
| Me | $CHF_2$ | Cl | F | $CO_2Et$ | Cl |
| Me | $CHF_2$ | Br | F | $CO_2Me$ | Cl |
| Me | $CHF_2$ | Cl | F | $CO_2CH_2CH_2Me$ | Cl |
| Me | $CHF_2$ | Cl | F | $C(O)NMe_2$ | Cl |
| Me | $CHF_2$ | Cl | Cl | $C(O)NHMe$ | Cl |
| Me | $CRF_2$ | Cl | F | $C(O)NHPh$ | Cl |
| Me | $CHF_2$ | Cl | F | $CO_2CH_2C\equiv CH$ | Cl |

TABLE 19-continued

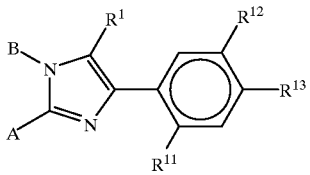

| A | B | $R^1$ | $R^{11}$ | $R^{12}$ | $R^{13}$ |
|---|---|---|---|---|---|
| Me | $CHF_2$ | Cl | F | $CO_2CH_2CH=CH_2$ | Cl |
| Me | $CHF_2$ | Cl | Cl | $C(O)NH(CH_2)_3Me$ | Cl |
| Me | $CHF_2$ | Cl | F | $CO_2N=CMe_2$ | Cl |
| Me | $CHF_2$ | Cl | F | $C(O)Me$ | Cl |
| Me | $CHF_2$ | Cl | F | $NHSO_2Me$ | Cl |
| Me | $CHF_2$ | Cl | F | $NHSO_2NHMe$ | Cl |
| Me | $CHF_2$ | Cl | Cl | $NHSO_2CF_3$ | Cl |
| Me | $CHF_2$ | Cl | F | $CH=CHCO_2Me$ | Cl |
| Me | $CHF_2$ | Br | F | $OCH_2CO_2Me$ | Cl |
| Me | $CH_2CF_3$ | Cl | F | H | Cl |
| Me | $CH_2CF_3$ | Cl | Cl | H | Br |
| Me | $CH_2CF_3$ | Br | F | H | Cl |
| Me | $CH_2CF_3$ | Br | Cl | H | Cl |
| Me | $CH_2CF_3$ | Cl | Br | H | Cl |
| Me | $CH_2CF_3$ | Cl | F | H | Br |
| Me | $CH_2CF_3$ | Cl | Cl | H | Br |
| Me | $CH_2CF_3$ | Cl | Cl | $OCH_2C\equiv CH$ | Cl |
| Me | $CH_2CF_3$ | Cl | F | $OCH_2C\equiv CH$ | Cl |
| Me | $CH_2CF_3$ | Cl | Br | $OCH_2C\equiv CH$ | Br |
| Me | $CH_2CF_3$ | Cl | F | $OCH_2CH=CH_2$ | Cl |
| Me | $CH_2CF_3$ | Cl | Cl | $OCH_2CH=CH_2$ | Cl |
| Me | $CH_2CF_3$ | Cl | Cl | $CO_2Me$ | Cl |
| Me | $CH_2CF_3$ | Cl | F | $CO_2Et$ | Cl |
| Me | $CH_2CF_3$ | Cl | F | $OCH_2CO_2Me$ | Cl |
| Me | $CH_2CF_3$ | Cl | Cl | $OCH_2CO_2Et$ | Cl |
| Me | $CH_2CF_3$ | Cl | Cl | $OCH_2C(O)NMe_2$ | Cl |
| Me | $CH_2CF_3$ | Cl | F | $OCH_2C(O)NHMe$ | Cl |
| Me | $CH_2CF_3$ | Cl | Cl | $NHSO_2Me$ | Cl |
| Me | $CH_2CF_3$ | Cl | F | $NHSO_2NHMe$ | Cl |
| Me | $CH_2CF_3$ | Cl | Cl | $C(O)NHPh$ | Cl |
| Et | $CHF_2$ | Cl | F | $OCH_2C\equiv CH$ | Cl |
| Et | $CHF_2$ | Cl | Cl | $OCH_2C\equiv CH$ | Cl |
| Et | $CHF_2$ | Cl | F | $CO_2Me$ | Cl |
| n-Pr | $CHF_2$ | Cl | F | $OCH_2C\equiv CH$ | Cl |
| Et | $CHF_2$ | Cl | F | $OCHMe_2$ | Cl |
| Et | $CH_2CF_3$ | Cl | F | $OCH_2C\equiv CH$ | Cl |
| $CHMe_2$ | $CH_2CF_3$ | Cl | F | $OCH_2C\equiv CH$ | Cl |
| n-Bu | $CH_2CF_3$ | Cl | F | $OCH_2C\equiv CH$ | Cl |
| Et | $CH_2CF_3$ | Cl | H | $OCH_2C\equiv CH$ | Br |
| OMe | $CHF_2$ | Cl | Cl | $OCH_2C\equiv CH$ | Cl |
| $OCH_2Me_2$ | $CHF_2$ | Cl | F | $OCH_2C\equiv CH$ | Cl |
| Cl | $CHF_2$ | Cl | F | $OCH_2C\equiv CH$ | Cl |
| OEt | $CH_2CF_3$ | Cl | F | $OCH_2C\equiv CH$ | Cl |
| Me | $CH_2CH=CH_2$ | Cl | F | H | Cl |
| Me | $CH_2C\equiv CH$ | Cl | F | H | Cl |
| Me | $CH_2CH=CH_2$ | Cl | F | $OCH_2C\equiv CH$ | Cl |
| Me | $CH_2CH=CH_2$ | Cl | Cl | $OCH_2C\equiv CH$ | Cl |
| Et | $CH_2CH=CH_2$ | Br | Cl | $CO_2Me$ | Cl |
| Et | $CH_2CH=CH_2$ | Cl | F | $OCH_2CO_2Me$ | Cl |
| n-Pr | $CH_2CH=CH_2$ | Cl | Br | $OCH_2CO_2Et$ | Cl |
| iso-Pr | $CH_2C\equiv CH$ | Cl | F | $OCH_2C\equiv CH$ | Cl |
| Me | $CH_2CH=CH_2$ | Cl | F | OEt | Cl |
| OMe | $CH_2CH=CH_2$ | Cl | Cl | $OCHMe_2$ | Cl |
| Me | Me | Cl | Cl | $OCH_2C\equiv CH$ | Cl |
| Me | Me | Cl | Cl | H | Cl |
| Me | Me | Cl | F | H | Cl |
| Me | Me | Br | F | H | Cl |
| Me | Me | Cl | F | $OCH_2C\equiv CH$ | Cl |
| Et | Me | Cl | F | $OCH_2C\equiv CH$ | Cl |
| Me | $CHMe_2$ | Cl | F | $OCH_2C\equiv CH$ | Cl |
| Me | n-Pr | Cl | Br | $OCH_2C\equiv CH$ | Br |
| Me | n-Pr | Br | Cl | $OCHMe_2$ | Cl |
| Me | $CHMe_2$ | Cl | F | $OCH_2CO_2Me$ | Cl |
| SMe | $CHF_2$ | Cl | F | $OCH_2C\equiv CH$ | Cl |
| SMe | $CH_2CF_3$ | Cl | Cl | H | Cl |
| SMe | $CHF_2$ | Cl | Cl | H | Cl |
| $CF_3$ | Me | Cl | F | H | Cl |

TABLE 19-continued

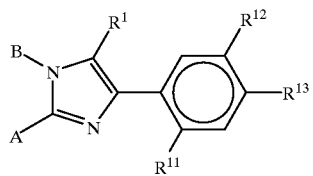

| A | B | R¹ | R¹¹ | R¹² | R¹³ |
|---|---|---|---|---|---|
| CF₃ | Me | Cl | Cl | OCH₂C≡CH | Cl |
| CF₃ | Et | Br | F | OCH₂C≡CH | Cl |
| CF₃ | Me | Cl | Cl | H | Cl |
| OMe | Me | Cl | Cl | H | Cl |
| OEt | Me | Cl | F | H | Cl |
| OMe | Me | Cl | Cl | OCH₂C≡CH | Cl |
| OEt | Me | Cl | F | OCH₂C≡CH | Cl |
| Cl | Me | Cl | F | H | Cl |
| Cl | Me | Cl | Cl | OCH₂C≡CH | Cl |
| Cl | Me | Cl | F | OCH₂C≡CH | Cl |
| SMe | Et | Cl | Cl | H | Cl |
| SMe | Et | Cl | F | OCH₂C≡CH | Cl |
| SMe | Et | Cl | F | H | Cl |
| t-Bu | CHF₂ | Cl | F | H | Cl |
| t-Bu | CH₂CF₃ | Cl | F | H | Cl |
| t-Bu | CHF₂ | Cl | F | OCHMe₂ | Cl |
| t-Bu | CHF₂ | Cl | F | OCH₂C≡CH | Cl |
| t-Bu | CHF₂ | Cl | Cl | OCH₂C≡CH | Cl |
| OCHF₂ | Me | Cl | Cl | H | Cl |
| OCHF₂ | Me | Cl | F | OCH₂C≡CH | Cl |
| OCH₂CF₃ | Me | Cl | Cl | OCH₂C≡CH | Cl |
| Me | CF₂CHF₂ | Cl | Cl | OCH₂C≡CH | Cl |
| Me | CF₂CHF₂ | Br | Cl | OCH₂C≡CH | Cl |
| Me | CF₂CHF₂ | Cl | F | OCH₂C≡CH | Cl |
| Me | CF₂CHF₂ | Cl | F | OCHMe₂ | Cl |
| Me | CH₂CH₂Cl | Cl | F | OCH₂C≡CH | Cl |

TABLE 20

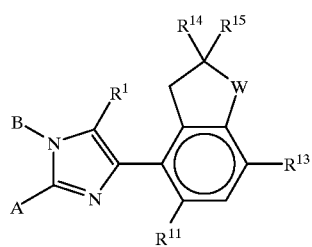

| A | B | R¹ | R¹¹ | R¹³ | R¹⁴ | R¹⁵ | W |
|---|---|---|---|---|---|---|---|
| Me | CHF₂ | Cl | F | Cl | H | H | O |
| Me | CHF₂ | Cl | Cl | Cl | H | H | O |
| Me | CHF₂ | Cl | F | Cl | Me | H | O |
| Me | CHF₂ | Cl | F | Cl | Me | Me | O |
| Me | CH₂CF₃ | Cl | F | Cl | Me | H | O |
| Me | CH₂CF₃ | Br | F | Cl | Me | H | O |
| Et | CH₂CF₃ | Cl | F | Cl | H | H | S |
| Me | CH₂CF₃ | Cl | Br | Br | H | H | O |
| Me | CH₂CH=CH₂ | Cl | F | Cl | Me | H | O |
| Me | CH₂C≡CH | Cl | F | Cl | Me | H | O |
| Me | CHMe₂ | Cl | Cl | Cl | H | H | O |
| Et | Et | Cl | F | Cl | Me | H | O |
| CF₃ | Me | Cl | F | Cl | Me | H | O |
| OMe | Me | Cl | F | Cl | Me | H | O |

TABLE 20-continued

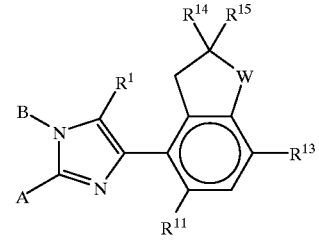

| A | B | R¹ | R¹¹ | R¹³ | R¹⁴ | R¹⁵ | W |
|---|---|---|---|---|---|---|---|
| OCHMe₂ | Me | Br | Cl | Cl | H | H | O |
| SMe | Et | Cl | Cl | Cl | Me | H | O |
| SEt | Me | Cl | F | Cl | Me | H | O |
| OMe | CHMe₂ | Br | Cl | Cl | Me | Me | O |
| Cl | Et | Cl | Cl | Cl | H | H | O |
| t-Bu | CHF₂ | Cl | Cl | Cl | Me | H | O |
| t-Bu | CH₂CF₃ | Cl | F | Cl | Me | H | O |
| Me | CF₂CHF₂ | Cl | F | Cl | H | H | O |
| Me | CH₂CH₂Cl | Cl | Cl | Cl | H | H | O |

TABLE 21

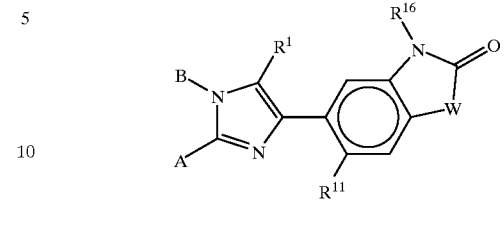

| A | B | R¹ | R¹¹ | R¹³ | R¹⁴ | R¹⁵ | W |
|---|---|---|---|---|---|---|---|
| Me | CHF$_2$ | Cl | F | Cl | H | H | O |
| Me | CHF$_2$ | Cl | Cl | Cl | H | H | O |
| Me | CHF$_2$ | Cl | Cl | Cl | Me | H | O |
| Me | CHF$_2$ | Cl | F | Cl | Me | Me | O |
| Me | CHF$_2$ | Cl | F | Cl | H | H | S |
| Me | CHF$_2$ | Br | F | Cl | H | Me | O |
| Me | CH$_2$CF$_3$ | Cl | F | Cl | H | Me | O |
| Et | CH$_2$CF$_3$ | Cl | Cl | Cl | H | H | O |
| OMe | CH$_2$CF$_3$ | Cl | F | Cl | H | Me | O |
| OCHMe$_2$ | CH$_2$CF$_3$ | Cl | Cl | Cl | H | H | O |
| Me | CH$_2$CH=CH$_2$ | Cl | F | Cl | H | H | O |
| Me | CH$_2$C≡CH | Cl | F | Cl | H | Me | O |
| Et | Et | Cl | Cl | Cl | H | H | O |
| Et | CHMe$_2$ | Cl | F | Cl | H | Me | O |
| CF$_3$ | Me | Cl | F | Cl | H | Me | O |
| OCH$_2$CF$_3$ | Me | Cl | F | Cl | H | H | O |
| Cl | Et | Cl | F | Cl | H | Me | O |
| OCHMe$_2$ | Me | Cl | F | Cl | H | Me | O |
| SMe | Et | Cl | Cl | Cl | H | H | O |
| t-Bu | CHF$_2$ | Cl | F | Cl | H | Me | O |
| Me | CF$_2$CHF$_2$ | Cl | Cl | Cl | H | H | O |
| Et | CF$_2$CHF$_2$ | Cl | F | Cl | H | H | O |
| Me | CH$_2$CH$_2$Cl | Cl | F | Cl | H | H | O |

TABLE 22

| A | B | R¹ | R¹¹ | R¹⁶ | W |
|---|---|---|---|---|---|
| Me | CHF$_2$ | Cl | F | Me | O |
| Me | CHF$_2$ | Cl | Cl | Et | O |
| Me | CHF$_2$ | Cl | F | CH$_2$CH=CH$_2$ | O |
| Et | CHF$_2$ | Cl | Cl | CH$_2$C≡CH | O |
| CHMe$_2$ | CHF$_2$ | Cl | Cl | CH$_2$C≡CH | O |
| Me | CHF$_2$ | Cl | Cl | CH$_2$C≡CH | S |
| Et | CHF$_2$ | Br | F | CH$_2$C≡CH | O |
| n-Pr | CHF$_2$ | Cl | Cl | CH$_2$CF$_3$ | O |
| Me | CH$_2$CF$_3$ | Cl | F | CH$_2$C≡CH | O |
| CHMe$_2$ | CH$_2$CF$_3$ | Cl | F | CH$_2$C≡CH | O |
| Me | CH$_2$CF$_3$ | Cl | Cl | n-Pr | O |
| Me | CH$_2$CH=CH$_2$ | Cl | F | CH$_2$C≡CH | O |
| Me | CH$_2$C≡CH | Cl | Cl | CH$_2$C≡CH | O |
| Et | Et | Cl | Cl | Me | O |
| OCH$_2$CF$_3$ | Me | Cl | Cl | CH$_2$C≡CH | O |
| CF$_3$ | Me | Cl | Cl | CH$_2$C≡CH | O |
| OMe | Me | Cl | F | CH$_2$C≡CH | O |
| OCHMe$_2$ | Me | Cl | F | CH$_2$C≡CH | O |
| SMe | Et | Cl | F | CH$_2$C≡CH | O |
| SMe | CHF$_2$ | Cl | F | CH$_2$OMe | O |
| t-Bu | CHF$_2$ | Cl | F | CH$_2$C≡CH | O |
| t-Bu | CHF$_2$ | Cl | Cl | CH$_2$C≡CH | O |
| Me | CF$_2$CHF$_2$ | Cl | Cl | CH$_2$C≡CH | O |
| Me | CF$_2$CHF$_2$ | Cl | F | Me | O |

TABLE 23

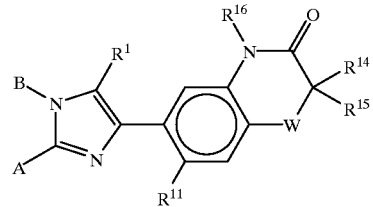

| A | B | R¹ | R¹¹ | R¹⁴ | R¹⁵ | R¹⁶ | W |
|---|---|---|---|---|---|---|---|
| Me | CHF$_2$ | Cl | F | H | H | Me | O |
| Me | CHF$_2$ | Cl | Cl | H | H | n-Pr | O |
| Me | CHF$_2$ | Cl | F | H | H | CH$_2$C≡CH | O |
| Et | CHF$_2$ | Cl | Cl | H | H | CH$_2$C≡CH | S |
| CHMe$_2$ | CHF$_2$ | Cl | F | H | H | CH$_2$C≡CH | O |
| Me | CHF$_2$ | Cl | F | H | H | CH$_2$CH=CH$_2$ | O |

TABLE 23-continued

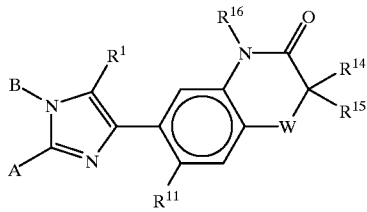

| A | B | R¹ | R¹¹ | R¹⁴ | R¹⁵ | R¹⁶ | W |
|---|---|---|---|---|---|---|---|
| Me | CHF₂ | Br | Cl | H | H | CH₂C≡CH | O |
| Me | CH₂CF₃ | Cl | F | H | H | CH₂C≡CH | O |
| Me | CH₂CF₃ | Cl | F | Me | Me | CH₂C≡CH | O |
| t-Bu | CH₂CF₃ | Cl | F | H | H | CH₂C≡CH | O |
| t-Bu | CHF₂ | Cl | F | H | H | CH₂C≡CH | O |
| Me | CH₂CH=CH | Me | Cl | F | H | CH₂C≡CH | O |
| Me | CH₂C≡CH | Cl | Cl | H | H | Et | O |
| Et | Et | Cl | Cl | H | H | CH₂C≡CH | O |
| CF₃ | Me | Cl | F | H | H | CH₂C≡CH | O |
| OCH₂CF₃ | Me | Cl | Cl | H | H | CH₂CH=CH₂ | O |
| OMe | Et | Cl | F | H | H | CH₂C≡CH | O |
| SMe | Me | Cl | F | Me | H | CH₂C≡CH | O |
| CHMe₂ | CH₂CF₃ | Cl | Cl | Me | H | CH₂C≡CH | O |
| Et | CHF₂ | Br | F | H | H | CH₂OMe | O |
| OCHMe₂ | Me | Cl | F | H | H | CH₂C≡CH | O |
| Me | CF₂CHF₂ | Cl | Cl | H | H | Me | O |
| Me | CH₂CH₂Cl | Cl | Cl | H | H | Et | O |

TABLE 24

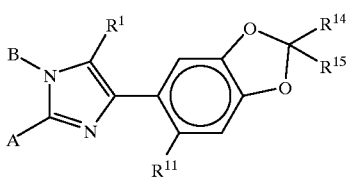

| A | B | R¹ | R¹¹ | R¹⁴ | R¹⁵ |
|---|---|---|---|---|---|
| Me | CHF₂ | Cl | Cl | H | H |
| Me | CHF₂ | Cl | F | H | H |
| Me | CHF₂ | Cl | F | F | F |
| Me | CHF₂ | Cl | Cl | F | F |
| Me | CH₂CF₃ | Cl | Cl | F | F |
| Me | CH₂CF₃ | Cl | F | H | H |
| Me | CH₂CF₃ | Br | Cl | H | H |
| Me | CH₂CF₃ | Cl | Br | F | F |
| Me | CH₂CH=CH₂ | Cl | Cl | F | F |
| Me | CH₂C≡CH | Cl | F | F | F |
| Et | Et | Cl | Cl | H | H |
| Et | OMe | Br | Cl | F | F |
| OCHMe₂ | Me | Cl | Cl | H | H |
| Me | CHF₂ | Cl | Cl | Me | Me |
| SMe | Et | Cl | F | H | H |
| t-Bu | CHF₂ | Cl | F | F | F |
| t-Bu | CHF₂ | Cl | Cl | F | F |
| t-Bu | CH₂CF₃ | Cl | Cl | H | H |
| n-Pr | Me | Cl | F | F | F |
| Et | CHF₂ | Cl | H | F | F |
| Me | CF₂CHF₂ | Cl | F | F | F |
| Et | CF₂CHF₂ | Cl | F | H | H |
| Me | CH₂CH₂Cl | Cl | F | F | F |

Formulation

Compounds of this invention will generally be used in formulation with an agriculturally suitable carrier comprising a liquid or solid diluent or an organic solvent. Use formulations include dusts, granules, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

|  | Weight Percent | | |
|---|---|---|---|
|  | Active Ingredient | Diluent | Surfactant |
| Wettable Powders | 25–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, N.J. Typical liquid diluents and solvents are described in Marsden, *Solvents Guide,* 2nd Ed., Interscience, New York, 1950. *McCutcheon's Detergents and Emulsifiers Annual,* Allured Publ. Corp., Ridgewood, N.J., as well as Sisely and Wood, *Encyclopedia of Surface Active Agents,* Chemical Publ. Co., Inc., New York, 1964, list surfactants and recommended uses. All formulations can contain minor amounts of additives to reduce foam, caking, corrosion, microbiological growth, etc.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations,* Washington, D.C., 1988, pp 251–259. Suspensions are prepared by wet-milling; see, for example, U.S. Pat. No. 3,060,084. Granules and pellets can be made by spraying the active material upon preformed granular a carriers or by agglomeration techniques. See Browning, "Agglomeration", *Chemical Engineering,* Dec. 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can also be prepared as taught in DE 3,246,493.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science,* John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are worked up in conventional ways. Compound numbers refer to compounds in Index Tables A and B.

Example A

| High Strength Concentrate | |
|---|---|
| Compound 1 | 98.5% |
| silica aerogel | 0.5% |
| synthetic amorphous fine silica | 1.0% |

Example B

| Wettable Powder | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 1 | 10.0% |
| attapulgite granules (low volatile matter, 0.71/0.30 mm; U.S.S. No. 25–50 sieves) | 90.0% |

Example D

| Extruded Pellet | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Utility

The compounds of the present invention are active postemergence and preemergence herbicides. Several compounds of this invention are useful for the control of selected grass and broadleaf weeds with tolerance to important agronomic crops such as, but not limited to, rice (*oryza sativa*), soybean (*Glycine max*), wheat (*Tritium aestivum*) and to plantation crops.

Alternatively, compounds of this invention can be used in areas where complete control of all vegetation is desired, such as around fuel storage tanks, industrial storage areas, oil well sites, drive-in theaters, around billboards, highways and railroad structures and in fence rows.

In general, effective application rates for the compounds of this invention are 10 to 5000 g/ha with a preferred rate range of 20 to 2000 g/ha. Effective rates of application for this invention are determined by a number of factors. These factors include: formulation selected, method of application, amount and type of vegetation present, growing conditions, etc. One skilled in the art can select the effective rates for a given situation.

The compounds of this invention may be used alone or in combination with other commercial herbicides, insecticides or fungicides. The following list exemplifies some of the herbicides suitable for use in mixtures. A combination of a compound from this invention with one or more of the following herbicides may be particularly useful for weed control in plantation crops.

Compounds of this invention can be used alone or in combination with other commercial herbicides, insecticides or fungicides. A mixture of one or more of the following herbicides with a compound of this invention may be particularly useful for weed control. Examples of other herbicides with which compounds of this invention can be formulated are: acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bromoxynil heptanoate, bromoxynil octanoate, butachlor, buthidazole, butralin, butylate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodim, clomazone, cloproxydim, clopyralid, calcium salt of methylarsonic acid, cyanazine, cycloate, cycluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumesulam, flumipropyn, fluometuron, fluorochloridone, fluorodifen, fluoroglycofen, flupoxam, fluridone, fluroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)-acetic acid, S,S'-dimethyl-2-(difluoromethyl)-4-(2-methylpropyl)-6-(trifluoromethyl)-3,5-pyridinedicarbothioate, mecoprop, mefenacet, mefluidide, methalpropalin, methabenzthiazuron, metham, methazole, methoxuron, metolachlor, metribuzin, 1,2-dihydropyridazine-3,6-dione, molinate, monolinuron, monuron, monuron salt and trichloroacetic acid, monosodium salt of methylarsonic acid, napropamide, naptalam, neburon, nicosulfuron, nitralin, nitrofen, nitrofluorfen, norea, norflurazon, oryzalin, oxadiazon, oxyfluorfen, paraquat, pebulate, pendimethalin, perfluidone, phenmedipham, picloram, 5-[2-chloro-4-(trifluoromethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlorac, quizalofop ethyl, rimsulfuron, secbumeton, sethoxydim, siduron, simazine, 1-(a,a-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, triallate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

In certain instances, combinations with other herbicides having a similiar spectrum of control but a different mode of action will be particularly advantageous for resistance management.

Selective herbicidal properties of the subject compounds were discovered in greenhouse tests as described below.

INDEX TABLE A

| Compound | $R^1$ | $R^{11}$ | $R^{12}$ | $R^{13}$ | m.p. ° C. |
|---|---|---|---|---|---|
| 2 | Br | Cl | H | Cl | 112–113 |
| 3 | Cl | Cl | H | Cl | 99–101 |
| 5 | Cl | F | H | Cl | 68–70 |
| 6 | Br | F | H | Cl | 86–88 |
| 7 | Br | F | H | F | 89–90 |
| 8 | Cl | Cl | $NO_2$ | Cl | 111–112 |
| 9 | Cl | F | OMe | Cl | 132–134 |
| 10 | Cl | F | $OCH_2C{\equiv}CH$ | Cl | 142–145 |
| 11 | F | Cl | $OCH_2CH_2CH_3$ | Cl | 48–50 |

| Compound | | | | | m.p. ° C. |
|---|---|---|---|---|---|
| 1 | | | | | 104–105 |
| 4 | | | | | oil |

INDEX TABLE B

| CMPD. | $R^1$ | $R^{11}$ | $R^{13}$ | $R^{12}$ | m.p. ° C. or Phys. Prop. |
|---|---|---|---|---|---|
| 12 | Cl | F | Br | H | 74–79 |
| 13 | Cl | F | Cl | H | 74–77 |
| 14 | Cl | F | Cl | OH | 177–178 |
| 15 | Br | Cl | Cl | H | 97–98 |
| 16 | Cl | F | Cl | $OCH_2C{\equiv}mCH$ | 123–124 |
| 17 | Cl | F | Cl | $OCH_2CH_3$ | 92–93 |
| 18 | Cl | F | Cl | $OCH_2CH{=}CH_2$ | 91–92 |
| 20 | Cl | F | Cl | $O(CH_2)_2OCH_3$ | <50 |
| 21 | Cl | F | Cl | $OCH(CH_3)_2$ | oil[a] |
| 22 | Cl | F | Cl | $OCH_2Ph$ | 108–109 |
| 23 | Cl | F | Cl | $O(CH_2)_2CH_3$ | oil[b] |
| 24 | Cl | F | Cl | O-cyclopentyl | oil[c] |
| 25 | Cl | F | Cl | $OSO_2CH_2CH_3$ | oil[d] |
| 26 | Br | F | Cl | $OCH_2C{\equiv}CH$ | 142–144 |
| 28 | Cl | F | Cl | $OCH(CH_3)CO_2CH_3$ | oil[e] |
| 29 | Cl | F | Cl | $OCH_3$ | 114–115 |
| 30 | Cl | F | Cl | $OCH_2CH(CH_3)_2$ | oil[f] |
| 35 | Cl | Cl | Cl | H | oil[g] |
| 36 | Cl | F | Cl | $OCH(CH_3)C{\equiv}CH$ | 116–120 |
| 37 | Br | F | Cl | $OCH_2CH{=}CH_2$ | 111–112 |
| 38 | Br | F | Cl | $OCH(CH_3)_2$ | oil[h] |
| 39 | Cl | F | Cl | $OCH_2CO_2CH(CH_3)_2$ | 102–104 |
| 40 | Cl | F | Cl | $OCH_2C(Cl){=}CH_2$ | 109–110 |
| 42 | Cl | F | Cl | $OCH_2CO_2CH_2CH_3$ | 82–84 |
| 43 | Cl | F | Cl | $CO_2CH_3$ | 101–105 |
| 44 | Cl | F | Cl | $CO_2CH(CH_3)_2$ | oil[i] |
| 45 | Cl | F | Cl | $COCH_3$ | 108–109 |
| 46 | Cl | F | Cl | $C_6H_5$ | solid[j] |
| 47 | Cl | F | Cl | $OCOCH_2CH_3$ | oil[k] |
| 48 | Cl | F | Cl | $OCH(CH_3)CH_2CH_3$ | oil[l] |
| 49 | Cl | F | Cl | $OCH_2CH_2Cl$ | oil[m] |
| 52 | Br | F | Cl | H | 84–85 |
| 58 | Cl | F | Cl | $OCH_2OCH_3$ | oil[n] |
| 59 | Cl | F | Cl | $OCH_2OCH_2CH_3$ | 79–81 |
| 60 | Cl | F | Cl | $OCH(CH_3)CN$ | oil[o] |
| 61 | Cl | F | Cl | $OCH_2CO_2CH_2C{\equiv}CH$ | 146–148 |
| 62 | Cl | F | Cl | $OCH_2CO_2CH_2CH{=}CH_2$ | 94–95 |
| 64 | Br | F | Cl | $OCH_2CO_2CH(CH_3)_2$ | 94–95 |
| 65 | Br | F | Cl | $OCH_2OCH_3$ | oil[p] |
| 66 | Br | F | Cl | $OCH(CH_3)C{\equiv}CH$ | oil[q] |
| 68 | Cl | Cl | Cl | OH | 150–152 |
| 69 | Cl | Cl | Cl | $OCH_2(C{-}C_3H_5)$ | oil[r] |

INDEX TABLE B-continued

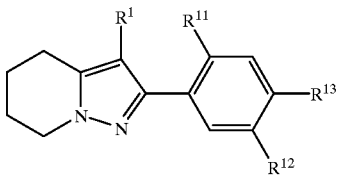

| CMPD. | R¹ | R¹¹ | R¹³ | R¹² | m.p. ° C. or Phys. Prop. |
|---|---|---|---|---|---|
| 70 | Cl | Cl | Cl | OCH(CH₃)₂ | oil(s) |
| 71 | Cl | Cl | Cl | OCH₂CH=CH₂ | oil(t) |
| 72 | Cl | Cl | Cl | OCH₂CH₂OCH₃ | oil(u) |
| 73 | Cl | Cl | Cl | OCH₂CO₂CH₂CH₃ | 83–87 |
| 74 | Cl | Cl | Cl | OCH(CH₃)C≡CH | oil(v) |
| 76 | Cl | Cl | Cl | O(CH₂)₆CH₃ | oil(w) |
| 77 | Cl | Cl | Cl | OCH₂COC(CH₃)₃ | 156–157 |
| 78 | Cl | F | Cl | CO₂CH₂CH₃ | 72–73 |
| 79 | Cl | F | Cl | OCH₂CH₂CH₂F | 80–81 |
| 81 | Br | F | Cl | OH | 179–180 |
| 82 | Cl | F | Cl | C(NOCH₃)CH₃ | 123–125 |
| 83 | Cl | F | Cl | OCH₂—epoxide | oil |
| 84 | Cl | F | Cl | OCH₂—dioxolane | oil |

(a)NMR (CDCl₃): δ 7.2 (2H), 4.5 (1H), 4.2 (2H), 2.8 (2H), 2.1 (2H), 1.9 (2H), 1.4 (6H)
(b)NMR (CDCl₃): δ 7.2 (1H), 7.1 (1H), 4.2 (2H), 4.0 (2H), 2.8 (2H), 2.1 (2H), 1.9 (2H), 1.8 (2H), 1.0 (3H)
(c)NMR (CDCl₃): δ 7.2 (1H), 7.1 (1H), 4.8 (1H), 4.2 (2H), 2.8 (2H), 2.1–1.6 (12H)
(d)NMR (CDCl₃): δ 7.7 (1H), 7.3 (1H), 4.3 (2H), 3.4 (2H), 2.8 (2H), 2.1 (2H), 1.9 (2H), 1.6 (3H)
(e)NMR (CDCl₃): δ 7.2 (1H), 7.1 (1H), 4.8 (1H), 4.2 (2H), 3.7 (3H), 2.8 (2H), 2.1 (2H), 1.9 (2H), 1.7 (3H)
(f)NMR (CDCl₃): δ 7.2 (1H), 7.1 (1H), 4.2 (2H), 3.8 (2H), 2.8 (2H), 2.3 (1H), 2.1 (2H), 1.9 (2H)
(g)NMR (CDCl₃): δ 7.5–7.1 (3H), 4.2 (2H), 2.8 (2H), 2.1 (2H), 1.9 (2H)
(h)NMR (CDCl₃): δ 7.2 (1H), 7.1 (1H), 4.5 (1H), 4.2 (2H), 2.7 (2H), 2.1 (2H), 1.9 (2H), 1.35 (6H)
(i)NMR (CDCl₃): δ 8.1 (1H), 7.2 (1H), 5.2 (1H), 4.2 (2H), 2.8 (2H), 2.1 (2H), 1.9 (2H), 1.4 (6H)
(j)NMR (CDCl₃): δ 7.6–7.2 (7H), 4.2 (2H), 2.8 (2H), 2.1 (2H), 1.9 (2H).
(k)NMR (CDCl₃): δ 7.4 (1H), 7.3 (1H), 4.2 (2H), 2.8 (2H), 2.6 (2H), 2.1 (2H), 1.9 (2H), 1.3 (3H)
(l)NMR (CDCl₃): δ 7.3–7.1 (2H), 4.3 (1H), 4.2 (2H), 2.8 (2H), 2.1 (2H), 1.9 (2H); 1.8–1.6 (2H), 1.3 (3H), 1.0 (3H)
(m)NMR (CDCl₃): δ 7.3–7.1 (2H), 4.3 (2H), 4.2 (2H), 3.8 (2H), 2.8 (2H), 2.1 (2H), 1.9 (2H)
(n)NMR (CDCl₃): δ 7.3 (1H), 7.2 (1H), 5.3 (1H), 4.2 (2H), 3.5 (3H), 2.8 (2H), 2.1 (2H), 1.9 (2H)
(o)NMR (CDCl₃): δ 7.7–7.2 (2H), 4.9 (1H), 4.2 (2H), 2.8 (2H), 2.1 (2H), 1.9 (2H), 1.8 (3H)
(p)NMR (CDCl₃): δ 7.3–7.2 (2H), 5.2 (1H), 4.2 (2H), 3.5 (3H), 2.7 (2H), 2.1 (2H), 1.9 (2H)
(q)NMR (CDCl₃): δ 7.3 (1H), 7.2; (1H), 4.9 (1H), 4.2 (2H), 2.7 (2H), 2.5 (1H), 2.1 (2H), 1.9 (2H), 1.2 (3H)
(r)NMR (CDCl₃): δ 7.5 (1H), 7.0 (1H), 4.2 (2H), 3.8 (2H), 2.8 (2H), 2.1 (2H), 1.9 (2H), 1.3 (1H), 0.6 (2H), 0.3 (2H)
(s)NMR (CDCl₃): δ 7.5 (1H), 7.0 (1H), 4.5 (1H), 4.2 (2H), 2.8 (2H), 2.1 (2H), 1.9 (2H), 1.4 (6H)
(t)NMR (CDCl₃): δ 7.5 (1H), 7.0 (1H), 6.1 (1H), 5.4 (1H), 4.6 (2H), 4.2 (2H), 2.8 (2H), 2.1 (2H), 1.9 (2H)
(u)NMR (CDCl₃): δ 7.5 (1H), 7.0 (1H), 4.2 (4H), 3.8 (2H), 3.5 (3H), 2.8 (2H), 2.1 (2H), 1.9 (2H)
(v)NMR (CDCl₃): δ 7.5 (1H), 7.0 (1H), 4.8 (1H), 4.2 (2H), 3.5 (3H), 2.8 (2H), 2.5 (1H), 2.1 (2H), 1.9 (2H), 1.7 (3H)
(w)NMR (CDCl₃): δ 7.5 (1H), 7.0 (1H), 4.2 (2H), 4.0 (2H), 2.8 (2H), 2.1 (2H), 1.9 (2H), 1.8 (2H), 1.5–0.9 (1H)

INDEX TABLE C

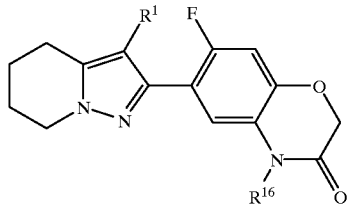

| CMPD. | R¹ | R¹⁶ | m.p. or Phys. Prop. |
|---|---|---|---|
| 31 | Cl | CH(CH₃)₂ | 153–154 |
| 32 | Cl | (CH₂)₂CH₃ | 129–130 |
| 33 | Cl | CH₂CH=CH₂ | 127–129 |
| 34 | Cl | CH₂C≡CH | 140–141 |
| 41 | Br | CH₂CH=CH₂ | 94–98 |
| 50 | Cl | CH(CH₃)C≡CH | solid(a) |
| 51 | Cl | H | 225–232 |
| 53 | Cl | CH₂CH₂OCH₃ | oil(b) |
| 54 | Cl | CH₂CH₃ | 150–151 |
| 55 | Cl | CH₂OCH₃ | 141–142 |
| 56 | Br | CH₂C≡CH | 164–165 |
| 57 | Cl | (CH₂)₃CH₃ | solid(c) |
| 63 | Br | (CH₂)₂CH₃ | 122–124 |
| 67 | Br | CH₂OCH₃ | solid(d) |
| 80 | Br | H | 201–203 |
| 85 | Cl | CH₂CH—epoxide | oil(e) |

27

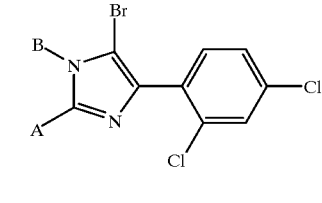

(a)NMR (CDCl₃): δ 7.9 (1H), 6.9 (1H), 6.0 (1H), 4.5 (2H), 4.2 (2H), 2.8 (2H), 2.1 (2H), 1.9 (2H), 1.6 (3H)
(b)NMR (CDCl₃): δ 7.3 (1H), 6.8 (1H), 4.6 (2H), 4.2 (2H), 4.1 (2H), 3.7 (2H), 3.4 (3H), 2.8 (2H), 2.1 (2H), 1.9 (2H)
(c)NMR (CDCl₃): δ 7.2 (1H), 6.9 (1H), 4.6 (2H), 4.3 (2H), 4.0 (2H), 2.8 (2H), 2.1 (2H), 1.9 (2H), 1.7 (2H), 1.4 (2H), 0.9 (3H)
(d)NMR (CDCl₃): δ 7.1 (1H), 6.8 (1H), 4.6 (2H), 4.2 (2H), 3.9 (2H), 2.8 (2H), 2.1 (2H), 1.9 (2H), 1.7 (2H), 1.0 (3H)
(e)NMR (CDCl₃): δ 7.4 (1H), 6.9 (1H), 4.7 (2H), 4.5 (2H), 4.2 (2H), 3.7 (1H), 3.2 (1H), 2.8 (2H), 2.7 (1H), 2.1 (2H), 1.9 (2H)

INDEX TABLE D

| CMPD. | B | A | m.p. or Phys. Prop. |
|---|---|---|---|
| 86 | CHF₂ | Me | 81–83 |
| 87 | CHF₂ | H | oil(a) |
| 88 | FCH₂CH₂ | H | oil(b) |

(a)NMR (CDCl₃): δ 7.16 (t, 1H), 7.30 (d, 1H), 7.38 (d, 1H), 7.51 (s, 1H), 8.07 (s, 1H)
(b)NMR (CDCl₃): δ 2.15–2.30 (m, 2H), 4.19 (t, 2H), 4.44 (t, TH), 4.56 (t, 1H), 7.30 (d, 1H), 7.40 (d, 1H), 7.50 (s, 1H), 7.71 (s, 1H)

INDEX TABLE E

| Structure | X | m.p. °C |
|---|---|---|
| (pyrazole fused with oxane, 2-(2-fluoro-4-chlorophenyl)) | Br | 126–127 |
|  | Cl | 125–126 |
| (pyrazole fused with oxane, 2-(2-fluoro-4-chloro-5-hydroxyphenyl)) | H | 209–211 |
| (pyrazole fused with oxane, 3-chloro substituent) | Cl | 100–101 |
|  | Br | 109–111 |
| (pyrazole fused with thiolane, 2-(2-fluoro-4-chlorophenyl)) | Br | 130–133 |
| (pyrazole fused with thiazoline) | Br | 121–125 |
| (pyrazole fused with cyclopentane) | Cl | 63–65 |
|  | Br | 84–86 |

Test A

Seeds of barnyardgrass (*Echinochchloa crus-galli*), cheatgrass (*Bromus secalinus*), cocklebur (*Xanthium pensylvanicum*), crabgrass (*Digitaria* spp.), giant foxtail (*Setaria faberii*), morningglory (*Ipomoea* spp.), sorghum (*Sorghum bicolor*), velvetleaf (*Abutilon theophrasti*), and wild oat (*Avena fatua*) were planted into a sandy loam soil and treated preemergence with test chemicals dissolved in a non-phytotoxic solvent. At the same time, these crop and weed species were also treated postemergence with test chemicals. Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (-) response means no test results.

TABLE A

| | COMPOUND | | | | COMPOUND | | |
|---|---|---|---|---|---|---|---|
| Rate (2000 g/ha) | 2 | 3 | 4 | Rate (2000 g/ha) | 2 | 3 | 4 |
| POSTEMERGENCE | | | | PREEMERGENCE | | | |
| Barnyardgrass | 9 | 9 | 4 | Barnyardgrass | 9 | 8 | 7 |
| Cheatgrass | 7 | 7 | 3 | Cheatgrass | 6 | 7 | 2 |
| Cocklebur | 10 | 10 | 8 | Cocklebur | 0 | — | 0 |
| Crabgrass | 7 | 7 | 4 | Crabgrass | 8 | 0 | 2 |
| Giant foxtail | 9 | 10 | 4 | Giant foxtail | 10 | 10 | 8 |
| Morningglory | 10 | 10 | 10 | Morningglory | 2 | 3 | 3 |
| Sorghum | 6 | 7 | 4 | Sorghum | 8 | 8 | 2 |
| Velvetleaf | 10 | 10 | 10 | Velvetleaf | 10 | 8 | 10 |
| Wild oats | 5 | 6 | 3 | Wild oats | 5 | 6 | 0 |

| | COMPOUND | | COMPOUND |
|---|---|---|---|
| Rate (1000 g/ha) | 1 | Rate (1000 g/ha) | 1 |
| POSTEMERGENCE | | PREEMERGENCE | |
| Barnyardgrass | 5 | Barnyardgrass | 2 |
| Cheatgrass | 4 | Cheatgrass | 0 |
| Cocklebur | 8 | Cocklebur | 0 |
| Crabgrass | 5 | Crabgrass | 0 |
| Giant foxtail | 4 | Giant foxtail | 5 |
| Morningglory | 10 | Morningglory | 0 |
| Sorghum | 4 | Sorghum | 0 |
| Velvetleaf | 10 | Velvetleaf | 8 |
| Wild oats | 3 | Wild oats | 0 |

Test B

Seeds of barley (*Hordeum vulgare*), barnyardgrass (*Echinochloa crus-galli*), bedstraw (*Galium aparine*), blackgrass (*Alopecurus myosuroides*), cheatgrass (*Bromus secalinus*), chickweed (*Stellaria media*), cocklebur (*Xanthium pensylvanicum*), corn (*Zea mays*), cotton (*Gossypium hirsutum*), crabgrass (*Digitaria* spp.), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), and wild oat (*Avena fatua*) and purple nutsedge. (*Cyperus rotundus*) tubers were planted and treated preemergence with test chemicals dissolved in a non-phytotoxic solvent. At the same time, these crop and weed species were also treated with postemergence applications of test chemicals. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (-) response means no test result.

TABLE B

| Rate (400 g/ha) | COMPOUND | | | | | | | |
|---|---|---|---|---|---|---|---|---|
| | 2 | 3 | 4 | 5 | 6 | 7 | 14 | 15 |
| POSTEMERGENCE | | | | | | | | |
| Barley | 2 | 2 | 3 | 2 | 5 | 3 | 6 | 6 |
| Barnyardgrass | 5 | 5 | 3 | 7 | 3 | 6 | 9 | 9 |
| Bedstraw | 3 | 8 | 3 | 8 | 8 | 6 | 10 | 8 |
| Blackgrass | 2 | 4 | 1 | 5 | 4 | 4 | 5 | 4 |
| Cheatgrass | 4 | 6 | 2 | 6 | 6 | 4 | 6 | 9 |
| Chickweed | 2 | 3 | 2 | 7 | 5 | 3 | 5 | 0 |
| Cocklebur | 8 | 7 | 6 | 8 | 7 | 8 | 9 | 7 |
| Corn | 4 | 4 | 3 | 4 | 3 | 4 | 5 | 5 |
| Cotton | 10 | 10 | 10 | 10 | 10 | 10 | 10 | 10 |
| Crabgrass | 7 | 4 | 3 | 6 | 7 | 4 | 4 | 5 |
| Giant foxtail | 6 | 6 | 4 | 5 | 5 | 5 | 5 | 6 |
| Lambsquarter | 9 | 10 | 9 | 8 | 10 | 9 | 10 | 10 |
| Morningglory | 9 | 9 | 9 | 8 | 9 | 9 | 8 | 8 |
| Nutsedge | 0 | 0 | 0 | 2 | 1 | 2 | 3 | 2 |
| Rape | 9 | 10 | 3 | 9 | 8 | 7 | 10 | 10 |
| Rice | 4 | 4 | 4 | 5 | 5 | 5 | 4 | 6 |
| Sorghum | 5 | 5 | 4 | 4 | 3 | 6 | 5 | 5 |
| Soybean | 7 | 7 | 5 | 8 | 6 | 8 | 9 | 9 |
| Sugar beet | 10 | 10 | 7 | 10 | 10 | 10 | 10 | 10 |
| Velvetleaf | 9 | 10 | 9 | 10 | 9 | 9 | 10 | 10 |
| Wheat | 2 | 3 | 1 | 5 | 5 | 5 | 5 | 6 |
| Wild buckwheat | 10 | 10 | 10 | 10 | 10 | 10 | 10 | 10 |
| Wild oat | 3 | 3 | 2 | 4 | 5 | 3 | 4 | 6 |
| PREEMERGENCE | | | | | | | | |
| Barley | 0 | 0 | 0 | 0 | 0 | 0 | 2 | 1 |
| Barnyardgrass | 2 | 4 | 0 | 3 | 3 | 2 | 3 | 8 |
| Bedstraw | 0 | 0 | 0 | 0 | 0 | 2 | 10 | 8 |
| Blackgrass | 0 | 0 | 0 | 2 | 3 | 2 | 7 | 5 |
| Cheatgrass | 0 | 2 | 0 | 2 | 3 | 0 | 5 | 9 |
| Chickweed | 0 | 0 | — | 2 | 2 | 3 | 0 | 0 |
| Cocklebur | 0 | 0 | — | 0 | 0 | 0 | 1 | 0 |
| Corn | 0 | 0 | 0 | 2 | 0 | 0 | 1 | 0 |
| Cotton | 2 | 0 | 0 | 0 | 2 | 0 | 2 | 2 |
| Crabgrass | — | 7 | 2 | 8 | 2 | 6 | 6 | 9 |
| Giant foxtail | 7 | 9 | 2 | 8 | 0 | 4 | 8 | 9 |
| Lambsquarter | — | 9 | 0 | 9 | 10 | 6 | 10 | 10 |
| Morningglory | 2 | 0 | 0 | 0 | 2 | 0 | 1 | 1 |
| Nutsedge | 0 | 0 | 0 | 10 | 0 | 2 | 0 | 0 |
| Rape | 0 | 0 | 0 | 1 | 2 | 0 | 2 | 7 |
| Rice | 0 | 1 | 0 | 2 | 0 | 0 | 1 | 0 |
| Sorghum | 0 | 0 | 0 | 0 | 0 | 0 | 0 | 3 |
| Soybean | 0 | 0 | 0 | 0 | 0 | 0 | 0 | 0 |
| Sugar beet | — | 0 | 0 | 2 | 3 | 0 | 8 | 7 |
| Velvetleaf | 4 | 2 | 3 | 4 | 10 | 5 | 9 | 9 |
| Wheat | 0 | 0 | 0 | 0 | 1 | 0 | 2 | 3 |
| Wild buckwheat | 0 | 0 | 0 | 4 | 9 | 3 | 10 | 8 |
| Wild oat | 0 | 0 | 0 | 0 | 2 | 0 | 5 | 5 |

| Rate (200 g/ha) | COMPOUND | | | | | | | | | | | | | | | | | | |
|---|---|---|---|---|---|---|---|---|---|---|---|---|---|---|---|---|---|---|---|
| | 1 | 2 | 3 | 8 | 9 | 10 | 11 | 12 | 13 | 16 | 17 | 18 | 20 | 21 | 22 | 23 | 24 | 25 | 26 | 28 |
| POSTEMERGENCE | | | | | | | | | | | | | | | | | | | | |
| Barley | 3 | 3 | 2 | 3 | 4 | 4 | 4 | 7 | 7 | 7 | 6 | 5 | 10 | 4 | 5 | 3 | 4 | 5 | 6 | 6 |
| Barnyardgrass | 3 | 3 | 3 | 6 | 6 | 3 | 6 | 9 | 10 | 10 | 9 | 7 | 9 | 9 | 5 | 9 | 6 | 5 | 7 | 10 |
| Bedstraw | 3 | 4 | 6 | 4 | 8 | 8 | 7 | 10 | 10 | 10 | 7 | 9 | 9 | 9 | 8 | 9 | 7 | 9 | 9 | 10 |
| Blackgrass | 1 | 1 | 2 | 3 | 5 | 4 | 4 | 5 | 4 | 7 | 5 | 6 | 8 | 5 | 3 | 6 | 6 | 2 | 5 | 6 |
| Cheatgrass | 2 | 3 | 4 | 3 | 4 | 5 | 3 | 8 | 10 | 10 | 7 | 1 | 8 | 8 | 4 | 8 | 5 | 3 | 7 | 9 |
| Chickweed | 2 | 2 | 3 | 1 | 9 | 9 | 6 | 5 | 5 | 10 | 7 | 7 | 10 | 7 | 7 | 9 | 9 | — | 10 | 9 |
| Cocklebur | 4 | 6 | 6 | 6 | 8 | 10 | 9 | 10 | 9 | 10 | 7 | 10 | 9 | 10 | 8 | 10 | 9 | 8 | 10 | 10 |
| Corn | 2 | 4 | 4 | 5 | 5 | 3 | 6 | 4 | 4 | 6 | 4 | 5 | 5 | 6 | 4 | 6 | 5 | 6 | 5 | 9 |
| Cotton | 8 | 9 | 10 | 9 | 10 | 10 | 10 | 10 | 10 | 10 | 10 | 10 | 10 | 10 | 10 | 10 | 10 | 10 | 10 | 10 |
| Crabgrass | 3 | 7 | 4 | 4 | 4 | 3 | 5 | 5 | 10 | 6 | 3 | — | 6 | 6 | 2 | 6 | 5 | 2 | 6 | 6 |
| Giant foxtail | 3 | 5 | 5 | 4 | 8 | 6 | 5 | 7 | 8 | 8 | 4 | 6 | 7 | 7 | 4 | 7 | 5 | 4 | 6 | 8 |
| Lambsquarter | 7 | 9 | 9 | 8 | 10 | 9 | 9 | 10 | 10 | 10 | 10 | 10 | 6 | 10 | 10 | 10 | 10 | 10 | 10 | 10 |
| Morningglory | 7 | 9 | 9 | 9 | 9 | 8 | 10 | 9 | 9 | 9 | 8 | 9 | 10 | 9 | 9 | 10 | 8 | 10 | 9 | 10 |
| Nutsedge | 0 | 0 | 0 | 2 | 3 | 2 | 5 | 2 | 4 | 3 | 1 | 2 | 4 | 3 | 2 | 3 | 4 | 8 | 4 | 5 |
| Rape | 3 | 9 | 7 | 5 | 10 | 10 | 7 | 10 | 10 | 10 | 10 | 10 | 10 | 10 | 7 | 10 | 7 | 10 | 10 | 10 |
| Rice | 3 | 4 | 4 | 3 | 4 | 5 | 6 | 5 | 7 | 6 | 5 | 6 | 5 | 6 | 5 | 6 | 5 | 9 | 6 | 7 |
| Sorghum | 4 | 5 | 5 | 5 | 4 | 3 | 8 | 5 | 7 | 6 | 5 | 6 | 6 | 6 | 5 | 6 | 6 | 5 | 6 | 9 |
| Soybean | 4 | 6 | 6 | 6 | 7 | 10 | 8 | 8 | 8 | 10 | 8 | 7 | 9 | 9 | 6 | 9 | 8 | 4 | 9 | 9 |

TABLE B-continued

| | | | | | | | | | | | | | | | | | | | |
|---|---|---|---|---|---|---|---|---|---|---|---|---|---|---|---|---|---|---|---|
| Sugar beet | 10 | 10 | 9 | 7 | 10 | 10 | 10 | 10 | 10 | 10 | 10 | 10 | 10 | 10 | 6 | 10 | 10 | 10 | 10 | 10 |
| Velvetleaf | 8 | 8 | 9 | 9 | 8 | 10 | 10 | 10 | 10 | 10 | 9 | 10 | 10 | 9 | 9 | 10 | 10 | 10 | 10 | 10 |
| Wheat | 2 | 2 | 2 | 3 | 7 | 9 | 4 | 6 | 7 | 8 | 7 | 6 | 3 | 8 | 4 | 6 | 4 | 4 | 5 | 9 |
| Wild buckwheat | 9 | 10 | 10 | 10 | 10 | 10 | 10 | 10 | 10 | 10 | 10 | 10 | 10 | 10 | 10 | 10 | 10 | 10 | 10 | 10 |
| Wild oat | 2 | 3 | 3 | 3 | 6 | 4 | 4 | 8 | 9 | 7 | 7 | 7 | 6 | 6 | 3 | 5 | 4 | 4 | 7 | 6 |

| | COMPOUND | | | | | | | | | | | | | | | | | | |
|---|---|---|---|---|---|---|---|---|---|---|---|---|---|---|---|---|---|---|---|
| Rate (200 g/ha) | 29 | 30 | 35 | 36 | 37 | 38 | 39 | 40 | 41 | 42 | 43 | 44 | 45 | 46 | 47 | 48 | 49 | 51 | 52 |
| POSTEMERGENCE | | | | | | | | | | | | | | | | | | | |
| Barley | 7 | 6 | 4 | 6 | 6 | 6 | 6 | 5 | 5 | 4 | 3 | 6 | 3 | 3 | 4 | 5 | 5 | 3 | 7 |
| Barnyardgrass | 10 | 10 | 9 | 9 | 7 | 8 | 6 | 4 | 6 | 8 | 9 | 10 | 5 | — | 9 | 8 | 7 | 9 | 9 |
| Bedstraw | 10 | 10 | 9 | 10 | 10 | 10 | 10 | — | 10 | 9 | 10 | 9 | 10 | 8 | 10 | 9 | 9 | 10 | 10 |
| Blackgrass | 6 | 5 | 4 | 7 | 7 | 7 | 4 | 3 | 5 | 3 | 8 | 9 | 3 | 3 | 8 | 6 | 6 | 6 | 5 |
| Cheatgrass | 8 | 7 | 5 | 7 | 7 | 5 | 4 | 4 | 5 | 3 | 9 | 10 | 6 | 4 | 4 | 7 | 7 | 4 | 7 |
| Chickweed | 8 | 8 | 3 | — | 10 | 10 | 10 | 10 | 10 | 8 | 10 | 10 | 7 | 3 | 9 | 8 | 9 | 10 | 7 |
| Cocklebur | 10 | 10 | 7 | 10 | 10 | 10 | 10 | 10 | 10 | 10 | 10 | 10 | 8 | — | 9 | 9 | 8 | 10 | 8 |
| Corn | 7 | 4 | 7 | 6 | 8 | 5 | 5 | 5 | 5 | 9 | 10 | 6 | 5 | — | 5 | 3 | 4 | 6 | 8 |
| Cotton | 10 | 10 | 10 | 10 | 10 | 10 | 10 | 10 | 10 | 10 | 10 | 10 | 10 | — | 10 | 10 | 10 | 10 | 10 |
| Crabgrass | 5 | 2 | 6 | 7 | 5 | 6 | 4 | 5 | 5 | 3 | — | 10 | — | — | 6 | 9 | — | 5 | 7 |
| Giant foxtail | 6 | 5 | 7 | 7 | 6 | 7 | 5 | 6 | 5 | 4 | 6 | 9 | 5 | — | 6 | 9 | 6 | 6 | 7 |
| Lambsquarter | 10 | 10 | 10 | 10 | 10 | 10 | 10 | 10 | 10 | 10 | 10 | 10 | 10 | 10 | 10 | 10 | 10 | 10 | 10 |
| Morningglory | 10 | 9 | 7 | 10 | 8 | 9 | 9 | 9 | 10 | 10 | 10 | 10 | 9 | — | 10 | 10 | 10 | 10 | 9 |
| Nutsedge | 4 | 5 | 3 | 5 | 4 | 4 | 4 | 4 | 4 | 5 | 3 | 8 | 6 | — | 8 | 5 | 6 | 3 | 5 |
| Rape | 10 | 9 | 9 | 10 | 10 | 10 | 10 | 8 | 10 | 10 | 10 | 10 | 10 | 4 | 6 | 6 | 6 | 10 | 10 |
| Rice | 7 | 5 | 6 | 6 | 6 | 6 | 6 | 5 | 7 | 6 | 9 | 9 | 6 | — | 5 | 8 | 6 | 5 | 6 |
| Sorghum | 6 | 6 | 6 | 6 | 6 | 6 | 5 | 5 | 6 | 5 | 8 | 5 | 5 | — | 4 | 6 | 5 | 6 | 7 |
| Soybean | 9 | 2 | 5 | 9 | 6 | 7 | 4 | 8 | 10 | 5 | 9 | 8 | 8 | — | 7 | 7 | 8 | 9 | 8 |
| Sugar beet | 10 | 10 | 10 | 10 | 10 | 10 | 10 | 10 | 10 | 10 | 10 | 10 | 10 | 9 | 10 | 10 | 10 | 10 | — |
| Velvetleaf | 10 | 10 | 10 | 10 | 10 | 10 | 10 | 10 | 10 | 10 | 10 | 10 | 10 | — | 9 | 10 | 10 | 10 | 10 |
| Wheat | 6 | 5 | 5 | 6 | 5 | 6 | 5 | 6 | 5 | 5 | 8 | 6 | 8 | 3 | 6 | 6 | 4 | 4 | 8 |
| Wild buckwheat | 10 | 10 | 10 | 10 | 10 | 10 | 10 | 10 | 9 | 10 | 10 | 10 | 10 | 10 | 9 | 10 | 10 | 10 | 10 |
| Wild oat | 7 | 6 | 4 | 6 | 6 | 5 | 3 | 5 | 4 | 3 | 7 | 8 | 3 | 2 | 3 | 6 | 4 | 3 | 8 |

| | COMPOUND | | | | | | | | | | | | | | | | | | |
|---|---|---|---|---|---|---|---|---|---|---|---|---|---|---|---|---|---|---|---|
| Rate (200 g/ha) | 58 | 59 | 64 | 65 | 66 | 68 | 69 | 70 | 71 | 72 | 73 | 74 | 75 | 77 | 78 | 79 | 80 | 81 | 82 |
| POSTEMERGENCE | | | | | | | | | | | | | | | | | | | |
| Barley | 8 | 4 | 3 | 6 | 6 | 3 | 4 | 4 | 4 | 5 | 3 | 4 | 1 | 3 | 5 | 4 | 4 | 3 | 3 |
| Barnyardgrass | 9 | 9 | 7 | 9 | 9 | 3 | 6 | 7 | 8 | 7 | 9 | 7 | 2 | 8 | 9 | 7 | 8 | 7 | 7 |
| Bedstraw | 9 | 8 | 10 | 10 | 10 | 9 | 7 | 7 | 9 | 9 | 8 | 9 | 4 | 5 | 9 | 7 | 10 | 10 | 9 |
| Blackgrass | 7 | 5 | 3 | 7 | 6 | 3 | 5 | 3 | 6 | 7 | 5 | 6 | 2 | 3 | 7 | 5 | 6 | 4 | 3 |
| Cheatgrass | 10 | 6 | 3 | 6 | 6 | 3 | 6 | 4 | 6 | 6 | 6 | 6 | 1 | 3 | 7 | 4 | 6 | 4 | 3 |
| Chickweed | 10 | 8 | 5 | 9 | — | 1 | 3 | 3 | 3 | 3 | 3 | 7 | 0 | 3 | 10 | 5 | 7 | 3 | 3 |
| Cocklebur | 10 | 10 | 10 | 10 | 10 | 7 | 8 | 8 | 8 | 10 | 10 | 10 | 3 | 9 | 10 | — | 10 | 10 | 8 |
| Corn | 6 | 5 | 3 | 5 | 3 | 4 | 3 | 4 | 3 | 5 | 8 | 4 | 2 | 3 | 9 | 5 | 5 | 3 | 4 |
| Cotton | 10 | 10 | 10 | 10 | 10 | 10 | 10 | 10 | 10 | 10 | 10 | 10 | 10 | 10 | 10 | 10 | 10 | 10 | 10 |
| Crabgrass | 3 | 5 | 5 | 7 | 5 | 4 | 4 | 6 | 3 | 2 | 6 | 5 | 3 | 6 | 5 | 5 | 6 | 6 | 4 |
| Giant foxtail | 6 | 7 | 3 | 8 | 6 | 4 | 5 | 5 | 6 | 5 | 5 | 5 | 2 | 6 | 6 | 6 | 7 | 8 | 5 |
| Lambsquarter | 10 | 10 | 10 | 10 | 10 | 10 | 8 | 10 | 10 | 10 | 10 | 10 | 4 | 10 | 10 | 10 | 10 | 10 | 9 |
| Morningglory | 10 | 10 | 10 | 10 | 10 | 8 | 7 | 8 | 10 | 9 | 9 | 9 | 1 | 9 | 10 | 10 | 10 | 10 | 10 |
| Nutsedge | 9 | 5 | 2 | 4 | 2 | 3 | 2 | 5 | 2 | 2 | 3 | 2 | 1 | 2 | 2 | 0 | 4 | 3 | 2 |
| Rape | 10 | 10 | 10 | 9 | 10 | 5 | 8 | 9 | 10 | 9 | 10 | 10 | 2 | 7 | 10 | 9 | 10 | 7 | 7 |
| Rice | 5 | 5 | 5 | 6 | 6 | 5 | 6 | 5 | 5 | 6 | 6 | 6 | 2 | 6 | 6 | 6 | 8 | 6 | 6 |
| Sorghum | 6 | 4 | 4 | 7 | 7 | 4 | 6 | 6 | 6 | 6 | 5 | 7 | 2 | 5 | 7 | 7 | 6 | 3 | 4 |
| Soybean | 9 | 7 | 5 | 8 | 8 | 6 | 5 | 6 | 7 | 7 | 5 | 6 | 2 | 7 | 9 | 8 | 9 | 7 | 6 |
| Sugar beet | 10 | 10 | 10 | 10 | 10 | 9 | 10 | 10 | 10 | 10 | 10 | 10 | 7 | 10 | 10 | 10 | 10 | 10 | 10 |
| Velvetleaf | 10 | 10 | 10 | 10 | 10 | 10 | 9 | 10 | 10 | 10 | 9 | 10 | 2 | 10 | 10 | 10 | 10 | 10 | 10 |
| Wheat | 8 | 6 | 2 | 5 | 5 | 4 | 6 | 5 | 6 | 5 | 4 | 5 | 2 | 5 | 7 | 6 | 4 | 4 | 4 |
| Wild buckwheat | 10 | 10 | 10 | 10 | 10 | 10 | 10 | 10 | 10 | 10 | 10 | 10 | 4 | 10 | 10 | 10 | 10 | 10 | 10 |
| Wild oat | 9 | 7 | 3 | 7 | 6 | 3 | 4 | 3 | 5 | 4 | 1 | 4 | 2 | 3 | 5 | 5 | 5 | 3 | 4 |

| | COMPOUND | | | | | | | | | | | | | | | | | | |
|---|---|---|---|---|---|---|---|---|---|---|---|---|---|---|---|---|---|---|---|
| Rate (200 g/ha) | 1 | 2 | 3 | 8 | 9 | 10 | 11 | 12 | 13 | 16 | 17 | 18 | 20 | 21 | 22 | 23 | 24 | 25 | 26 | 28 |
| PREEMERGENCE | | | | | | | | | | | | | | | | | | | | |
| Barley | 0 | 0 | 0 | 0 | 0 | 0 | 0 | 1 | 6 | 3 | 10 | 2 | 4 | 2 | 0 | 0 | 0 | 0 | 1 | 0 |
| Barnyardgrass | 0 | 0 | 0 | 0 | 0 | 0 | 0 | 7 | 9 | 9 | 4 | 6 | 7 | 7 | 5 | 6 | 4 | 6 | 7 | 1 |
| Bedstraw | 0 | 3 | 0 | 0 | 0 | 0 | 1 | 5 | 9 | 10 | 4 | 7 | 10 | 9 | 10 | 5 | 5 | 10 | 10 | 10 |
| Blackgrass | 0 | 0 | 0 | 0 | 1 | 0 | 0 | 7 | 9 | 8 | 4 | 5 | 7 | 7 | 5 | 7 | 8 | 3 | 6 | 4 |
| Cheatgrass | 0 | 0 | 1 | 0 | 1 | 2 | 0 | 9 | 10 | 7 | 8 | 7 | 6 | 6 | 3 | 6 | 4 | 3 | 7 | 6 |
| Chickweed | 0 | 0 | 0 | 0 | 8 | 10 | 4 | 1 | 10 | 10 | 8 | 9 | 10 | 7 | 2 | 6 | 3 | 9 | 10 | 7 |
| Cocklebur | 0 | 0 | 0 | 0 | 0 | 0 | 0 | 0 | 2 | 2 | 0 | 5 | 2 | 2 | 1 | 8 | 1 | 1 | 9 | 1 |

TABLE B-continued

| | | | | | | | | | | | | | | | | | | | |
|---|---|---|---|---|---|---|---|---|---|---|---|---|---|---|---|---|---|---|---|
| Corn | 0 | 0 | 0 | 0 | 0 | 0 | 0 | 4 | 8 | 3 | 4 | 1 | 5 | 1 | 4 | 6 | 1 | 0 | 6 | 2 |
| Cotton | 0 | 0 | 0 | 0 | 0 | 0 | 0 | 8 | 7 | 10 | 0 | 5 | 9 | 7 | 4 | 5 | 8 | 5 | 9 | 0 |
| Crabgrass | 0 | 0 | 7 | 1 | 0 | 0 | 0 | 9 | 10 | 9 | 9 | 9 | 9 | 8 | 4 | 9 | 7 | 7 | 9 | 2 |
| Giant foxtail | 0 | 0 | 3 | 6 | 0 | 0 | 0 | 10 | 10 | 10 | 10 | 8 | 10 | 9 | 9 | 9 | 8 | 7 | 10 | 5 |
| Lambsquarter | 0 | 6 | 3 | 10 | 8 | 10 | 7 | 10 | 10 | 10 | 10 | 10 | 10 | 10 | 9 | 10 | 10 | 10 | 10 | 10 |
| Morningglory | 0 | 0 | 0 | 0 | 0 | 0 | 0 | 0 | 1 | 5 | 4 | 5 | 9 | 2 | 2 | 8 | 5 | 5 | 9 | 3 |
| Nutsedge | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 2 | 2 | 0 | 0 | 9 | 10 | 10 | 7 | 7 | 10 | 8 | 1 | 6 | 8 | 9 | 10 | 10 |
| Rice | 0 | 0 | 0 | 0 | 0 | 0 | 0 | 0 | 0 | 1 | 0 | 0 | 0 | 2 | 2 | 2 | 0 | 0 | 3 | 2 |
| Sorghum | 0 | 0 | 0 | 0 | 0 | 0 | 0 | 0 | 5 | 4 | 1 | 5 | 5 | 2 | 3 | 2 | 1 | 2 | 4 | 0 |
| Soybean | 0 | 0 | 0 | 0 | 0 | 0 | 0 | 0 | 5 | 7 | 2 | 2 | 7 | 2 | 2 | 7 | 2 | 0 | 3 | 0 |
| Sugar beet | 0 | 0 | 0 | 2 | 4 | 2 | 0 | 9 | 10 | 10 | 3 | 10 | 10 | 9 | 9 | 10 | 9 | 10 | 10 | 10 |
| Velvetleaf | 0 | 0 | 2 | 0 | 9 | 0 | 0 | 10 | 10 | 10 | 7 | 10 | 3 | 10 | 5 | 10 | 9 | 10 | 10 | 10 |
| Wheat | 0 | 0 | 0 | 0 | 0 | 0 | 0 | 2 | 9 | 3 | 3 | 4 | 4 | 2 | 1 | 2 | 1 | 2 | 2 | 2 |
| Wild buckwheat | 0 | 0 | 0 | 0 | 4 | 6 | 0 | 9 | 10 | 10 | 10 | 8 | 10 | 9 | 5 | 10 | 5 | 10 | 10 | 7 |
| Wild oat | 0 | 0 | 0 | 0 | 0 | 0 | 0 | 7 | 9 | 7 | 6 | 7 | 8 | 6 | 1 | 6 | 2 | 4 | 6 | 2 |

| | COMPOUND | | | | | | | | | | | | | | | | | |
|---|---|---|---|---|---|---|---|---|---|---|---|---|---|---|---|---|---|---|
| Rate (200 g/ha) | 29 | 30 | 35 | 36 | 37 | 38 | 39 | 40 | 41 | 42 | 43 | 44 | 45 | 46 | 47 | 48 | 49 | 51 | 52 |
| PREEMERGENCE | | | | | | | | | | | | | | | | | | | |
| Barley | 4 | 2 | 0 | 2 | 0 | 1 | 0 | 1 | 1 | 0 | 0 | 2 | 2 | 0 | 0 | 0 | 0 | 0 | 3 |
| Barnyardgrass | 8 | 6 | 7 | 5 | 4 | 1 | 2 | 3 | 6 | 0 | 2 | 8 | 5 | — | 0 | 3 | 5 | 9 | 9 |
| Bedstraw | 9 | 9 | 8 | — | 8 | 7 | 9 | 9 | 10 | 9 | 9 | 10 | 4 | 2 | 9 | 9 | 9 | 10 | 7 |
| Blackgrass | 7 | 0 | 4 | 10 | 6 | 1 | 2 | 2 | 7 | 0 | 5 | 6 | 3 | 0 | 3 | 5 | 2 | 6 | 6 |
| Cheatgrass | 8 | 4 | 5 | 6 | 6 | 3 | 2 | 4 | 5 | 0 | 3 | 6 | 2 | 0 | 0 | 2 | 2 | 5 | 10 |
| Chickweed | 7 | 3 | 9 | — | 9 | 0 | 5 | 5 | 10 | 0 | 10 | 9 | 2 | 2 | 2 | 4 | 8 | 10 | 9 |
| Cocklebur | 4 | 4 | 2 | 2 | 0 | 5 | 1 | 8 | 5 | 0 | 0 | 9 | 4 | — | 3 | 0 | 0 | 9 | 0 |
| Corn | 6 | 1 | 3 | 4 | 3 | 2 | 0 | 1 | 2 | 0 | 0 | 3 | 1 | — | 0 | 1 | 2 | 0 | 4 |
| Cotton | 7 | 6 | 4 | 6 | 7 | 9 | 0 | 7 | 2 | 0 | 1 | 8 | 0 | — | 2 | 9 | 2 | 5 | 3 |
| Crabgrass | 9 | 9 | 9 | 9 | 7 | 8 | 2 | 8 | 6 | 0 | 0 | 9 | 6 | — | 0 | 9 | 5 | 9 | 10 |
| Giant foxtail | 9 | 8 | 9 | 9 | 5 | 9 | 2 | 9 | 3 | 0 | 0 | 8 | 5 | — | 5 | 9 | 10 | 8 | 10 |
| Lambsquarter | 10 | 10 | 10 | 10 | 10 | 10 | 10 | 10 | 10 | 10 | 10 | 10 | 10 | 9 | 9 | 10 | 10 | 10 | 10 |
| Morningglory | 5 | 5 | 2 | 2 | 1 | 4 | 2 | 4 | 7 | 3 | 0 | 10 | 4 | — | 3 | 3 | 6 | 10 | 2 |
| Nutsedge | 0 | 0 | 2 | 2 | 0 | 0 | 0 | 0 | 0 | 0 | 0 | 3 | 0 | — | 0 | 0 | 0 | 0 | 0 |
| Rape | 10 | 3 | — | 8 | 6 | 8 | 10 | 6 | 10 | 3 | 9 | 8 | 7 | 0 | 2 | 9 | 6 | 10 | 9 |
| Rice | 2 | 2 | 2 | 4 | 0 | 2 | 0 | 0 | 0 | 2 | 2 | 2 | 3 | — | 0 | 2 | 0 | 2 | 1 |
| Sorghum | 1 | 0 | 3 | 1 | 1 | 1 | 0 | 1 | 1 | 0 | 2 | 2 | 1 | — | 0 | 1 | 1 | 0 | 3 |
| Soybean | 5 | 2 | 3 | 2 | 4 | 4 | 0 | 2 | 0 | 0 | 3 | 3 | 2 | — | 0 | 0 | 3 | 8 | 0 |
| Sugar beet | 10 | 9 | 4 | 9 | 9 | 10 | 10 | 9 | 10 | 10 | 10 | 10 | 9 | 7 | 8 | 10 | 10 | 10 | 10 |
| Velvetleaf | 10 | 10 | 10 | 10 | 9 | 7 | 4 | 8 | 10 | 6 | 10 | 8 | 0 | — | 4 | 4 | 1 | 10 | 10 |
| Wheat | 4 | 2 | 7 | 5 | 3 | 2 | 0 | 2 | 3 | 0 | 2 | 3 | 5 | 0 | 2 | 2 | 2 | 2 | 7 |
| Wild buckwheat | 10 | 6 | 1 | 10 | 10 | 10 | 10 | 9 | 10 | 7 | 10 | 9 | 10 | 4 | 9 | 10 | 10 | 10 | 10 |
| Wild oat | 7 | 3 | 3 | 6 | 7 | 5 | 0 | 4 | 6 | 0 | 4 | 6 | 2 | 0 | 2 | 3 | 4 | 2 | 4 |

| | COMPOUND | | | | | | | | | | | | | | | | | |
|---|---|---|---|---|---|---|---|---|---|---|---|---|---|---|---|---|---|---|
| Rate (200 g/ha) | 58 | 59 | 64 | 65 | 66 | 68 | 69 | 70 | 71 | 72 | 73 | 74 | 75 | 77 | 78 | 79 | 80 | 81 | 82 |
| PREEMERGENCE | | | | | | | | | | | | | | | | | | | |
| Barley | 4 | 5 | 0 | 2 | 2 | 0 | 0 | 0 | 0 | 0 | 0 | 0 | 0 | 0 | 0 | 2 | 0 | 0 | 0 |
| Barnyardgrass | 7 | 8 | 1 | 9 | 7 | 0 | 1 | 0 | 5 | 3 | 0 | 1 | 0 | 3 | 6 | 6 | 6 | 0 | 6 |
| Bedstraw | 9 | 10 | 1 | 5 | 10 | 2 | 6 | 6 | 6 | 8 | 9 | 9 | 0 | 10 | 9 | 7 | 2 | 9 | 9 |
| Blackgrass | 7 | 5 | 2 | 7 | 7 | 8 | 2 | 0 | 0 | 4 | 0 | 8 | 0 | 3 | 7 | 5 | 3 | 3 | 4 |
| Cheatgrass | 8 | 5 | 2 | 4 | 6 | 3 | 4 | 2 | 2 | 3 | 2 | 4 | 0 | 5 | 4 | 4 | 3 | 4 | 6 |
| Chickweed | 10 | 9 | 0 | 3 | 5 | 2 | 0 | 0 | 0 | 9 | 4 | 5 | 0 | 1 | 8 | 3 | 3 | 9 | 0 |
| Cocklebur | 9 | 8 | 2 | 4 | 0 | 0 | 0 | 0 | 0 | 0 | 0 | 0 | 0 | 1 | 0 | 6 | 0 | 0 | 0 |
| Corn | 4 | 2 | 0 | 4 | 0 | 0 | 0 | 0 | 2 | 2 | 0 | 0 | 0 | 0 | 0 | 0 | 0 | 0 | 3 |
| Cotton | 0 | 7 | 0 | 4 | 0 | 0 | 0 | 0 | 0 | 0 | 0 | 0 | 0 | 0 | 2 | 0 | 0 | 0 | 1 |
| Crabgrass | 9 | 10 | 0 | 2 | 3 | 2 | 5 | 2 | 5 | 9 | 0 | 6 | 2 | 3 | 8 | 6 | 3 | 0 | 7 |
| Giant foxtail | 10 | 10 | 0 | 10 | 6 | 0 | 5 | 4 | 8 | 7 | 0 | 6 | 2 | 2 | 9 | 9 | 2 | 2 | 6 |
| Lambsquarter | 10 | 10 | 10 | 10 | 10 | 0 | 10 | 10 | 10 | 10 | 10 | 0 | 10 | 10 | 10 | 10 | 10 | 10 | 10 |
| Morningglory | 4 | 6 | 8 | 2 | 2 | 0 | 0 | 0 | 0 | 0 | 0 | 0 | 0 | 0 | 10 | 7 | 10 | 0 | 2 |
| Nutsedge | 0 | 0 | 0 | 0 | 0 | 0 | 0 | 0 | 5 | 4 | 0 | 0 | 0 | 0 | 0 | 0 | 0 | 0 | 0 |
| Rape | 5 | 10 | 0 | 10 | 5 | 0 | 3 | 3 | 3 | 6 | 2 | 7 | 0 | 6 | 9 | 6 | 10 | 7 | 6 |
| Rice | 0 | 1 | 2 | 3 | 0 | 0 | 0 | 0 | 0 | 0 | 0 | 0 | 0 | 0 | 2 | 0 | 4 | 0 | 2 |
| Sorghum | 3 | 5 | 0 | 0 | 0 | 0 | 0 | 0 | 0 | 0 | 0 | 0 | 0 | 0 | 3 | 0 | 0 | 0 | 2 |
| Soybean | 0 | 4 | 0 | 2 | 0 | 0 | 0 | 0 | 0 | 0 | 0 | 0 | 0 | 0 | 1 | 0 | 0 | 0 | 6 |
| Sugar beet | 10 | 10 | 10 | 10 | 10 | 9 | 6 | 10 | 10 | 9 | 5 | 10 | 0 | 3 | 10 | 10 | 9 | 9 | 10 |
| Velvetleaf | 10 | 10 | 6 | 9 | 9 | 9 | 9 | 5 | 10 | 10 | 7 | 9 | 0 | 7 | 10 | 10 | 10 | 10 | 10 |
| Wheat | 7 | 4 | 0 | 5 | 3 | 3 | 2 | 3 | 2 | 3 | 2 | 0 | 0 | 0 | 4 | 2 | 2 | 2 | 2 |
| Wild buckwheat | 10 | 10 | 10 | 10 | 10 | 4 | 0 | 8 | 10 | 2 | 3 | 9 | 0 | 9 | 10 | 9 | 3 | 10 | 9 |
| Wild oat | 9 | 7 | 0 | 8 | 5 | 0 | 0 | 3 | 2 | 3 | 2 | 3 | 0 | 0 | 6 | 6 | 7 | 3 | 7 |

COMPOUND

TABLE B-continued

| Rate (100 g/ha) | 2 | 3 | 4 | 5 | 6 | 7 | 14 | 15 |
|---|---|---|---|---|---|---|---|---|
| POSTEMERGENCE | | | | | | | | |
| Barley | 2 | 2 | 2 | 2 | 4 | 2 | 5 | 4 |
| Barnyardgrass | 3 | 4 | 3 | 3 | 3 | 4 | 7 | 6 |
| Bedstraw | 3 | 6 | 3 | 4 | — | 4 | 10 | 7 |
| Blackgrass | 1 | 2 | 1 | 3 | — | 3 | 4 | 2 |
| Cheatgrass | 2 | 3 | 1 | 5 | — | 3 | 4 | 4 |
| Chickweed | 2 | 2 | 2 | 4 | — | 3 | 6 | 0 |
| Cocklebur | 7 | 6 | 5 | 6 | 6 | 7 | 9 | 5 |
| Corn | 3 | 4 | 3 | 3 | 2 | 3 | 4 | 4 |
| Cotton | 10 | 9 | 7 | 10 | 10 | 9 | 10 | 10 |
| Crabgrass | 3 | 3 | 3 | — | 6 | 4 | 3 | 2 |
| Giant foxtail | 4 | 4 | 3 | 5 | 6 | 5 | 5 | 4 |
| Lambsquarter | 9 | 9 | 7 | 8 | — | 8 | 9 | 9 |
| Morningglory | 9 | 9 | 5 | 8 | 9 | 8 | 7 | 5 |
| Nutsedge | 0 | 0 | 0 | 1 | — | 1 | 2 | 1 |
| Rape | 3 | 7 | 1 | 6 | 5 | 5 | 7 | 8 |
| Rice | 4 | 3 | 3 | 4 | 4 | 5 | 4 | 4 |
| Sorghum | 4 | 4 | 3 | 3 | 3 | 5 | 4 | 5 |
| Soybean | 6 | 6 | 4 | 6 | 6 | 8 | 8 | 7 |
| Sugar beet | 9 | 9 | 8 | 9 | 10 | 9 | 10 | 10 |
| Velvetleaf | 8 | 9 | 4 | 8 | 10 | 7 | 10 | 5 |
| Wheat | 2 | 2 | 1 | 3 | 4 | 3 | 5 | 3 |
| Wild buckwheat | 10 | 10 | 10 | 9 | — | 9 | 10 | 10 |
| Wild oat | 2 | 2 | 1 | 4 | 4 | 2 | 4 | 4 |
| PREEMERGENCE | | | | | | | | |
| Barley | 0 | 0 | 0 | 0 | 0 | 0 | 0 | 0 |
| Barnyardgrass | 0 | 0 | 0 | 0 | 1 | 1 | 0 | 0 |
| Bedstraw | 0 | 0 | 0 | — | 0 | 0 | 10 | 2 |
| Blackgrass | 0 | 0 | 0 | 0 | 0 | 0 | 3 | 2 |
| Cheatgrass | 0 | 0 | 0 | 0 | 0 | 0 | 3 | 3 |
| Chickweed | 0 | 0 | 0 | 0 | 0 | 0 | 0 | 0 |
| Cocklebur | 0 | 0 | 0 | 0 | 0 | 0 | 0 | 0 |
| Corn | 0 | 0 | 0 | 0 | 0 | 0 | 0 | 0 |
| Cotton | 0 | 0 | 0 | 0 | 0 | 0 | 0 | 0 |
| Crabgrass | 0 | 0 | 0 | 0 | 0 | 2 | 2 | 8 |
| Giant foxtail | 0 | 2 | 0 | 0 | 0 | 3 | 2 | 3 |
| Lambsquarter | 0 | 0 | 0 | 5 | 8 | 0 | 9 | 10 |
| Morningglory | 0 | 0 | 0 | 0 | 0 | 0 | 0 | 0 |
| Nutsedge | 0 | 0 | 0 | 0 | 0 | 0 | 0 | 0 |
| Rape | 0 | 0 | 0 | 0 | 0 | 0 | 0 | 1 |
| Rice | 0 | 0 | 0 | 0 | 0 | 0 | 0 | 0 |
| Sorghum | 0 | 0 | 0 | 0 | 0 | 0 | 0 | 0 |
| Soybean | 0 | 0 | 0 | 0 | 0 | 0 | 0 | 0 |
| Sugar beet | 0 | 0 | 0 | 0 | 0 | 0 | 6 | 3 |
| Velvetleaf | — | 0 | 0 | 2 | 2 | 1 | 0 | 2 |
| Wheat | 0 | 0 | 0 | 0 | 0 | 0 | 0 | 1 |
| Wild buckwheat | 0 | 0 | 0 | 0 | — | 0 | 10 | 0 |
| Wild oat | 0 | 0 | 0 | 0 | 0 | 0 | 0 | 0 |

| | COMPOUND | | | | | | | | | | | | | | | | | | | | | | |
|---|---|---|---|---|---|---|---|---|---|---|---|---|---|---|---|---|---|---|---|---|---|---|---|
| Rate (50 g/ha) | 1 | 2 | 3 | 8 | 9 | 10 | 11 | 12 | 13 | 16 | 17 | 18 | 20 | 21 | 22 | 23 | 24 | 25 | 26 | 28 | 29 | 30 | 31 | 32 |
| POSTEMERGENCE | | | | | | | | | | | | | | | | | | | | | | | | |
| Barley | 3 | 2 | 1 | 2 | 3 | 4 | 4 | 6 | 6 | 6 | 5 | 4 | 3 | 6 | 4 | 3 | 4 | 4 | 4 | 6 | 5 | 5 | 5 | 5 |
| Barnyardgrass | 2 | 3 | 3 | 5 | 3 | 1 | 4 | 5 | 7 | 8 | 6 | 4 | 6 | 6 | 3 | 7 | 4 | 3 | 5 | 7 | 8 | 6 | 6 | 5 |
| Bedstraw | 3 | 3 | 6 | 3 | 5 | 8 | 3 | 9 | 9 | 10 | 6 | 7 | 8 | 6 | 8 | 7 | 6 | 9 | 9 | 9 | 7 | 8 | 10 | 10 |
| Blackgrass | 0 | 1 | 1 | 1 | 4 | 4 | 3 | 2 | 3 | 4 | 3 | 4 | 5 | 3 | 3 | 6 | 2 | 2 | 4 | 4 | 3 | 5 | 4 | 5 |
| Cheatgrass | 2 | 2 | 3 | 2 | 3 | 4 | 3 | 8 | 8 | 7 | 5 | 5 | 5 | 5 | 3 | 6 | 3 | 3 | 5 | 6 | 4 | 6 | 6 | 5 |
| Chickweed | 0 | 1 | 1 | 0 | 6 | 9 | 3 | 2 | 2 | 9 | 5 | 7 | 8 | 8 | — | — | 8 | — | 10 | — | — | 5 | 10 | — |
| Cocklebur | 4 | 7 | 6 | 5 | 6 | 7 | 7 | 5 | — | 10 | 7 | 9 | 10 | 8 | 7 | 8 | 8 | 7 | 10 | 9 | 6 | 7 | 9 | 10 |
| Corn | 2 | 3 | 3 | 5 | 4 | 2 | 5 | 3 | 4 | 4 | 4 | 4 | 4 | 5 | 3 | 4 | 5 | 3 | 5 | 6 | 6 | 4 | 3 | 4 |
| Cotton | 7 | 9 | 9 | 9 | 10 | 10 | 9 | 10 | 10 | 10 | 10 | 10 | 10 | 10 | 10 | 10 | 10 | 10 | 10 | 10 | 10 | 10 | 10 | 10 |
| Crabgrass | 2 | 3 | 2 | 3 | 3 | 2 | 3 | 4 | 6 | 4 | 4 | 3 | 3 | 2 | 3 | 2 | 5 | 3 | 2 | 5 | 4 | 3 | 4 | 5 |
| Giant foxtail | 3 | 4 | 3 | 4 | 4 | 4 | 6 | 6 | 6 | 6 | 4 | 4 | 5 | 4 | 3 | 5 | 4 | 3 | 4 | 5 | 3 | 4 | 5 | 5 |
| Lambsquarter | 4 | 9 | 9 | 8 | 9 | 10 | 8 | 10 | 10 | 9 | 10 | 10 | 10 | 10 | 8 | 10 | 9 | 9 | 10 | 10 | 10 | 10 | 10 | 10 |
| Morningglory | 6 | 9 | 9 | 8 | 8 | 8 | 9 | 7 | 6 | 9 | 7 | 10 | 9 | 10 | 5 | 8 | 9 | 8 | 9 | 8 | 8 | 8 | 10 | 10 |
| Nutsedge | 0 | 0 | 0 | 0 | 2 | 1 | 3 | 1 | 2 | 3 | 0 | 1 | 2 | 1 | 2 | 2 | 3 | 2 | — | 2 | 4 | 2 | 5 | 4 |
| Rape | 1 | 5 | 4 | 5 | 8 | 9 | 5 | 10 | 10 | 10 | 9 | 7 | 10 | 6 | 4 | 6 | 5 | 10 | 9 | 10 | 8 | 5 | 9 | 10 |
| Rice | 4 | 3 | 3 | 3 | 4 | 3 | 5 | 3 | 5 | 5 | 5 | 5 | 6 | 5 | 4 | 4 | 5 | 4 | 5 | 5 | 4 | 5 | 7 | 7 |
| Sorghum | 4 | 4 | 4 | 5 | 3 | 3 | 4 | 4 | 5 | 5 | 5 | 5 | 6 | 5 | 5 | 4 | 5 | 4 | 5 | 7 | 5 | 4 | 4 | 6 |
| Soybean | 4 | 6 | 6 | 4 | 6 | 10 | 9 | 6 | 8 | 9 | 7 | 7 | 8 | 9 | 5 | 8 | 6 | 8 | 8 | 8 | 8 | 7 | 7 | 8 |
| Sugar beet | 8 | 9 | 9 | 7 | 10 | 10 | 8 | 10 | 10 | 10 | 10 | 10 | 10 | 10 | 9 | 10 | 10 | 10 | 10 | 10 | 10 | 10 | 10 | 10 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Velvetleaf | 3 | 9 | 9 | 7 | 7 | 10 | 7 | 6 | 10 | 10 | 9 | 8 | 10 | 10 | 6 | 9 | 10 | 8 | 10 | 10 | 8 | 7 | 10 | 10 |
| Wheat | 1 | 1 | 1 | 2 | 4 | 7 | 3 | 6 | 5 | 5 | 5 | 4 | 2 | 3 | 3 | 2 | 3 | 3 | 4 | 7 | 4 | 4 | 5 | 5 |
| Wild buckwheat | 5 | 10 | 10 | 5 | 10 | 10 | 9 | 10 | 10 | 10 | 10 | 10 | 10 | 10 | 10 | 10 | 10 | 10 | 10 | 9 | 10 | 10 | 10 | 10 |
| Wild oat | 2 | 2 | 2 | 2 | 5 | 3 | 2 | 6 | 6 | 6 | 5 | 5 | 4 | 4 | 3 | 3 | 3 | 3 | 5 | 5 | 5 | 5 | 6 | 4 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (50 g/ha) | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 |

POSTEMERGENCE

| | | | | | | | | | | | | | | | | | | | | | | | | |
|---|---|---|---|---|---|---|---|---|---|---|---|---|---|---|---|---|---|---|---|---|---|---|---|---|
| Barley | 4 | 4 | 2 | 5 | 4 | 4 | 4 | 4 | 5 | 3 | 3 | 4 | 4 | 2 | 5 | 7 | 4 | 4 | 3 | 5 | 6 | 4 | 4 | 7 |
| Barnyardgrass | 7 | 5 | 5 | 6 | 5 | 6 | 4 | 4 | 3 | 5 | 7 | 8 | 3 | — | 6 | 4 | 3 | 4 | 8 | 9 | 6 | 5 | 6 | 4 |
| Bedstraw | 9 | 10 | 7 | 10 | 7 | — | — | 10 | 10 | 10 | 10 | 9 | 8 | 6 | 9 | 9 | 9 | 10 | 10 | 10 | 10 | 9 | 10 | 10 |
| Blackgrass | 5 | 6 | 3 | 5 | 4 | 3 | 4 | 2 | 2 | 2 | 7 | 8 | 6 | 2 | 4 | 6 | 4 | 6 | 6 | 4 | 5 | 6 | 7 | 7 |
| Cheatgrass | 4 | 5 | 3 | 5 | 4 | 4 | 4 | 4 | 3 | 1 | 6 | 7 | 4 | 3 | 4 | 6 | 4 | 6 | 4 | 4 | 4 | 7 | 8 | 6 |
| Chickweed | 10 | 10 | — | — | 5 | 9 | 8 | 10 | 10 | 4 | — | — | 8 | 3 | 9 | 9 | 7 | 10 | 10 | 5 | 9 | 10 | 10 | 10 |
| Cocklebur | 10 | 1 | 5 | 9 | 7 | 8 | 10 | 5 | 10 | 10 | 8 | 9 | 7 | — | 6 | 7 | 9 | 10 | 9 | 6 | 10 | 10 | 10 | 10 |
| Corn | 4 | 4 | 4 | 5 | 6 | 4 | 5 | 4 | — | 7 | 8 | 4 | 5 | — | 4 | 3 | 3 | 4 | 6 | 4 | 3 | 5 | 3 |
| Cotton | 10 | 10 | 9 | 9 | 10 | 9 | 10 | 10 | 10 | 10 | 10 | 10 | 10 | — | 10 | 10 | 10 | 10 | 10 | 10 | 10 | 10 | 10 | 10 |
| Crabgrass | 5 | 4 | 3 | 5 | 4 | 5 | 5 | 4 | 3 | 2 | 4 | — | — | — | 3 | 8 | 4 | 4 | 4 | 6 | 4 | 3 | 3 | 6 |
| Giant foxtail | 4 | 5 | 4 | 6 | 5 | 5 | 4 | 5 | 4 | 3 | 5 | 6 | 5 | — | 4 | 6 | 4 | 4 | 4 | 5 | 6 | 4 | 6 | 6 |
| Lambsquarter | 10 | 10 | 10 | 10 | 9 | 10 | 9 | 9 | 10 | 9 | 8 | 10 | 10 | 9 | 7 | 10 | — | 10 | 10 | 9 | 10 | 10 | 10 | 10 |
| Morningglory | 10 | 1 | 5 | 8 | 7 | 8 | 8 | 3 | 9 | 9 | 10 | 9 | 8 | — | 9 | 10 | 10 | 10 | 9 | 9 | 10 | 9 | 10 | 9 |
| Nutsedge | 5 | 0 | 1 | 4 | 2 | 3 | 5 | 2 | 4 | 2 | 3 | 4 | — | — | 2 | 4 | 2 | 5 | 3 | 3 | 6 | 2 | 2 | 7 |
| Rape | 10 | 10 | 6 | 10 | 9 | 8 | 5 | 4 | 10 | 9 | 9 | 9 | 3 | 4 | 3 | 8 | 7 | 10 | 7 | 8 | 10 | 10 | 10 | 10 |
| Rice | 7 | 5 | 5 | 6 | 5 | 5 | 4 | 5 | 6 | 4 | 7 | 5 | 6 | — | 4 | 3 | 5 | 4 | 3 | 4 | 4 | 4 | 4 | 4 |
| Sorghum | 6 | 6 | 5 | 5 | 5 | 5 | 5 | 4 | 5 | 4 | 5 | 4 | 4 | — | 3 | 4 | 3 | 3 | 4 | 4 | 3 | 3 | 4 | 2 |
| Soybean | 9 | 10 | 4 | 9 | 5 | 5 | 2 | 5 | 9 | 4 | 8 | 8 | 8 | — | 7 | 7 | 8 | 9 | 8 | 10 | 9 | 9 | 9 | 8 |
| Sugar beet | 10 | 10 | 9 | 10 | 10 | 10 | 10 | 10 | 10 | 10 | 10 | 10 | 7 | 10 | 10 | 10 | 10 | 10 | 10 | 10 | 10 | 10 | 10 | 10 |
| Velvetleaf | 9 | 1 | 8 | 10 | 10 | 6 | 9 | 2 | 10 | 10 | 10 | 9 | 9 | — | 8 | 9 | 9 | 10 | 9 | 9 | 10 | 9 | 9 | 9 |
| Wheat | 5 | 5 | 2 | 5 | 4 | 4 | 4 | 4 | 5 | 2 | 3 | 6 | 3 | 2 | 3 | 5 | 5 | 4 | 3 | 4 | 7 | 6 | 6 | 7 |
| Wild buckwheat | 10 | 10 | 6 | 10 | 9 | 10 | 10 | 9 | 10 | 9 | 10 | 10 | 6 | 10 | 10 | 10 | 10 | 10 | 10 | 10 | 10 | 10 | 0 | 10 |
| Wild oat | 5 | 5 | 3 | 5 | 4 | 3 | 3 | 4 | 3 | 1 | 5 | 5 | 2 | 2 | 3 | 4 | 3 | 4 | 2 | 5 | 7 | 7 | 7 | 6 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (50 g/ha) | 57 | 58 | 59 | 60 | 61 | 62 | 63 | 64 | 65 | 66 | 67 | 68 | 69 | 70 | 71 | 72 | 73 | 74 | 77 | 78 | 79 | 80 | 81 | 82 |

POSTEMERGENCE

| | | | | | | | | | | | | | | | | | | | | | | | | |
|---|---|---|---|---|---|---|---|---|---|---|---|---|---|---|---|---|---|---|---|---|---|---|---|---|
| Barley | 4 | 6 | 4 | 4 | 2 | 1 | 5 | 2 | 3 | 5 | 6 | 3 | 4 | 3 | 3 | 4 | 2 | 2 | 2 | 3 | 4 | 3 | 3 | 2 |
| Barnyardgrass | 3 | 6 | 5 | 4 | 2 | 3 | 5 | 5 | 7 | 5 | 6 | 2 | 4 | 6 | 6 | 5 | 7 | 5 | 4 | 8 | 4 | 6 | 8 | 6 |
| Bedstraw | 9 | 10 | 10 | 9 | 9 | 9 | 8 | 10 | 10 | 10 | 10 | 7 | 5 | 8 | 8 | 7 | 7 | 8 | 4 | 6 | 5 | 8 | 9 | 8 |
| Blackgrass | 7 | 6 | 4 | 3 | 3 | 2 | 4 | 2 | 7 | 4 | 5 | 2 | 3 | — | 4 | 5 | 5 | 6 | 2 | 4 | 3 | 3 | 2 | 2 |
| Cheatgrass | 6 | 7 | 4 | 3 | 3 | 2 | 4 | 2 | 3 | 3 | 6 | 2 | 3 | 3 | 4 | 5 | 3 | 6 | 2 | 2 | 3 | 5 | 3 | 2 |
| Chickweed | 10 | 9 | 6 | 7 | 2 | 3 | 9 | 2 | 5 | — | 9 | 0 | 2 | 2 | 2 | 2 | 2 | 6 | 2 | 6 | 4 | 4 | 2 | 2 |
| Cocklebur | 9 | 6 | 7 | 8 | 8 | 9 | 9 | 10 | 10 | 9 | 9 | 6 | 8 | 8 | 7 | 8 | 8 | 9 | 7 | 8 | 8 | 9 | 8 | 7 |
| Corn | 4 | 5 | 4 | 3 | 5 | 5 | 2 | 5 | 4 | 3 | 4 | 3 | 4 | 3 | 3 | 5 | 2 | 3 | 7 | 3 | 4 | 2 | 3 |
| Cotton | 10 | 10 | 10 | 10 | 10 | 10 | 10 | 10 | 10 | 10 | 10 | 10 | 10 | 10 | 10 | 10 | 10 | 10 | 9 | 10 | 10 | 10 | 10 | 10 |
| Crabgrass | 3 | 3 | 4 | 2 | 2 | 2 | 3 | 3 | 4 | 4 | 6 | 3 | 4 | 3 | 3 | 2 | 3 | 3 | 5 | 4 | 3 | 4 | 4 | 3 |
| Giant foxtail | 6 | 6 | 6 | 4 | 2 | 3 | 3 | 3 | 5 | 7 | 6 | 4 | 5 | 5 | 5 | 4 | 5 | 5 | 5 | 4 | 4 | 4 | 4 | 4 |
| Lambsquarter | 10 | 10 | 10 | 10 | 9 | 9 | 10 | 9 | 10 | 10 | 10 | 10 | 8 | 9 | 10 | 10 | 9 | 9 | 10 | 9 | 10 | 10 | 10 | 7 |
| Morningglory | 10 | 9 | 8 | 7 | 10 | 9 | 10 | 9 | 10 | 10 | 10 | 8 | 7 | 7 | 10 | 7 | 10 | 9 | 8 | 10 | 10 | 10 | 9 | 10 |
| Nutsedge | 4 | 5 | 2 | 2 | 2 | 0 | 6 | 2 | 3 | 2 | 3 | 2 | 2 | 1 | 2 | 2 | 2 | 2 | 1 | 0 | 2 | — | 2 |
| Rape | 10 | 9 | 10 | 10 | 8 | 6 | 9 | 7 | 8 | 10 | 10 | 3 | 6 | 7 | 8 | 9 | 7 | 10 | 6 | 8 | 8 | 10 | 3 | 5 |
| Rice | 3 | 4 | 5 | 4 | 4 | 3 | 5 | 4 | 5 | 5 | 7 | 5 | 5 | 4 | 4 | 6 | 3 | 4 | 3 | 5 | 6 | 6 | 4 |
| Sorghum | 4 | 4 | 3 | 3 | 3 | 2 | 5 | 4 | 6 | 5 | 6 | 3 | 4 | 5 | 6 | 4 | 5 | 5 | 4 | 6 | 4 | 3 | 2 |
| Soybean | 8 | 7 | 8 | 4 | 3 | 8 | 5 | 6 | | 6 | 9 | 4 | 2 | 5 | 6 | 6 | 2 | 6 | 5 | 10 | 7 | 8 | 6 | 4 |
| Sugar beet | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 | 10 |
| Velvetleaf | 9 | 9 | 8 | 8 | 10 | 10 | 10 | 10 | 10 | 10 | 10 | 8 | 10 | 10 | 10 | 9 | 6 | 10 | 10 | 10 | 8 | 9 | 9 | 10 |
| Wheat | 7 | 7 | 7 | 4 | 3 | 2 | 5 | 3 | 6 | 5 | 6 | 3 | 4 | 4 | 4 | 5 | 2 | 4 | 2 | A | 5 | 4 | 3 | 3 |
| Wild buckwheat | 10 | 10 | 10 | 10 | 9 | 10 | 10 | 10 | 10 | 10 | 10 | 10 | 10 | 10 | 10 | 10 | 10 | 10 | 10 | 10 | 10 | 10 | 10 | 10 |
| Wild oat | 7 | 7 | 7 | 4 | 2 | 2 | 6 | 3 | 7 | 5 | 7 | 2 | 3 | 2 | 3 | 3 | 1 | 4 | 1 | 3 | 4 | 4 | 2 | 2 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (50 g/ha) | 1 | 2 | 3 | 8 | 9 | 10 | 11 | 12 | 13 | 16 | 17 | 18 | 20 | 21 | 22 | 23 | 24 | 25 | 26 | 28 | 29 | 30 | 31 | 32 |

PREEMERGENCE

| | | | | | | | | | | | | | | | | | | | | | | | | |
|---|---|---|---|---|---|---|---|---|---|---|---|---|---|---|---|---|---|---|---|---|---|---|---|---|
| Barley | 0 | 0 | 0 | 0 | 0 | 0 | 0 | 1 | 1 | 1 | 0 | 0 | 1 | 0 | 0 | 0 | 0 | 0 | 0 | 0 | 0 | 0 | 0 | 0 |
| Barnyardgrass | 0 | 0 | 0 | 0 | 0 | 0 | 0 | 2 | 3 | 3 | 1 | 2 | 6 | 2 | 2 | 4 | 1 | 2 | 2 | 0 | 4 | 2 | 3 | 1 |
| Bedstraw | 0 | 0 | 0 | 0 | 0 | 0 | 3 | 5 | 8 | 0 | 1 | 10 | 2 | — | 5 | 3 | 5 | 10 | 8 | 7 | 0 | — | — |
| Blackgrass | 0 | 0 | 0 | 0 | 0 | 0 | 0 | 1 | 3 | 5 | 2 | 3 | 5 | 6 | 0 | 6 | 2 | 0 | 4 | 2 | 5 | 0 | 6 | 5 |
| Cheatgrass | 0 | 0 | 0 | 0 | 0 | 0 | 2 | 0 | 7 | 9 | 0 | 4 | 2 | 5 | 4 | 0 | 4 | 0 | 0 | 6 | 4 | 5 | 0 | 6 | 5 |
| Chickweed | 0 | 0 | 0 | 0 | — | 10 | 0 | 1 | 5 | 10 | 0 | 9 | 7 | 2 | 0 | 0 | 0 | 0 | 10 | 1 | 3 | 0 | — | — |
| Cocklebur | 0 | 0 | 0 | 0 | 0 | 0 | 0 | — | 0 | 0 | 0 | 0 | 0 | 0 | 2 | 0 | 0 | 0 | 1 | 0 | 2 | 0 | 3 | 5 |
| Corn | 0 | 0 | 0 | 0 | 0 | 0 | 0 | 0 | 5 | 1 | 0 | 1 | 0 | 0 | 2 | 0 | 0 | 0 | 4 | 0 | 0 | 0 | 0 | 0 |

TABLE B-continued

| | | | | | | | | | | | | | | | | | | | | | | | |
|---|---|---|---|---|---|---|---|---|---|---|---|---|---|---|---|---|---|---|---|---|---|---|---|
| Cotton | 0 | 0 | 0 | 0 | 0 | 0 | 0 | 2 | 3 | 3 | 0 | 0 | 2 | 2 | 2 | 5 | 3 | 4 | 3 | 0 | 1 | 2 | 0 | 8 |
| Crabgrass | 0 | 0 | 0 | 0 | 0 | 0 | 0 | 6 | 10 | 2 | 3 | 4 | 6 | 2 | 2 | 2 | 0 | 5 | 5 | 0 | 8 | 6 | 2 | 3 |
| Giant foxtail | 0 | 0 | 0 | 0 | 0 | 0 | 0 | 7 | 9 | 7 | 7 | 4 | 10 | 5 | 3 | 6 | 3 | 2 | 6 | 0 | 8 | 7 | 3 | 4 |
| Lambsquarter | 0 | 0 | 0 | 0 | 4 | 6 | 0 | 10 | 10 | 10 | 10 | 10 | 10 | 10 | 6 | 10 | 9 | 9 | 10 | 10 | 10 | 8 | 10 | 10 |
| Morningglory | 0 | 0 | 0 | 0 | 0 | 0 | 0 | 0 | 0 | 0 | 2 | 1 | 1 | 2 | 2 | 3 | 1 | 1 | 2 | 3 | 2 | 2 | 5 | 2 |
| Nutsedge | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Rape | 0 | 0 | 0 | 0 | 0 | 0 | 0 | 3 | 5 | 1 | 1 | 1 | 3 | 3 | 0 | 3 | 2 | 0 | 3 | 9 | 8 | 0 | 1 | 2 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 |
| Sorghum | 0 | 0 | 0 | 0 | 0 | 0 | 0 | 0 | 0 | 0 | 0 | 0 | 1 | 0 | 0 | 0 | 0 | 0 | 2 | 0 | 0 | 0 | 0 | 2 |
| Soybean | 0 | 0 | 0 | 0 | 0 | 0 | 0 | 0 | 0 | 3 | 0 | 0 | 2 | 0 | 0 | 1 | 0 | 0 | 1 | 0 | 1 | 0 | 0 | 0 |
| Sugar beet | 0 | 0 | 0 | 0 | 0 | 0 | 0 | 8 | 9 | 7 | 9 | 9 | 9 | 10 | 1 | 9 | 9 | 7 | 9 | 10 | 7 | 5 | 10 | 7 |
| Velvetleaf | 0 | 0 | 0 | 0 | 2 | 0 | 0 | 6 | 10 | 8 | 3 | 5 | 5 | 1 | 4 | 1 | 1 | 1 | 10 | 5 | 10 | 5 | 9 | 10 |
| Wheat | 0 | 0 | 0 | 0 | 0 | 0 | 0 | 1 | 4 | 1 | 1 | 1 | 4 | 3 | 0 | 0 | 0 | 0 | 1 | 0 | 0 | 0 | 1 | 0 |
| Wild buckwheat | — | 0 | 0 | 0 | 0 | 0 | 0 | 2 | 8 | 8 | 5 | 6 | 10 | 7 | 2 | 0 | 3 | 8 | 7 | 7 | 8 | 0 | 10 | 8 |
| Wild oat | 0 | 0 | 0 | 0 | 0 | 0 | 0 | 5 | 7 | 3 | 3 | 1 | 6 | 4 | 0 | 3 | 0 | 0 | 3 | 0 | 3 | 0 | 4 | 5 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (50 g/ha) | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| PREEMERGENCE | | | | | | | | | | | | | | | | | | | | | | | | |
| Barley | 1 | 2 | 0 | 0 | 0 | 0 | 0 | 0 | 1 | 0 | 0 | 1 | 0 | 0 | 0 | 0 | 0 | 0 | 0 | 2 | 1 | 2 | 3 | 2 |
| Barnyardgrass | 3 | 4 | 1 | 3 | 0 | 0 | 0 | 1 | 4 | 0 | 0 | 5 | 0 | — | 0 | 2 | 0 | 0 | 9 | 5 | 2 | 3 | 6 | 0 |
| Bedstraw | — | — | 0 | 10 | — | 0 | 4 | 9 | 2 | 7 | 0 | 8 | 2 | 0 | 9 | 3 | 8 | 10 | 5 | 5 | 9 | 9 | 10 | 9 |
| Blackgrass | 5 | 6 | 0 | 4 | 0 | 1 | 0 | — | 6 | 0 | 2 | 4 | 2 | 0 | 2 | 0 | 0 | 6 | 2 | 4 | 6 | 3 | 7 | 6 |
| cheatgrass | 6 | 6 | 1 | 4 | 5 | 0 | 0 | 0 | 3 | 0 | 2 | 2 | 2 | 0 | 0 | 0 | 0 | 3 | 3 | 6 | 4 | 3 | 5 | 5 |
| Chickweed | — | — | — | — | — | 0 | 0 | 0 | 10 | 0 | 0 | 9 | 3 | 0 | 0 | — | 0 | 10 | 6 | 9 | 10 | 10 | 10 | 10 |
| Cocklebur | 5 | 2 | 0 | 0 | 0 | 0 | 0 | 5 | 2 | 0 | 0 | 6 | 0 | — | 2 | — | 0 | 0 | 2 | 0 | 1 | 0 | 2 | 2 |
| Corn | 0 | 0 | 0 | 0 | 0 | 0 | 0 | 0 | 0 | 0 | 0 | 2 | 0 | — | 0 | 0 | 0 | 0 | 1 | 0 | 0 | 1 | 0 | 0 |
| Cotton | 0 | 0 | 0 | 4 | 0 | 0 | 0 | 1 | 4 | 0 | 0 | 1 | 0 | — | 0 | 2 | 0 | 1 | 0 | 2 | 2 | 1 | 0 | 0 |
| Crabgrass | 6 | 9 | 4 | 5 | 0 | 0 | 0 | 0 | 0 | 0 | 3 | 0 | — | 0 | 2 | 0 | 0 | 2 | 2 | 6 | 0 | 6 | 3 | 3 |
| Giant foxtail | 7 | 6 | 2 | 5 | 2 | 2 | 5 | 9 | 1 | 0 | 0 | 7 | 2 | — | 0 | 6 | 4 | 3 | 2 | 9 | 8 | 8 | 8 | 0 |
| Lambsquarter | 10 | 10 | 10 | 10 | 10 | 10 | 10 | 10 | 10 | 9 | 9 | 10 | 10 | 0 | 9 | 10 | 10 | 10 | 10 | 10 | 10 | 10 | 10 | 10 |
| Morningglory | 10 | 2 | 0 | 0 | 0 | 0 | 0 | 1 | 0 | 0 | 0 | 7 | 2 | — | 1 | 1 | 1 | 2 | 9 | 0 | 10 | 3 | 8 | 6 |
| Nutsedge | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 4 |
| Rape | 5 | 6 | 0 | 5 | — | 8 | 8 | 8 | 10 | 2 | 0 | 2 | 2 | 0 | 1 | 4 | 1 | 8 | 8 | 1 | 2 | 6 | 6 | 3 |
| Rice | 3 | 2 | 0 | 0 | 0 | 0 | 0 | 0 | 0 | 0 | 1 | 1 | 0 | — | 0 | 1 | 0 | 2 | 0 | 0 | 1 | 0 | 0 | 0 |
| Sorghum | 0 | 2 | 0 | 0 | 0 | 0 | 0 | 0 | 0 | 0 | 0 | 1 | 0 | — | 0 | 0 | 0 | 0 | 0 | 2 | 6 | 1 | 0 | 0 |
| Soybean | 2 | 6 | 0 | 0 | 0 | 0 | 0 | 0 | 0 | 0 | 4 | 0 | — | 0 | 0 | 0 | 0 | 3 | 1 | 0 | 0 | 0 | 0 | 0 |
| Sugarbeet | 10 | 9 | 0 | 9 | 9 | 8 | 8 | 9 | 10 | 10 | 9 | 10 | 7 | 0 | 1 | 9 | 9 | 10 | 10 | 9 | 9 | 9 | 10 | 9 |
| Velvetleaf | 9 | 10 | 2 | 8 | 1 | 0 | 2 | 2 | 2 | 0 | 5 | 4 | 2 | — | 2 | 0 | 0 | 0 | 10 | 8 | 9 | 10 | 10 | 10 |
| Wheat | 2 | 3 | 0 | 5 | 0 | 0 | 0 | 0 | 1 | 0 | 0 | 3 | 2 | 0 | 0 | 0 | 0 | 0 | 0 | 4 | 7 | 3 | 4 | 4 |
| Wild buckwheat | — | 8 | 0 | 10 | 9 | 8 | 10 | — | 10 | 0 | 8 | 9 | 3 | 0 | 0 | 9 | 7 | 7 | 10 | 7 | 9 | 10 | 10 | 9 |
| Wild oat | 7 | 7 | 0 | 3 | 2 | 0 | 0 | 0 | 2 | 0 | 2 | 4 | 2 | 0 | 0 | 0 | 0 | 3 | 0 | 4 | 8 | 2 | 9 | 5 |

| | COMPOUND | | | | | | | | | | | | | | | | | | | | | | | |
|---|---|---|---|---|---|---|---|---|---|---|---|---|---|---|---|---|---|---|---|---|---|---|---|---|
| Rate (50 g/ha) | 57 | 58 | 59 | 60 | 61 | 62 | 63 | 64 | 65 | 66 | 67 | 68 | 69 | 70 | 71 | 72 | 73 | 74 | 77 | 78 | 79 | 80 | 81 | 82 |
| PREEMERGENCE | | | | | | | | | | | | | | | | | | | | | | | | |
| Barley | 0 | 1 | 2 | 0 | 0 | 0 | 0 | 0 | 0 | 0 | 2 | 0 | 0 | 0 | 0 | 0 | 0 | 0 | 0 | 2 | 0 | 0 | 0 | 0 |
| Barnyardgrass | 3 | 4 | 6 | 0 | 0 | 0 | 0 | 0 | 4 | 0 | 6 | 0 | 0 | 0 | 0 | 3 | 0 | 0 | 0 | 2 | 3 | 0 | 0 | 2 |
| Bedstraw | 8 | 6 | 8 | 6 | 5 | 7 | 10 | 0 | 5 | 9 | 3 | 0 | 0 | 1 | 2 | 0 | 2 | 0 | 3 | 2 | 2 | 0 | 0 | 0 |
| Blackgrass | 6 | 4 | 4 | 0 | 2 | 0 | 3 | 1 | 7 | — | 8 | 2 | — | 0 | 0 | 0 | 0 | 0 | 2 | 4 | 1 | 0 | 0 | 0 |
| Cheatgrass | 5 | 4 | 4 | 2 | 2 | 0 | 2 | 2 | 2 | 1 | 6 | — | 0 | 0 | 0 | 0 | 0 | 4 | 3 | 2 | 2 | 2 | 0 | 2 |
| Chickweed | 9 | 10 | 4 | 4 | 3 | 0 | 9 | 0 | 1 | 4 | 6 | 2 | 0 | 0 | 0 | 0 | 2 | 0 | 0 | 6 | 0 | 0 | 0 | 6 |
| Cocklebur | 3 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Corn | 0 | 2 | 1 | 0 | 0 | 0 | 0 | 0 | 0 | 0 | 2 | 0 | 0 | 0 | 0 | 0 | 0 | 0 | 0 | 0 | 0 | 0 | 0 | 0 |
| Cotton | 2 | 0 | 4 | 5 | 0 | 0 | 2 | 0 | 0 | 0 | 1 | 0 | 0 | 0 | 0 | 0 | 0 | 0 | 0 | 0 | 0 | 0 | 0 | 0 |
| Crabgrass | 0 | 0 | 5 | 0 | 0 | 0 | 0 | 0 | 2 | 0 | 2 | 0 | 2 | 0 | 0 | 0 | 0 | 2 | 2 | 2 | 4 | 0 | 0 | 3 |
| Giant foxtail | 2 | 9 | 9 | 2 | 0 | 0 | 1 | 0 | 6 | 0 | 2 | 0 | 2 | 0 | 0 | 3 | 0 | 2 | 2 | 2 | 3 | 0 | 0 | 3 |
| Lambsquarter | 10 | 10 | 10 | 9 | 9 | 9 | 10 | 10 | 10 | 9 | 10 | 6 | 9 | 7 | 10 | 9 | 9 | 9 | 10 | 10 | 9 | 10 | 9 | 10 |
| Morningglory | 10 | 4 | 2 | 3 | 3 | 0 | 0 | 0 | 0 | 0 | 2 | 0 | 0 | 0 | 0 | 0 | 0 | 0 | 0 | 0 | 0 | 5 | 0 | 0 |
| Nutsedge | 0 | 0 | 0 | 0 | 10 | 0 | 0 | 0 | 0 | 0 | 0 | 0 | 0 | 0 | 0 | 0 | 0 | 0 | 0 | 0 | 0 | 0 | 0 | 0 |
| Rape | 0 | 5 | 5 | 6 | 4 | 0 | 6 | 0 | 0 | 1 | 3 | 0 | 2 | 2 | 0 | 0 | 2 | 0 | 0 | 4 | 3 | 4 | 0 | 0 |
| Rice | 0 | 0 | 0 | 1 | 0 | 0 | 0 | 0 | 1 | 0 | 0 | 0 | 0 | 0 | 0 | 0 | 0 | 0 | 0 | 0 | 0 | 2 | 0 | 0 |
| Sorghum | 0 | 2 | 1 | 2 | 0 | 0 | 0 | 0 | 0 | 0 | 2 | 0 | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Sugar beet | 9 | 9 | 9 | 9 | 9 | 10 | 10 | 10 | 9 | 9 | 8 | 9 | 0 | 3 | 6 | 5 | 0 | 5 | 0 | 3 | 9 | 9 | 8 | 8 |
| Velvetleaf | 10 | 10 | 10 | 6 | 10 | 2 | 2 | 7 | 3 | 9 | 6 | 1 | 0 | 1 | 0 | 0 | 0 | 2 | 5 | 3 | 10 | 5 | 9 | 3 | 0 |
| Wheat | 2 | 2 | 4 | 2 | 0 | 2 | 2 | 0 | 0 | 0 | 0 | 0 | 0 | 2 | 0 | 0 | 0 | 0 | 0 | 3 | 0 | 0 | 0 | 0 |

TABLE B-continued

| | | | | | | | | | | | | | | | | | | | | | | | | |
|---|---|---|---|---|---|---|---|---|---|---|---|---|---|---|---|---|---|---|---|---|---|---|---|---|
| Wild buckwheat | — | 9 | 10 | 7 | 0 | 0 | 10 | 5 | 10 | 4 | 10 | 0 | 0 | 8 | 0 | 0 | 0 | 5 | 8 | 9 | 0 | 3 | 0 | 7 |
| Wild oat | 5 | 6 | 2 | 3 | 2 | 0 | 3 | 0 | 2 | 2 | 5 | 0 | 0 | 2 | 2 | 0 | 0 | 0 | 0 | 3 | 3 | 2 | 0 | 2 |

| | COMPOUND | | | | | | | | | | | | | |
|---|---|---|---|---|---|---|---|---|---|---|---|---|---|---|
| Rate (10 g/ha) | 31 | 32 | 33 | 34 | 50 | 53 | 54 | 55 | 56 | 57 | 60 | 61 | 62 | 63 | 67 |
| POSTEMERGENCE | | | | | | | | | | | | | | | |
| Barley | 5 | 5 | 4 | 4 | 3 | 4 | 4 | 5 | 6 | 4 | 3 | 1 | 1 | 4 | 4 |
| Barnyardgrass | 4 | 3 | 4 | 4 | 3 | 3 | 3 | 2 | 3 | 3 | 3 | 2 | 2 | 3 | 5 |
| Bedstraw | 10 | 8 | 8 | 10 | 10 | 8 | 9 | 9 | 8 | 9 | 7 | 5 | 8 | 6 | 8 |
| Blackgrass | 4 | 4 | 4 | 4 | 6 | 5 | 5 | 5 | 6 | 4 | 3 | 2 | 1 | 4 | 4 |
| Cheatgrass | 5 | 4 | 4 | 4 | 5 | 5 | 5 | 6 | 5 | 4 | 3 | 2 | 1 | 4 | 5 |
| Chickweed | 10 | 10 | 10 | 10 | 9 | 9 | e | 9 | 9 | 8 | 3 | 2 | 0 | 5 | 7 |
| Cocklebur | 9 | 9 | 10 | 10 | 9 | 9 | 9 | 10 | 10 | 9 | 6 | 4 | 5 | 8 | 8 |
| Corn | 4 | 3 | 3 | 4 | 3 | 4 | 3 | 3 | — | 3 | 3 | 3 | 2 | 2 | 3 |
| Cotton | 10 | 10 | 10 | 10 | 9 | 10 | 10 | 10 | 10 | 10 | 9 | 9 | 10 | 9 | 10 |
| Crabgrass | 4 | 3 | 3 | 3 | 3 | 3 | 2 | 2 | 4 | 2 | 2 | 2 | 1 | 3 | 5 |
| Giant foxtail | 5 | 4 | 4 | 4 | 4 | 3 | 4 | 4 | 4 | 5 | 3 | 2 | 1 | 3 | 5 |
| Lambsquarter | 10 | 10 | 9 | 9 | 9 | 10 | 10 | 10 | 10 | 9 | 10 | 9 | 8 | 9 | 9 |
| Morningglory | 9 | 10 | 9 | 9 | 10 | 9 | 9 | 10 | 10 | 10 | 7 | 7 | 6 | 8 | 10 |
| Nutsedge | 2 | 2 | 0 | — | 4 | 6 | 2 | 2 | 4 | 2 | 1 | 0 | 0 | 1 | 1 |
| Rape | 5 | 6 | 10 | 10 | 9 | 10 | 10 | 10 | 10 | 10 | 6 | 1 | 1 | 9 | 9 |
| Rice | 4 | 4 | 6 | 5 | 6 | 4 | 3 | 3 | 3 | 3 | 3 | 2 | 3 | 3 | 6 |
| Sorghum | 5 | 6 | 6 | 4 | 4 | 3 | 3 | 3 | 3 | 2 | 3 | 2 | 2 | 3 | 5 |
| Soybean | 7 | 7 | 8 | 8 | 6 | 9 | 8 | 7 | 9 | 6 | 6 | 2 | 2 | 6 | 8 |
| Sugar beet | 10 | 10 | 10 | 10 | 10 | 10 | 10 | 10 | 10 | 10 | 10 | 10 | 10 | 10 | 10 |
| Velvetleaf | 10 | 10 | 10 | 10 | 9 | 9 | 8 | 10 | 9 | 6 | 7 | 2 | 7 | 8 | 9 |
| Wheat | 5 | 5 | 3 | 5 | 4 | 7 | 6 | 8 | 7 | 7 | 3 | 2 | 2 | 4 | 5 |
| Wild buckwheat | 10 | 9 | 10 | 10 | 10 | 10 | 10 | 10 | 10 | 10 | 9 | 3 | 2 | 9 | 10 |
| Wild oat | 5 | 4 | 4 | 5 | 3 | 6 | 4 | 6 | 6 | 4 | 2 | 1 | 1 | 4 | 6 |
| PREEMERGENCE | | | | | | | | | | | | | | | |
| Barley | 0 | 0 | 0 | 0 | 0 | 1 | 0 | 0 | 0 | 0 | 0 | 0 | 0 | 0 | 0 |
| Barnyardgrass | 0 | 0 | 2 | 3 | 0 | 2 | 0 | 0 | 0 | 0 | 0 | 0 | 0 | 0 | 2 |
| Bedstraw | — | — | — | — | 3 | 8 | 8 | 3 | 4 | 6 | — | 0 | 7 | 4 | 0 |
| Blackgrass | 3 | 5 | 3 | 4 | 4 | 4 | 3 | 3 | 3 | 3 | 0 | 0 | 0 | 0 | 3 |
| Cheatgrass | 2 | 2 | 3 | 3 | 2 | 3 | 1 | 1 | 5 | 3 | 0 | 0 | 0 | 2 | 2 |
| Chickweed | — | 0 | — | — | 0 | 10 | 9 | 9 | 9 | 6 | — | — | — | 0 | 0 |
| Cocklebur | 0 | 0 | 0 | 0 | 0 | 0 | 0 | — | 2 | 0 | 0 | 0 | 0 | 0 | 0 |
| Cotton | 0 | 0 | 0 | 0 | 0 | 0 | 1 | 6 | 0 | 0 | 0 | 0 | 0 | 0 | 0 |
| Crabgrass | 0 | 2 | 2 | 3 | 0 | 2 | 0 | 0 | 0 | 0 | 0 | 0 | 0 | 0 | 0 |
| Giant foxtail | 0 | 2 | 2 | 3 | 0 | 2 | 0 | 2 | 0 | 0 | 0 | 0 | 0 | 0 | 0 |
| Lambsquarter | 9 | 9 | 9 | 9 | 10 | 10 | 10 | 10 | 10 | 8 | 9 | 5 | 5 | — | 9 |
| Morningglory | 0 | 0 | 2 | 2 | 0 | 7 | — | 2 | 2 | 5 | 0 | 0 | 0 | 0 | 1 |
| Nutsedge | 0 | 0 | 0 | 0 | 0 | 0 | 0 | 0 | 0 | 0 | 0 | 0 | 0 | 0 | 0 |
| Rape | 0 | 3 | 2 | 3 | 0 | 2 | 0 | 0 | — | 0 | 0 | 0 | 0 | 2 | 0 |
| Rice | 0 | 0 | 0 | 2 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 | 0 | 0 | 0 |
| Soybean | 0 | 0 | 0 | 6 | 0 | 0 | 0 | 0 | 0 | 0 | 0 | 0 | 0 | 0 | 0 |
| Sugar beet | 5 | 6 | 6 | 4 | 6 | 6 | 4 | 9 | 6 | 0 | 4 | 6 | 1 | 10 | 8 |
| Velvetleaf | 0 | 2 | 0 | 0 | 0 | 0 | 0 | 2 | 0 | 3 | 1 | 0 | 0 | 1 | 0 |
| Wheat | 0 | 0 | 0 | 0 | 0 | 2 | 1 | 0 | 2 | 0 | 0 | 0 | 0 | 0 | 0 |
| Wild buckwheat | 0 | — | 0 | 2 | 3 | 10 | 9 | 2 | 5 | 6 | 0 | 0 | 0 | 0 | 10 |
| Wild oat | 2 | 2 | 2 | 3 | 2 | 7 | 3 | 3 | 3 | 3 | 2 | 2 | 0 | 3 | 3 |

Test C

The compounds evaluated in this test were formulated in a non-phytoxic solvent and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barley (*Hordeum vulgare*), bedstraw (*Galium aparine*), blackgrass (*Alopecurus myosuroides*), chickweed (*Stellaria media*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), pigweed (*Amaranthusretroflexus*), rape (*Brassica napus*), ryegrass (*Lolium multiflorum*), sorghum (*Sorghum bicolor*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the preemergence portion-of this test. Plantings of these species were adjusted to produce plants of appropriate size for the post-emergence portion of the test. Plant species in the flood test consisted of rice (*Oryza sativa*), umbrella sedge (*Cyperus difformis*), duck salad (*Heteranthera limosa*) and barnyardgrass (*Echinochloa crus-galli*) grown to the 1 and 2 leaf stage for testing.

All plant species were grown using normal greenhouse practices. Visual evaluations of injury expressed on treated plants, when compared to untreated controls, were recorded approximately fourteen to twenty one days after application of the test compound. Plant response ratings, summarized in Table C, were recorded on a 0 to 100 scale where 0 is no effect and 100 is complete control. A dash (-) response means no test result.

TABLE C

| Rate (250 g/ha) | COMPOUND | | | | | | | | | | | |
|---|---|---|---|---|---|---|---|---|---|---|---|---|
| | 13 | 20 | 26 | 28 | 29 | 30 | 43 | 44 | 48 | 49 | 50 | 66 |
| POSTEMERGENCE | | | | | | | | | | | | |
| Barley Igri | 85 | 50 | 50 | 50 | 90 | 70 | 60 | 60 | 40 | 60 | 50 | 60 |
| Barnyardgrass 2 | — | — | — | — | — | — | — | 100 | 100 | 100 | — | 100 |
| Barnyardgrass | 100 | 100 | 100 | 100 | 100 | 100 | 100 | — | — | — | 100 | — |
| Bedstraw | 100 | 100 | 100 | 100 | 100 | 100 | 100 | 100 | 100 | 100 | 100 | 100 |
| Blackgrass | 98 | 70 | 70 | 70 | 90 | 80 | 90 | 80 | 60 | 70 | 60 | 80 |
| Chickweed | 70 | 100 | 100 | 80 | 95 | 70 | 100 | 100 | 80 | 80 | 100 | 100 |
| Corn | 100 | 70 | 50 | 90 | 50 | 40 | 90 | 90 | 50 | 50 | 60 | 60 |
| Cotton | 100 | 100 | 100 | 100 | 100 | 100 | 100 | 100 | 100 | 100 | 100 | 100 |
| Crabgrass | 100 | 60 | 40 | 50 | 50 | 20 | 60 | 50 | 40 | 40 | 50 | 50 |
| Downy Brome | 100 | 90 | 70 | 100 | 95 | 90 | 80 | 90 | 70 | 70 | 60 | 80 |
| Duck salad | 100 | 90 | 90 | 70 | 100 | 60 | 45 | 90 | 80 | 95 | 90 | 90 |
| Giant foxtail | 100 | 100 | 70 | 100 | 100 | 80 | 85 | 100 | 90 | 60 | 50 | 90 |
| Lambsquarters | 100 | 100 | 100 | 100 | 100 | 100 | 100 | 100 | 100 | 100 | 100 | 100 |
| Morningglory | 80 | 90 | 100 | 100 | 100 | 90 | 100 | 100 | 95 | 100 | 100 | 100 |
| Pigweed | 100 | 100 | 100 | 100 | 100 | 100 | 100 | 100 | 100 | 100 | 100 | 100 |
| Rape | 100 | 100 | 100 | 100 | 100 | 100 | 100 | 100 | 90 | 100 | 100 | 100 |
| Rice Japonica | 90 | 95 | 85 | 85 | 90 | 60 | 75 | 85 | 60 | 60 | 90 | 25 |
| Ryegrass | 100 | 80 | 50 | 70 | 90 | 80 | 85 | 90 | 50 | 60 | 50 | 75 |
| Sorghum | 100 | 40 | 50 | 100 | 50 | 40 | 100 | 100 | 70 | 60 | 50 | 60 |
| Soybean | 90 | 80 | 60 | 80 | 100 | 50 | 90 | 70 | 50 | 80 | 90 | 70 |
| Speedwell | 100 | 100 | 100 | — | — | — | — | — | — | 100 | — | 100 |
| Sugar beet | 100 | 100 | 100 | 100 | 100 | 100 | 80 | 100 | 100 | 100 | 100 | 100 |
| Umbrella sedge | 95 | 100 | 100 | 70 | 95 | 80 | 70 | 100 | 70 | 95 | 95 | 80 |
| Velvetleaf | 100 | 100 | 100 | 100 | 100 | 100 | 100 | 100 | 90 | 100 | 100 | 100 |
| Wheat | 90 | 60 | 60 | 100 | 95 | 90 | 60 | 80 | 50 | 70 | 60 | 70 |
| Wild buckwheat | 100 | 100 | 100 | 90 | 100 | 100 | 100 | 100 | 100 | 100 | 100 | 100 |
| Wild oat | 90 | 60 | 50 | 70 | 90 | 80 | 60 | 60 | 60 | 60 | 50 | 60 |

| Rate (250 g/ha) | COMPOUND | | | | |
|---|---|---|---|---|---|
| | 13 | 20 | 26 | 63 | 66 |
| PREEMERGENCE | | | | | |
| Barley Igri | 30 | 20 | 20 | 40 | 20 |
| Bedstraw | 80 | 50 | 100 | 100 | 90 |
| Blackgrass | 30 | 50 | 40 | 90 | 70 |
| Chickweed | 0 | 100 | 100 | 50 | 80 |
| Corn | 10 | 40 | 30 | 30 | 60 |
| Cotton | 50 | 100 | 100 | 70 | 90 |
| Crabgrass | 100 | 100 | 60 | 70 | 100 |
| Downy Brome | 50 | 30 | 20 | 50 | 70 |
| Giant foxtail | 100 | 100 | 100 | 75 | 100 |
| Lambsquarters | 100 | 100 | 100 | 100 | 100 |
| Morningglory | 0 | — | 100 | 100 | 60 |
| Pigweed | 100 | 100 | 100 | 100 | 100 |
| Rape | 50 | 20 | 30 | 100 | 30 |
| Ryegrass | 60 | 50 | 20 | 80 | 70 |
| Sorghum | 30 | 100 | 50 | 20 | 30 |
| Soybean | 0 | 100 | 100 | 20 | 20 |
| Speedwell | 100 | 100 | 100 | 100 | 100 |
| Sugar beet | 100 | 100 | 100 | 100 | 100 |
| Velvetleaf | 100 | 100 | 100 | 100 | 100 |
| Wheat | 60 | 40 | 10 | 50 | 70 |
| Wild buckwheat | 100 | 100 | 100 | 100 | 100 |
| Wild oat | 30 | 30 | 30 | 85 | 30 |

| Rate (125 g/ha) | COMPOUND | | | | | | | |
|---|---|---|---|---|---|---|---|---|
| | 13 | 36 | 39 | 40 | 41 | 42 | 52 | 58 | 59 |
| POSTEMERGENCE | | | | | | | | | |
| Barley Igri | 70 | 50 | 40 | 40 | 60 | 40 | 50 | 60 | 60 |
| Barnyardgrass 2 | — | — | — | — | — | 60 | 100 | 100 | 100 |
| Barnyardgrass | 100 | 100 | 95 | 100 | 100 | — | — | — | — |
| Bedstraw | 100 | 100 | 100 | 60 | 90 | 100 | 100 | 100 | 100 |

TABLE C-continued

| | | | | | | | | | |
|---|---|---|---|---|---|---|---|---|---|
| Blackgrass | 80 | 70 | 40 | 70 | 60 | 30 | 60 | 85 | 70 |
| Chickweed | 20 | 100 | 70 | 90 | 100 | 60 | — | 100 | 90 |
| Corn | 60 | 60 | 30 | 30 | 50 | 40 | 50 | 65 | 65 |
| Cotton | 100 | 100 | 100 | 100 | 100 | 100 | 100 | 100 | 100 |
| Crabgrass | 70 | 60 | 30 | 10 | 30 | 40 | 70 | 70 | 70 |
| Downy Brome | 100 | 50 | 40 | 60 | 60 | 50 | 90 | 90 | 90 |
| Duck salad. | 95 | 50 | 0 | 85 | 30 | 20 | 85 | 85 | 80 |
| Giant foxtail | 100 | 85 | 60 | 70 | 50 | 70 | 85 | 100 | 90 |
| Lambsquarters | 100 | 100 | 100 | 100 | 100 | 100 | — | 100 | 95 |
| Moringglory | 70 | 100 | 100 | 70 | 100 | 100 | 100 | 100 | 85 |
| Pigweed | 100 | 100 | 100 | 100 | 100 | 90 | 100 | 100 | 100 |
| Rape | 100 | 100 | 70 | 70 | 100 | 100 | 100 | 100 | 100 |
| Rice Japonica | 85 | 50 | 30 | 40 | 85 | 40 | 60 | 50 | 40 |
| Ryegrass | 70 | 50 | 20 | 40 | 40 | 40 | 60 | 85 | 80 |
| Sorghum | 70 | 70 | 60 | 50 | 50 | 70 | 60 | 85 | 70 |
| Soybean | 80 | 100 | 70 | 60 | 100 | 80 | 70 | 85 | 70 |
| Speedwell | 100 | — | 100 | 100 | 100 | 100 | 100 | 100 | 100 |
| Sugar beet | 100 | 100 | 100 | 100 | 100 | 100 | 100 | 100 | 100 |
| Umbrella sedge | 90 | 80 | 70 | 70 | 90 | 90 | 80 | 100 | 0 |
| Velvetleaf | 100 | 100 | 100 | 100 | 100 | 100 | 100 | 100 | 100 |
| Wheat | 80 | 50 | 20 | 50 | 60 | 40 | 50 | 60 | 70 |
| Wild buckwheat | 100 | 100 | 100 | 100 | 100 | 100 | 100 | 100 | 100 |
| Wild oat | 70 | 50 | 30 | 40 | 50 | 30 | 60 | 75 | 60 |

| | COMPOUND | | | |
|---|---|---|---|---|
| Rate (125 g/ha) | 13 | 52 | 58 | 59 |
| PREEMERGENCE | | | | |
| Barley Igri | 20 | 10 | 30 | 10 |
| Bedstraw | 70 | 80 | 70 | 70 |
| Blackgrass | 0 | 50 | 70 | 90 |
| Chickweed | 0 | 20 | 70 | 30 |
| Corn | 10 | 0 | 30 | 0 |
| Cotton | 0 | 0 | 40 | 50 |
| Crabgrass | 100 | 80 | 100 | 90 |
| Downy Brome | 30 | 50 | 70 | 60 |
| Giant foxtail | 100 | 90 | 100 | 90 |
| Lambsquarters | 100 | 100 | 100 | 100 |
| Moringglory | 0 | 0 | 30 | 10 |
| Pigweed | 100 | 100 | 100 | 100 |
| Rape | 20 | 60 | 70 | 40 |
| Ryegrass | 30 | 50 | 100 | 90 |
| Sorghum | 20 | 10 | 20 | 20 |
| Soybean | 0 | 0 | 0 | 0 |
| Speedwell | 100 | 100 | 100 | 100 |
| Sugar beet | 100 | 100 | 100 | 100 |
| velvetleaf | 100 | 100 | 100 | 100 |
| Wheat | 40 | 60 | 30 | 10 |
| Wild buckwheat | 100 | 100 | 100 | 100 |
| Wild oat | 20 | 20 | 75 | 30 |

| | COMPOUND | | | | | | | | | | | |
|---|---|---|---|---|---|---|---|---|---|---|---|---|
| Rate (62 g/ha) | 13 | 20 | 26 | 28 | 29 | 30 | 31 | 32 | 33 | 34 | 36 | 38 | 39 |
| POSTEMERGENCE | | | | | | | | | | | | | |
| Barley Igri | 40 | 50 | 40 | 40 | 60 | 50 | 50 | 50 | 60 | 40 | 30 | 50 | 30 |
| Barnyardgrass 2 | — | — | — | — | — | — | — | — | — | — | — | 100 | — |
| Barnyardgrass | 100 | 100 | 100 | 95 | 100 | 100 | 100 | 100 | 100 | 100 | 100 | — | 90 |
| Bedstraw | 80 | 100 | 100 | 100 | 100 | 100 | 100 | 100 | 100 | 100 | 100 | 90 | 70 |
| Blackgrass | 70 | 50 | 40 | 50 | 50 | 60 | 40 | 50 | 60 | 60 | 50 | 40 | 30 |
| Chickweed | 0 | 90 | 100 | 80 | 60 | 50 | 90 | 100 | 100 | 100 | 80 | 30 | 40 |
| Corn | 50 | 40 | 50 | 80 | 40 | 30 | 50 | 50 | 40 | 50 | 50 | 50 | 30 |
| Cotton | 100 | 100 | 100 | 100 | 100 | 100 | 100 | 100 | 100 | 100 | 100 | 100 | 100 |
| Crabgrass | 60 | 40 | 20 | 20 | 20 | 0 | 50 | 40 | 20 | 60 | 50 | 40 | 20 |
| Downy Brome | 80 | 70 | 50 | 60 | 80 | 60 | 40 | 50 | 60 | 50 | 40 | 40 | 30 |
| Duck salad | 95 | 80 | 70 | 30 | 95 | 40 | 40 | 60 | 80 | 40 | 30 | 50 | 0 |
| Giant foxtail | 70 | 70 | 50 | 100 | 70 | 50 | 40 | 70 | 70 | 70 | 75 | 50 | 30 |
| Lambsquarters | 100 | 100 | 100 | 80 | 100 | 90 | 95 | 100 | 100 | 100 | 100 | 70 | 100 |
| Moringglory | 70 | 70 | 70 | 100 | 80 | 80 | 100 | 100 | 100 | 100 | 100 | 95 | 100 |
| Pigweed | 100 | 100 | 100 | 100 | 100 | 100 | 100 | 100 | 100 | 100 | 100 | 100 | 100 |
| Rape | 100 | 100 | 100 | 100 | 100 | 100 | 100 | 100 | 100 | 100 | 100 | 80 | 60 |
| Rice Japonica | 70 | 90 | 80 | 65 | 70 | 50 | 50 | 75 | 85 | 90 | 40 | 30 | 30 |
| Ryegrass | 70 | 50 | 30 | 60 | 70 | 60 | 40 | 40 | 60 | 30 | 30 | 50 | — |
| Sorghum | 70 | 30 | 50 | 100 | 20 | 20 | 50 | 60 | 40 | 70 | 60 | 70 | 50 |
| Soybean | 60 | 80 | 60 | 70 | 60 | 50 | 80 | 90 | 100 | 100 | 80 | 60 | 60 |

TABLE C-continued

| | | | | | | | | | | | | | |
|---|---|---|---|---|---|---|---|---|---|---|---|---|---|
| Speedwell | 100 | 100 | 100 | — | — | — | — | — | — | — | — | — | 95 |
| Sugar beet | 100 | 100 | 100 | 100 | 100 | 100 | 100 | 100 | 100 | 100 | 100 | 100 | 100 |
| Umbrella sedge | 85 | 90 | 95 | 20 | 90 | 30 | 80 | 60 | 80 | 80 | 70 | 50 | 60 |
| Velvetleaf | 100 | 100 | 100 | 100 | 100 | 100 | 100 | 100 | 100 | 100 | 100 | 90 | 100 |
| Wheat | 60 | 50 | 40 | 70 | 80 | 60 | 40 | 50 | 60 | 50 | 50 | 50 | 10 |
| Wild buckwheat | 100 | 100 | 100 | 70 | 100 | 80 | 100 | 95 | 100 | 100 | 100 | 100 | 90 |
| Wild oat | 50 | 40 | 30 | 50 | 60 | 60 | 50 | 50 | 60 | 30 | 30 | 50 | 20 |

| | COMPOUND | | | | | | | | | | | | |
|---|---|---|---|---|---|---|---|---|---|---|---|---|---|
| Rate (62 g/ha) | 40 | 41 | 42 | 43 | 44 | 48 | 49 | 50 | 54 | 55 | 56 | 66 | 67 |
| POSTEMERGENCE | | | | | | | | | | | | | |
| Barley Igri | 30 | 50 | 30 | 50 | 40 | 30 | 40 | 40 | 50 | 50 | 50 | 50 | 50 |
| Barnyardgrass 2 | — | — | 40 | — | 100 | 95 | 100 | — | 100 | 100 | — | 100 | 95 |
| Barnyardgrass | 100 | 100 | — | 100 | — | — | — | 95 | — | — | — | — | — |
| Bedstraw | — | 80 | 100 | 70 | 80 | 100 | 70 | 100 | 100 | 100 | 100 | 100 | 80 |
| Blackgrass | 50 | 50 | 30 | 60 | 60 | 50 | 50 | 60 | 60 | 60 | 80 | 60 | 60 |
| Chickweed | 60 | 100 | 50 | 90 | 95 | 60 | 50 | 100 | 100 | 100 | 100 | 95 | 100 |
| Corn | 30 | 40 | 40 | 90 | 50 | 40 | 40 | 50 | 50 | 50 | 50 | 40 | 40 |
| Cotton | 100 | 100 | 100 | 100 | 100 | 100 | 100 | 100 | 100 | 100 | 100 | 100 | 100 |
| Crabgrass | 10 | 20 | 10 | 20 | 40 | 30 | 20 | 40 | 50 | 40 | 20 | 40 | 40 |
| Downy Brome- | 50 | 50 | 30 | 50 | 50 | 40 | 60 | 50 | 60 | 70 | 70 | 60 | 60 |
| Duck salad | 80 | 30 | 0 | 25 | 70 | 60 | 90 | 0 | 100 | 50 | — | 75 | 10 |
| Giant foxtail | 60 | 30 | 50 | 50 | 60 | 40 | 50 | 50 | 70 | 50 | 40 | 70 | 40 |
| Lambsquarters | 80 | 100 | 100 | 100 | 100 | 100 | 100 | 100 | 100 | 100 | 100 | 100 | 100 |
| Morningglory | 50 | 100 | 100 | 90 | 95 | 60 | 100 | 100 | 100 | 100 | 100 | 85 | 100 |
| Pigweed | 100 | 100 | 90 | 100 | 100 | 100 | 100 | 100 | 100 | 100 | 100 | 100 | 100 |
| Rape | 70 | 100 | 95 | 100 | 100 | 50 | 70 | 100 | 100 | 100 | 100 | 100 | 100 |
| Rice Japonica | 40 | 80 | 20 | 70 | 60 | 30 | 50 | 65 | 85 | 90 | — | 10 | 90 |
| Ryegrass | 30 | 30 | 30 | 50 | 50 | 30 | 50 | 40 | 60 | 60 | 50 | 50 | 60 |
| Sorghum | 30 | 40 | 60 | 100 | 60 | 50 | 50 | 50 | 60 | 60 | 60 | 50 | 60 |
| Soybean | 50 | 70 | 60 | 70 | 50 | 40 | 70 | 90 | 95 | 95 | 95 | 60 | 95 |
| Speedwell | 100 | 100 | 100 | — | — | — | 100 | 100 | 100 | 100 | 100 | 100 | 100 |
| Sugar beet | 100 | 100 | 100 | 60 | 100 | 100 | 100 | 100 | 100 | 100 | 100 | 100 | 100 |
| Umbrella sedge | 10 | 80 | 70 | 60 | 80 | 40 | 90 | 75 | 70 | 90 | — | 0 | 70 |
| Velvetleaf | 100 | 100 | 100 | 100 | 100 | 90 | 100 | 100 | 100 | 100 | 100 | 75 | 100 |
| Wheat | 40 | 50 | 30 | 50 | 50 | 30 | 50 | 50 | 60 | 60 | 60 | 60 | 60 |
| Wild buckwheat | 100 | 100 | 100 | 100 | 100 | 100 | 100 | 100 | 100 | 100 | 100 | 100 | 100 |
| Wild oat | 30 | 40 | 30 | 50 | 50 | 40 | 50 | 30 | 60 | 60 | 60 | 50 | 60 |

| | COMPOUND | | | | | | |
|---|---|---|---|---|---|---|---|
| Rate (62 g/ha) | 13 | 20 | 26 | 38 | 54 | 63 | 66 |
| PREEMERGENCE | | | | | | | |
| Barley Igri | 0 | 0 | 0 | 0 | 10 | 10 | 0 |
| Bedstraw | 70 | 50 | 100 | 50 | 50 | 100 | 80 |
| Blackgrass | 0 | 30 | 20 | 30 | 70 | 50 | 70 |
| Chickweed | 0 | 50 | 100 | — | 100 | 30 | 50 |
| Corn | 0 | — | 0 | 0 | 40 | 20 | 0 |
| Cotton | 0 | 0 | 0 | 0 | 40 | 20 | 40 |
| Crabgrass | 50 | 70 | 20 | 30 | 50 | 0 | 50 |
| Downy Brome | 20 | 20 | 0 | 0 | 30 | 20 | 30 |
| Giant foxtail | 100 | 100 | 70 | 0 | 60 | 20 | 20 |
| Lambsquarters | 100 | 100 | 100 | — | 100 | 95 | 100 |
| Morningglory | 0 | 20 | 20 | 20 | 20 | 40 | 10 |
| Pigweed | 100 | 100 | 100 | 100 | 100 | 100 | 100 |
| Rape | 0 | 20 | 20 | 30 | 10 | 85 | 20 |
| Ryegrass | 20 | — | 0 | 0 | 70 | 40 | 50 |
| Sorghum | 0 | 30 | 30 | 20 | 40 | 0 | 10 |
| Soybean | 0 | 0 | 0 | 0 | 10 | 0 | 0 |
| Speedwell | 100 | 100 | 100 | 20 | 100 | 100 | 100 |
| Sugar beet | 100 | 100 | 100 | 70 | 100 | 100 | 100 |
| Velvetleaf | 100 | 100 | 100 | 100 | 100 | 100 | 70 |
| Wheat | 0 | 20 | 0 | 0 | 50 | 0 | 30 |
| Wild buckwheat | 100 | 100 | 100 | 90 | 100 | 100 | 100 |
| Wild oat | 0 | 20 | 20 | 0 | 50 | 40 | 10 |

| | COMPOUND | | | | | | | |
|---|---|---|---|---|---|---|---|---|
| Rate (31 g/ha) | 13 | 36 | 39 | 40 | 41 | 42 | 52 | 58 | 59 |
| POSTEMERGENCE | | | | | | | | |
| Barley Igri | 40 | 30 | 30 | 30 | 40 | 30 | 40 | 50 | 50 |
| Barnyardgrass 2 | — | — | — | — | — | 20 | 100 | 100 | 100 |

TABLE C-continued

| | | | | | | | | | |
|---|---|---|---|---|---|---|---|---|---|
| Barnyardgrass | 100 | 100 | 80 | 100 | 100 | — | — | — | — |
| Bedstraw | 80 | 100 | 60 | 30 | 70 | 90 | 70 | — | 100 |
| Blackgrass | 50 | 40 | 10 | 30 | 40 | 20 | 40 | 65 | 50 |
| Chickweed | 0 | 80 | 30 | 30 | 90 | 40 | — | 100 | 70 |
| Corn | 40 | 40 | 30 | 30 | 40 | 30 | 40 | 50 | 50 |
| Cotton | 100 | 100 | 100 | 100 | 100 | 100 | 95 | 100 | 100 |
| Crabgrass | 60 | 30 | 10 | 10 | 10 | 10 | 40 | 60 | 40 |
| Downy Brome | 70 | 30 | 20 | 40 | 40 | 30 | 50 | 70 | 70 |
| Duck salad | 90 | 0 | 0 | 65 | 10 | 0 | 20 | 80 | 40 |
| Giant foxtail | 70 | 60 | 20 | 40 | 30 | 30 | 50 | 70 | 70 |
| Lambsquarters | 100 | 95 | 100 | 70 | 100 | 100 | — | 100 | 85 |
| Morningglory | 70 | 80 | 100 | 50 | 100 | 95 | 50 | 90 | 85 |
| Pigweed | 100 | 100 | 100 | 95 | 100 | 90 | 50 | 100 | 100 |
| Rape | 100 | 90 | 50 | 70 | 100 | 70 | 70 | 70 | 70 |
| Rice Japonica | 60 | 35 | 30 | 35 | 65 | 10 | 45 | 0 | 0 |
| Ryegrass | 20 | 30 | 10 | 20 | 20 | 20 | 40 | 60 | 40 |
| Sorghum | 40 | 50 | 30 | 20 | 30 | 50 | 50 | 50 | 60 |
| Soybean | 50 | 50 | 50 | 40 | 70 | 40 | 40 | 70 | 60 |
| Speedwell | 100 | — | 90 | 95 | 100 | 100 | 100 | 100 | 100 |
| Sugar beet | 100 | 100 | 100 | 100 | 100 | 100 | 100 | 100 | 100 |
| Umbrella sedge | 80 | 20 | 0 | 0 | 60 | 10 | 25 | 70 | 0 |
| Velvetleaf | 100 | 100 | 100 | 90 | 100 | 100 | 100 | 80 | 90 |
| Wheat | 50 | 30 | 10 | 30 | 50 | 20 | 30 | 50 | 60 |
| Wild buckwheat | 80 | 70 | 70 | 50 | 100 | 70 | 80 | 100 | 100 |
| Wild oat | 30 | 20 | 20 | 20 | 30 | 10 | 30 | 50 | 40 |

| | COMPOUND | | | |
|---|---|---|---|---|
| Rate (31 g/ha) | 13 | 52 | 58 | 59 |
| PREEMERGENCE | | | | |
| Barley Igri | 0 | 0 | 0 | 0 |
| Bedstraw | 20 | 10 | 50 | 50 |
| Blackgrass | 0 | 0 | 60 | 50 |
| Chickweed | 0 | 0 | 10 | 10 |
| Corn | 0 | 0 | 0 | 0 |
| Cotton | 0 | 0 | 10 | 10 |
| Crabgrass | 30 | 10 | 50 | 30 |
| Downy Brome | 0 | 0 | 30 | 30 |
| Giant foxtail | 90 | 30 | 60 | 50 |
| Lambsquarters | 100 | 50 | 100 | 100 |
| Morningglory | 0 | 0 | 0 | 10 |
| Pigweed | 100 | 100 | 100 | 100 |
| Rape | 0 | 10 | 10 | 0 |
| Ryegrass | 0 | 10 | 50 | 50 |
| Sorghum | 0 | 0 | 10 | 10 |
| Soybean | 0 | 0 | 0 | 0 |
| Speedwell | 100 | 20 | 100 | 100 |
| Sugar beet | 100 | 70 | 90 | 50 |
| Velvetleaf | 100 | 100 | 100 | 95 |
| Wheat | 0 | 0 | 10 | 0 |
| Wild buckwheat | 90 | 10 | 100 | 50 |
| Wild oat | 0 | 0 | 10 | 0 |

| | COMPOUND | | | | | | | | | | | | |
|---|---|---|---|---|---|---|---|---|---|---|---|---|---|
| Rate (16 g/ha) | 20 | 26 | 28 | 29 | 30 | 31 | 32 | 33 | 34 | 36 | 38 | 39 | 40 |
| POSTEMERGENCE | | | | | | | | | | | | | |
| Barley Igri | 40 | 20 | 30 | 40 | 30 | 40 | 30 | 50 | 40 | 20 | 40 | 20 | 20 |
| Barnyardgrass 2 | — | — | — | — | — | — | — | — | — | — | 75 | — | — |
| Barnyardgrass | 100 | 100 | 50 | 100 | 95 | 90 | 100 | 95 | 95 | 100 | — | 50 | 100 |
| Bedstraw | 70 | 80 | 100 | 100 | 70 | 100 | 100 | 100 | 100 | 90 | 50 | — | 30 |
| Blackgrass | 40 | 40 | 30 | 30 | 20 | 30 | 30 | 50 | 50 | 30 | 20 | 10 | 20 |
| Chickweed | 60 | 80 | 50 | 40 | 20 | 80 | 90 | 85 | 100 | 70 | 20 | 20 | 30 |
| Corn | 25 | 40 | 25 | 20 | 20 | 40 | 40 | 30 | 40 | 30 | 40 | 20 | 30 |
| Cotton | 100 | 100 | 100 | 100 | 100 | 100 | 100 | 100 | 100 | 100 | 90 | 100 | 100 |
| Crabgrass | 20 | 0 | 0 | 20 | 0 | 30 | 30 | 0 | 30 | 20 | 30 | 10 | 10 |
| Downy Brome | 50 | 40 | 40 | 60 | 40 | 40 | 40 | 60 | 40 | 20 | 30 | 10 | 30 |
| Duck salad | 75 | 60 | 0 | 85 | 30 | 40 | 30 | 65 | 0 | 0 | 20 | 0 | 0 |
| Giant foxtail | 20 | 40 | 60 | 20 | 20 | 30 | 50 | 20 | 40 | 50 | 40 | 10 | 30 |
| Lambsquarters | 80 | 80 | 80 | 60 | 70 | 100 | 100 | 80 | 100 | 90 | 70 | 70 | 70 |
| Morningglory | 70 | 70 | 80 | 80 | 50 | 100 | 100 | 90 | 100 | 80 | 95 | 60 | 50 |
| Pigweed | 100 | 100 | 100 | 100 | 100 | 100 | 100 | 100 | 100 | 100 | 100 | 90 | 90 |
| Rape | 80 | 90 | 70 | 100 | 80 | 95 | 95 | 100 | 100 | 85 | 40 | 20 | 50 |
| Rice Japonica | 50 | 65 | 45 | 65 | 40 | 35 | 30 | 60 | 35 | 20 | 10 | 20 | 35 |
| Ryegrass | 20 | 20 | 40 | 60 | 40 | 30 | 30 | 50 | 30 | 20 | 30 | 10 | 10 |

TABLE C-continued

| | | | | | | | | | | | | |
|---|---|---|---|---|---|---|---|---|---|---|---|---|
| Sorghum | 20 | 30 | 50 | 0 | 0 | 50 | 50 | 20 | 50 | 40 | 60 | 20 | 20 |
| Soybean | 60 | 50 | 30 | 50 | 20 | 60 | 70 | 80 | 100 | 50 | 40 | 30 | 40 |
| Speedwell | 100 | 100 | — | — | — | — | — | — | — | — | — | 90 | 90 |
| Sugar beet | 100 | 100 | 100 | 90 | 100 | 100 | 100 | 100 | 100 | 95 | 100 | 100 | 100 |
| Umbrella sedge | 70 | 70 | 0 | 30 | 25 | 0 | 70 | 70 | 60 | 0 | 20 | 0 | 0 |
| Velvetleaf | 100 | 100 | 100 | 100 | 60 | 100 | 100 | 100 | 100 | 100 | 80 | 100 | 90 |
| Wheat | 40 | 20 | 60 | 30 | 30 | 30 | 30 | 50 | 40 | 20 | 30 | 10 | 20 |
| Wild buckwheat | 70 | 80 | 60 | 90 | 70 | 100 | 90 | — | 100 | 70 | 100 | — | 50 |
| Wild oat | 20 | 30 | 30 | 40 | 40 | 30 | 30 | 50 | 20 | 10 | 30 | 10 | 20 |

| | COMPOUND | | | | | | | | | | | |
|---|---|---|---|---|---|---|---|---|---|---|---|---|
| Rate (16 g/ha) | 41 | 42 | 43 | 44 | 48 | 49 | 50 | 54 | 55 | 56 | 66 | 67 |

POSTEMERGENCE

| | | | | | | | | | | | | |
|---|---|---|---|---|---|---|---|---|---|---|---|---|
| Barley Igri | 30 | 20 | 40 | 30 | 20 | 20 | 30 | 50 | 40 | 50 | 30 | 30 |
| Barnyardgrass 2 | — | 0 | — | 100 | 40 | 100 | — | 95 | 90 | — | 90 | 90 |
| Barnyardgrass | 90 | — | 95 | — | — | — | 70 | — | — | — | — | — |
| Bedstraw | 70 | 80 | 60 | 80 | 40 | 50 | 60 | 100 | 100 | 95 | 85 | 80 |
| Blackgrass | 40 | 10 | 30 | 40 | 30 | 40 | 50 | 50 | 50 | 65 | 40 | 50 |
| Chickweed | 90 | 20 | 80 | 80 | 30 | 50 | 80 | 100 | 100 | 100 | 70 | 95 |
| Corn | 40 | 20 | 50 | 40 | 30 | 30 | 40 | 40 | 50 | 40 | 30 | 30 |
| Cotton | 100 | 100 | 90 | 100 | 100 | 90 | 100 | 100 | 100 | 100 | 85 | 100 |
| Crabgrass | 10 | 10 | 20 | 30 | 20 | 10 | 20 | 30 | 30 | 10 | 20 | 30 |
| Downy Brome | 30 | 20 | 40 | 40 | 20 | 40 | 40 | 50 | 60 | 60 | 40 | 60 |
| Duck salad | 0 | 0 | 0 | 30 | 10 | 70 | 0 | 35 | 10 | — | 30 | 0 |
| Giant foxtail | 20 | 30 | 50 | 40 | 30 | 40 | 50 | 40 | 40 | 30 | 50 | 30 |
| Lambsquarters | 85 | 100 | 100 | 100 | 60 | 100 | 100 | 75 | 100 | 100 | 80 | 100 |
| Morningglory | 70 | 90 | 60 | 70 | 50 | 50 | 100 | 100 | 100 | 100 | 50 | 100 |
| Pigweed | 90 | 90 | 100 | 100 | 90 | 100 | 100 | 100 | 100 | 100 | 100 | 100 |
| Rape | 95 | 50 | 100 | 70 | 30 | 60 | 50 | 100 | 100 | 100 | 60 | 90 |
| Rice Japonica | 45 | 0 | 60 | 30 | 20 | 30 | 60 | 55 | 70 | — | 0 | 50 |
| Ryegrass | 10 | 10 | 40 | 30 | 20 | 40 | 30 | 40 | 40 | 40 | 30 | 50 |
| Sorghum | 20 | 40 | 60 | 40 | 40 | 40 | 50 | 50 | 50 | 50 | 40 | 40 |
| Soybean | 60 | 20 | 50 | 30 | 30 | 50 | 70 | 85 | 90 | 90 | 50 | 80 |
| Speedwell | 100 | 95 | — | — | — | 100 | 100 | 100 | 100 | 100 | 100 | 100 |
| Sugar beet | 100 | 100 | 40 | 100 | 100 | 100 | 100 | 100 | 100 | 100 | 100 | 100 |
| Umbrella sedge | 60 | 0 | 0 | 60 | 10 | 70 | 0 | 10 | 70 | — | 0 | 30 |
| Velvetleaf | 100 | 100 | 100 | 90 | 80 | 90 | 100 | 100 | 100 | 100 | 65 | 100 |
| Wheat | 40 | 10 | 40 | 30 | 20 | 20 | 30 | 60 | 50 | 60 | 40 | 50 |
| Wild buckwheat | 95 | 60 | 100 | 90 | 85 | 100 | 80 | 100 | 100 | 100 | 100 | 100 |
| Wild oat | 20 | 10 | 40 | 30 | 30 | 40 | 20 | 40 | 40 | 50 | 20 | 50 |

| | COMPOUND | | | | | |
|---|---|---|---|---|---|---|
| Rate (16 g/ha) | 20 | 26 | 38 | 54 | 63 | 66 |

PREEMERGENCE

| | | | | | | |
|---|---|---|---|---|---|---|
| Barley Igri | 0 | 0 | 0 | 0 | 0 | 0 |
| Bedstraw | 20 | 60 | 20 | 30 | 10 | 20 |
| Blackgrass | 0 | 0 | 0 | 20 | 30 | 20 |
| Chickweed | 30 | 50 | — | 20 | 20 | 0 |
| Corn | 0 | 0 | 0 | 0 | 0 | 0 |
| Cotton | 0 | 0 | 0 | 0 | 0 | 0 |
| Crabgrass | 20 | 0 | 10 | 0 | 0 | 0 |
| Downy Brome | 0 | 0 | 0 | 20 | 0 | 0 |
| Giant foxtail | 80 | 30 | 0 | 0 | 0 | 0 |
| Lambsquarters | 100 | 100 | — | 100 | 20 | 70 |
| Morningglory | 0 | 0 | 0 | 0 | 10 | 0 |
| Pigweed | 100 | 100 | 90 | 100 | 100 | 90 |
| Rape | 0 | 0 | 20 | 0 | 20 | 0 |
| Ryegrass | 20 | 0 | 0 | 30 | 0 | 20 |
| Sorghum | 20 | 20 | 10 | 0 | 0 | 0 |
| Soybean | 0 | 0 | 0 | 0 | 0 | 0 |
| Speedwell | 100 | 100 | 0 | 100 | 90 | 90 |
| Sugar beet | 20 | 20 | 30 | 100 | 100 | 50 |
| Velvetleaf | 100 | 90 | 100 | 80 | 20 | 70 |
| Wheat | 0 | 0 | 0 | 10 | 0 | 0 |

TABLE C-continued

| | | | | | | | |
|---|---|---|---|---|---|---|---|
| Wild buckwheat | 70 | 80 | 20 | 100 | | 50 | 75 |
| Wild oat | 0 | 0 | 0 | 10 | | 0 | 0 |

| | COMPOUND | | | | COMPOUND | | |
|---|---|---|---|---|---|---|---|
| Rate (8 g/ha) | 52 | 58 | 59 | Rate (8 g/ha) | 52 | 58 | 59 |
| POSTEMERGENCE | | | | PREEMERGENCE | | | |
| Barley Igri | 20 | 40 | 40 | Barley Igri | 0 | 0 | 0 |
| Barnyardgrass 2 | 95 | 95 | 90 | Bedstraw | 0 | 10 | 0 |
| Barnyardgrass | — | — | — | Blackgrass | 0 | 20 | 20 |
| Bedstraw | 70 | 100 | 75 | Chickweed | 0 | — | 0 |
| Blackgrass | 20 | 50 | 30 | Corn | 0 | 0 | 0 |
| Chickweed | — | 70 | 40 | Cotton | 0 | 0 | 0 |
| Corn | 30 | 40 | 40 | Crabgrass | 0 | 0 | 0 |
| Cotton | 95 | 100 | 100 | Downy Brome | 0 | 0 | 0 |
| Crabgrass | 30 | 30 | 30 | Giant foxtail | 10 | 0 | 10 |
| Downy Brome | 20 | 40 | 50 | Lambsquarters | 0 | 100 | 95 |
| Duck salad | 0 | 20 | 0 | Morningglory | 0 | 0 | 0 |
| Giant foxtail | 40 | 40 | 40 | Pigweed | 50 | 100 | 100 |
| Lambsquarters | — | 85 | 70 | Rape | 0 | 0 | 0 |
| Morningglory | 30 | 70 | 70 | Ryegrass | 0 | 0 | 20 |
| Pigweed | 50 | 100 | 30 | Sorghum | 0 | 0 | 0 |
| Rape | 40 | 50 | 40 | Soybean | 0 | 0 | 0 |
| Rice Japonica | 20 | 0 | 0 | Speedwell | 0 | 100 | 50 |
| Ryegrass | 20 | 30 | 20 | Sugar beet | 0 | 85 | 30 |
| Sorghum | 40 | 50 | 40 | Velvetleaf | 30 | 40 | 40 |
| Soybean | 30 | 50 | 50 | Wheat | 0 | 0 | 0 |
| Speedwell | 30 | 70 | 100 | Wild buckwheat | 0 | 40 | 0 |
| Sugar beet | 70 | 100 | 100 | Wild oat | 0 | 0 | 0 |
| Umbrella sedge | 20 | 30 | 0 | | | | |
| Velvetleaf | 90 | 75 | 70 | | | | |
| Wheat | 20 | 40 | 40 | | | | |
| Wild buckwheat | 40 | 100 | 100 | | | | |
| Wild oat | 20 | 30 | 30 | | | | |

| | COMPOUND | | | | | | | | |
|---|---|---|---|---|---|---|---|---|---|
| Rate (4 g/ha) | 20 | 26 | 28 | 29 | 30 | 31 | 32 | 33 | 34 | 38 |
| POSTEMERGENCE | | | | | | | | | | |
| Barley Igri | 10 | 20 | 20 | 20 | 30 | 30 | 30 | 40 | 30 | 30 |
| Barnyardgrass 2 | — | — | — | — | — | — | — | — | — | 20 |
| Barnyardgrass | 90 | 100 | 35 | 100 | 85 | 65 | 55 | 65 | 75 | — |
| Bedstraw | 60 | 70 | 90 | 90 | 50 | 85 | 90 | 90 | 95 | 50 |
| Blackgrass | 20 | 30 | 20 | 20 | 10 | 20 | 30 | 50 | 30 | 10 |
| Chickweed | 40 | 50 | 20 | 10 | 10 | 20 | 60 | 60 | 75 | 10 |
| Corn | 25 | 30 | 20 | 20 | 20 | 30 | 30 | 30 | 30 | 20 |
| Cotton | 100 | 100 | 100 | 100 | 100 | 100 | 100 | 100 | 100 | 80 |
| Crabgrass | 0 | 0 | 0 | 0 | 0 | 20 | 20 | 0 | 20 | 20 |
| Downy Brome | 20 | 20 | 10 | 20 | 20 | 20 | 30 | 40 | 30 | 20 |
| Duck salad | 0 | 55 | 0 | 20 | 0 | 0 | 0 | 0 | 0 | 0 |
| Giant foxtail | 0 | 0 | 20 | 0 | 0 | 20 | 30 | 0 | 30 | 30 |
| Lambsquarters | 70 | 80 | 50 | 30 | 50 | — | 80 | 70 | 100 | 60 |
| Morningglory | 50 | 50 | 50 | 70 | 30 | 100 | 70 | 70 | 100 | 30 |
| Pigweed | 100 | 100 | 100 | 50 | 100 | 100 | 100 | 100 | 100 | 30 |
| Rape | 80 | 80 | 50 | 90 | 50 | 60 | 85 | 100 | 100 | 30 |
| Rice Japonica | 45 | 40 | 0 | 30 | 35 | 0 | 20 | 50 | 25 | 10 |
| Ryegrass | 0 | 20 | 20 | 30 | 20 | 20 | 20 | 40 | 20 | 10 |
| Sorghum | 20 | 20 | 20 | 0 | 0 | 40 | 40 | 20 | 40 | 30 |
| Soybean | 50 | 20 | 0 | 10 | 0 | 40 | 50 | 40 | 70 | 20 |
| Speedwell | 100 | 90 | — | — | — | — | — | — | — | — |
| Sugar beet | 100 | 100 | 100 | — | 80 | 100 | 100 | 100 | 80 | 70 |
| Umbrella sedge | 0 | 0 | 0 | 20 | 10 | 0 | 0 | 20 | 0 | 0 |
| Velvetleaf | 90 | 90 | 100 | 50 | 0 | 95 | — | 100 | 100 | 10 |
| Wheat | 40 | 20 | 40 | 20 | 20 | 30 | 30 | 40 | 30 | 20 |
| Wild buckwheat | 70 | 50 | 30 | 80 | 50 | 70 | 60 | 90 | 50 | 100 |
| Wild oat | 20 | 20 | 20 | 20 | 20 | 30 | 30 | 40 | 20 | 10 |

| | COMPOUND | | | | | | | | |
|---|---|---|---|---|---|---|---|---|---|
| Rate (4 g/ha) | 43 | 44 | 48 | 49 | 50 | 54 | 55 | 56 | 66 | 67 |
| POSTEMERGENCE | | | | | | | | | | |
| Barley Igri | 30 | 10 | 10 | 10 | 20 | 40 | 30 | 30 | 30 | 30 |
| Barnyardgrass 2 | — | 65 | 20 | 90 | — | 10 | 60 | — | 10 | 20 |

TABLE C-continued

| | | | | | | | | | | |
|---|---|---|---|---|---|---|---|---|---|---|
| Barnyardgrass | 45 | — | — | — | 60 | — | — | — | — | — |
| Bedstraw | 40 | 60 | 20 | 20 | 20 | 85 | 90 | 80 | 60 | 70 |
| Blackgrass | 20 | 30 | 20 | 10 | 30 | 40 | 40 | 40 | 20 | 40 |
| Chickweed | 60 | 30 | 10 | 20 | 30 | 75 | 70 | 80 | 30 | 70 |
| Corn | 20 | 30 | 10 | 10 | 30 | 30 | 40 | 30 | 30 | 20 |
| Cotton | 90 | 90 | 90 | 90 | 100 | 95 | 100 | 100 | 70 | 100 |
| Crabgrass | 10 | 20 | 10 | 10 | 20 | 20 | 10 | 0 | 10 | 20 |
| Downy Brome | 30 | 20 | 0 | 30 | 30 | 30 | 40 | 50 | 20 | 50 |
| Duck salad | 0 | 0 | 0 | 20 | 0 | 0 | 0 | — | 0 | 0 |
| Giant foxtail | 40 | 20 | 20 | 30 | 30 | 20 | 30 | 10 | 30 | 20 |
| Lambsquarters | 90 | 90 | 60 | 100 | 100 | 50 | 100 | 100 | 30 | 100 |
| Morningglory | 40 | 50 | 30 | 40 | 70 | 100 | 100 | 100 | 50 | 70 |
| Pigweed | 90 | 90 | 80 | 70 | 100 | 100 | 100 | 100 | 30 | 70 |
| Rape | 80 | 40 | 30 | 50 | 0 | 50 | 100 | 100 | 40 | 70 |
| Rice Japonica | 35 | 10 | 10 | 10 | 25 | 0 | 30 | — | 0 | 0 |
| Ryegrass | 30 | 20 | 10 | 20 | 20 | 30 | 30 | 40 | 10 | 40 |
| Sorghum | 40 | 30 | 30 | 30 | 50 | 40 | 40 | 30 | 30 | 30 |
| Soybean | 40 | 10 | 30 | 40 | 60 | 65 | 70 | 60 | 20 | 50 |
| Speedwell | — | — | — | 85 | 70 | 100 | 100 | 100 | 100 | 100 |
| Sugar beet | 30 | 80 | 100 | 100 | 100 | 100 | 100 | 100 | 80 | 100 |
| Umbrella sedge | 0 | 30 | 10 | 40 | 0 | 0 | 30 | — | 0 | 0 |
| Velvetleaf | 50 | 80 | 30 | 50 | 90 | 100 | 100 | 100 | 60 | 85 |
| Wheat | 20 | 20 | 10 | 10 | 20 | 40 | 40 | 50 | 20 | 30 |
| Wild buckwheat | 60 | 70 | 60 | 100 | 20 | 100 | 100 | 100 | 100 | 70 |
| Wild oat | 20 | 20 | 20 | 20 | 20 | 30 | 30 | 40 | 10 | 30 |

| | COMPOUND | | | | | |
|---|---|---|---|---|---|---|
| Rate (4 g/ha) | 20 | 26 | 38 | 54 | 63 | 66 |
| PREEMERGENCE | | | | | | |
| Barley Igri | 0 | 0 | 0 | 0 | 0 | 0 |
| Bedstraw | 0 | 20 | 0 | 0 | 0 | 0 |
| Blackgrass | 0 | 0 | 0 | 10 | 10 | 0 |
| Chickweed | 0 | 50 | — | 0 | 10 | 0 |
| Corn | 0 | 0 | 0 | 0 | 0 | 0 |
| Cotton | 0 | 0 | 0 | 0 | 0 | 0 |
| Crabgrass | 0 | 0 | 0 | 0 | 0 | 0 |
| Downy Brome | 0 | 0 | 0 | 0 | 0 | 0 |
| Giant foxtail | 30 | 0 | 0 | 0 | 0 | 0 |
| Lambsquarters | 90 | 80 | — | 60 | 10 | 0 |
| Morningglory | 0 | 0 | 0 | 0 | 0 | 0 |
| Pigweed | 20 | 30 | 0 | 90 | 0 | 0 |
| Rape | 0 | 0 | 10 | 0 | 0 | 0 |
| Ryegrass | 0 | 0 | 0 | 0 | 0 | 0 |
| Sorghum | 0 | 0 | 0 | 0 | 0 | 0 |
| Soybean | 0 | 0 | 0 | 0 | 0 | 0 |
| Speedwell | 80 | 90 | 0 | 100 | 0 | 0 |
| Sugar beet | 0 | 0 | 0 | 10 | 10 | 0 |
| Velvetleaf | 50 | 50 | 20 | 0 | 0 | — |
| Wheat | 0 | 0 | 0 | 0 | 0 | 0 |
| Wild buckwheat | 30 | 20 | 0 | 0 | 0 | 0 |
| Wild oat | 0 | 0 | 0 | 0 | 0 | 0 |

| | COMPOUND | | | | COMPOUND | | |
|---|---|---|---|---|---|---|---|
| Rate (2 g/ha) | 52 | 58 | 59 | Rate (2 g/ha) | 52 | 58 | 59 |
| POSTEMERGENCE | | | | PREEMERGENCE | | | |
| Barley Igri | 10 | 30 | 30 | Barley Igri | 0 | 0 | 0 |
| Barnyardgrass 2 | 25 | 0 | 0 | Bedstraw | 0 | 0 | 0 |
| Barnyardgrass | — | — | — | Blackgrass | 0 | 0 | 0 |
| Bedstraw | 50 | 60 | 50 | Chickweed | 0 | 10 | 0 |
| Blackgrass | 10 | 20 | 20 | Corn | 0 | 0 | 0 |
| Chickweed | — | 20 | 20 | Cotton | 0 | 0 | 0 |
| Corn | 20 | 40 | 30 | Crabgrass | 0 | 0 | 0 |
| Cotton | 70 | 95 | 95 | Downy Brome | 0 | 0 | 0 |
| Crabgrass | 10 | 20 | 10 | Giant foxtail | 0 | 0 | 0 |
| Downy Brome | 10 | 20 | 20 | Lambsquarters | 0 | 0 | 0 |
| Duck salad | 0 | 0 | 0 | Morningglory | 0 | 0 | 0 |
| Giant foxtail | 20 | 20 | 20 | Pigweed | 0 | 0 | 0 |
| Lambsquarters | — | 50 | 30 | Rape | 0 | 0 | 0 |
| Morningglory | 20 | 50 | 70 | Ryegrass | 0 | 0 | 0 |
| Pigweed | 20 | 90 | 30 | Sorghum | 0 | 0 | 0 |
| Rape | 10 | 30 | 20 | soybean | 0 | 0 | 0 |
| Rice Japonica | 0 | 0 | 0 | Speedwell | 0 | 0 | — |
| Ryegrass | 10 | 10 | 10 | Sugar beet | 0 | 10 | 0 |

TABLE C-continued

| | | | | | | | | |
|---|---|---|---|---|---|---|---|---|
| Sorghum | 30 | 30 | 20 | Velvetleaf | 0 | 0 | 0 | |
| Soybean | 10 | 50 | 30 | Wheat | 0 | 0 | 0 | |
| Speedwell | — | 40 | 100 | Wild buckwheat | 0 | 0 | 0 | |
| Sugar beet | 70 | 100 | 90 | Wild oat | 0 | 0 | 0 | |
| Umbrella sedge | 10 | 25 | 90 | | | | | |
| Velvetleaf | 50 | 40 | 50 | | | | | |
| Wheat | 10 | 30 | 10 | | | | | |
| Wild buckwheat | — | 100 | 100 | | | | | |
| Wild oat | 10 | 20 | 10 | | | | | |

| | COMPOUND | | | | | | | | | |
|---|---|---|---|---|---|---|---|---|---|---|
| Rate (1 g/ha) | 31 | 32 | 33 | 34 | 38 | 50 | 54 | 55 | 56 | 67 |
| POSTEMERGENCE | | | | | | | | | | |
| Barley Igri | 20 | 20 | 20 | 20 | 10 | 0 | 30 | 20 | 30 | 20 |
| Barnyardgrass 2 | — | — | — | — | 10 | — | 0 | 10 | — | 0 |
| Barnyardgrass | 20 | 30 | 35 | 60 | — | — | — | — | — | — |
| Bedstraw | 75 | 85 | 80 | 30 | 20 | 10 | 65 | 30 | 70 | 40 |
| Blackgrass | 10 | 10 | 30 | 20 | 10 | 20 | 30 | 30 | 30 | 30 |
| Chickweed | — | 30 | 40 | 75 | 0 | 20 | 60 | 30 | 65 | 70 |
| Corn | 20 | 20 | 20 | 20 | 10 | 20 | 30 | 30 | 20 | 10 |
| Cotton | 90 | 95 | 100 | 100 | 60 | 70 | 70 | 90 | 100 | 95 |
| Crabgrass | 10 | 10 | 0 | 10 | 10 | 10 | 10 | 10 | 0 | 10 |
| Downy Brome | 10 | 20 | 30 | 20 | 10 | 0 | 10 | 30 | 40 | 20 |
| Duck salad | 0 | 0 | 0 | 0 | 0 | — | 0 | 0 | — | 0 |
| Giant foxtail | 10 | 20 | 0 | 20 | 20 | 20 | 10 | 20 | 10 | 10 |
| Lambsquarters | 40 | 70 | 50 | 80 | 60 | — | 10 | 100 | 85 | 100 |
| Morningglory | 70 | 50 | 50 | 60 | 20 | 50 | 60 | 80 | 50 | 50 |
| Pigweed | 95 | 95 | 100 | 90 | 10 | 85 | 95 | 100 | 100 | — |
| Rape | 30 | 60 | 100 | 85 | 20 | 0 | 50 | 60 | 100 | 70 |
| Rice Japonica | 0 | 0 | 20 | 20 | 0 | — | 0 | 10 | — | 0 |
| Ryegrass | 10 | 10 | 30 | 10 | 0 | 0 | 10 | 10 | 20 | 20 |
| Sorghum | 20 | 30 | 0 | 30 | 20 | 30 | 20 | 30 | 20 | 20 |
| Soybean | 30 | 20 | 30 | 50 | 20 | 40 | 50 | 40 | 40 | 30 |
| Speedwell | — | — | — | — | — | 0 | 100 | 60 | 100 | 90 |
| Sugar beet | 60 | 80 | 100 | — | 20 | 20 | 100 | 100 | 100 | 100 |
| Umbrella sedge | 0 | 0 | 10 | 0 | 0 | — | 0 | 10 | — | 0 |
| Velvetleaf | 85 | 100 | 70 | 100 | 10 | 70 | 70 | 80 | 100 | 70 |
| Wheat | 10 | 10 | 30 | 20 | 0 | 0 | 20 | 30 | 30 | 10 |
| Wild buckwheat | 70 | 30 | 80 | — | 40 | 0 | 100 | 60 | 100 | — |
| Wild oat | 10 | 20 | 30 | 10 | 0 | 10 | 20 | 20 | 30 | 10 |

| | COMPOUND | |
|---|---|---|
| Rate (1 g/ha) | 38 | 54 |
| PREEMERGENCE | | |
| Barley Igri | 0 | 0 |
| Bedstraw | 0 | 0 |
| Blackgrass | 0 | 0 |
| Chickweed | — | 0 |
| Corn | 0 | 0 |
| Cotton | 0 | 0 |
| Crabgrass | 0 | 0 |
| Downy Brome | 0 | 0 |
| Giant foxtail | 0 | 0 |
| Lambsquarters | — | 0 |
| Morningglory | 0 | 0 |
| Pigweed | 0 | 0 |
| Rape | 0 | 0 |
| Ryegrass | 0 | 0 |
| Sorghum | 0 | 0 |
| Soybean | 0 | 0 |
| Speedwell | 0 | 50 |
| Sugar beet | 0 | 0 |
| Velvetleaf | 0 | 0 |
| Wheat | 0 | 0 |
| Wild buckwheat | 0 | 0 |
| Wild oat | 0 | 0 |

Test D

Plastic pots were partially filled with silt loam soil. The soil was then saturated with water. Japonica rice (*Oryza sativa*) seedlings at the 2.0 to 2.5 leaf stage, seeds selected from barnyardgrass (*Echinochloa crus-galli*), duck salad (*Heteranthera limosa*), umbrella sedge (*Cyperus difformis*), and tubers selected from arrowhead (Sagittaria spp.), and waterchestnut (Eleocharis spp.), were planted into this soil.

After planting, water levels were raised to 3 cm above the soil surface and maintained at this level throughout the test. Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table D, are reported on a 0 to 100 scale where 0 is no effect and 100 is complete control. A dash (-) response means no test result.

TABLE D

| Rate (500 g/ha) | COMPOUND 52 | Rate (125 g/ha) | COMPOUND 52 |
|---|---|---|---|
| PADDY | | PADDY | |
| Arrowhead | 40 | Arrowhead | 40 |
| Barnyardgrass 2 | 100 | Barnyardgrass 2 | 100 |
| Duck salad | 100 | Duck salad | 80 |
| Japonica rice | 30 | Japonica rice | 25 |
| Umbrella sedge | 80 | Umbrella sedge | 20 |
| Waterchestnut | 65 | Waterchestnut | 25 |

| Rate (250 g/ha) | 52 |
|---|---|
| PADDY | |
| Arrowhead | 30 |
| Barnyardgrass 2 | 100 |
| Duck salad | 80 |
| Japonica rice | 25 |
| Umbrella sedge | 50 |
| Waterchestnut | 40 |

| | COMPOUND | | | | | | | | |
|---|---|---|---|---|---|---|---|---|---|
| Rate (64 g/ha) | 13 | 16 | 31 | 34 | 36 | 40 | 49 | 52 | 55 |
| PADDY | | | | | | | | | |
| Arrowhead | 55 | 85 | 100 | 100 | 0 | 0 | 0 | 10 | 30 |
| Barnyardgrass 2 | 100 | 100 | 60 | 50 | 100 | 100 | 100 | 100 | 100 |
| Duck salad | 100 | 90 | 0 | 60 | 60 | 45 | 10 | 10 | 10 |
| Japonica rice | 35 | 40 | 30 | 50 | 25 | 30 | 20 | 20 | 25 |
| Umbrella sedge | 80 | 80 | 75 | 80 | 80 | 80 | 50 | 0 | 80 |
| Waterchestnut | 80 | 90 | — | 20 | 20 | 60 | 20 | 15 | 20 |
| Rate (32 g/ha) | 13 | 16 | 31 | 34 | 36 | 40 | 49 | 52 | 55 |
| PADDY | | | | | | | | | |
| Arrowhead | 40 | 70 | 100 | 100 | 0 | 0 | — | 10 | 20 |
| Barnyardgrass 2 | 100 | 100 | 40 | 30 | 100 | 100 | 70 | 100 | 40 |
| Duck salad | 85 | 40 | 0 | 0 | 30 | 0 | 0 | 0 | 0 |
| Japonica rice | 30 | 35 | 25 | 40 | 20 | 20 | 15 | 20 | 25 |
| Umbrella sedge | 85 | 70 | 65 | 70 | 70 | 30 | 0 | 0 | 80 |
| Waterchestnut | 60 | 80 | — | 20 | 20 | 30 | 10 | 0 | 15 |

| | | | | | | | | |
|---|---|---|---|---|---|---|---|---|
| Rate (16 g/ha) | 13 | 16 | 31 | 34 | 36 | 40 | 49 | 55 |
| PADDY | | | | | | | | |
| Arrowhead | 80 | 70 | 85 | 90 | 0 | 0 | 0 | 20 |
| Barnyardgrass 2 | 100 | 100 | 30 | 20 | 80 | 70 | 30 | 10 |
| Duck salad | 35 | 0 | 0 | 0 | 20 | 0 | 0 | 0 |
| Japonica rice | 25 | 30 | 20 | 55 | 15 | 15 | 10 | 20 |
| Umbrella sedge | 65 | 50 | 20 | 50 | 60 | 15 | 0 | 20 |
| Waterchestnut | 30 | 60 | — | — | 20 | 30 | 0 | 10 |

| | COMPOUND | | | | | | | |
|---|---|---|---|---|---|---|---|---|
| Rate (8 g/ha) | 13 | 16 | 31 | 34 | 36 | 40 | 49 | 55 |
| PADDY | | | | | | | | |
| Arrowhead | 20 | 70 | 60 | 90 | 0 | 0 | 0 | 0 |
| Barnyardgrass 2 | 60 | 80 | 0 | 10 | 65 | 65 | 20 | 0 |
| Duck salad | 0 | 0 | 0 | 0 | 0 | 0 | 0 | 0 |
| Japonica rice | 20 | 25 | 15 | 30 | 10 | 10 | 10 | 10 |
| Umbrella sedge | 45 | 30 | 0 | 20 | 0 | 0 | 0 | 0 |
| Waterchestnut | 20 | 35 | — | 20 | 10 | 20 | 0 | 0 |
| Rate (4 g/ha) | 13 | 16 | 31 | 34 | 36 | 40 | 49 | 55 |
| PADDY | | | | | | | | |
| Arrowhead | 10 | 70 | 50 | 85 | 0 | 0 | 0 | 0 |
| Barnyardgrass 2 | 30 | 30 | 0 | 0 | 30 | 20 | 0 | 0 |
| Duck salad | 0 | 0 | 0 | 0 | 0 | 0 | 0 | 0 |
| Japonica rice | 10 | 20 | 10 | 20 | 10 | 10 | 10 | 10 |

TABLE D-continued

| | | | | | | | | |
|---|---|---|---|---|---|---|---|---|
| Umbrella sedge | 30 | 20 | 0 | 0 | 0 | 0 | 0 | 0 |
| Waterchestnut | 20 | — | — | 20 | 10 | 20 | 0 | 0 |

Test E

Plastic pots were partially filled with silt loam soil. The soil was then flooded with water, Japonica rice (*oryza sativa*) sprouted seeds and 1.5 leaf transplants were planted in the soil. Seeds of barnyardgrass (*Echinochloa crus-galli*) were planted in saturated soil and plants grown to the I leaf, 2 leaf and 3 leaf stages for testing. At testing, the water level for all plantings was raised to 2 cm above the soil surface.

Chemical treatments were formulated in a non-phytotoxic solvent and applied directly to the paddy water. Treated plants and controls were maintained in a greenhouse for approximately 21 days, after which all species were compared to controls and visually evaluated. Plant response ratings, summarized in Table E are reported on a 0 to 100 scale where 0 is no effect and 100 is complete control. A dash (-) response means no test result.

TABLE E

| | COMPOUND | | COMPOUND | | | | |
|---|---|---|---|---|---|---|---|
| Rate (1000 g/ha) | 13 | Rate (250 g/ha) | 13 | 15 | 16 | 34 | |
| Flood | | Flood | | | | | |
| Barnyardgrass 2 | 100 | Barnyardgrass 2 | 100 | 100 | 100 | 100 | |
| Barnyardgrass 3 | 100 | Barnyardgrass 3 | 100 | — | 100 | 95 | |
| Japonica 1 | 95 | Japonica 1 | 60 | 65 | 80 | 100 | |
| Japonica 2 | 98 | Japonica 2 | 45 | 25 | 50 | 95 | |

| | |
|---|---|
| Rate (500 g/ha) | 13 |
| Flood | |
| Barnyardgrass 2 | 100 |
| Barnyardgrass 3 | 100 |
| Japonica 1 | 75 |
| Japonica 2 | 85 |

| | COMPOUND | | | | | | | |
|---|---|---|---|---|---|---|---|---|
| Rate (125 g/ha) | 13 | 15 | 16 | 34 | 36 | 40 | 41 | 50 | 52 |
| Flood | | | | | | | | | |
| Barnyardgrass 2 | 100 | 100 | 100 | 100 | 100 | 85 | 98 | 55 | 100 |
| Barnyardgrass 3 | 100 | — | 100 | 50 | 75 | 50 | 55 | 60 | 100 |
| Japonica 1 | 70 | 25 | 60 | 98 | 25 | 20 | 95 | 75 | 55 |
| Japonica 2 | 50 | 20 | 45 | 60 | 20 | 20 | 55 | 45 | 40 |

| Rate (64 g/ha) | 13 | 15 | 16 | 34 | 36 | 40 | 41 | 49 | 50 | 52 | 55 |
|---|---|---|---|---|---|---|---|---|---|---|---|
| Flood | | | | | | | | | | | |
| Barnyardgrass 2 | 100 | 100 | 100 | 95 | 65 | 60 | 65 | 100 | 35 | 100 | 100 |
| Barnyardgrass 3 | 100 | — | 100 | 45 | 50 | 40 | 45 | 70 | 35 | 100 | 75 |
| Japonica 1 | 45 | 15 | 55 | 95 | 25 | 15 | 65 | 25 | 50 | 35 | 98 |
| Japonica 2 | 35 | 15 | 35 | 45 | 15 | 15 | 45 | 30 | 35 | 25 | 35 |

| Rate (32 g/ha) | 13 | 15 | 16 | 34 | 36 | 40 | 41 | 49 | 50 | 52 | 55 |
|---|---|---|---|---|---|---|---|---|---|---|---|
| Flood | | | | | | | | | | | |
| Barnyardgrass 2 | 100 | 100 | 98 | 90 | 55 | 45 | 55 | 90 | 25 | 100 | 80 |
| Barnyardgrass 3 | 100 | — | 95 | 45 | 40 | 35 | 35 | 55 | 20 | 65 | 50 |
| Japonica 1 | 30 | 10 | 30 | 85 | 20 | 15 | 45 | 0 | 40 | 20 | 85 |
| Japonica 2 | 30 | 10 | 20 | 30 | 15 | 20 | 30 | 30 | 30 | 20 | 25 |

| Rate (16 g/ha) | 13 | 15 | 16 | 34 | 36 | 40 | 41 | 49 | 50 | 52 | 55 |
|---|---|---|---|---|---|---|---|---|---|---|---|
| Flood | | | | | | | | | | | |
| Barnyardgrass 2 | 100 | 95 | 100 | 85 | 40 | 25 | 30 | 45 | 15 | 45 | 70 |
| Barnyardgrass 3 | 100 | — | 80 | 35 | 35 | 20 | 25 | 45 | 15 | 55 | 40 |
| Japonica 1 | 25 | 10 | 20 | 75 | 20 | 10 | 35 | 0 | 20 | 10 | 75 |
| Japonica 2 | 25 | 10 | 15 | 25 | 0 | 15 | 20 | 20 | 20 | 15 | 20 |

| Rate (8 g/ha) | 13 | 36 | 40 | 41 | 49 | 50 | 52 | 55 |
|---|---|---|---|---|---|---|---|---|
| Flood | | | | | | | | |
| Barnyardgrass 2 | 100 | 30 | 15 | 25 | 25 | 15 | 40 | 15 |
| Barnyardgrass 3 | 90 | 30 | 25 | 20 | 35 | 10 | 35 | 20 |
| Japonica 1 | 20 | 15 | 15 | 25 | 0 | 0 | 0 | 25 |
| Japonica 2 | 20 | 10 | 10 | 15 | 0 | 15 | 10 | 15 |

Test F

Compounds evaluated in this test were formulated in a non-phytoxic solvent and applied to the soil surface before plant seedlings emerged (preemergence application) and to plants that were in the one-to-four leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include winter barley (*Hordeum vulgare* cv. 'Igri'), blackgrass (*Alopecurus myosuroides*), chickweed (*Stellaria media*), downy brome (*Bromus tectorum*), field violet (*Viola arvensis*), galium (*Galium aparine*), green foxtail (*Setaria viridis*), kochia (*Kochia scoparia*), lambsquarters (*Chenopodium album*), speedwell (*Veronica persica*), rape (*Brassica napus*), ryegrass (*Lolium multiflorum*), sugar beet (*Beta vulgaris* cv. 'US1'), sunflower (*Helianthus annuus* cv. 'Russian Giant'), spring wheat (*Triticum aestivum* cv. 'ERA'), winter wheat (*Triticum aestivum* cv. 'Talent'), wild buckwheat (*Polygonum convolvulus*), wild mustard (*Sinapis arvensis*), wild oat (*Avena fatua*), and wild radish (*Raphanus raphanistrum*).

Blackgrass, galium and wild oat were treated at two growth stages. The first stage (1) was when the plants had two to three leaves. The second stage (2) was when the plants had approximately four leaves or in the initial stages of tillering. Treated plants and untreated controls were maintained in a greenhouse for approximately 21 to 28 days, after which all treated plants were compared to untreated controls and visually evaluated. Plant response ratings, summarized in Table F, are based upon a 0 to 100 scale where 0 is no effect and 100 is complete control. A dash response (-) means no test result.

TABLE F

| Rate (250 g/ha) | COMPOUND 26 | Rate (250 g/ha) | COMPOUND 13 | COMPOUND 26 |
|---|---|---|---|---|
| POSTEMERGENCE | | PREEMERGENCE | | |
| Blackgrass (1) | 30 | Blackgrass (1) | 95 | 40 |
| Blackgrass (2) | 15 | Blackgrass (2) | 40 | 40 |
| Chickweed | 100 | Chickweed | 30 | 100 |
| Downy brome | 10 | Downy brome | 100 | 40 |
| Field violet | 100 | Field violet | 100 | 100 |
| Galium (1) | 100 | Galium (1) | 100 | 100 |
| Galium (2) | 100 | Galium (2) | 100 | 100 |
| Green foxtail | 50 | Green foxtail | 100 | 100 |
| Kochia | 100 | Kochia | — | — |
| Lambsquarters | 100 | Lambsquarters | — | — |
| Persn Speedwell | 100 | Persn Speedwell | 100 | 100 |
| Rape | 100 | Rape | 60 | 100 |
| Ryegrass | 55 | Ryegrass | 60 | 80 |
| Sugar beet | 100 | Sugar beet | 100 | 100 |
| Sunflower | 60 | Sunflower | 0 | 60 |
| Wheat (Spring) | 20 | Wheat (Spring) | 55 | 20 |
| Wheat (Winter) | 20 | Wheat (Winter) | 20 | 20 |
| Wild buckwheat | 100 | Wild buckwheat | 100 | 100 |
| Wild mustard | 100 | Wild mustard | — | — |
| Wild oat (1) | 50 | Wild oat (1) | 50 | 30 |
| Wild oat (2) | 30 | Wild oat (2) | 80 | 50 |
| Wild radish | 60 | Wild radish | 100 | 100 |
| Winter Barley | 30 | Winter Barley | 20 | 20 |

| Rate (125 g/ha) | COMPOUND 26 | COMPOUND 50 | Rate (125 g/ha) | COMPOUND 13 | COMPOUND 26 |
|---|---|---|---|---|---|
| POSTEMERGENCE | | | PREEMERGENCE | | |
| Blackgrass (1) | 10 | 40 | Blackgrass (1) | 60 | 20 |
| Blackgrass (2) | 10 | 20 | Blackgrass (2) | 40 | 40 |
| Chickweed | 100 | 100 | Chickweed | 0 | 100 |
| Downy brome | 50 | 0 | Downy brome | 100 | 30 |
| Field violet | 100 | 100 | Field violet | 100 | 100 |
| Galium (1) | 100 | 100 | Galium (1) | 100 | 100 |
| Galium (2) | 100 | 100 | Galium (2) | 100 | 100 |
| Green foxtail | 80 | 50 | Green foxtail | 100 | 100 |
| Kochia | 100 | 100 | Kochia | — | 100 |
| Lambsquarters | 100 | 100 | Lambsquarters | — | 100 |
| Persn Speedwell | 100 | 100 | Persn Speedwell | 100 | 100 |
| Rape | 100 | 100 | Rape | 20 | 80 |
| Ryegrass | 30 | 10 | Ryegrass | 40 | 60 |
| Sugar beet | 100 | 100 | Sugar beet | 100 | 100 |
| Sunflower | 100 | 100 | Sunflower | 0 | 10 |
| Wheat (Spring) | 15 | 10 | Wheat (Spring) | 40 | 15 |
| Wheat (Winter) | 30 | 0 | Wheat (Winter) | 20 | 10 |

TABLE F-continued

| | | | | | | |
|---|---|---|---|---|---|---|
| Wild buckwheat | 100 | 100 | Wild buckwheat | 100 | | 100 |
| Wild mustard | 100 | 100 | Wild mustard | — | | 70 |
| Wild oat (1) | 45 | 0 | Wild oat (1) | 50 | | 20 |
| Wild oat (2) | 20 | 0 | Wild oat (2) | 50 | | 30 |
| Wild radish | 60 | 70 | Wild radish | 95 | | 70 |
| Winter Barley | 30 | 50 | Winter Barley | 20 | | 15 |

| | COMPOUND | | | | COMPOUND | | |
|---|---|---|---|---|---|---|---|
| Rate (64 g/ha) | 20 | 26 | 50 | Rate (64 g/ha) | 13 | 20 | 26 |
| POSTEMERGENCE | | | | PREEMERGENCE | | | |
| Blackgrass (1) | 10 | 0 | 0 | Blackgrass (1) | 20 | 40 | 0 |
| Blackgrass (2) | 5 | 10 | 0 | Blackgrass (2) | 0 | 20 | 0 |
| Chickweed | 60 | 100 | 100 | Chickweed | 0 | 60 | 100 |
| Downy brome | 20 | 30 | 0 | Downy brome | 60 | 30 | 0 |
| Field violet | 100 | 100 | 100 | Field violet | 100 | 100 | 100 |
| Galium (1) | 60 | 100 | 100 | Galium (1) | 100 | 0 | 100 |
| Galium (2) | 100 | 100 | 100 | Galium (2) | 100 | 30 | 100 |
| Green foxtail | 70 | 70 | 50 | Green foxtail | 100 | 100 | 100 |
| Kochia | 100 | 100 | 100 | Kochia | 0 | — | 100 |
| Lambsquarters | 90 | 100 | 100 | Lambsquarters | 100 | — | 100 |
| Persn Speedwell | 100 | 100 | 100 | Persn Speedwell | 100 | 100 | 100 |
| Rape | 100 | 100 | 100 | Rape | 100 | 0 | 60 |
| Ryegrass | 40 | 20 | 0 | Ryegrass | 35 | 30 | 40 |
| Sugar beet | 100 | 100 | 100 | Sugar beet | 100 | 100 | 100 |
| Sunflower | 100 | 60 | 60 | Sunflower | 0 | 40 | 0 |
| Wheat (Spring) | 15 | 15 | 0 | Wheat (Spring) | 10 | 10 | 0 |
| Wheat (Winter) | 20 | 20 | 0 | Wheat (Winter) | 0 | 10 | 0 |
| Wild buckwheat | 100 | 100 | 100 | Wild buckwheat | 70 | — | 100 |
| Wild mustard | 70 | 100 | 100 | Wild mustard | 30 | — | 80 |
| Wild oat (1) | 30 | 40 | 0 | Wild oat (1) | 20 | 20 | 10 |
| Wild oat (2) | 40 | 15 | 0 | Wild oat (2) | 0 | 10 | 20 |
| Wild radish | 100 | 60 | 55 | Wild radish | 80 | 100 | 40 |
| Winter Barley | 40 | 30 | 0 | Winter Barley | 0 | 10 | 0 |

| | COMPOUND | | | | | |
|---|---|---|---|---|---|---|
| Rate (32 g/ha) | 20 | 26 | 36 | 42 | 49 | 50 |
| POSTEMERGENCE | | | | | | |
| Blackgrass (1) | 5 | 0 | 5 | 0 | 0 | 0 |
| Blackgrass (2) | 0 | 0 | 20 | 0 | 10 | 0 |
| Chickweed | — | 90 | 100 | 0 | 60 | 100 |
| Downy brome | 10 | 0 | 5 | 0 | 10 | 0 |
| Field violet | 100 | 100 | 100 | 80 | 100 | 100 |
| Galium (1) | 60 | 50 | 60 | 60 | 40 | 100 |
| Galium (2) | 60 | 60 | 70 | 60 | 40 | 100 |
| Green foxtail | 50 | 60 | 50 | 60 | 60 | 0 |
| Kochia | 100 | 100 | 100 | 100 | 100 | 100 |
| Lambsquarters | 80 | 100 | 60 | 100 | 70 | 50 |
| Persn Speedwell | 100 | 100 | 100 | 100 | 100 | 100 |
| Rape | 40 | 100 | 100 | 100 | 20 | 100 |
| Ryegrass | 20 | 5 | 35 | 30 | 20 | 0 |
| Sugar beet | 100 | 100 | 100 | 100 | 100 | 100 |
| Sunflower | 100 | 20 | 60 | 100 | 0 | 60 |
| Wheat (Spring) | 15 | 15 | 20 | 10 | 20 | 0 |
| Wheat (Winter) | 20 | 15 | 50 | 10 | 20 | 0 |
| Wild buckwheat | 100 | 100 | 100 | — | 100 | 100 |
| Wild mustard | — | 100 | 100 | 100 | 100 | 70 |
| Wild oat (1) | 30 | 25 | 20 | 10 | 30 | 0 |
| Wild oat (2) | 40 | 15 | 20 | 10 | 20 | 0 |
| Wild radish | 100 | 60 | 100 | 20 | — | 50 |
| Winter Barley | 25 | 20 | 25 | 10 | 20 | 0 |

| | COMPOUND | | |
|---|---|---|---|
| Rate (32 g/ha) | 13 | 20 | 26 |
| PREEMERGENCE | | | |
| Blackgrass (1) | 10 | 40 | 0 |
| Blackgrass (2) | 0 | 0 | 0 |
| Chickweed | 0 | 50 | 50 |
| Downy brome | 20 | 0 | 0 |
| Field violet | 100 | 100 | 100 |
| Galium (1) | 100 | 0 | 100 |

TABLE F-continued

| | | | |
|---|---|---|---|
| Galium (2) | 100 | 0 | 100 |
| Green foxtail | 100 | 70 | 50 |
| Kochia | 0 | — | 80 |
| Lambsquarters | 100 | — | 100 |
| Persn speedwell | 100 | 100 | 100 |
| Rape | 0 | 0 | 20 |
| Ryegrass | 20 | 20 | 20 |
| Sugar beet | 100 | 100 | 70 |
| Sunflower | 0 | 0 | 0 |
| Wheat (Spring) | 0 | 0 | 0 |
| Wheat (Winter) | 0 | 0 | 0 |
| Wild buckwheat | 0 | 100 | 100 |
| Wild mustard | 30 | — | 50 |
| Wild oat (1) | 0 | 0 | 0 |
| Wild oat (2) | 0 | 10 | 0 |
| Wild radish | 0 | 95 | 0 |
| Winter Barley | 0 | 10 | 0 |

| | COMPOUND | | | | | |
|---|---|---|---|---|---|---|
| Rate (16 g/ha) | 20 | 26 | 36 | 42 | 49 | 50 |
| POSTEMERGENCE | | | | | | |
| Blackgrass (1) | 0 | 0 | 0 | 0 | 0 | 0 |
| Blackgrass (2) | 0 | 0 | 10 | 0 | 0 | 0 |
| Chickweed | 60 | 100 | 100 | 0 | 50 | 70 |
| Downy brome | 10 | 0 | 0 | 0 | 10 | 0 |
| Field violet | 100 | 100 | 100 | 70 | 60 | 100 |
| Galium (1) | — | 30 | 50 | 40 | 40 | 100 |
| Galium (2) | 45 | 100 | 60 | 60 | 40 | 100 |
| Green foxtail | 50 | 50 | 50 | 10 | 50 | 0 |
| Kochia | 100 | 100 | 60 | 100 | 100 | 100 |
| Lambsquarters | 70 | 50 | 60 | 100 | 50 | 30 |
| Persn Speedwell | 100 | 190 | 100 | 100 | 100 | 100 |
| Rape | 40 | 50 | 100 | 70 | 0 | 100 |
| Ryegrass | 10 | 0 | 20 | 0 | 0 | 0 |
| Sugar beet | 100 | 100 | 100 | 100 | — | 100 |
| Sunflower | 100 | 0 | 50 | 60 | 0 | 40 |
| Wheat (Spring) | 15 | 0 | 15 | 10 | 10 | 0 |
| Wheat (Winter) | 15 | 0 | 20 | 10 | 10 | 0 |
| Wild buckwheat | 100 | 100 | 100 | 100 | 100 | 40 |
| Wild mustard | 60 | 100 | 100 | 100 | — | 70 |
| Wild oat (1) | 20 | 0 | 20 | 0 | 20 | 0 |
| Wild oat (2) | 20 | 0 | 20 | 0 | 0 | 0 |
| Wild radish | 50 | 60 | 100 | 20 | 100 | 50 |
| Winter Barley | 20 | 0 | 20 | 10 | 10 | 0 |

| | COMPOUND | | |
|---|---|---|---|
| Rate (16 g/ha) | 13 | 20 | 26 |
| PREEMERGENCE | | | |
| Blackgrass (1) | 0 | 0 | 0 |
| Blackgrass (2) | 0 | 0 | 0 |
| Chickweed | 0 | — | 45 |
| Downy brome | 0 | 0 | 0 |
| Field violet | — | 100 | 70 |
| Galium (1) | 0 | 0 | 0 |
| Galium (2) | 0 | 0 | 40 |
| Green foxtail | 100 | 60 | 20 |
| Kochia | 0 | — | 80 |
| Lambsquarters | 40 | — | 80 |
| Persn Speedwell | 0 | 0 | 100 |
| Rape | 0 | 0 | 0 |
| Ryegrass | 0 | 0 | 0 |
| Sugar beet | — | 100 | 60 |
| Sunflower | 0 | 0 | 0 |
| Wheat (Spring) | 0 | 0 | 0 |
| Wheat (Winter) | 0 | 0 | 0 |
| Wild buckwheat | 0 | 100 | 30 |
| Wild mustard | — | — | 40 |
| Wild oat (1) | 0 | 0 | 0 |
| Wild oat (2) | 0 | 0 | 0 |

TABLE F-continued

| | | | |
|---|---|---|---|
| Wild radish | — | 0 | 0 |
| Winter Barley | 0 | 0 | 0 |

| | COMPOUND | | | | |
|---|---|---|---|---|---|
| Rate (8 g/ha) | 20 | 26 | 36 | 42 | 49 |

POSTEMERGENCE

| | | | | | |
|---|---|---|---|---|---|
| Blackgrass (1) | 0 | 0 | 0 | 0 | 0 |
| Blackgrass (2) | 0 | 0 | 0 | 0 | 0 |
| Chickweed | 40 | 40 | 100 | 0 | 20 |
| Downy brome | 10 | 0 | 0 | 0 | 0 |
| Field violet | 100 | 100 | 100 | 10 | 60 |
| Galium (1) | 30 | 0 | 50 | 40 | 35 |
| Galium (2) | 40 | 50 | 60 | 30 | 30 |
| Green foxtail | 40 | 0 | 40 | 0 | 20 |
| Kochia | — | 100 | 60 | 80 | 80 |
| Lambsquarters | 50 | 50 | 50 | 60 | — |
| Persn Speedwell | 100 | 60 | 100 | 100 | 60 |
| Rape | 20 | 0 | 40 | 40 | 0 |
| Ryegrass | 5 | 0 | 10 | 0 | 0 |
| Sugar beet | 100 | 100 | 100 | 100 | 100 |
| Sunflower | 100 | 0 | 40 | 30 | 0 |
| Wheat (Spring) | 15 | 0 | 15 | 0 | 0 |
| Wheat (Winter) | 15 | 0 | 20 | 10 | 10 |
| Wild buckwheat | 100 | 100 | — | 100 | 100 |
| Wild mustard | 40 | 70 | 100 | — | 100 |
| Wild oat (1) | 20 | 0 | 20 | 0 | 20 |
| Wild oat (2) | 20 | 0 | 10 | 0 | 0 |
| Wild radish | 50 | 20 | 100 | 10 | 10 |
| Winter Barley | 20 | 0 | 20 | 10 | 10 |

| | COMPOUND | | |
|---|---|---|---|
| Rate (8 g/ha) | 13 | 20 | 26 |

PREEMERGENCE

| | | | |
|---|---|---|---|
| Blackgrass (1) | 0 | 0 | 0 |
| Blackgrass (2) | 0 | 0 | 0 |
| Chickweed | 0 | 0 | 0 |
| Downy brome | 0 | 0 | 0 |
| Field violet | — | 100 | 0 |
| Galium (1) | 0 | 0 | 0 |
| Galium (2) | 0 | 0 | 20 |
| Green foxtail | 50 | 0 | 0 |
| Kochia | 0 | — | 0 |
| Lambsquarters | 0 | — | 70 |
| Persn speedwell | 0 | — | 80 |
| Rape | 0 | 0 | 0 |
| Ryegrass | 0 | 0 | 0 |
| Sugar beet | 0 | 70 | 50 |
| Sunflower | 0 | 0 | 0 |
| Wheat (Spring) | 0 | 0 | 0 |
| Wheat (Winter) | 0 | 0 | 0 |
| Wild buckwheat | 0 | 100 | 0 |
| Wild mustard | 0 | — | 0 |
| Wild oat (1) | 0 | 0 | 0 |
| Wild oat (2) | 0 | 0 | 0 |
| Wild radish | — | 0 | 0 |
| Winter Barley | 0 | 0 | 0 |

| | COMPOUND | | | | |
|---|---|---|---|---|---|
| Rate (4 g/ha) | 20 | 26 | 36 | 42 | 49 |

POSTEMERGENCE

| | | | | | |
|---|---|---|---|---|---|
| Blackgrass (1) | 0 | 0 | 0 | 0 | 0 |
| Blackgrass (2) | 0 | 0 | 0 | 0 | 0 |
| Chickweed | 40 | 30 | 50 | 0 | 0 |
| Downy brome | 10 | 0 | 0 | 0 | 0 |
| Field violet | 100 | 100 | 100 | 0 | — |
| Galium (1) | 0 | 0 | 20 | 0 | 30 |
| Galium (2) | 40 | 50 | 40 | 0 | 30 |
| Green foxtail | 30 | 0 | 0 | 0 | 0 |
| Kochia | — | 100 | 20 | 80 | 60 |
| Lambsquarters | 50 | — | 50 | 60 | 50 |

TABLE F-continued

| | | | | | |
|---|---|---|---|---|---|
| Persn Speedwell | 100 | 60 | 100 | 100 | 50 |
| Rape | 20 | 0 | — | 20 | 0 |
| Ryegrass | 0 | 0 | 0 | 0 | 0 |
| Sugar beet | 100 | 100 | 100 | — | 100 |
| Sunflower | 40 | 0 | 0 | 20 | 0 |
| Wheat (Spring) | 15 | 0 | 15 | 0 | 0 |
| Wheat (Winter) | 15 | 0 | 20 | 0 | 10 |
| Wild buckwheat | 50 | 100 | — | 60 | 100 |
| Wild mustard | 40 | 70 | 100 | 100 | 100 |
| Wild oat (1) | 10 | 0 | 10 | 0 | 10 |
| Wild oat (2) | 10 | 0 | 10 | 0 | 0 |
| Wild radish | 50 | 0 | 100 | 0 | 0 |
| Winter Barley | 15 | 0 | 20 | 10 | 0 |

| | COMPOUND | | |
|---|---|---|---|
| Rate (4 g/ha) | 13 | 20 | 26 |

PREEMERGENCE

| | | | |
|---|---|---|---|
| Blackgrass (1) | 0 | 0 | 0 |
| Blackgrass (2) | 0 | 0 | 0 |
| Chickweed | 0 | 0 | 0 |
| Downy brome | 0 | 0 | 0 |
| Field violet | — | 100 | 0 |
| Galium (1) | 0 | 0 | 0 |
| Galium (2) | 0 | 0 | 0 |
| Green foxtail | 0 | 0 | 0 |
| Kochia | 0 | — | 0 |
| Lambsquarters | 0 | — | 0 |
| Persn Speedwell | 0 | — | 50 |
| Rape | 0 | 0 | 0 |
| Ryegrass | 0 | 0 | 0 |
| Sugar beet | 0 | 20 | 0 |
| Sunflower | 0 | 0 | 0 |
| Wheat (Spring) | 0 | 0 | 0 |
| Wheat (Winter) | 0 | 0 | 0 |
| Wild buckwheat | 0 | 50 | 0 |
| Wild mustard | 0 | — | 0 |
| Wild oat (1) | 0 | 0 | 0 |
| Wild oat (2) | 0 | 0 | 0 |
| Wild radish | — | 0 | 0 |
| Winter Barley | 0 | 0 | 0 |

| | COMPOUND | |
|---|---|---|
| Rate (2 g/ha) | 42 | 49 |

POSTEMERGENCE

| | | |
|---|---|---|
| Blackgrass (1) | 0 | 0 |
| Blackgrass (2) | 0 | 0 |
| Chickweed | 0 | 0 |
| Downy brome | 0 | 0 |
| Field violet | 0 | — |
| Galium (1) | 0 | 0 |
| Galium (2) | 0 | 0 |
| Green foxtail | 0 | 0 |
| Kochia | 75 | 20 |
| Lambsquarters | 55 | — |
| Persn Speedwell | 100 | 50 |
| Rape | 0 | 0 |
| Ryegrass | 0 | 0 |
| Sugar beet | 100 | 70 |
| Sunflower | 0 | 0 |
| Wheat (Spring) | 0 | 0 |
| Wheat (Winter) | 0 | 0 |
| Wild buckwheat | 60 | 100 |
| Wild mustard | 40 | 90 |
| Wild oat (1) | 0 | 0 |
| Wild oat (2) | 0 | 0 |
| Wild radish | 0 | 0 |
| Winter Barley | 10 | 0 |

Test G

Seeds, rhizomes, or plant parts of alfalfa (*Medicago ativa*), annual bluegrass (*Poa annua*), bermudagrass (*Cynodon dactylon*), broadleaf signalgrass (*Brachiaria plantaginea*), common purslane (*Portulaca oleracea*), common ragweed (*Ambrosia elatior*), dallisgrass (*Paspalum* dilatatum), goosegrass (*Eleusine indica*), guineagrass (*Panicum maximum*), itchgrass (*Rottboellia exaltata*), johnsongrass (*Sorghum halepense*), large crabgrass (*Digitaria sanguinalis*), peanut (*Arachis hypoagaea*), pitted morningglory (*Ipomoea lacunosa*), purple nutsedge (*Cyperus rotundus*), sandbur (*Cenchrus echinatus*), smooth crabgrass (*Digitaria ischaemum*) and yellow nutsedge (*Cyperus esculentus*) were planted into greenhouse pots containing greenhouse planting medium. Each pot contained only one plant species.

The test compound was dissolved in a non-phytotoxic solvent and applied preemergence and/or postemergence to the plants. Preemergence applications were made within one day of planting the seeds or plant parts. Postemergence applications were applied when the plants were in the two to four leaf stage (three to twenty cm). Test chemicals were dissolved in a non-phytotoxic solvent and applied preemergence and postemergence to the plants. Untreated control plants and treated plants were placed in the greenhouse and visually evaluated for injury at 13 to 21 days after herbicide application. Plant response ratings, summarized in Table G, are based on a 0 to 100 scale where 0 is no injury and 100 is complete control. A dash (-) response indicates no test result.

TABLE G

| Rate (250 g/ha) | COMPOUND | | | | | | | | | | | | | | | | |
|---|---|---|---|---|---|---|---|---|---|---|---|---|---|---|---|---|---|
| | 14 | 16 | 18 | 20 | 21 | 22 | 23 | 24 | 25 | 26 | 28 | 29 | 30 | 31 | 32 | 33 | 34 |
| POSTEMERGENCE | | | | | | | | | | | | | | | | | |
| Alfalfa Var. | 10 | 30 | 70 | 50 | 0 | 0 | 0 | 20 | 0 | 50 | 0 | 70 | 0 | 10 | 0 | 0 | 60 |
| Ann Bluegrass | 0 | 0 | 20 | 0 | 0 | 0 | 0 | 0 | 0 | 0 | 0 | 0 | 0 | 0 | 0 | 0 | 0 |
| Bermudagrass | 0 | 0 | 70 | 0 | 0 | 0 | 0 | 0 | 0 | 0 | 0 | 0 | 0 | 0 | 0 | 0 | 0 |
| Brdlf Sgnlgrass | 0 | 0 | 0 | 0 | 0 | 0 | 0 | 0 | 0 | 0 | 0 | 0 | 0 | 0 | 0 | 0 | 0 |
| Cmn Purslane | 40 | 80 | 100 | 70 | 90 | 70 | 50 | 70 | 60 | 90 | 60 | 80 | 60 | 80 | 80 | 80 | 100 |
| Cmn Ragweed | 20 | 100 | 20 | 20 | 100 | 20 | 20 | 0 | 0 | 100 | 60 | 60 | 0 | 100 | 60 | 50 | 100 |
| Dallisgrass | 0 | 0 | 0 | 0 | 0 | 0 | 0 | 0 | 0 | 0 | 0 | 0 | 0 | 0 | 0 | 0 | 0 |
| Goosegrass | 0 | 0 | 0 | 0 | 0 | 0 | 0 | 0 | 0 | 0 | 0 | 0 | 0 | 0 | 0 | 0 | 0 |
| Guineagrass | 0 | 0 | 0 | 0 | 0 | 0 | 0 | 0 | 0 | 0 | 0 | 0 | 0 | 0 | 0 | 0 | 0 |
| Itchgrass | 0 | 0 | 0 | 0 | 0 | 0 | 0 | 0 | 0 | 0 | 0 | 0 | 0 | 20 | 0 | 0 | 0 |
| Johnsongrass | 0 | 0 | 0 | 0 | 0 | 0 | 0 | 0 | 0 | 0 | 0 | 0 | 0 | 0 | 0 | 0 | 0 |
| Large Crabgrass | 0 | 0 | 0 | 0 | 0 | 0 | 0 | 0 | 0 | 0 | 0 | 0 | 0 | 0 | 0 | 0 | 0 |
| Peanuts | 0 | 0 | 0 | 0 | 0 | 0 | 0 | 0 | 0 | 0 | 0 | 0 | 0 | 0 | 0 | 0 | 0 |
| Pit Morninglory | 0 | 40 | 0 | 0 | 20 | 0 | 0 | 30 | 0 | 40 | 0 | 70 | 20 | 50 | 30 | 100 | 50 |
| Purple Nutsedge | — | — | — | — | — | — | — | — | — | — | — | — | — | — | — | — | — |
| S. Sandbur | 0 | 0 | 80 | 0 | 0 | 0 | 0 | 0 | 0 | 0 | 0 | 0 | 0 | 0 | 0 | 0 | 0 |
| Smooth Crabgras | 20 | 0 | 0 | 0 | 0 | 0 | 0 | 0 | 0 | 0 | 0 | 0 | 0 | 0 | 0 | 0 | 0 |
| Yellow Nutsedge | — | — | — | — | — | — | — | — | — | — | — | — | — | — | — | — | — |

| Rate (250 g/ha) | COMPOUND | | | | | | | | | | | | | | | | |
|---|---|---|---|---|---|---|---|---|---|---|---|---|---|---|---|---|---|
| | 14 | 16 | 18 | 20 | 21 | 22 | 23 | 24 | 25 | 26 | 28 | 29 | 30 | 31 | 32 | 33 | 34 |
| PREEMERGENCE | | | | | | | | | | | | | | | | | |
| Alfalfa Var. | 0 | 60 | 0 | 0 | 0 | 0 | 0 | 0 | 0 | 60 | 0 | 0 | 0 | 30 | 0 | 0 | 100 |
| Ann Bluegrass | 0 | 0 | 0 | 0 | 0 | 0 | 0 | 0 | 0 | 0 | 0 | 0 | 0 | 0 | 0 | 0 | 50 |
| Bermudagrass | 0 | 0 | 0 | 0 | 0 | 0 | 50 | 0 | 0 | 0 | 0 | 50 | 0 | 0 | 0 | 0 | 0 |
| Brdlf Sgnlgrass | 0 | 30 | 0 | 0 | 0 | 0 | 0 | 0 | 0 | 0 | 0 | 0 | 0 | 0 | 0 | 0 | 0 |
| Cmn Purslane | 0 | 100 | 100 | 100 | 0 | 0 | 100 | 0 | 0 | 100 | 0 | 100 | 0 | 100 | 100 | 40 | 100 |
| Cmn Ragweed | 0 | 100 | 100 | 0 | 50 | 0 | 0 | 0 | 0 | 20 | 0 | 40 | 0 | 70 | 0 | 0 | 0 |
| Dallisgrass | 0 | 50 | 20 | 0 | 40 | 0 | 20 | 30 | 0 | 20 | 0 | 90 | 0 | 0 | 0 | 0 | 80 |
| Goosegrass | 0 | 60 | 80 | 100 | 70 | 0 | 40 | 40 | 0 | 20 | 0 | 100 | 30 | 0 | 0 | 0 | 30 |
| Guineagrass | 0 | 30 | 70 | 70 | 0 | 0 | 0 | 0 | 0 | 30 | 0 | 100 | 0 | 100 | 0 | 0 | 0 |
| Itchgrass | 0 | 100 | 30 | 30 | 0 | 0 | 0 | 20 | 0 | 50 | 0 | 40 | 0 | 70 | 0 | 0 | 20 |
| Johnsongrass | 0 | 0 | 0 | 0 | 0 | 0 | 0 | 0 | 0 | 0 | 0 | 0 | 0 | 0 | 0 | 0 | 0 |
| Large Crabgrass | 0 | 100 | 80 | 90 | 60 | 0 | 70 | 90 | 0 | 90 | 0 | 100 | 70 | 0 | 0 | 0 | 60 |
| Peanuts | 0 | 40 | 0 | 0 | 20 | 0 | 0 | 0 | 0 | 0 | 0 | 0 | 0 | 0 | 0 | 0 | 0 |
| Pit Morninglory | 0 | 40 | 0 | 0 | 20 | 0 | 0 | 50 | 0 | 20 | 0 | 30 | 0 | 0 | 0 | 0 | 30 |
| Purple Nutsedge | — | — | — | — | — | — | — | — | — | — | — | — | — | — | — | — | — |
| S. Sandbur | 0 | 0 | 20 | 0 | 0 | 0 | 0 | 0 | 0 | 0 | 0 | 0 | 0 | 0 | 0 | 0 | 0 |
| Smooth Crabgras | 0 | 100 | 40 | 70 | 20 | 0 | 20 | 0 | 0 | 40 | 0 | 100 | 0 | 0 | 0 | 0 | 80 |
| Yellow Nutsedge | — | — | — | — | — | — | — | — | — | — | — | — | — | — | — | — | — |

| Rate (125 g/ha) | COMPOUND | | | | | | | | | | | | | | | | |
|---|---|---|---|---|---|---|---|---|---|---|---|---|---|---|---|---|---|
| | 14 | 16 | 18 | 20 | 21 | 22 | 23 | 24 | 25 | 26 | 28 | 29 | 30 | 31 | 32 | 33 | 34 |
| POSTEMERGENCE | | | | | | | | | | | | | | | | | |
| Alfalfa Var. | 0 | 50 | 0 | 0 | 0 | 0 | 0 | 0 | 0 | 20 | 0 | 0 | 0 | 0 | 0 | 0 | 40 |
| Ann Bluegrass | 0 | 0 | 0 | 0 | 0 | 0 | 0 | 0 | 0 | 0 | 0 | 0 | 0 | 0 | 0 | 0 | 0 |
| Bermudagrass | 0 | 0 | 0 | 0 | 0 | 20 | 0 | 0 | 0 | 0 | 0 | 0 | 0 | 0 | 0 | 0 | 0 |
| Brdlf Sgnlgrass | 0 | 0 | 0 | 0 | 0 | 0 | 0 | 0 | 0 | 0 | 0 | 0 | 0 | 0 | 0 | 0 | 0 |
| Cmn Purslane | 50 | 100 | 80 | 100 | 70 | 80 | 70 | 80 | 100 | 100 | 30 | 90 | 70 | 100 | 100 | 100 | 100 |
| Cmn Ragweed | 30 | 100 | 60 | 40 | 0 | 70 | 60 | 50 | 50 | 80 | 100 | 20 | 40 | 100 | 100 | 80 | 70 |
| Dallisgrass | 0 | 0 | 0 | 0 | 0 | 0 | 0 | 0 | 0 | 0 | 0 | 0 | 0 | 0 | 0 | 0 | 0 |

TABLE G-continued

| | | | | | | | | | | | | | | | | | |
|---|---|---|---|---|---|---|---|---|---|---|---|---|---|---|---|---|---|
| Goosegrass | 0 | 0 | 0 | 0 | 0 | 0 | 0 | 0 | 0 | 0 | 0 | 0 | 0 | 0 | 0 | 0 | 0 |
| Guineagrass | 0 | 0 | 0 | 0 | 0 | 0 | 0 | 0 | 0 | 0 | 0 | 0 | 0 | 0 | 0 | 0 | 0 |
| Itchgrass | 0 | 0 | 0 | 0 | 0 | 0 | 0 | 0 | 0 | 0 | 0 | 0 | 0 | 0 | 0 | 0 | 0 |
| Johnsongrass | 0 | 0 | 0 | 0 | 0 | 0 | 0 | 0 | 0 | 0 | 0 | 0 | 0 | 0 | 0 | 0 | 0 |
| Large Crabgrass | 20 | 0 | 0 | 0 | 0 | 0 | 0 | 0 | 0 | 0 | 0 | 0 | 0 | 0 | 0 | 0 | 0 |
| Peanuts | 20 | 70 | 0 | 0 | 0 | 0 | 0 | 0 | 0 | 0 | 0 | 0 | 0 | 0 | 0 | 0 | 30 |
| Pit Morninglory | 0 | 70 | 0 | 0 | 0 | 20 | 0 | 0 | 0 | 0 | 0 | 0 | 0 | 50 | 70 | 30 | 30 |
| Purple Nutsedge | 0 | 10 | 0 | 0 | 0 | 0 | 0 | 0 | 0 | 0 | 0 | 0 | 0 | 10 | 10 | 10 | 20 |
| S. Sandbur | 0 | 0 | 0 | 0 | 0 | 0 | 0 | 0 | 0 | 0 | 0 | 0 | 0 | 0 | 0 | 0 | 0 |
| Smooth Crabgras | 0 | 0 | 0 | 0 | 0 | 0 | 0 | 0 | 0 | 0 | 0 | 0 | 0 | 0 | 0 | 0 | 0 |
| Yellow Nutsedge | 0 | 0 | 0 | 0 | 0 | 0 | 0 | 0 | 0 | 0 | 0 | 0 | 0 | 0 | 0 | 0 | 0 |

| | COMPOUND | | | | | | | | | | | | | | | | |
|---|---|---|---|---|---|---|---|---|---|---|---|---|---|---|---|---|---|
| Rate (125 g/ha) | 14 | 16 | 18 | 20 | 21 | 22 | 23 | 24 | 25 | 26 | 28 | 29 | 30 | 31 | 32 | 33 | 34 |
| PREEMERGENCE | | | | | | | | | | | | | | | | | |
| Alfalfa Var. | 0 | 0 | 0 | 0 | 0 | 0 | 0 | 0 | 0 | 0 | 0 | 0 | 0 | 0 | 0 | 0 | 0 |
| Ann Bluegrass | 0 | 0 | 0 | 0 | 30 | 0 | 0 | 30 | 0 | 0 | 0 | 0 | 0 | 0 | 0 | 0 | 0 |
| Bermudagrass | 0 | 80 | 0 | 0 | 20 | 0 | 0 | 30 | 0 | 0 | 0 | 0 | 0 | 0 | 0 | 0 | 0 |
| Brdlf Sgnlgrass | 0 | 0 | 0 | 0 | 0 | 0 | 0 | 100 | 0 | 0 | 0 | 0 | 0 | 0 | 0 | 0 | 0 |
| Cmn Purslane | 0 | 100 | 0 | 0 | 100 | 0 | 0 | 0 | 0 | 30 | 0 | 0 | 0 | 0 | 0 | 0 | 0 |
| Cmn Ragweed | 20 | 100 | 0 | 0 | 50 | 0 | 0 | 40 | 0 | 0 | 0 | 20 | 0 | 0 | 0 | 0 | 0 |
| Dallisgrass | 0 | 0 | 0 | 0 | 20 | 0 | 0 | 20 | 0 | 20 | 0 | 80 | 0 | 0 | 0 | 0 | 0 |
| Goosegrass | 0 | 100 | 0 | 0 | 100 | 0 | 90 | 90 | 0 | 70 | 0 | 90 | 0 | 0 | 0 | 0 | 0 |
| Guineagrass | 0 | 100 | 0 | 0 | 100 | 0 | 0 | 0 | 0 | 0 | 0 | 0 | 0 | 0 | 0 | 0 | 0 |
| Itchgrass | 0 | 20 | 0 | 0 | 60 | 0 | 0 | 100 | 0 | 0 | 0 | 100 | 0 | 0 | 0 | 0 | 0 |
| Johnsongrass | 0 | 0 | 0 | 0 | 30 | 0 | 0 | 0 | 0 | 0 | 0 | 0 | 0 | 0 | 0 | 0 | 0 |
| Large Crabgrass | 0 | 100 | 0 | 0 | 100 | 0 | 0 | 80 | 0 | 90 | 0 | 80 | 0 | 0 | 0 | 0 | 0 |
| Peanuts | 0 | — | 0 | 0 | 0 | 0 | 0 | 0 | 0 | — | 0 | 0 | 0 | 0 | 0 | 0 | 0 |
| Pit Morninglory | 0 | 0 | 0 | 0 | 0 | 0 | 0 | 0 | 0 | 0 | 0 | 0 | 0 | 0 | 0 | 0 | 0 |
| Purple Nutsedge | 0 | 0 | 0 | — | 0 | 0 | 0 | 0 | 0 | 0 | 0 | 0 | 0 | 0 | 0 | 0 | 0 |
| S. Sandbur | 0 | 50 | 0 | 0 | 0 | 0 | 0 | 40 | 0 | 0 | 0 | 0 | 0 | 0 | 0 | 0 | 0 |
| Smooth Crabgras | 0 | 70 | 0 | 0 | 70 | 0 | 0 | 0 | 0 | 0 | 0 | 0 | 0 | 0 | 0 | 0 | 0 |
| Yellow Nutsedge | 0 | 0 | 0 | 0 | 0 | 0 | 0 | 0 | 0 | 0 | 0 | 0 | 0 | 0 | 0 | 0 | 0 |

Test H

Seeds of barnyardgrass (*Echinochloa crus-galli*), black nightshade (*Solanum ptycanthum dunal*), cocklebur (*Xanthium pensylvanicum*), common ragweed (*Ambrosia elatior*), corn (*Zea mays*), cotton (*Gossypium hirsutam*), crabgrass (Digitaria spp.), giant foxtail (*Setaria faberii*), jimsonweed (*Datura stramonium*), johnson grass (*Sorghum halepense*), morningglory (Ipomoea spp.), smartweed (*Polygonum pensylvanicum*), soybean (*Glycine max*), velvetleaf (*Abutilon theophrasti*) and purple nutsedge (*Cyperus rotundus*) tubers were planted into a silt loam soil. These crops and weeds were grown in the greenhouse until the plants ranged in height from two to eighteen cm (one to four leaf stage), then treated postemergence with the test chemicals dissolved in a non-phytotoxic solvent. Pots receiving these postemergence treatments were placed in the greenhouse and maintained according to routine greenhouse procedures.

Treated plants and untreated controls were maintained in the greenhouse approximately 21 days after application of the test compound. Visual evaluations of plant injury responses were then recorded. Plant response ratings, summarized in Table H, are reported on a 0 to 10 scale where 0 is no effect and 10 is complete control.

TABLE H

| | COMPOUND | | COMPOUND |
|---|---|---|---|
| Rate (500 g/ha) | 13 | Rate (250 g/ha) | 13 |
| PREEMERGENCE | | PREEMERGENCE | |
| Barnyardgrass | 10 | Barnyardgrass | 10 |
| Black Nightshade | 10 | Black Nightshade | 10 |

TABLE H-continued

| | | | |
|---|---|---|---|
| Cocklebur | 8 | Cocklebur | 0 |
| Common Ragweed | 10 | Common Ragweed | 6 |
| Corn G4689A | 10 | Corn G4689A | 4 |
| Cotton | 7 | Cotton | 0 |
| Crabgrass | 10 | Crabgrass | 10 |
| Giant Foxtail | 10 | Giant Foxtail | 10 |
| Jimson weed | 10 | Jimson weed | 10 |
| Johnson Grass | 10 | Johnson Grass | 5 |
| Morningglory | 0 | Morningglory | 0 |
| Nutsedge | 2 | Nutsedge | 0 |
| Smartweed | 10 | Smartweed | 10 |
| Soybean | 2 | Soybean | 0 |
| Velvetleaf | 10 | Velvetleaf | 10 |

| | COMPOUND | | COMPOUND |
|---|---|---|---|
| Rate (125 g/ha) | 13 | Rate (16 g/ha) | 34 |
| PREEMERGENCE | | POSTEMERGENCE | |
| Barnyardgrass | 6 | Barnyardgrass | 0 |
| Black Nightshade | 10 | Black Nightshade | 10 |
| Cocklebur | 0 | Cocklebur | 10 |
| Common Ragweed | 4 | Common Ragweed | 2 |
| Corn G4689A | 0 | Corn G4689A | 2 |
| Cotton | 0 | Cotton | 10 |
| Crabgrass | 7 | Crabgrass | 0 |
| Giant Foxtail | 7 | Giant Foxtail | 0 |
| Jimson weed | 10 | Jimson weed | 10 |
| Johnson Grass | 5 | Johnson Grass | 0 |
| Morningglory | 0 | Morningglory | 10 |
| Nutsedge | 0 | Nutsedge | 0 |
| Smartweed | 10 | Smartweed | 8 |
| Soybean | 0 | Soybean | 10 |

TABLE H-continued

| | Velvetleaf | 10 | Velvetleaf | 10 |

| Rate (62 g/ha) | COMPOUND 13 | Rate (31 g/ha) | COMPOUND 13 |
|---|---|---|---|
| PREEMERGENCE | | PREEMERGENCE | |
| Barnyardgrass | 0 | Barnyardgrass | 0 |
| Black Nightshade | 10 | Black Nightshade | 8 |
| Cocklebur | 0 | Cocklebur | 0 |
| Common Ragweed | 1 | Common Ragweed | 0 |
| Corn G4689A | 0 | Corn G4689A | 0 |
| Cotton | 0 | Cotton | 0 |
| Crabgrass | 3 | Crabgrass | 0 |
| Giant Foxtail | 4 | Giant Foxtail | 0 |
| Jimson weed | 2 | Jimson weed | 0 |
| Johnson Grass | 0 | Johnson Grass | 0 |
| Morningglory | 0 | Morningglory | 0 |
| Nutsedge | 0 | Nutsedge | 0 |
| Smartweed | 2 | Smartweed | 0 |
| Soybean | 0 | Soybean | 0 |
| Velvetleaf | 8 | Velvetleaf | 6 |

| Rate (8 g/ha) | COMPOUND 34 | Rate (4 g/ha) | COMPOUND 34 |
|---|---|---|---|
| POSTEMERGENCE | | POSTEMERGENCE | |
| Barnyardgrass | 0 | Barnyardgrass | 0 |
| Black Nightshade | 10 | Black Nightshade | 5 |
| Cocklebur | 10 | Cocklebur | 5 |
| Common Ragweed | 1 | Common Ragweed | 0 |
| Corn G4689A | 1 | Corn G4689A | 1 |
| Cotton | 10 | Cotton | 10 |
| Crabgrass | 0 | Crabgrass | 0 |
| Giant Foxtail | 0 | Giant Foxtail | 0 |
| Jimson weed | 10 | Jimson weed | 10 |
| Johnson Grass | 0 | Johnson Grass | 0 |
| Morningglory | 10 | Morningglory | 10 |
| Nutsedge | 0 | Nutsedge | 0 |
| Smartweed | 7 | Smartweed | 5 |
| Soybean | 7 | Soybean | 7 |
| Velvetleaf | 10 | Velvetleaf | 10 |

Test I

Plastic pots were partially filled with clay loam soil. Tansplanted seedlings of Japonica rice (*Oryza sative*) and seeds of barnyardgrass (*Echinoghloa oryzicola*) were planted in flooded pots. Plants were then grown to the 2 leaf, 2.5 leaf and 3 leaf stages for testing. At test, water levels for all plantings were kept to 3 cm above the soil surface. Chemical treatments were formulated in a non-phytotoxic solvent and applied directly to the paddy water. Treated plants and controls were maintained in a greenhouse for approximately 21 to 28 days, after which all species were compared to controls and visually evaluated. Plant response ratings, summarized in Table I are reported on a 0 to 10 scale where 0 is no effect and 10 is complete control.

TABLE I

| | COMPOUND | | | | COMPOUND | | |
|---|---|---|---|---|---|---|---|
| Rate (64 g/ha) | 13 | 15 | 16 | Rate (16 g/ha) | 13 | 15 | 16 |
| FLOOD | | | | FLOOD | | | |
| Barnyardgrass 2.5 | 6 | 3 | 5 | Barnyardgrass 2.5 | 3 | 1 | 2 |
| Barnyardgrass 2 | 8 | 3 | 6 | Barnyardgrass 2 | 6 | 2 | 4 |
| Rice 1 | 4 | 2 | 6 | Rice 1 | 2 | 1 | 3 |
| Rice 2 | 4 | 3 | 6 | Rice 2 | 3 | 2 | 4 |
| Rate (32 g/ha) | 13 | 15 | 16 | Rate (8 g/ha) | 13 | 15 | 16 |
| FLOOD | | | | FLOOD | | | |
| Barnyardgra 2.5 | 3 | 2 | 4 | Barnyardgra 2.5 | 2 | 1 | 2 |
| Barnyardgrass 2 | 7 | 2 | 5 | Barnyardgrass 2 | 2 | 0 | 5 |
| Rice 1 | 2 | 2 | 5 | Rice 1 | 2 | 2 | 3 |
| Rice 2 | 3 | 2 | 5 | Rice 2 | 3 | 1 | 3 |

What is claimed is:

1. A compound of Formula I

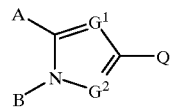

I wherein

Q is

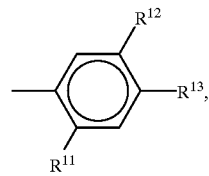

Q-1

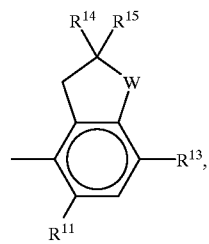

Q-2

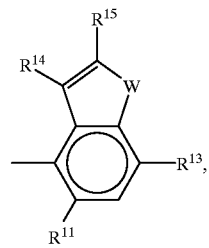

Q-3

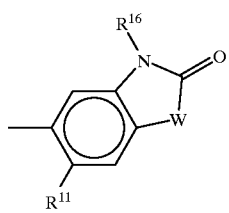

Q-4

-continued

Q-5

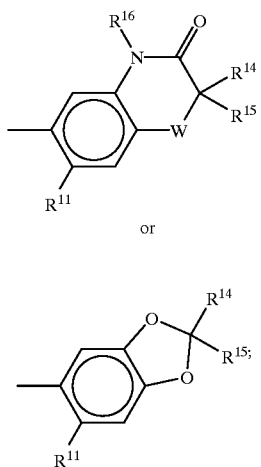

or

Q-6

$G^1$ is $CR^1$ or N;

$G^2$ is $CR^4$ or N;

A is $C_1$–$C_4$ alkyl, $C_1$–$C_4$ haloalkyl, $C_2$–$C_4$ alkenyl, $C_2$–$C_4$ alkynyl, $OR^{10}$, $SR^{10}$ or halogen;

B is $C_1$–$C_4$ alkyl, $C_1$–$C_4$ haloalkyl, $C_3$–$C_4$ alkenyl or $C_3$–$C_4$ alkynyl;

A and B can be taken together as X—Y—Z to form a fused ring such that X is connected to nitrogen and Z is connected to carbon;

X is $CHR^2$, $CH_2CH_2$ or $CR^2$=$CR^3$;

Y is $CHR^5$, $CR^5$=$CR^6$, $CHR^5CHR^6$, $NR^7$, O or $S(O)_n$;

Z is $CHR^8$, $CH_2CH_2$, $CR^8$=$CR^9$, $NR^7$, O or $S(O)_n$;

n is 0, 1 or 2;

$R^1$ and $R^4$ are independently halogen or CN;

$R^2$, $R^3$, $R^5$, $R^6$, $R^8$ and $R^9$ are independently H, halogen, $C_1$–$C_4$ alkyl or $C_1$–$C_4$ haloalkyl;

$R^7$ is H, $C_1$–$C_4$ alkyl or $C_1$–$C_4$ haloalkyl;

W is O or S;

$R^{10}$ is $C_1$–$C_4$ alkyl or $C_1$–$C_4$ haloalkyl;

$R^{11}$ is halogen;

$R^{12}$ is H, $C_1$–$C_8$ alkyl, $C_1$–$C_8$ haloalkyl, halogen, OH, $OR^{17}$, SH, $S(O)_nR^{17}$, $COR^{17}$, $CO_2R^{17}$, $C(O)SR^{17}$, $CH_2CHR^{27}CO_2R^{17}$, $C(O)NR^{19}R^{20}$, CHO, $CR^{19}$=$NOR^{26}$, CH=$CR^{27}CO_2R^{17}$, $CO_2N$=$CR^{21}R^{22}$, $NO_2$, CN, $NHSO_2R^{23}$, $NHSO_2NHR^{23}$, $NR^{17}R^{28}$, $NH_2$ or phenyl optionally substituted with $R^{29}$;

$R^{13}$ is $C_1$–$C_2$ alkyl, $C_1$–$C_2$ haloalkyl, $OCH_3$, $SCH_3$, $OCHF_2$, halogen, CN or $NO_2$;

$R^{14}$ is H, $C_1$–$C_3$ alkyl or halogen;

$R^{15}$ is H, $C_1$–$C_3$ alkyl, halogen, $C_1$–$C_3$ haloalkyl, cyclopropyl, vinyl, $C_2$ alkynyl, CN, $C(O)R^{28}$, $CO_2R^{28}$, $C(O)NR^{28}R^{30}$, $CR^{24}R^{25}CN$, $CR^{24}R^{25}C(O)R^{28}$, $CR^{24}R^{25}CO_2R^{28}$, $CR^{24}R^{25}C(O)NR^{28}R^{30}$, $CHR^{24}OH$, $CHR^{24}OC(O)R^{28}$ or $OCHR^{24}OC(O)NR^{28}R^{30}$;

when Q is Q-2 or Q-6, $R^{14}$ and $R^{15}$ together with the carbon to which they are attached can be C=O;

$R^{16}$ is H, $C_1$–$C_6$ alkyl, $C_1$–$C_6$ haloalkyl, $C_2$–$C_6$ alkoxyalkyl, $C_3$–$C_6$ alkenyl, $C_3$–$C_6$ alkynyl or

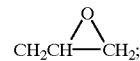

$R^{17}$ is $C_1$–$C_8$ alkyl; $C_3$–$C_8$ cycloalkyl; $C_3$–$C_8$ alkenyl; $C_3$–$C_8$ alkynyl; $C_1$–$C_8$ haloalkyl; $C_2$–$C_8$ alkoxyalkyl; $C_2$–$C_8$ alkylthioalkyl; $C_2$–$C_8$ alkylsulfinylalkyl; $C_2$–$C_8$ alkylsulfonylalkyl; $C_4$–$C_8$ alkoxyalkoxyalkyl; $C_4$–$C_8$ cycloalkylalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with halogen, $C_1$–$C_3$ alkyl or $C_1$–$C_3$ haloalkyl; $C_4$–$C_8$ trialkylsilylalkyl; $C_3$–$C_8$ cyanoalkyl; $C_3$–$C_8$ halocycloalkyl; $C_3$–$C_8$ haloalkenyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $C_2$–$C_8$ alkyl carbonyl; benzyl optionally substituted with halogen, $C_1$–$C_3$ alkyl or $C_1$–$C_3$ haloalkyl; $CHR^{24}COR^{18}$; $CHR^{24}P(O)(OR^{18})_2$; $CHR^{24}P(S)(OR^{18})_2$; $CHR^{24}C(O)NR^{19}R^{20}$; $CHR^{24}C(O)NH_2$; $CHR^{24}CO_2R^{18}$; $CO_2R^{18}$; $SO_2R^{18}$; phenyl optionally substituted with $R^{29}$;

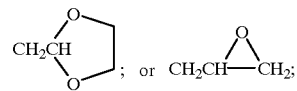

$R^{18}$ is $C_1$–$C_6$ alkyl, $C_1$–$C_6$ haloalkyl, $C_3$–$C_6$ alkenyl or $C_3$–$C_6$ alkynyl;

$R^{19}$ and $R^{21}$ are independently H or $C_1$–$C_4$ alkyl;

$R^{20}$ and $R^{22}$ are independently $C_1$–$C_4$ alkyl or phenyl optionally substituted with halogen, $C_1$–$C_3$ alkyl or $C_1$–$C_3$ haloalkyl;

$R^{19}$ and $R^{20}$ may be taken together as —$(CH_2)_5$—, —$(CH_2)_4$— or —$CH_2CH_2OCH_2CH_2$—, each ring optionally substituted with $C_1$–$C_3$ alkyl, phenyl or benzyl;

$R^{21}$ and $R^{22}$ may be taken together with the carbon to which they are attached to form $C_3$–$C_8$ cycloalkyl;

$R^{23}$ is $C_1$–$C_4$ alkyl or $C_1$–$C_4$ haloalkyl;

$R^{24}$ and $R^{25}$ are independently H or $C_1$–$C_4$ alkyl;

$R^{26}$ is H, $C_1$–$C_6$ alkyl, $C_3$–$C_6$ alkenyl or $C_3$–$C_6$ alkynyl;

$R^{27}$ is H, $C_1$–$C_4$ alkyl or halogen;

$R^{28}$ and $R^{30}$ are independently H or $C_1$–$C_4$ alkyl; and $R^{29}$ is $C_1$–$C_2$ alkyl, $C_1$–$C_2$ haloalkyl, $OCH_3$, $SCH_3$, $OCHF_2$, halogen, CN or $NO_2$;

and their corresponding N-oxides and agriculturally suitable salts provided that 1) the sum of X, Y, and Z is no greater than 5 atoms in length and only one of Y and Z can be other than a carbon containing link;

2) when A and B are other than taken together as X—Y—Z then $G^1$ is N and $G^2$ is $CR^4$;

3) when $R^{12}$ is $CO_2R^{17}$, $C(O)SR^{17}$, CH=$CR^{27}CO_2R^{17}$ or $CH_2CHR^{27}CO_2R^{17}$ then $R^{17}$ is other than $C_1$ haloalkyl and when $R^{17}$ is $CHR^{24}CO_2R^{18}$ or $CO_2R^{18}$ then $R^{18}$ is other than $C_1$ haloalkyl;

4) when $G^1$ is N then $G^2$ is $CR^4$, and when $G^2$ is N then $G^1$ is $CR^1$;

5) when $G^1$ is N and A and B are taken together as $CH_2CH_2CH_2CH_2$, then Q is Q-2 or Q-3;

6) when Q is Q-1, $G^1$ is $CR^1$, $G^2$ is N,
   A and B are taken together as X—Y—Z to form a fused ring such that X is connected to nitrogen and Z is connected to carbon, Y is $CHR^5CHR^6$, and Z is $CHR^8$, then X is $CH_2CH_2$ or $CR^2$=$CR^3$; and 7) when Q is Q-1, $G^1$ is N, $G^2$ is $CR^4$,
   A is $C_1$–$C_4$ alkyl, $C_1$–$C_4$ haloalkyl, $C_2$–$C_4$ alkenyl, $C_2$–$C_4$ alkynyl, $OR^{10}$, $SR^{10}$ or halogen,
   B is $C_1$–$C_4$ alkyl, $C_1$–$C_4$ haloalkyl, $C_3$–$C_4$ alkenyl or $C_3$–$C_4$ alkynyl,
   $R^{12}$ is H, $C_1$–$C_8$ alkyl, $C_1$–$C_8$ haloalkyl, halogen, OH, $OR^{17}$, SH, $S(O)_nR^{17}$, $COR^{17}$, $CO_2R$, $C(O)SR$ $CH_2CHR^{27}CO_2R^{17}$, $C(O)NR^{19}R^{20}$, CHO, $CR^{19}$=$NOR^{26}$, CH=$CR^{27}CO_2R^7$, $NO_2$, CN, $NHSO_2R^{23}$, $NH_2$ or phenyl optionally substituted with $R^{29}$; then,
   $R^{17}$ is $C_2$–$C_8$ alkylthioalkyl; $C_2$–$C_8$ alkylsulfinylalkyl; $C_2$–$C_8$ alkylsulfonylalkyl, $C_4$–$C_8$ alkoxyalkoxyalkyl; $C_4$–$C_8$ alkenoxyalkyl; $C_4$–$C_8$ alkynoxyalkyl; $C_6$–$C_8$ cycloalkoxyalkyl; $C_4$–$C_8$ alkenyloxyalkyl; $C_4$–$C_8$ alkynyloxyalkyl; $C_3$–$C_8$ haloalkoxyalkyl; $C_4$–$C_8$ haloalkenoxyalkyl; $C_4$–$C_8$ haloalkynoxyalkyl; $C_6$–$C_8$ cycloalkylthioalkyl; $C_4$–$C_8$ alkenylthioalkyl; $C_4$–$C_8$ alkynylthioalkyl; $C_1$–$C_4$ alkyl substituted with phenoxy or benzyloxy, each ring optionally substituted with halogen, $C_1$–$C_3$ alkyl or $C_1$–$C_3$ haloalkyl; $C_4$–$C_8$ trialkylsilylalkyl; $C_3$–$C_8$ halocycloalkyl; $C_5$–$C_8$ alkoxyalkenyl; $C_5$–$C_8$ haloalkoxyalkenyl; $C_5$–$C_8$ alkylthioalkenyl; $C_3$–$C_8$ haloalkynyl; $C_5$–$C_8$ alkoxyalkynyl; $C_5$–$C_8$ haloalkoxyalkynyl; $C_5$–$C_8$ alkylthioalkynyl; $CHR^{24}P(O)$ $(OR^{18})_2$; $CHR^{24}P(S)$ $(OR^{18})_2$; $CO_2R^{18}$; or phenyl optionally substituted with $R^{29}$.

2. A compound of Formula I of claim 1 wherein $R^2$, $R^3$, $R^5$, $R^6$, $R^8$ and $R^9$ are independently H, F, $CH_3$ or $CF_3$.

3. A compound of claim 2 wherein
   $R^{12}$ is H, $OR^{17}$, $SR^{17}$ or $CO_2R^{17}$; and
   $R^{13}$ is halogen or CN.

4. A compound of claim 3 wherein
   Q is Q-1, Q-2, Q-4 or Q-5;
   A and B are taken together as X—Y—Z;
   X is $CHR^2$;
   Y is $CHR^5$ or $CHR^5CHR^6$;
   Z is $CHR^8$;
   $R^2$, $R^3$, $R^5$, $R^6$, $R^8$ and $R^9$ are independently H or F; and
   $R^{17}$ is $C_1$–$C_4$ alkyl, $C_3$–$C_4$ alkenyl, $C_3$–$C_4$ alkynyl, $C_2$–$C_4$ alkoxyalkyl, $C_1$–$C_4$ haloalkyl, $C_3$–$C_4$ haloalkenyl or $C_3$–$C_4$ haloalkynyl provided that when Q is Q-1, then Y is $CHR^5$.

5. The compound of claim 4 which is:
   3-chloro-2-[4-chloro-2-fluoro-5-(2-propynyloxy)-5,6,7,8-tetrahydroimidazo[1,2-a]pyridine.

6. An agriculturally suitable composition for controlling the growth of undesired vegetation comprising an effective amount of a compound of any one of claims 1–4 and 6 and at least one of the following: surfactant, solid diluent or liquid diluent.

7. A method for controlling the growth of undesired vegetation which comprises applying to the locus to be protected an effective amount of a compound of any one of claims 1–4 or 6.

8. A compound of claim 1 which is 6-(3-chloro-4,5,6,7-tetrahydropyrazolo[1,5-a]pyridin-2-yl-7-fluoro-4-(2-propynl)-2H-1,4-benzoxazin-3-(4H)-one.

* * * * *